(12) United States Patent
Sehgal et al.

(10) Patent No.: US 7,481,998 B2
(45) Date of Patent: Jan. 27, 2009

(54) EX VIVO AND IN VIVO EXPRESSION OF THE THROMBOMODULIN GENE FOR THE TREATMENT OF CARDIOVASCULAR AND PERIPHERAL VASCULAR DISEASES

(75) Inventors: Lakshman R. Sehgal, Monarch Beach, CA (US); Jonathan Wong, Palo Alto, CA (US)

(73) Assignee: BioVec, LLC, Chicago, IL (US)

( * ) Notice: Subject to any disclaimer, the term of this patent is extended or adjusted under 35 U.S.C. 154(b) by 22 days.

(21) Appl. No.: 11/650,479

(22) Filed: Jan. 8, 2007

(65) Prior Publication Data

US 2007/0212334 A1    Sep. 13, 2007

Related U.S. Application Data

(63) Continuation-in-part of application No. 10/725,013, filed on Dec. 2, 2003, now Pat. No. 7,179,459.

(60) Provisional application No. 60/430,099, filed on Dec. 2, 2002.

(51) Int. Cl.
    *A01N 63/00* (2006.01)
    *A61K 39/235* (2006.01)
    *A61K 31/715* (2006.01)
    *C12N 15/86* (2006.01)
    *C07H 21/04* (2006.01)

(52) U.S. Cl. .................. 424/93.6; 424/233.1; 514/44; 435/456; 536/23.5; 536/24.1; 536/24.2

(58) Field of Classification Search .................. None
See application file for complete search history.

(56) References Cited

U.S. PATENT DOCUMENTS

| 4,826,811 | A | 5/1989 | Sehgal et al. |
| 5,981,225 | A | 11/1999 | Kochanek et al. |
| 6,290,949 | B1 | 9/2001 | French et al. |
| 7,179,459 | B2 | 2/2007 | Sehgal et al. |

OTHER PUBLICATIONS

Esmon (Ann. Med. 34: 598-605, 2002).*
Borroni et al (Alzheimer Disease and Associated Disorders 16(3): 150-155, 2002).*
Li et al (J. Vasc. Surg. 32: 804-813, 2000).*
Tohda et al (Arteriosclerosis, Thrombosis, and Vascular Biology;18:1861-1869, 1998).*
Tabuchi et al (Eur. J. Card. Thor. Surg. 26: 995-1000, 2004).*
Zushi et al, Aspartic acid 349 in the fourth epidermal growth factor-like structure of human thrombomodulin plays a role in its Ca(2+)-mediated binding to Protein C. The Journal of Biological Chemistry, (Oct. 25, 1991) vol. 266, No. 30, pp. 19886-19893*
Tsiang et al, Functional domains of membrane-bound human thrombomodulin. EGF-like domains four to six and the serine/threonine-rich domain are required for cofactor activity. The Journal of Biological Chemistry, (Mar. 25, 1992) vol. 267, No. 9, pp. 6164-6170.*
Nagashima et al, Alanine-scanning mutagenesis of the epidermal growth factor-like domains of human thrombomodulin identifies critical residues for its cofactor activity. The Journal of Biological Chemistry, (Feb. 5, 1993) vol. 268, No. 4, pp. 2888-2892.*
Gerlitz et al, Identification of the predominant glycosaminoglycan-attachment site in soluble recombinant human thrombomodulin: potential regulation of functionality by glycosyltransferase competition for serine474. The Biochemical Journal, (Oct. 1, 1993) vol. 295 (Pt 1), pp. 131-140.*
Lin et al, Modulation of glycosaminoglycan addition in naturally expressed and recombinant human thrombomodulin. The Journal of Biological Chemistry, (Oct. 7, 1994) vol. 269, No. 40, pp. 25021-25030.*
Adler et al, The structure of a 19-residue fragment from the C-loop of the fourth epidermal growth factor-like domain of thrombomodulin. The Journal of Biological Chemistry, (Oct. 6, 1995) vol. 270, No. 40, pp. 23366-23372.*
Weiler-Guettler et al, A targeted point mutation in thrombomodulin generates viable mice with a prethrombotic state. The Journal of Clinical Investigation, (May 1, 1998) vol. 101, No. 9, pp. 1983-1991.*
Zuckerbraun, Brian S., et al., "Vascular Gene Therapy, A Reality of the 21$^{st}$ Century," Arch. Surg., vol. 137, pp. 854-861 (2002).
Kibbe, Melina R., et al., "Gene Therapy for Restenosis," Circ. Res., vol. 86, pp. 829-833 (2000).
Shears, Larry L., et al., "Efficient Inhibition of Intimal Hyperplasia by Adenovirus-Mediated Inducible Nitric Oxide Synthase Gene Transfer to Rats and Pigs In Vivo," J. Am. Coll. Surg., vol. 187, No. 3, pp. 295-306 (1998).
Russell Ross, "The pathogenesis of atherosclerosis: a perspective for the 1990s," Nature, vol. 362, pp. 801-809 (1993).
Sadler, J. Evan, "Thrombomodulin Structure and Function," Tehomb Haemost., vol. 78, pp. 392-395 (1997).
Esmon, Charles T., "Thrombomodulin as a model of molecular mechanisms that modulate protease specificity and function at the vessel surface," Faseb J., vol. 9; pp. 946-955 (1995).
Salomaa, Veikko, et al., "Soluble thrombomodulin as a predicctor of incident coronary heart disease and symptomless carotid artery atherosclerosis in the Atherosclerosis Risk in Communities (ARIC) Study: a case-cohort study," Lancet, vol. 353, pp. 1729-1734 (1999).
Palmer, R.M.J., et al., "Nitric oxide release accounts for the biological activity of endothelium-derived relaxing factor," Nature, vol. 327, pp. 524-526 (1987).

(Continued)

*Primary Examiner*—Richard Schnizer
(74) *Attorney, Agent, or Firm*—Ping Wang; Morris, Manning & Martin, LLP

(57) ABSTRACT

The present invention relates to methods and compositions for treatment of cardiovascular and peripheral vascular diseases using ex vivo and in vivo gene delivery technologies. One aspect of the present invention relates to a method for treating a vascular disease by introducing a DNA sequence encoding a TM protein or its variant into a segment of a blood vessel ex vivo using a gutless adenovirus vector. Another aspect of the present invention is to provide a gutless adenovirus vector carrying a transgene, such as a gene encoding TM protein or its variant.

9 Claims, 7 Drawing Sheets
(1 of 7 Drawing Sheet(s) Filed in Color)

OTHER PUBLICATIONS

Kubes, P., et al., "Nitric oxide: An endogenous modulator of leukocyte adhesion," Proc. Natl. Acad. Sci. USA, vol. 88, pp. 4651-4655 (1991).

Steg, P. Gabriel, M.D., et al., "Reduction of Restenosis After Angioplasty in an Atheromatous Rabbit Model by Suicide Gene Therapy," Circulation, vol. 96, pp. 401-411 (1997).

Van Belle, Eric, et al., "Accelerated Endothelialization by Local Delivery of Recombinant Human Vascular Endothelial Growth Factor Reduces In-Stent Intimal Formation," Biochem. and Biophs. Res. Communications, vol. 235, pp. 311-316 (1997).

Salyapongse, A. Neil, M.D., et al., "Gene Therapy and Tissue Engineering," Tissue Engineering, vol. 26, No. 4, pp. 663-676 (1999).

Kon, T., et al., "Bone Morphogenetic Protein-2-Stimulates Differentiation of Cultured Spinal Ligament Cells from Patients with Ossification of the Posterior Longitudinal Ligament," Calcif. Tissue Int., vol. 60; pp. 291-296 (1997).

Kibbe et al. (J. Vasc. Surg. 34: 156-65, 2001).

He et al. (PNAS, 95: 2509-2514).

Marmur, J., et al., "Strand Separation and Specific Recombination in Deoxyribonucleic Acids: Biological Studies," PNAS USA, vol. 46, pp. 453-461 (1960).

Doty, P., et al., "Strand Separation and Specific Recombination in Deoxyribonucleic Acids: Physical Chemical Studies," PNAS USA, vol. 46, pp. 461-476 (1960).

Sambrook, J. Fritsch, et al., "Analysis of Genomic DNA by Southern Hybridization," *Molecular Cloning: A Laboratory Manual* (Cold Spring Harbor Lab. Press, Plainview, NY), vol. II, pp. 9.31-9.62 (1989).

Curiel, David T., "Strategies to Adapt Adenoviral Vectors for Targeted Delivery," *Ann NY Acad Sci* 886, pp. 158-171 (1991).

Haj-Ahmand, Yousef, et al., "Development of a Helper-Independent Human Adenovirus Vector and Its Use in the Transfer of the Herpes Simplex Virus Thymidine Kinase Gene," *J. Virol.* vol. 57, No. 1, 267-274 (1986).

Ragot, Thierry, et al., "Efficient adenivirus-mediated transfer of a human minidystrophin gene to skeletal muscle of *mdx* mice," *Nature*, vol. 361, pp. 647-650 (1993).

Howell, John McC., et al., "High-Level Dystrophin Expression after Adenovirus-Mediated Dystrophin Minigene Transfer to Skeletal Muscle of Dystrophic Dogs: Prolongation of Expression with Immunosuppression," *Hum Gene Ther.*, vol. 9, pp. 629-634 (1998).

Parks, Robin J., et al., "A helper-dependent adenovirus vector system: Removal of helper virus by Cre-mediated excision of the viral packaging signal," *PNAS*, vol. 93, pp. 13565-13570 (1996).

Lieber, André, et al., "Recombinant Adenoviruses with Large Deletions Generated by Cre-Mediated Excision Exhibit Different Biological Properties Compared with First-Generation Vectors In Vitro and In Vivo," *J. Virol*, vol. 70, pp. 8944-8960 (1996).

Gossen, Manfred, et al., "Tight control of gene expression in mammalian cells by tetracycline-responsive promoters," *PNAS USA*, vol. 89, pp. 5547-5551 (1992).

Gossen, Manfred, et al., "Transcriptional Activation by Tetraclines in Mammalian Cells," *Science*, vol. 268, pp. 1766-1769 (1995).

Kistner, Andreas, et al., "Doxycycline-mediated quantitative and tissue-specific control of gene expression in transgenic mice," *PNAS USA*, vol. 93, pp. 10933-10938 (1996).

No, David, et al., "Ecdysone-inducible gene expression in mammalian cells and transgenic mice," *PNAS USA*, vol. 93, pp. 3346-3351 (1996).

Wang, Yaolin, et al., "A regulatory system for use in gene transfer," *PNAS USA*, vol. 91, pp. 8180-8184 (1994).

Wang, Yaolin, et al., "Ligand-inducible and liver-specific target gene expression in transgenic mice," *Nat. Biotech.*, vol. 15, pp. 239-243 (1997).

Magari, Shannon R., et al., "Pharmacologic Control of a Humanized Gene Therapy System Implanted into Nude Mice," *J. Clin. Invest.*, vol. 100, No. 11, pp. 2865-2872 (1997).

Ye, Xuehai, et al., "Regulated Delivery of Therapeutic Proteins After in Vivo Somatic Cell Gene Transfer," *Science*, vol. 283, pp. 88-91 (1999).

Suzuki, Koji, et al., "Structure and expression of human thrombomodulin, a thrombin receptor on endothelium acting as a cofactor for protein C activation," *EMBO J.*, vol. 6, No. 7, pp. 1891-1897 (1987).

Dittman, William A., et al., "Human Thrombomodulin: Complete cDNA Sequence and Chromosome Localization of the Gene," *Biochemistry*, vol. 26, pp. 4350-4357 (1987).

Beauchamp, Cindy, et al., "Development of a FLP/frt Syste for Generating Helper-Dependent Adenoviral Vectors," *Molecular Therapy*, vol. 3, No. 5, pp. 809-815 (2001).

Umana, Pablo, et al., "Efficient FLPe recombinase enables scalable production of helper-dependent adenoviral vectors with negligible helper-virus contamination," *Nature Biotechnology*, vol. 19, pp. 582-585 (2001).

* cited by examiner

SEQUENCE LISTING

<160> NUMBER OF SEQ ID NOS: 16

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 1

```
catcatcaat aatataccct attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tactggtacc gcggccgcct    360
cgagtctaga actagtggat ccccgggct gcaggaattc tgatggctct caaaattcct    420
gcctccttta gggataaaag actttaagac ttttaacaa aaagaaaaa gaaaaaaaa     480 attcctgcct cctggtgtac acacacagaa gggttccctc cccttgaatg tgaccaggat    540
ctgtgaaaat aacgggatag ccgctcctgt gattaggtta tgtggtagac tagagcaaga    600
ttctcctgct ggttttgaag aagtcagctg ccatgttgtg agactgtcat gggctagggc    660
atgagccttt aaatatctgg gagcaacccc tggccagcag ccagtgagaa aacgggccct    720
cagtcctaca atcacaagga actaaattct gccaacaacc tgaaggaact ttgaagagga    780
tcatgagtcc cttgattcag cttgatgagc ccctgagcag aggatacagc taacttgtac    840
tagggaagta taaaaacat gcatgggaat gatatatatc aactttaagg ataattgtca    900
tacttctggg aatgaaggga agaaatggg gctttagttg tattatgatc tttaatttct    960
caaaaaaaat aagatcagaa gcaaatatgg caaatgtta atactttgtg gggtacgtag   1020
gtattcagca tacccttttt tctgagttca aaatatttta taattaaaat gaaatgcagg   1080
ccaggcacag tggctcatgc ctataatacc agcactttgc gaggccgagg tgggaggatg   1140
gcttgaggcc agaccagcct ggccaacatg gcaaaccccc atctctactt aaaaaaaaaa   1200
aaactatata tatatatatg tgtgtgtgtg tgtatatata tatgtgtata tatttata     1260 tatgtgtgta tatatatata tgtatatata tttatatatg tgtgtgtata tatatata    1320 cacacacaca catatataca tacatacata cacacacaca cacacacaat tagccaggca   1380
tggtggcgca cacctgtagt cccagctact tgggaggctg agacatgaga attgcttgaa   1440
```

```
cctgggaggc agagtagtta gtgagctgag atcataccac tgcactccag cctggtgaca    1500
gagtgagact ctgtcttaaa aaaataaaa attaaaatta aatgcaaaag gtccaagtga    1560
attgaagagg aaagggtat caaggaaggt tttgtggagg tgacgtttga gctgggtctt    1620
aaatgactta aacatgggat aagaagggag ggaataagga catttcaggt acgagaaata    1680
aggagcaaac agtggaaaca acctaacgtc tgtcaaccag tgaatggata acaaaaatgt    1740
aattcagatg gtatccaact tacgatggtt caacatgaga ttttctgac tttaggatag    1800 atttatcaaa gtagtaaatc cattttcaac ttatgatatt ttcaacttca gatgggttta    1860
tcaggacaca gttgaggaac acctgtctat ccatacaatt tggcaataaa aggaaatga    1920 gtgcagatat actccacaac atgaatgaac cttgaaaaca ttaagtgaga aagccagat    1980 acaaaaggcc acatattgta tgattctatt tatacaaaat gtccagaata ggcaaatctt    2040
atagacagca agtaggtaga tgatcagttt gctaggtgct gggggaaggg gaaatgggga    2100
gtgatggcta aggggattgg gtttctttgt ggggcaatga aaatgtttta aaattgagcg    2160
tgataatgat tgcacaatgc tgcatatata taatctat agattatata tatataaga    2220 gaggctgtta gacagtgata agtgatatat atatatatat acatagagag agagagagag    2280
agagagagag gctgttagtg ataagtgatc aggaaaataa aagtattgag gaggaatacg    2340
aagttgacgg tgtgaaaaca tgagatttta tataggatgg ccaggaaagg ccttaatgag    2400
aaagtgactt atgagtaaaa acaagggatc ctaaaccttta gcatgcatca gaatcactcg    2460
gaaacttgtt aaagcatagc ttgctgggcc tcatcacaga tattttgatt cggtaggttc    2520
ttgtctgata ttaatacttt tggtctaggg aaccacattt tgagaaccac tgagctaaag    2580
gaagtaaagg tttcccttag tttactagct ggtaaccta ggaaactgct tagcctctcg    2640
gtgctaagat acaaaatact ttagcacata ataacacatg gaaaatagtc tataaattat    2700
aaatattatt ttttatgtac caaatattac ataagacaaa atctaagcaa gatatatata    2760
tatatacata aaatataaga tatatatgta tatattatat atagataaat agagagagag    2820
agttatgttt agaaagaaaa tacttcaaac taaaaaaaga gaggtaggaa gtataccatt    2880
ccattattgg taaaaacaaa ttactaagta gtctttacaa aaaaccaatc tcactccttt    2940
agaacacaag cccaccatta aaactgatgc agaggaattt ctctccctgg cttacccttta    3000 ggatggtgca tactaagtta gaaaagtcat aaatgttata ttaaaagtaa atgtgaactt    3060
acttccacaa tcaagacatt ctagaagaaa aagagaaatg aaaatcagta caatgaataa    3120
aacggtattt ccaattataa gtcaaatcac atcataacaa ccctaaggaa ttatccaaac    3180
tcttgttttt agatgcttta ttatatcaaa ctctccttta aacaagtggc ccatctgctg    3240
ggatttggaa gcctgtaata ctgaaatttt catcataatg gaaattttaa aaacagaatt    3300
tgacccacct gtttttaaaa cactttcatt acttaacaag aggtctaatc ttgggcaagt    3360
cttgaaattt ctctggcctt agtttcccat gtgttaaatg aaacttgaag cagttggtct    3420
cttatagtct cctgactcta acattctaag aattatattt gtacaataac tcaaaaatca    3480
cataatttaa tttaccatat ggactccaaa atatattttc tcattaggct aaacttgatc    3540
tgcattttct ggatgtgtcc atattcttgg actacactaa aacatgatac caatgcttcc    3600
tctcaccata aaccctcact tcgctttcta catttaagaa ttttatagct ggaagagtcc    3660
ttaacagaaa ataccatcta ataattaccc ctcaaaatcg agaaagtcct atctgttctt    3720
atgctagtta taagaatgag gcagcatttc acataatggt tataaacact gccacaagaa    3780
gattcatgat gtgttgttta tctgtagctc tcatcatact ctgtcatata actatagcat    3840
```

```
taagattttta atgttctata tattcttcta agacagtgtt taccagagta aggcacaaaa    3900
gatccactgg tttgcaagaa agattagaac ttttaaattt tttacctcac cttgtttaat    3960
ctatatttt gtatgtattt tgtaacatat atattattat taccataaat catatataat    4020
ttaaaatgca tatattaggg gtaaatgctc aggaaacttt ttataaattg ggcatgcaaa    4080
tacaagtttg aagactcact gttctaggta ttaaaagtaa agttataacc aagtaaagct    4140
tccaccttt catgtctcaa agcagtttat tgttggaggt aagatctctt agaagcctaa    4200
acaggtccaa gtacagaatg aagtaaggct agcccataac ttgtggcaag caattcatac    4260
tatttctctc atgctgagct ctcctcagtg aagcagctac tatagacaac tgcagcctat    4320
tggtagccta ttttacaggc aggaaaaaaa ttactttta ttcaaagtgg aactcaggac    4380
atggggagaa aatgaataca aaaataggg tcaatccaaa ggcacacagc aaatgagtaa    4440
cacagttatg tttttttccc atttgtatga ggtcccagta aattctaagt aaactgcaaa    4500
tttaataata cactaaaaaa gccatgcaat tgttcaaatg aatcccagca tggtacaagg    4560
agtacagaca ctagagtcta aaaacaaaa gaatgccatt attgagtttt tgaattatat    4620
caagtagtta catctctact taataaatga gaaaacgag gataagaggc catttgataa    4680
aatgaaaata gccaagaagt ggtattagag acttgaatac aggtattcgg gtccaaagtt    4740
catctgctca aatactaact ggggaaaaga gggaaaaata tttatataca tatatatctg    4800
cacacaaaaa tacccccaaa agacaaaatg aggccaggca gggtggctca cacccgtaat    4860
cccggtactt tgggaggctg aggcaggtgg atacctgaga tcaggagttg agatcagcc    4920
tggtcaacat ggtgaaaccc tgtctctact aaagataaaa aaattagcca ggcatggtgg    4980
cgtgcgcctg taatcccagc tacttgggag tctgaggcag gagaatcact tgaactggga    5040
aggggaggtt gcagtgagcc aagatcgtac tactgcactc cagcctgggc agcagagtga    5100
gactccatca caaaaataaa taaataaata aaatacaatg aaacagaaag ttcaaataat    5160
cccataatct taccaccaag aaataacttt cactcgttat acttattgat ttttccataa    5220
taaatgtact ttactgtgac tatcatgaaa agaaagttat tttagaaaca gagaactgtt    5280
tcagatcaaa tctatgtagt agaacagagc cattaggtgg gaaagacgag atcaaactaa    5340
atctcagaag gcctaaaagg ctaggtccat tccagcacta aaaactgacc agacaagtaa    5400
tggcttcaac agcttctaaa tatggacaaa gcatgctgaa agggaaggac aggtctaaca    5460
gtggtatatg aaatgaacag gaggggcaaa gctcatttct cctctgaagt tttccaaaga    5520
tgctgaggag gacattagtt tgacatgacc ctgatatggg acaagataat ttcacagaag    5580
ttttacatgt taaagttttc ttatagatac tcattcaagt aagcaatgaa cactaaaatc    5640
taaagaaaga aaagagcttt agagtcaggt ctgtattcaa attcaagctc taccacttac    5700
tggttctgtg actttgggca agtcttttaa ccttattaag tcttaatttc ctgatttgta    5760
aaatggggat atcgtctccc tcacaggatt gttgtgaaac tttatgaga ttaatgcctt    5820
tatatttggc atagtgtaag taaacaataa ctggcagctt caaaaaaaaa aagcagtagc    5880
attccatcat ttattattgg ttactctcaa aaagttttc aatgtactag aagataaata    5940
ttcaaatacc ttaatatctc cattattttc aggtaaacag catgctcctg aacaaccaat    6000
gggtcaacaa ataaattaaa agggaaatct aaaaacatct tgatattaaa ctacatggaa    6060
gcacaatata ccaaaaccaa tggttcacac taggagaatt ttaaggtaca agaaaactct    6120
ttgagatttc ttaaaataat agtatgtctg aatttattga gtgatttacc agaaactgtt    6180
gtaagagctc tacttgcatt atagcactta atcctcttaa ctctatggct gctattatca    6240
```

```
acctcaccct aatcacatat gggacacaga gaggttaagt aacttgccca aggtcagagt    6300
taggaagtac taagccatgc tttgaatcag ttgtcaggct ccggaactca cactttcagc    6360
cactacataa tactgctttg ctatctttta ggaaactatg tgagtctacc tcacatagac    6420
tcacataggt ttgttttttt tttttttta aaggctatct tttcccccat caatgttttt    6480
tgaaggatcc caaattagag tcccacagag gcagacagca gtacttgaca atatggacat    6540
ttaaggttaa tgttggattc tactgtcttt ttactacatg acctagggaa cgataattaa    6600
cctagactgc ttccaagggt taaataaccc atttagttat actatgtaaa ttatctctta    6660
gtgattgatt gaaagcacac tgttactaat tgactcggta tgaagtgctt ttttttcttc    6720
cctttcaaga tacatacctt tccagttaaa gttgagagat catctccacc aattactttt    6780 atgtccctg ttgactggtc attctagtta aaaaaaaaa aaactatata tatatatatc    6840
tacacacaca tatgtatatg tatatcctta tgtacacaca caaacttcaa attaaatgag    6900
aactagaaga tttgagaagt tagctagcta atatccatag cattatgata ttctaaatga    6960
tatgaattat aagaattagg tttcctgaaa tgaatgacta gaaaactttc aagtagagat    7020
tagtaaaaat taaaaagtcc taatcggcca ttactgattt tgatgttttta agagtcctaa    7080 aaaatgggtt acatccattt ttaagtgggt agtattataa cagccaccca tcttcaatca    7140
cagtgatttc tgaattgtga gggaagttat tagcatgaca ggtgtctggt tctgccctg    7200 tacgattccc atgagtcaag caaattgtaa gggctggtct atatcacacc caccccaag    7260 gatatgtccc tcaaaagtct agcccaggcc ccgtcatctt cagcatcatc tgggaaacca    7320
ggtctgatta gtagtccttt aaggaatacc tcttaggctc ccattttact gctatcacag    7380
aatccaataa aacccttaca ggagattcaa tgggaaatgc tcaacaccca ctgtagttgg    7440
tggtgacaat gaccataatt tggctgtgct ggattcagga cagaaaattt gggtgaaaga    7500
gcaggtgaac aaaagagctt cgacttgccc tagcagagag caagccatac ataccacaa    7560 agccacagca attacaacgg tgcagtacca gcacagtaaa tgaacaaagt agagcccaga    7620
aacagaccca gaactatatg aggatttagt atacaataaa gatggtattt cgagtcagta    7680
gggaaaagat gaattattca ataaatgatg tttggccaac tagtaaccca tttgggaaaa    7740
aataaaagta tggtccctac ctcacagcat acacaaaaat aaattccaga cggattaaaa    7800
tctaaatgta aaaaataaag ccataagtgg actggaagaa aatagagaat ttttttaac    7860 atccgtagaa agggtaaaaa cccaggcatg acatgaacca aaactgaaga ggttctgtaa    7920 caaataccc ctttttatata ttgggctcca acaataagaa cccataggaa aatggagaat    7980
gaacacaaat agacaattta tagaagagaa ggttataagg tgtaaaatta tatctatctg    8040
agaaacaaac actaaaacaa tgtgattcta ctgttctccc acccatactg gcaaaactta    8100
agcctgataa tatgctgagg ggaaataagc actcttgttg gtgagagtat taattggcat    8160
agcttctttt gaaaatgaca tagcaatacc tgttaaaatt gcaaacatgc atgtcactta    8220
atccagtaat cccacttctg ggaatcaatg ctacaaaaac actgacaagt atacaaagat    8280
acattcaaga gtgttcactg gccgggtgc ggtggcttca tgcctgtaat cccagggagg    8340
cagaggcaag acgatcgctt gaccccagga gttcaaggcc agcccgagaa acacagcaag    8400
accctgtctc tcttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaacaccaag tagtggaaca ctgtgttgcc tatgacacca tttttattca    8640
```

```
acatttaaac aaatttgtaa cagcaattac atgagtagtg acaatggcgt ttatgagact    8700
tttcactttt atgtgcttct attttttgtta tgcttctata tatacatcca tttattatgg    8760
agtgttactt tcaaaaatca caaatgggcc agtattattt ggtgttgcaa ggtgagcata    8820
tgacttctga tatcaacctt tgcatattac ttctcaattt agggaaatta cagacatccc    8880
ttattctaac taacttaaaa cccagcattt caaacataca gaattgatgg ggaaaaaaaa    8940
gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
agttgatgtc tttacagaga caagaggaat aaaggaaaaa atattcaaga actgaaaagt    9120
atggagtcat ggaaaaattg ctgtgatcca aaggctacgg tgataggaca agaaacaaga    9180
gaactccaag cagtaagaca ctgctgttct attagcatcc aaacctccat actcctgttt    9240
gccccaaggc tttttaaaa aatagagaca ggatctcact attttgctca ggctggtctt    9300
gaactcctgg actcaagcta tcctcctgcc tcggcctcct aaagtgccga gattacaggc    9360
ttgagtcacc atacctggct atttattttt tcttaactct cttgcctggc ctatagccac    9420
catgaagct aataaagaat attaatttaa gagtaatggt atagttcact acattggaat    9480
acaggtataa gtgcctacat tgtacatgaa tggcatacat ggatcaatta ccccacctgg    9540
gtggccaaag gaactgcgcg aacctccctc cttggctgtc tggaacaagc ttcccactag    9600
atcccttttac tgagtgcctc cctcatcttt aattatggtt aagtctagga taacaggact    9660
ggcaaaggtg aggggaaagc ttcctccaga gttgctctac cctctcctct accgtcctat    9720
ctcctcactc ctctcagcca aggagtccaa tctgtcctga actcagagcg tcactgtcaa    9780
ctacataaaa ttgccagaga agctctttgg gactacaaac atacccctt aatgtcttta    9840
tttctatttt gtctacctct tcagtctagg tgaaaaata ggaaggataa tagggaagaa    9900
ctttgtttat gcctacttat ccgccccctag gaattttgaa aacctctagg tagcaataag    9960
aactgcagca tggtatagaa aaagaggagg aaagctgtat agaaatgcat aataaatggg   10020
caggaaaaga actgcttgga acaaacaggg aggttgaact ataaggagag aaagcagaga   10080
ggctaatcaa caaggctggg ttcccaagag ggcatgatga gactattact aaggtaggaa   10140
ttactaaggg ctccatgtcc ccttagtggc ttagtactat gtagcttgct ttctgcagtg   10200
aacttcagac ccttctttta ggatcctaga atggactttt ttttttttatc ggaaaacagt   10260
cattctctca acattcaagc aggccccaag tctaccacac tcaatcacat tttctcttca   10320
tatcataatc tctcaaccat tctctgtcct tttaactgtt tttctatacc ctgatcaaat   10380
gccaacaaaa gtgagaatgt tagaatcatg tatttttaga ggtagactgt atctcagata   10440
aaaaaaaagg gcagatattc cattttccaa atatgtatg cagaaaaaat aagtatgaaa   10500
ggacatatgc tcaggtaaca agttaatttg tttacttgta ttttatgaat tccctaaaac   10560
ctacgtcacc cgccccgttc ccacgccccg cgccacgtca caaactccac cccctcatta   10620
tcatattggc ttcaatccaa ataaggtat attattgatg atgttaatta acatgcatgg   10680
atccatatgc ggtgtgaaat accgcacaga tgcgtaagga gaaataccg catcaggcgc   10740
tcttccgctt cctcgctcac tgactcgctg cgctcggtcg ttcggctgcg gcgagcggta   10800
tcagctcact caaaggcggt aatacggtta tccacagaat caggggataa cgcaggaaag   10860
aacatgtgag caaaaggcca gcaaaaggcc aggaaccgta aaaaggccgc gttgctggcg   10920
tttttccata ggctccgccc ccctgacgag catcacaaaa atcgacgctc aagtcagagg   10980
tggcgaaacc cgacaggact ataaagatac caggcgtttc ccctggaag ctccctcgtg   11040
```

```
cgctctcctg ttccgaccct gccgcttacc ggatacctgt ccgcctttct cccttcggga   11100
agcgtggcgc tttctcatag ctcacgctgt aggtatctca gttcggtgta ggtcgttcgc   11160
tccaagctgg gctgtgtgca cgaaccccc gttcagcccg accgctgcgc cttatccggt    11220
aactatcgtc ttgagtccaa cccggtaaga cacgacttat cgccactggc agcagccact   11280
ggtaacagga ttagcagagc gaggtatgta ggcggtgcta cagagttctt gaagtggtgg   11340
cctaactacg gctacactag aaggacagta tttggtatct gcgctctgct gaagccagtt   11400
accttcggaa aaagagttgg tagctcttga tccggcaaac aaaccaccgc tggtagcggt   11460 ggttttttg tttgcaagca gcagattacg cgcagaaaaa aaggatctca agaagatcct    11520
ttgatctttt ctacggggtc tgacgctcag tggaacgaaa actcacgtta agggattttg   11580
gtcatgagat tatcaaaaag gatcttcacc tagatccttt taaattaaaa atgaagtttt   11640
aaatcaatct aaagtatata tgagtaaact tggtctgaca gttaccaatg cttaatcagt   11700
gaggcaccta tctcagcgat ctgtctattt cgttcatcca tagttgcctg actcccgtc    11760 gtgtagataa ctacgatacg ggagggctta ccatctggcc ccagtgctgc aatgataccg   11820
cgagacccac gctcaccggc tccagattta tcagcaataa accagccagc cggaagggcc   11880
gagcgcagaa gtggtcctgc aactttatcc gcctccatcc agtctattaa ttgttgccgg   11940
gaagctagag taagtagttc gccagttaat agtttgcgca acgttgttgc cattgctgca   12000
gccatgagat tatcaaaaag gatcttcacc tagatccttt tcacgtagaa agccagtccg   12060
cagaaacggt gctgaccccg gatgaatgtc agctactggg ctatctggac aagggaaaac   12120
gcaagcgcaa agagaaagca ggtagcttgc agtgggctta catggcgata gctagactgg   12180
gcggttttat ggacagcaag cgaaccggaa ttgccagctg ggcgccctc tggtaaggtt    12240 gggaagccct gcaaagtaaa ctggatggct ttcttgccgc caaggatctg atggcgcagg   12300
ggatcaagct ctgatcaaga gacaggatga ggatcgtttc gcatgattga acaagatgga   12360
ttgcacgcag gttctccggc cgcttgggtg gagaggctat tcggctatga ctgggcacaa   12420
cagacaatcg gctgctctga tgccgccgtg ttccggctgt cagcgcaggg gcgcccggtt   12480 cttttgtca agaccgacct gtccggtgcc ctgaatgaac tgcaagacga ggcagcgcgg    12540
ctatcgtggc tggccacgac gggcgttcct tgcgcagctg tgctcgacgt tgtcactgaa   12600
gcgggaaggg actggctgct attgggcgaa gtgccggggc aggatctcct gtcatctcac   12660
cttgctcctg ccgagaaagt atccatcatg gctgatgcaa tgcggcggct gcatacgctt   12720
gatccggcta cctgcccatt cgaccaccaa gcgaaacatc gcatcgagcg agcacgtact   12780
cggatggaag ccggtcttgt cgatcaggat gatctggacg aagagcatca ggggctcgcg   12840
ccagccgaac tgttcgccag gctcaaggcg agcatgcccg acggcgagga tctcgtcgtg   12900
acccatggcg atgcctgctt gccgaatatc atggtggaaa atggccgctt ttctggattc   12960
atcgactgtg gccggctggg tgtggcggac cgctatcagg acatagcgtt ggctacccgt   13020
gatattgctg aagagcttgg cggcgaatgg gctgaccgct tcctcgtgct ttacggtatc   13080
gccgctcccg attcgcagcg catcgccttc tatcgccttc ttgacgagtt cttctgaatt   13140
ttgttaaaat ttttgttaaa tcagctcatt ttttaaccaa taggccgaaa tcggcaaaat   13200
cccttataaa tcaaagaat agaccgagat agggttgagt gttgttccag tttggaacaa    13260
gagtccacta ttaaagaacg tggactccaa cgtcaaaggg cgaaaaaccg tctatcaggg   13320
cgatggccca ctacgtgaac catcacccta atcaagtttt tggggtcga ggtgccgtaa    13380 agcactaaat cggaacccta agggagcccc cgatttaga gcttgacggg gaaagccggc   13440
```

-continued

```
gaacgtggcg agaaaggaag ggaagaaagc gaaaggagcg ggcgctaggg cgctggcaag    13500
tgtagcggtc acgctgcgcg taaccaccac acccgccgcg cttaatgcgc cgctacaggg    13560
cgcgtccatt cgccattcag gatcgaatta attcttaatt aa                      13602
```

<210> SEQ ID NO 2
<211> LENGTH: 575
<212> TYPE: PRT
<213> ORGANISM: Homo sapiens

<400> SEQUENCE: 2

```
Met Leu Gly Val Leu Val Leu Gly Ala Leu Ala Leu Ala Gly Leu Gly
 1               5                  10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
    65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
               100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
    145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
               180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
        210                 215                 220

Thr Ala Pro Pro Gly Ala Val Gln Gly His Trp Ala Arg Glu Ala Pro
    225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
                260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
        290                 295                 300

Ser Tyr Ser Cys Met Cys Glu Thr Gly Tyr Arg Leu Ala Ala Asp Gln
    305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
                340                 345                 350
```

```
Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
    450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Ala Val Gly Leu
            500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
    530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575

<210> SEQ ID NO 3
<211> LENGTH: 1725
<212> TYPE: DNA
<213> ORGANISM: Homo sapiens

<400> SEQUENCE: 3
atgcttgggg tcctggtcct tggcgcgctg gccctggccg gcctgggggtt ccccgcaccc    60 gcagagccgc agccgggtgg cagccagtgc gtcgagcacg actgcttcgc gctctacccg   120
ggccccgcga ccttcctcaa tgccagtcag atctgcgacg gactgcgggg ccacctaatg   180
acagtgcgct cctcggtggc tgccgatgtc atttccttgc tactgaacgg cgacggcggc   240
gttggccgcc ggcgcctctg gatcggcctg cagctgccac ccggctgcgg cgaccccaag   300
cgcctcgggc ccctgcgcgg cttccagtgg gttacgggag acaacaacac cagctatagc   360
aggtgggcac ggctcgacct caatggggct cccctctgcg gccgttgtg cgtcgctgtc   420 tccgctgctg aggccactgt gcccagcgag ccgatctggg aggagcagca gtgcgaagtg   480
aaggccgatg gcttcctctg cgagttccac ttccagcca cctgcaggcc actggctgtg   540
gagcccggcg ccgcggctgc cgccgtctcg atcacctacg caccccgtt cgcggcccgc   600 ggagcggact ccaggcgct gccggtgggc agctccgccg cggtggctcc cctcggctta   660
cagctaatgt gcaccgcgcc gcccggagcg gtccaggggc actgggccag ggaggcgccg   720
ggcgcttggg actgcagcgt ggagaacggc ggctgcgagc acgcgtgcaa tgcgatccct   780
ggggctcccc gctgccagtg cccagccggc gccgccctgc aggcagacgg cgctcctgc   840 accgcatccg cgacgcagtc ctgcaacgac ctctgcgagc acttctgcgt tcccaacccc   900
```

| | |
|---|---|
| gaccagccgg gctcctactc gtgcatgtgc gagaccggct accggctggc ggccgaccaa | 960 |
| caccggtgcg aggacgtgga tgactgcata ctggagccca gtccgtgtcc gcagcgctgt | 1020 |
| gtcaacacac agggtggctt cgagtgccac tgctaccctaactacgacct ggtggacggc | 1080 |
| gagtgtgtgg agcccgtgga cccgtgcttc agagccaact gcgagtacca gtgccagccc | 1140 |
| ctgaaccaaa ctagctacct ctgcgtctgc gccgagggct tcgcgcccat tccccacgag | 1200 |
| ccgcacaggt gccagatgtt ttgcaaccag actgcctgtc cagccgactg cgaccccaac | 1260 |
| acccaggcta gctgtgagtg ccctgaaggc tacatcctgg acgacggttt catctgcacg | 1320 |
| gacatcgacg agtgcgaaaa cggcggcttc tgctccgggg tgtgccacaa cctccccggt | 1380 |
| accttcgagt gcatctgcgg gcccgactcg gcccttgccc gccacattgg caccgactgt | 1440 |
| gactccggca aggtggacgg tggcgacagc ggctctggcg agccccgcc cagcccgacg | 1500 |
| cccggctcca ccttgactcc tccggccgtg gggctcgtgc attcgggctt gctcataggc | 1560 |
| atctccatcg cgagcctgtg cctggtggtg gcgcttttgg cgctcctctg ccacctgcgc | 1620 |
| aagaagcagg gcgccgccag ggccaagatg gagtacaagt gcgcggcccc ttccaaggag | 1680 |
| gtagtgctgc agcacgtgcg gaccgagcgg acgccgcaga gactc | 1725 |

<210> SEQ ID NO 4
<211> LENGTH: 649
<212> TYPE: DNA
<213> ORGANISM: Homo sapiens
<220> FEATURE:
<221> NAME/KEY: modified_base
<222> LOCATION: (335)
<223> OTHER INFORMATION: a, c, g, t, unknown or other

<400> SEQUENCE: 4

| | |
|---|---|
| tctagacgcg ttgacattga ttattgacta gttattaata gtaatcaatt acgggtcat | 60 |
| tagttcatag cccatgatat catatggagt tccgcgttac ataacttacg gtaaatggcc | 120 |
| cgcctggctg accgcccaac gacccccgcc cattgacgtc aataatgacg tatgttccca | 180 |
| tagtaacgcc aatagggact ttccattgac gtcaatgggt ggagtattta cggtaaactg | 240 |
| cccacttggc agtacatcaa gtgtatcata tgccaagtac gccccctat tgacgtcaat | 300 |
| gacggtaaat ggcccgcctg gcattatgcc cagtncatga ccttatggga ctttcctact | 360 |
| tggcagacat ctacgtatta gtcatcgcta ttaccatggt gatgcggttt tggcagtaca | 420 |
| tcaatgggcg tggatagcgg tttgactcac ggggatttc caagtctcca ccccattgac | 480 |
| gtcaatggga gtttgttttg gcaccaaaat caacgggact ttccaaaatg tcgtaacaac | 540 |
| tccgccccat tgacgcaaat gggcggtagg cgtgtacggt gggaggtcta tataagcaga | 600 |
| gctctctggc taactagaga acccctgctt actggcttat cgagatatc | 649 |

<210> SEQ ID NO 5
<211> LENGTH: 3693
<212> TYPE: DNA
<213> ORGANISM: Homo sapiens

<400> SEQUENCE: 5

| | |
|---|---|
| ggcagcgcgc agcggcaaga agtgtctggg ctgggacgga caggagaggc tgtcgccatc | 60 |
| ggcgtcctgt gcccctctgc tccggcacgg ccctgtcgca gtgcccgcgc tttcccggc | 120 |
| gcctgcacgc ggcgcgcctg gtaacatgc ttggggtcct ggtccttggc gcgctggccc | 180 |
| tggccggcct ggggttcccc gcacccgcag agccgcagcc gggtggcagc cagtgcgtcg | 240 |
| agcacgactg cttcgcgctc taccccggcc ccgcgacctt cctcaatgcc agtcagatct | 300 |

```
gcgacggact gcggggccac ctaatgacag tgcgctcctc ggtggctgcc gatgtcattt      360
ccttgctact gaacggcgac ggcggcgttg gccgccggcg cctctggatc ggcctgcagc      420
tgccacccgg ctgcggcgac cccaagcgcc tcgggcccct cgcgcggctt cagtgggtta      480
cgggagacaa caacaccagc tatagcaggt gggcacggct cgacctcaat ggggctcccc      540
tctgcggccc gttgtgcgtc gctgtctccg ctgctgaggc cactgtgccc agcgagccga      600 tctggggagga gcagcagtgc gaagtgaagg ccgatggctt cctctgcgag ttccacttcc      660
cagccacctg caggccactg gctgtggagc ccggcgccgc ggctgccgcc gtctcgatca      720
cctacggcac cccgttcgcg gcccgcggag cggacttcca ggcgctgccg gtgggcagct      780
ccgccgcggt ggctcccctc ggcttacagc taatgtgcac cgcgccgccc ggagcggtcc      840
aggggcactg ggccagggag cgccgggcg cttgggactg cagcgtggag aacggcggct      900
gcgagcacgc gtgcaatgcg atccctgggg ctccccgctg ccagtgccca gccggcgccg      960
ccctgcaggc agacgggcgc tcctgcaccg catccgcgac gcagtcctgc aacgacctct     1020
gcgagcactt ctgcgttccc aaccccgacc agccgggctc ctactcgtgc atgtgcgaga     1080
ccggctaccg gctggcggcc gaccaacacc ggtgcgagga cgtggatgac tgcatactgg     1140
agcccagtcc gtgtccgcag cgctgtgtca acacacaggg tggcttcgag tgccactgct     1200
accctaacta cgacctggtg gacggcgagt gtgtggagcc cgtggacccg tgcttcagag     1260
ccaactgcga gtaccagtgc cagcccctga ccaaactagc tacctctgc gtctgcgccg     1320 agggcttcgc gcccattccc cacgagccgc acaggtgcca gatgttttgc aaccagactg     1380
cctgtccagc cgactgcgac cccaacaccc aggctagctg tgagtgccct gaaggctaca     1440
tcctggacga cggtttcatc tgcacggaca tcgacgagtg cgaaaacggc ggcttctgct     1500
ccggggtgtg ccacaacctc cccggtacct tcgagtgcat ctgcgggccc gactcggccc     1560
ttgcccgcca cattggcacc gactgtgact ccggcaaggt ggacggtggc gacagcggct     1620
ctggcgagcc cccgcccagc ccgacgcccg gctccacctt gactcctccg gccgtggggc     1680
tcgtgcattc gggcttgctc ataggcatct ccatcgcgag cctgtgcctg gtggtggcgc     1740 tttggcgct cctctgccac ctgcgcaaga agcagggcgc cgccagggcc aagatggagt     1800
acaagtgcgc ggccccttcc aaggaggtag tgctgcagca cgtgcggacc gagcggacgc     1860
cgcagagact ctgagcggcc tccgtccagg agcctggctc cgtccaggag cctgtgcctc     1920
ctcaccccca gctttgctac caaagcacct tagctggcat tacagctgga gaagaccctc     1980
cccgcacccc ccaagctgtt ttcttctatt ccatggctaa ctggcgaggg ggtgattaga     2040
gggaggagaa tgagcctcgg cctcttccgt gacgtcactg gaccactggg caatgatggc     2100
aattttgtaa cgaagacaca gactgcgatt tgtcccaggt cctcactacc gggcgcagga     2160
gggtgagcgt tattggtcgg cagccttctg ggcagacctt gacctcgtgg gctagggatg     2220
actaaaatat ttattttttt taagtattta ggttttttgtt tgtttccttt gttcttacct     2280
gtatgtctcc agtatccact ttgcacagct ctccggtctc tctctctcta caaactccca     2340
cttgtcatgt gacaggtaaa ctatcttggt gaatttttt ttcctagccc ctcacattt     2400 atgaagcaag ccccacttat tccccattct tcctagtttt ctcctcccag gaactgggcc     2460
aactcacctg agtcaccta cctgtgcctg accctacttc ttttgctctt agctgtctgc     2520
tcagacagaa cccctacatg aaacagaaac aaaaacacta aaataaaaa tggccatttg     2580 ctttttcacc agatttgcta atttatcctg aaatttcaga ttcccagagc aaaataattt     2640
taaacaaagg ttgagatgta aaaggtatta aattgatgtt gctggactgt catagaaatt     2700
```

-continued

```
acacccaaag aggtatttat ctttactttt aaacagtgag cctgaatttt gttgctgttt    2760
tgatttgtac tgaaaaatgg taattgttgc taatcttctt atgcaatttc cttttttgtt    2820
attattactt attttttgaca gtgttgaaaa tgttcagaag gttgctctag attgagagaa    2880
gagacaaaca cctcccagga gacagttcaa gaaagcttca aactgcatga ttcatgccaa    2940
ttagcaattg actgtcactg ttccttgtca ctggtagacc aaaataaaac cagctctact    3000
ggtcttgtgg aattgggagc ttgggaatgg atcctggagg atgcccaatt agggcctagc    3060
cttaatcagg tcctcagaga atttctacca tttcagagag ccttttggaa atgtggcccc    3120
tgaacaagaa ttggaagctg ccctgcccat gggagctggt tagaaatgca gaatcctagg    3180
ctccacccca tccagttcat gagaatctat atttaacaag atctgcaggg ggtgtgtctg    3240
ctcagtaatt tgaggacaac cattccagac tgcttccaat tttctggaat acatgaaata    3300
tagatcagtt ataagtagca ggccaagtca ggcccttatt tcaagaaac tgaggaattt     3360
tctttgtgta gctttgctct ttggtagaaa aggctaggta cacagctcta gacactgcca    3420
cacagggtct gcaaggtctt tggttcagct aagctaggaa tgaaatcctg cttcagtgta    3480
tggaaataaa tgtatcatag aaatgtaact tttgtaagac aaaggttttc ctcttctatt    3540
ttgtaaactc aaaatatttg tacatagtta tttatttatt ggagataatc tagaacacag    3600
gcaaaatcct tgcttatgac atcacttgta caaaataaac aataacaat gtgaaaaaaa     3660
aaaaaaaaaa aaaaaaaaa aaaaaaaaaa aaa                                  3693
```

<210> SEQ ID NO 6
<211> LENGTH: 4457
<212> TYPE: DNA
<213> ORGANISM: Homo sapiens
<220> FEATURE:
<221> NAME/KEY: modified_base
<222> LOCATION: (349)
<223> OTHER INFORMATION: a, c, g, t, unknown or other

<400> SEQUENCE: 6

```
gtttaaacgg gccctctaga cgcgttgaca ttgattattg actagttatt aatagtaatc      60
aattacgggg tcattagttc atagcccatg atatcatatg gagttccgcg ttacataact     120
tacggtaaat ggcccgcctg gctgaccgcc caacgacccc cgcccattga cgtcaataat     180
gacgtatgtt cccatagtaa cgccaatagg gactttccat tgacgtcaat gggtggagta     240
tttacggtaa actgcccact tggcagtaca tcaagtgtat catatgccaa gtacgccccc     300
ctattgacgt caatgacggt aaatggcccg cctggcatta tgcccagtnc atgaccttat     360
gggactttcc tacttggcag acatctacgt attagtcatc gctattacca tggtgatgcg     420
gttttggcag tacatcaatg ggcgtggata gcggtttgac tcacggggat ttccaagtc      480
tccacccat tgacgtcaat gggagtttgt tttggcacca aaatcaacgg gactttccaa      540
aatgtcgtaa caactccgcc ccattgacgc aaatgggcgg taggcgtgta cggtgggagg     600
tctatataag cagagctctc tggctaacta gagaacccct gcttactggc ttatcgagat     660
atctgcagaa ttcatctgtc gactgctacc ggcagcgcgc agcggcaaga agtgtctggg     720
ctgggacgga caggagaggc tgtcgccatc ggcgtcctgt gcccctctgc tccggcacgg     780
ccctgtcgca gtgcccgcgc tttccccggc gcctgcacgg ggcgcgcctg ggtaacatgc     840
ttggggtcct ggtccttggc gcgctggccc tggccggcct ggggttcccc gcacccgcag    900
agccgcagcc gggtggcagc cagtgcgtcg agcacgactg cttcgcgctc taccccggcc     960
ccgcgacctt cctcaatgcc agtcagatct gcgacggact gcggggccac ctaatgacag    1020
```

-continued

```
tgcgctcctc ggtggctgcc gatgtcattt ccttgctact gaacggcgac ggcggcgttg    1080
gccgccggcg cctctggatc ggcctgcagc tgccacccgg ctgcgcgac  cccaagcgcc    1140
tcgggcccct cgcgggcttc cagtgggtta cgggagacaa caacaccagc tatagcaggt    1200
gggcacggct cgacctcaat ggggctcccc tctgcggccc gttgtgcgtc gctgtctccg    1260
ctgctgaggc cactgtgccc agcgagccga tctgggagga gcagcagtgc gaagtgaagg    1320
ccgatggctt cctctgcgag ttccacttcc cagccacctg caggccactg gctgtggagc    1380
ccggcgccgc ggctgccgcc gtctcgatca cctacggcac cccgttcgcg gcccgcggag    1440
cggacttcca ggcgctgccg gtgggcagct ccgccgcggt ggctcccctc ggcttacagc    1500
taatgtgcac cgcgccgccc ggagcggtcc aggggcactg gccagggag  cgccgggcg     1560
cttgggactg cagcgtggag aacgcggct  gcgagcacgg gtgcaatgcg atccctgggg    1620
ctccccgctg ccagtgccca gccggcgccg ccctgcaggc agacgggcgc tcctgcaccg    1680
catccgcgac gcagtcctgc aacgacctct gcgagcactt ctgcgttccc aaccccgacc    1740
agccgggctc ctactcgtgc atgtgcgaga ccggctaccg gctggcggcc gaccaacacc    1800
ggtgcgagga cgtggatgac tgcatactgg agcccagtcc gtgtccgcag cgctgtgtca    1860
acacacaggg tggcttcgag tgccactgct accctaacta cgacctggtg gacggcgagt    1920
gtgtggagcc cgtggacccg tgcttcagag ccaactgcga gtaccagtgc agcccctga    1980
accaaactag ctacctctgc gtctgcgccg agggcttcgc gcccattccc cacgagccgc    2040
acaggtgcca gatgttttgc aaccagactg cctgtccagc cgactgcgac cccaacaccc    2100
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc cccgcccagc ccgacgcccg    2340
gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
tgctgcagca cgtgcggacc gagcggacgc cgcagagact ctgagcggcc tccgtccagg    2580
agcctggctc cgtccaggag cctgtgcctc ctcacccca  gctttgctac caaagcacct    2640
tagctggcat tacagctgga gaagaccctc cccgcacccc ccaagctgtt ttcttctatt    2700
ccatggctaa ctgcgagggg ggtgattaga gggaggagaa tgagcctcgg cctcttccgt    2760
gacgtcactg gaccactggg caatgatggc aattttgtaa cgaagacaca gactgcgatt    2820
tgtcccaggt cctcactacc gggcgcagga gggtgagcgt tattggtcgg cagccttctg    2880
ggcagacctt gacctcgtgg gctagggatg actaaaatat ttatttttt  taagtattta    2940
ggttttgtt  tgtttccttt gttcttacct gtatgtctcc agtatccact ttgcacagct    3000
ctccggtctc tctctctcta caaactccca cttgtcatgt gacaggtaaa ctatcttggt    3060
gaattttttt ttcctagccc tctcacattt atgaagcaag ccccacttat tccccattct    3120
tcctagtttt ctcctcccag gaactgggcc aactcacctg agtcacccta cctgtgcctg    3180
acctacttc  ttttgctctt agctgtctgc tcagacagaa cccctacatg aaacagaaac    3240
aaaaacacta aaaataaaaa tggccatttg cttttttcacc agatttgcta atttatcctg    3300
aaatttcaga ttcccagagc aaaataaatt taaacaaagg ttgagatgta aaaggtatta    3360
aattgatgtt gctggactgt catagaaatt acacccaaag aggtatttat ctttactttt    3420
```

```
aaacagtgag cctgaattt gttgctgttt tgatttgtac tgaaaaatgg taattgttgc    3480
taatcttctt atgcaatttc ctttttgtt attattactt atttttgaca gtgttgaaaa    3540
tgttcagaag gttgctctag attgagagaa gagacaaaca cctcccagga gacagttcaa    3600
gaaagcttca aactgcatga ttcatgccaa ttagcaattg actgtcactg ttccttgtca    3660
ctggtagacc aaaataaaac cagctctact ggtcttgtgg aattgggagc ttgggaatgg    3720
atcctggagg atgcccaatt agggcctagc cttaatcagg tcctcagaga atttctacca    3780
tttcagagag gccttttgga atgtggcccc tgaacaagaa ttggaagctg ccctgcccat    3840
gggagctggt tagaaatgca gaatcctagg ctccacccca tccagttcat gagaatctat    3900
atttaacaag atctgcaggg ggtgtgtctg ctcagtaatt tgaggacaac cattccagac    3960
tgcttccaat tttctggaat acatgaaata tagatcagtt ataagtagca ggccaagtca    4020
ggcccttatt ttcaagaaac tgaggaattt tctttgtgta gctttgctct ttggtagaaa    4080
aggctaggta cacagctcta gacactgcca cacagggtct gcaaggtctt tggttcagct    4140
aagctaggaa tgaaatcctg cttcagtgta tggaaataaa tgtatcatag aaatgtaact    4200
tttgtaagac aaaggttttc ctcttctatt ttgtaaactc aaaatatttg tacatagtta    4260
tttatttatt ggagataatc tagaacacag gcaaaatcct tgcttatgac atcacttgta    4320
caaaataaac aaataacaat gtgaaaaaaa aaaaaaaaa aaaaaaaaa aaaaaaaaa    4380 aaaggtagca gtcgacagat gaattccacc acactggact agtggatccg agctcggtac    4440
caagcttaag tttaaac                                                  4457

<210> SEQ ID NO 7
<211> LENGTH: 17534
<212> TYPE: DNA
<213> ORGANISM: Artificial Sequence
<220> FEATURE:
<221> NAME/KEY: modified_base
<222> LOCATION: (730)
<223> OTHER INFORMATION: a, c, g, t, unknown or other
<220> FEATURE:
<223> OTHER INFORMATION: Description of Artificial Sequence: Synthetic
      plasmid

<400> SEQUENCE: 7
catcatcaat aatataccct atttttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttg    180 gtgtgcgccg gtgtacacag gaagtgacaa ttttcgcgcg gttttaggcg gatgttgtag    240
taaatttggg cgtaaccgag taagatttgg ccatttccgc gggaaaactg aataagagga    300
agtgaaatct gaataatttt tgttactca tagcgcgtaa tactggtacc gcggccgcct    360
cgagtctaga actagtggat cccccaaacg ggccctctag acgcgttgac attgattatt    420
gactagttat taatagtaat caattacggg gtcattagtt catagcccat gatatcatat    480
ggagttccgc gttacataac ttacggtaaa tggcccgcct ggctgaccgc ccaacgaccc    540
ccgcccattg acgtcaataa tgacgtatgt tcccatagta acgccaatag ggactttcca    600
ttgacgtcaa tgggtggagt atttacggta aactgcccac ttggcagtac atcaagtgta    660
tcatatgcca agtacgcccc cctattgacg tcaatgacgg taaatggccc gcctggcatt    720
atgcccagtn catgacctta tgggactttc ctacttggca gacatctacg tattagtcat    780
cgctattacc atggtgatgc ggttttggca gtacatcaat gggcgtggat agcggtttga    840
```

```
ctcacgggga ttttccaagt ctccacccca ttgacgtcaa tgggagtttg ttttggcacc      900
aaaatcaacg ggactttcca aaatgtcgta acaactccgc cccattgacg caaatgggcg      960
gtaggcgtgt acggtgggag gtctatataa gcagagctct ctggctaact agagaacccc     1020
tgcttactgg cttatcgaga tatctgcaga attcatctgt cgactgctac cggcagcgcg     1080
cagcggcaag aagtgtctgg gctgggacgg acaggagagg ctgtcgccat cggcgtcctg     1140
tgcccctctg ctccggcacg gccctgtcgc agtgcccgcg cttccccgg cgcctgcacg      1200 cggcgcgcct gggtaacatg cttggggtcc tggtccttgg cgcgctggcc ctggccggcc     1260
tggggttccc cgcacccgca gagccgcagc cgggtggcag ccagtgcgtc gagcacgact     1320
gcttcgcgct ctacccgggc cccgcgacct tcctcaatgc cagtcagatc tgcgacggac     1380
tgcggggcca cctaatgaca gtgcgctcct cggtggctgc cgatgtcatt tccttgctac     1440
tgaacggcga cggcggcgtt ggccgccggc gcctctggat cggcctgcag ctgccacccg     1500
gctgcggcga ccccaagcgc ctcgggcccc tgcgcggctt ccagtgggtt acgggagaca     1560
acaacaccag ctatagcagg tgggcacggc tcgacctcaa tggggctccc ctctgcggcc     1620
cgttgtgcgt cgctgtctcc gctgctgagg ccactgtgcc cagcgagccg atctgggagg     1680
agcagcagtg cgaagtgaag gccgatggct tcctctgcga gttccacttc ccagccacct     1740
gcaggccact ggctgtggag cccggcgccg gcgctgccgc cgtctcgatc acctacggca     1800
ccccgttcgc ggcccgcgga gcggacttcc aggcgctgcc ggtgggcagc tccgccgcgg     1860
tggctcccct cggcttacag ctaatgtgca ccgcgccgcc cggagcggtc caggggcact     1920
gggccaggga ggcgccgggc gcttgggact gcagcgtgga gaacggcggc tgcgagcacg     1980
cgtgcaatgc gatccctggg gctcccgct gccagtgccc agccgcgcc gcctgcagg       2040 cagacgggcg ctcctgcacc gcatccgcga cgcagtcctg caacgacctc tgcgagcact     2100
tctgcgttcc caaccccgac cagccgggct cctactcgtg catgtgcgag accggctacc     2160
ggctggcggc cgaccaacac cggtgcgagg acgtggatga ctgcatactg gagcccagtc     2220
cgtgtccgca gcgctgtgtc aacacacagg gtggcttcga gtgccactgc tacccctaact    2280 acgacctggt ggacggcgag tgtgtggagc ccgtggaccc gtgcttcaga gccaactgcg     2340
agtaccagtg ccagcccctg aaccaaacta gctacctctg cgtctgcgcc gagggcttcg     2400
cgcccattcc ccacgagccg cacaggtgcc agatgttttg caaccagact gcctgtccag     2460
ccgactgcga ccccaacacc caggctagct gtgagtgccc tgaaggctac atcctggacg     2520
acggtttcat ctgcacggac atcgacgagt gcgaaaacgg cggcttctgc tccggggtgt     2580
gccacaacct ccccggtacc ttcgagtgca tctgcgggcc cgactcggcc cttgcccgcc     2640
acattggcac cgactgtgac tccggcaagg tggacgtgg cgacagcggc tctggcgagc      2700 cccgcccag cccgacgccc ggctccacct tgactcctcc ggccgtgggg ctcgtgcatt      2760
cgggcttgct cataggcatc tccatcgcga gcctgtgcct ggtggtggcg cttttggcgc     2820
tcctctgcca cctgcgcaag aagcagggcg ccgccagggc caagatggag tacaagtgcg     2880 cggcccttc caaggaggta gtgctgcagc acgtgcggac cgagcggacg ccgcagagac     2940
tctgagcggc ctccgtccag gagcctggct ccgtccagga gcctgtgcct cctcaccccc     3000
agctttgcta ccaaagcacc ttagctggca ttacagctgg agaagaccct ccccgcaccc     3060
cccaagctgt tttcttctat tccatggcta actggcgagg gggtgattag agggaggaga     3120
atgagcctcg gcctcttccg tgacgtcact ggaccactgg gcaatgatgg caattttgta     3180
acgaagacac agactgcgat ttgtcccagg tcctcactac cgggcgcagg agggtgagcg     3240
```

```
ttattggtcg gcagccttct gggcagacct tgacctcgtg ggctagggat gactaaaata    3300
tttatttttt ttaagtattt aggttttttgt ttgtttcctt tgttcttacc tgtatgtctc   3360
cagtatccac tttgcacagc tctccggtct ctctctctct acaaactccc acttgtcatg    3420
tgacaggtaa actatcttgg tgaattttttt tttcctagcc ctctcacatt tatgaagcaa   3480
gccccactta ttccccattc ttcctagttt tctcctccca ggaactgggc caactcacct    3540
gagtcaccct acctgtgcct gaccctactt cttttgctct tagctgtctg ctcagacaga    3600
acccctacat gaaacagaaa caaaaacact aaaaataaaa atggccattt gcttttttcac   3660
cagatttgct aatttatcct gaaatttcag attcccagag caaaataatt ttaaacaaag    3720
gttgagatgt aaaaggtatt aaattgatgt tgctggactg tcatagaaat tacacccaaa    3780
gaggtattta tctttacttt taaacagtga gcctgaattt tgttgctgtt ttgatttgta    3840
ctgaaaaatg gtaattgttg ctaatcttct tatgcaattt ccttttttgt tattattact    3900
tatttttgac agtgttgaaa atgttcagaa ggttgctcta gattgagaga agagacaaac    3960
acctcccagg agacagttca agaaagcttc aaactgcatg attcatgcca attagcaatt    4020
gactgtcact gttccttgtc actggtagac caaaataaaa ccagctctac tggtcttgtg    4080
gaattgggag cttgggaatg atcctggag gatgcccaat tagggcctag ccttaatcag     4140
gtcctcagag aatttctacc atttcagaga ggccttttgg aatgtggccc ctgaacaaga    4200
attggaagct gccctgccca tgggagctgg ttagaaatgc agaatcctag gctccacccc    4260
atccagttca tgagaatcta tatttaacaa gatctgcagg gggtgtgtct gctcagtaat    4320
ttgaggacaa ccattccaga ctgcttccaa ttttctggaa tacatgaaat atagatcagt    4380
tataagtagc aggccaagtc aggcccttat tttcaagaaa ctgaggaatt ttctttgtgt    4440
agctttgctc tttggtagaa aaggctaggt acacagctct agacactgcc acacagggtc    4500
tgcaaggtct ttggttcagc taagctagga atgaaatcct gcttcagtgt atggaaataa    4560
atgtatcata gaaatgtaac ttttgtaaga caaaggtttt cctcttctat tttgtaaact    4620
caaaatattt gtacatagtt atttatttat tggagataat ctagaacaca ggcaaaatcc    4680
ttgcttatga catcacttgt acaaaataaa caaataacaa tgtgaaaaaa aaaaaaaaaa    4740
aaaaaaaaaa aaaaaaaaaa aaaggtagc agtcgacaga tgaattccac cacactggac    4800
tagtggatcc gagctcggta ccaagcttaa gtttgggctg caggaattct gatggctctc    4860
aaaattcctg cctcctttag ggataaaaga ctttaagact ttttaacaaa aagaaaaag    4920
aaaaaaaaa ttcctgcctc ctggtgtaca cacacagaag ggttccctcc ccttgaatgt    4980
gaccaggatc tgtgaaaata acgggatagc cgctcctgtg attaggttat gtggtagact    5040
agagcaagat tctcctgctg gttttgaaga agtcagctgc catgttgtga gactgtcatg    5100
ggctagggca tgagcccttta aatatctggg agcaacccct ggccagcagc cagtgagaaa    5160
acgggccctc agtcctacaa tcacaaggaa ctaaattctg ccaacaacct gaaggaactt    5220
tgaagaggat catgagtccc ttgattcagc ttgatgagcc cctgagcaga ggatacagct    5280
aacttgtact agggaagtat aaaaaacatg catgggaatg atatatatca actttaagga    5340
taattgtcat acttctggga atgaagggaa agaaatgggg ctttagttgt attatgatct    5400
ttaatttctc aaaaaaaata agatcagaag caaatatggc aaaatgttaa acttttgtg    5460
ggtacgtagg tattcagcat accctttttt ctgagttcaa aatattttat aattaaaatg    5520
aaatgcaggc caggcacagt ggctcatgcc tataatacca gcactttgcg aggccgaggt    5580
gggaggatgg cttgaggcca gaccagcctg gccaacatgg caaaacccca tctctactta    5640
```

```
aaaaaaaaaa aactatatat atatatatgt gtgtgtgtgt gtatatatat atatgtatat    5700
atatttatat atgtgtgtat atatatatat gtatatatat ttatatatgt gtgtgtatat    5760
atatatatac acacacacac atatatacat acatacatac acacacacac acacacaatt    5820
agccaggcat ggtggcgcac acctgtagtc ccagctactt gggaggctga gacatgagaa    5880
ttgcttgaac ctgggaggca gagtagttag tgagctgaga tcataccact gcactccagc    5940
ctggtgacag agtgagactc tgtcttaaaa aaaataaaaa ttaaaattaa atgcaaaagg    6000
tccaagtgaa ttgagagga aaggggtatc aaggaaggtt ttgtggaggt gacgtttgag    6060
ctgggtctta aatgacttaa acatgggata agaaggagg gaataaggac atttcaggta    6120
cgagaaataa ggagcaaaca gtggaaacaa cctaacgtct gtcaaccagt gaatggataa    6180
caaaaatgta attcagatgg tatccaactt acgatggttc aacatgagat ttttctgact    6240
ttaggataga tttatcaaag tagtaaatcc attttcaact tatgatattt tcaacttcag    6300
atgggtttat caggacacag ttgaggaaca cctgtctatc catacaattt ggcaataaaa    6360
aggaaatgag tgcagatata ctccacaaca tgaatgaacc ttgaaaacat taagtgagag    6420
aagccagata caaaaggcca catattgtat gattctattt atacaaaatg tccagaatag    6480
gcaaatctta tagacagcaa gtaggtagat gatcagtttg ctaggtgctg ggggaagggg    6540
aaatggggag tgatggctaa ggggattggg tttctttgtg gggcaatgaa aatgttttaa    6600
aattgagcgt gataatgatt gcacaatgct gcatatatat ataatctata gattatatat    6660
atataaagag aggctgttag acagtgataa gtgatatata tatatatata catagagaga    6720
gagagagaga gagagagagg ctgttagtga taagtgatca ggaaaataaa agtattgagg    6780
aggaatacga agttgacggt gtgaaaacat gagattttat ataggatggc cagggaaggc    6840
cttaatgaga aagtgactta tgagtaaaaa caagggatcc taaaccttag catgcatcag    6900
aatcactcgg aaacttgtta aagcatagct tgctgggcct catcacagat attttgattc    6960
ggtaggttct tgtctgatat taatacttt ggtctaggga accacatttt gagaaccact    7020
gagctaaagg aagtaaaggt ttcccttagt ttactagctg gtaacactgg cccaggaggc    7080
cttctggtg accctaagg aattatccaa actcttgttt ttagatgctt tattatatca    7140
aactctcctt taaacaagtg gcccatctgc tgggatttgg aagcctgtaa tactgaaatt    7200
ttcatcataa tggaaatttt aaaaacagaa tttgacccac ctgttttaa aacactttca    7260
ttacttaaca agaggtctaa tcttgggcaa gtcttgaaat ttctctggcc ttagtttccc    7320
atgtgttaaa tgaaacttga agcagttggt ctcttatagt ctcctgactc taacattcta    7380
agaattatat ttgtacaata actcaaaaat cacataattt aatttaccat atggactcca    7440
aaatatattt tctcattagg ctaaacttga tctgcatttt ctggatgtgt ccatattctt    7500
ggactacact aaaacatgat accaatgctt cctctcacca taaaccctca cttcgctttc    7560
tacatttaag aattttatag ctggaagagt ccttaacaga aaataccatc taataattac    7620
ccctcaaaat cgagaaagtc ctatctgttc ttatgctagt tataagaatg aggcagcatt    7680
tcacataatg gttataaaca ctgccacaag aagattcatg atgtgttgtt tatctgtagc    7740
tctcatcata ctctgtcata taactatagc attaagattt taatgttcta tatattcttc    7800
taagacagtg tttaccagag taaggcacaa aagatccact ggtttgcaag aaagattaga    7860
actttttaaat ttttttacctc accttgttta atctatattt ttgtatgtat tttgtaacat    7920
atatattatt attaccataa atcatatata atttaaaatg catatattag gggtaaatgc    7980
tcaggaaact ttttataaat tgggcatgca aatacaagtt tgaagactca ctgttctagg    8040
```

```
tattaaaagt aaagttataa ccaagtaaag cttccacctt ttcatgtctc aaagcagttt    8100
attgttggag gtaagatctc ttagaagcct aaacaggtcc aagtacagaa tgaagtaagg    8160
ctagcccata acttgtggca agcaattcat actatttctc tcatgctgag ctctcctcag    8220
tgaagcagct actatagaca actgcagcct attggtagcc tattttacag gcaggaaaaa    8280
aattactttt tattcaaagt ggaactcagg acatggggag aaaatgaata caaaaaatag    8340
ggtcaatcca aaggcacaca gcaaatgagt aacacagtta tgttttttc ccatttgtat     8400 gaggtcccag taaattctaa gtaaactgca aatttaataa tacactaaaa aagccatgca    8460
attgttcaaa tgaatcccag catggtacaa ggagtacaga cactagagtc taaaaaacaa    8520
aagaatgcca ttattgagtt tttgaattat atcaagtagt tacatctcta cttaataaat    8580
gagaaaaacg aggataagag gccatttgat aaaatgaaaa tagccaagaa gtggtattag    8640
agacttgaat acaggtattc gggtccaaag ttcatctgct caaatactaa ctggggaaaa    8700
gagggaaaaa tatttatata catatatatc tgcacacaaa ataccccca aaagacaaaa     8760 tgaggccagg cagggtggct cacacccgta atcccggtac tttgggaggc tgaggcaggt    8820
ggatacctga gatcaggagt tggagatcag cctggtcaac atggtgaaac cctgtctcta    8880
ctaaagataa aaaattagc caggcatggt ggcgtgcgcc tgtaatccca gctacttggg     8940
agtctgaggc aggagaatca cttgaactgg gaagggggagg ttgcagtgag ccaagatcgt    9000
actactgcac tccagcctgg gcagcagagt gagactccat cacaaaaata aataaataaa    9060
taaaatacaa tgaaacagaa agttcaaata atcccataat cttaccacca agaaataact    9120
ttcactcgtt atacttattg atttttccat aataaatgta ctttactgtg actatcatga    9180
aaagaaagtt atttttagaaa cagagaactg tttcagatca aatctatgta gtagaacaga    9240
gccattaggt gggaaagacg agatcaaact aaatctcaga aggcctaaaa ggctaggtcc    9300
attccagcac taaaaactga ccagacaagt aatggcttca acagcttcta aatatggaca    9360
aagcatgctg aaagggaagg acaggtctaa cagtggtata tgaaatgaac aggagggggca   9420 aagctcattt ctcctctgaa gttttccaaa gatgctgagg aggacattag tttgacatga    9480
ccctgatatg ggacaagata atttcacaga agttttacat gttaaagttt tcttatagat    9540
actcattcaa gtaagcaatg aacactaaaa tctaaagaaa gaaaagagct ttagagtcag    9600
gtctgtattc aaattcaagc tctaccactt actggttctg tgactttggg caagtctttt    9660
aaccttatta agtcttaatt tcctgatttg taaaatgggg atatcgtctc cctcacagga    9720
ttgttgtgaa acttttatga gattaatgcc tttatatttg gcatagtgta agtaaacaat    9780
aactggcagc ttcaaaaaaa aaagcagta gcattccatc atttattatt ggttactctc     9840 aaaaagttttt tcaatgtact agaagataaa tattcaaata ccttaatatc tccattattt   9900
tcaggtaaac agcatgctcc tgaacaacca atgggtcaac aaataatta aagggaaat      9960 ctaaaaacat cttgatatta aactacatgg aagcacaata taccaaaacc aatggttcac   10020
actaggagaa ttttaaggta caagaaaact ctttgagatt tcttaaaata atagtatgtc   10080
tgaatttatt gagtgattta ccagaaactg ttgtaagagc tctacttgca ttatagcact   10140
taatcctctt aactctatgg ctgctattat caacctcacc ctaatcacat atgggacaca   10200
gagaggttaa gtaacttgcc caaggtcaga gttaggaagt actaagccat gctttgaatc   10260
agttgtcagg ctccggaact cacactttca gccactacat aatactgctt tgctatcttt   10320
taggaaacta tgtgagtcta cctcacatag actcacatag gtttgttttt ttttttttt    10380 taaaggctat cttttccccc atcaatgttt tttgaaggat cccaaattag agtcccacag   10440
```

```
aggcagacag cagtacttga caatatggac atttaaggtt aatgttggat tctactgtct   10500
ttttactaca tgacctaggg aacgataatt aacctagact gcttccaagg gttaaataac   10560
ccatttagtt atactatgta aattatctct tagtgattga ttgaaagcac actgttacta   10620
attgactcgg tatgaagtgc ttttttttct tcccttcaa gatacatacc tttccagtta   10680
aagttgagag atcatctcca ccaattactt ttatgtcccc tgttgactgg tcattctagt   10740
taaaaaaaaa aaaactata tatatata tctacacaca catatgtata tgtatatcct   10800
tatgtacaca cacaaacttc aaattaaatg agaactagaa gatttgagaa gttagctagc   10860
taatatccat agcattatga tattctaaat gatatgaatt ataagaatta ggtttcctga   10920
aatgaatgac tagaaaactt tcaagtagag attagtaaaa attaaaaagt cctaatcggc   10980
cattactgat ttgatgtttt taagagtcct aaaaaatggg ttacatccat ttttaagtgg   11040
gtagtattat aacagccacc catcttcaat cacagtgatt tctgaattgt gagggaagtt   11100
attagcatga caggtgtctg ttctggccc tgtacgattc ccatgagtca agcaaattgt   11160
aagggctggt ctatatcaca cccaaccca aggatatgtc cctcaaaagt ctagcccagg   11220
ccccgtcatc ttcagcatca tctgggaaac caggtctgat tagtagtcct ttaaggaata   11280
cctcttaggc tcccatttta ctgctatcac agaatccaat aaaaccctta caggagattc   11340
aatgggaaat gctcaacacc cactgtagtt ggtggtgaca atgaccataa tttggctgtg   11400
ctggattcag gacagaaaat ttgggtgaaa gagcaggtga acaaagagc ttcgacttgc   11460 cctagcagag agcaagccat accataccac aaagccacag caattacaac ggtgcagtac   11520
cagcacagta aatgaacaaa gtagagccca gaaacagacc cagaactata tgaggattta   11580
gtatacaata aagatggtat ttcgagtcag tagggaaaag atgaattatt caataaatga   11640
tgtttggcca actagtaacc catttgggaa aaaataaag tatggtccct acctcacagc   11700
atacacaaaa ataaattcca gacggattaa aatctaaatg taaaaaataa agccataagt   11760
ggactggaag aaaatagaga attttttta acatccgtag aaagggtaaa aacccaggca   11820
tgacatgaac caaaactgaa gaggttctgt aacaaatacc cccttttata tattgggctc   11880
caacaataag aacccatagg aaaatggaga atgaacacaa atagacaatt tatagaagag   11940
aaggttataa ggtgtaaaat tatatctatc tgagaaacaa acactaaaac aatgtgattc   12000
tactgttctc ccacccatac tggcaaaact taagcctgat aatatgctga ggggaaataa   12060
gcactcttgt tggtgagagt attaattggc atagcttctt ttgaaaatga catagcaata   12120
cctgttaaaa ttgcaaacat gcatgtcact taatccagta atcccacttc tgggaatcaa   12180
tgctacaaaa acactgacaa gtatacaaag atacattcaa gagtgttcac tgggccgggt   12240
gcggtggctt catgcctgta atcccaggga ggcagaggca agacgatcgc ttgacccag   12300 gagttcaagg ccagcccgag aaacacagca agaccctgtc tctctttttt ttatttaaaa   12360
aataaatgtt cactgtatca gttgttcaca aaaacaaacc aacatgtcca ttaacaggga   12420
accatttaaa ttaatcaagt tcatctacac aatgtaatac catgcaacta ttaaaaagca   12480
cctgataatc caaagcacac tgagacagaa taatgctatt aaaaacacca agtagtgaa   12540 cactgtgttg cctatgacac catttttatt caacatttaa acaaatttgt aacagcaatt   12600
acatgagtag tgacaatggc gtttatgaga cttttcactt ttatgtgctt ctattttgt   12660 tatgcttcta tatatacatc catttattat ggagtgttac tttcaaaaat cacaaatggg   12720
ccagtattat ttggtgttgc aaggtgagca tatgacttct gatatcaacc tttgcatatt   12780
acttctcaat ttagggaaat tacagacatc ccttattcta actaacttaa aacccagcat   12840
```

-continued

```
ttcaaacata cagaattgat ggggaaaaaa aagaaagaag aaagaaagaa aaggcaacaa    12900
gcttcagatg acagtgactc acatcaaatt atttataaaa tctgttaaat agtgccatct    12960
tctggagata cctggtatta cagtccaact ccagttgatg tctttacaga gacaaggaga    13020
ataaaggaaa aaatattcaa gaactgaaaa gtatggagtc atggaaaaat tgctgtgatc    13080
caaaggctac ggtgatagga caagaaacaa gagaactcca agcagtaaga cactgctgtt    13140
ctattagcat ccaaacctcc atactcctgt ttgccccaag gcttttttaa aaaatagaga    13200
caggatctca ctattttgct caggctggtc ttgaactcct ggactcaagc tatcctcctg    13260
cctcggcctc ctaaagtgcc gagattacag gcttgagtca ccatacctgg ctatttattt    13320
tttcttaact ctcttgcctg gcctatagcc accatggaag ctaataaaga atattaattt    13380
aagagtaatg gtatagttca ctacattgga atacaggtat aagtgcctac attgtacatg    13440
aatggcatac atggatcaat taccccacct gggtggccaa aggaactgcg cgaacctccc    13500
tccttggctg tctggaacaa gcttcccact agatcccttt actgagtgcc tccctcatct    13560
ttaattatgg ttaagtctag gataacagga ctggcaaagg tgaggggaaa gcttcctcca    13620
gagttgctct accctctcct ctaccgtcct atctcctcac tcctctcagc caaggagtcc    13680
aatctgtcct gaactcagag cgtcactgtc aactacataa aattgccaga gaagctcttt    13740
gggactacaa acacataccc ttaatgtctt tatttctatt ttgtctacct cttcagtcta    13800
ggtgaaaaaa taggaaggat aatagggaag aactttgttt atgcctactt atccgcccct    13860
aggaattttg aaaacctcta ggtagcaata agaactgcag catggtatag aaaaagagga    13920
ggaaagctgt atagaaatgc ataataaatg ggcaggaaaa gaactgcttg gaacaaacag    13980
ggaggttgaa ctataaggag agaaagcaga gaggctaatc aacaaggctg ggttcccaag    14040
agggcatgat gagactatta ctaaggtagg aattactaag ggctccatgt cccccttagtg   14100 gcttagtact atgtagcttg ctttctgcag tgaacttcag acccttcttt taggatccta    14160
gaatggactt tttttttta tcggaaaaca gtcattctct caacattcaa gcaggcccca    14220
agtctaccac actcaatcac attttctctt catatcataa tctctcaacc attctctgtc    14280
cttttaactg ttttttctata ccctgatcaa atgccaacaa aagtgagaat gttagaatca    14340
tgtattttta gaggtagact gtatctcaga taaaaaaaaa gggcagatat tccattttcc    14400
aaaatatgta tgcagaaaaa ataagtatga aaggacatat gctcaggtaa caagttaatt    14460
tgtttacttg tatttatga attccctaaa acctacgtca cccgcccgt tcccacgccc      14520 cgcgccacgt cacaaactcc accccctcat tatcatattg gcttcaatcc aaaataaggt    14580
atattattga tgatgttaat taacatgcat ggatccatat gcggtgtgaa ataccgcaca    14640
gatgcgtaag gagaaaatac cgcatcaggc gctcttccgc ttcctcgctc actgactcgc    14700
tgcgctcggt cgttcggctg cggcgagcgg tatcagctca ctcaaaggcg gtaatacggt    14760
tatccacaga atcaggggat aacgcaggaa agaacatgtg agcaaaaggc cagcaaaagg    14820
ccaggaaccg taaaaaggcc gcgttgctgg cgtttttcca taggctccgc cccctgacg    14880 agcatcacaa aaatcgacgc tcaagtcaga ggtggcgaaa cccgacagga ctataaagat    14940
accaggcgtt ccccctggaa gctccctcg tgcgctctcc tgttccgacc ctgccgctta    15000
ccggatacct gtccgccttt ctcccttcgg aagcgtggc gctttctcat agctcacgct    15060
gtaggtatct cagttcggtg taggtcgttc gctccaagct gggctgtgtg cacgaacccc    15120
ccgttcagcc cgaccgctgc gccttatccg gtaactatcg tcttgagtcc aacccggtaa    15180
gacacgactt atcgccactg gcagcagcca ctggtaacag gattagcaga gcgaggtatg    15240
```

```
taggcggtgc tacagagttc ttgaagtggt ggcctaacta cggctacact agaaggacag   15300
tatttggtat ctgcgctctg ctgaagccag ttaccttcgg aaaaagagtt ggtagctctt   15360
gatccggcaa acaaaccacc gctggtagcg gtggttttttt tgtttgcaag cagcagatta  15420
cgcgcagaaa aaaggatct caagaagatc ctttgatctt ttctacgggg tctgacgctc    15480
agtggaacga aaactcacgt taagggattt tggtcatgag attatcaaaa aggatcttca   15540
cctagatcct tttaaattaa aaatgaagtt ttaaatcaat ctaaagtata tatgagtaaa   15600
cttggtctga cagttaccaa tgcttaatca gtgaggcacc tatctcagcg atctgtctat   15660
ttcgttcatc catagttgcc tgactccccg tcgtgtagat aactacgata cgggagggct   15720
taccatctgg ccccagtgct gcaatgatac cgcgagaccc acgctcaccg gctccagatt   15780
tatcagcaat aaaccagcca gccggaaggg ccgagcgcag aagtggtcct gcaacttttat  15840
ccgcctccat ccagtctatt aattgttgcc gggaagctag agtaagtagt tcgccagtta   15900
atagtttgcg caacgttgtt gccattgctg cagccatgag attatcaaaa aggatcttca   15960
cctagatcct tttcacgtag aaagccagtc gcagaaacg tgctgacccc ggatgaatg     16020
tcagctactg ggctatctgg acaagggaaa acgcaagcgc aaagagaaag caggtagctt   16080
gcagtgggct tacatggcga tagctagact gggcggtttt atggacagca agcgaaccgg   16140
aattgccagc tggggcgccc tctggtaagg ttgggaagcc ctgcaaagta aactggatgg   16200
ctttcttgcc gccaaggatc tgatggcgca ggggatcaag ctctgatcaa gagacaggat   16260
gaggatcgtt tcgcatgatt gaacaagatg gattgcacgc aggttctccg gccgcttggg   16320
tggagaggct attcggctat gactgggcac aacagacaat cggctgctct gatgccgccg   16380
tgttccggct gtcagcgcag gggcgcccgg ttcttttgt caagaccgac ctgtccggtg   16440
ccctgaatga actgcaagac gaggcagcgc ggctatcgtg gctggccacg acgggcgttc   16500
cttgcgcagc tgtgctcgac gttgtcactg aagcgggaag ggactggctg ctattgggcg   16560
aagtgccggg gcaggatctc ctgtcatctc accttgctcc tgccgagaaa gtatccatca   16620
tggctgatgc aatgcggcgg ctgcatacgc ttgatccggc tacctgccca ttcgaccacc   16680
aagcgaaaca tcgcatcgag cgagcacgta ctcggatgga agccggtctt gtcgatcagg   16740
atgatctgga cgaagagcat caggggctcg cgccagccga actgttcgcc aggctcaagg   16800
cgagcatgcc cgacggcgag gatctcgtcg tgacccatgg cgatgcctgc ttgccgaata   16860
tcatggtgga aaatggccgc ttttctggat tcatcgactg tggccggctg ggtgtggcgg   16920
accgctatca ggacatagcg ttggctaccc gtgatattgc tgaagagctt ggcggcgaat   16980
gggctgaccg cttcctcgtg ctttacggta tcgccgctcc cgattcgcag cgcatcgcct   17040
tctatcgcct tcttgacgag ttcttctgaa ttttgttaaa attttttgtta aatcagctca   17100
ttttttaacc aataggccga aatcggcaaa atcccttata aatcaaaaga atagaccgag   17160
atagggttga gtgttgttcc agtttggaac aagagtccac tattaaagaa cgtggactcc   17220
aacgtcaaag ggcgaaaaac cgtctatcag ggcgatggcc cactacgtga accatcaccc   17280
taatcaagtt ttttggggtc gaggtgccgt aaagcactaa atcggaaccc taaagggagc   17340
ccccgattta gagcttgacg gggaaagccg gcgaacgtgg cgagaaagga agggaagaaa   17400
gcgaaaggag cgggcgctag ggcgctggca agtgtagcgg tcacgctgcg cgtaaccacc   17460
acacccgccg cgcttaatgc gccgctacag ggcgcgtcca ttcgccattc aggatcgaat   17520
taattcttaa ttaa                                                   17534
```

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gtaacactgg cccaggaggc ctttctggtg acccc                          35

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
tgaccgggtc ctccggaaag accactgggg att                            33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tagttccttc tgcctggaat ac                                        22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
caagtcacaa ggatggacta ca                                        22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct    60
acttgccctc tggaaccagc tctagggtca ccacatctct gcttctgagt gcctcctcag   120
acacagtctg tatttcctct tccaagctct catcacaaac attgtgctgt attatatgtt   180
tctgtgtggt cttccttcta tgaggaagcc ttggaaagca ggagacttat tttagtcttc   240
tttatgtttc ttttattccc aacacattat gtctgcccca tagaccttt caataaatga   300 ttattgagtt agtgactcct tttacatgct gacaaatgtg gctcttatta ctccccattt   360
cagtatcaca tatttgtaaa agtgaatcct tcttaatcgt tttactttc tcctagtaaa   420 ttcctcatct atgcctgtct gctgctgttc tctgtgctgc tggcccttcg tttggatggc   480
atcatacagt ggagttactg ggctgtcttt gctccaatat ggctgtggaa gttaatggtc   540
attgttggag cctcagttgg aactggagtc tgggcacgaa atcctcaata tcggtaatac   600

```
tgctttatac aacccattgg tctctagcat gagggagcaa tatcttgact tttctcactt    660
ttgatgaagt aaggaccatt ttattttcta cctatctggg gtcttagaac tatagtataa    720
gctaacagat ctcttctgtg tttttgaaaa tttagtcttt ggtatgtatt ttcttacaaa    780
agcagtgcca tttgggggta agttgccagc cagctcacag atgcctatat aatccaaaat    840
gcacccaaaa tacagaactg gtatgccata ctagactaag cagcatgaaa ccaccctgtt    900
tttaggaaaa gacactcata ttatgtttgg tcatgaaaga tctttctcca atacagtttt    960
ggaactgggg ctccccttgt cccaccctcc tagtcccaga gctttaggac tattagcagt   1020 gtagggagg tggcttgacc aggagaccat gagtccctga cacagcagct ggggaatgag    1080
gaaagtcaaa gattggatgc cgagaaggaa agcagagcct ttgggggcag gggagagggg   1140 tacccttac cgtttccaac tcttgccctc cctgctcttg gatgcctccg ctggcccaaa    1200
ttcctgggag ttgctcacgc cagcatgcaa cctgcttgtt gctgggacct gcgagagtct   1260
ttcccttctc tgccacagag actgtaacta cataaaggga aaaaggggga cttaagactg   1320
ggaggctatt atgaacctcc actgggaaaa tgaggagtac aggaattccc agaaggcagc   1380
tgctcatgtg ggaaaagtgt aaagttgaaa ctaccgcacc tttttttttt tttttttttt   1440
tttttttttt ttgagacaga gtttcgctct tgttcccag gctggagtgc aatggtgtga   1500
tctcggccca ctgcagcctc cacatcccgg gttcaagtga ttctcctgcc tcggcctcct   1560
gagtagctgg gattacaggc acctgccacc atgcccagct aattttttgt attttttagta  1620 gagatagggg ttcaccatgc caggctagtt ttgaactcct gacatcaggt gatccacccg   1680
ccttggcctc ctgaagtgct gggattacag gtgtgagcca ccacgtccgg ccactacatc   1740
aactttttaa atttttgttt actaaatatg aaaatgattc agattgtgta aattacatat   1800
cacatacatg tctaagaact gtaaaacagt tacacagaga gccttggcag gtgagggaca   1860
ttcatgtata gctgtttcag agttcttaga ttttttttga agattgatg acctgtgtgg     1920 ctgtatgtgt tttattttt tatgagatat tttcagatat ctaatattaa ttgcttctca     1980
aagaatgcaa agttaaataa acatttaggt tctactaatt gatatttaga atatattcaa   2040
acttctcttt gttggtctta tttaagatgt tttgagcaag gaaaggaatt gtgtatgtgg   2100
ggttgaatgt aaggaatgta caggcgtggt cattctcatg ttaacattaa ccagtggaac   2160
atggttgggt cctacaggaa taacctctga tagcattttc tctatgatct aacttccggt   2220
gtatttgtca cccacaatac atgtatatca taaatgttca tctgtatttt gaataaacat   2280
tgtaggcctt tcagatgcat tatagagcct tttcctgatt agcggcctta ccattgctca   2340
attgtagatc tgttaaggtt attgtgcatg atacttagct aattaaactg attttgtttg   2400
agaacagttt taactcttgt tcttctttct ctttcatgtg caggtgttaa tttatcttaa   2460
tggaatagaa aggaaaatga aaatcattta tacgttttat ttgcatttaa aaatagcacc   2520
taacaatagt tactactatc ttgaaatata actggcactt gttcatagaa ctagagttat   2580
ttttataata ttgtgtgaag ggtggtttac atggtttctt gaaaaatgag gatcatgaga   2640 cttaagggt atttgcctgg ttttagcagc agaagcaaat cagcttgaat aatcttggaa    2700
gtaactcttg ttgttgaatt taaagatgtg aacagaagtg tttatgtaca ttgtcaggga   2760
aataagaact ggctattact tttgagaata tccttatacg gttaaaacat taaattctgg   2820
tttggttgta atgttcattt tgtattatgt agtagttctt cgatgtttca gagattgcct   2880
accaaagctt aggtttaagt tagctttcta cctgattttcc ctttgctttt gtcaaatttt   2940
caagtaaaat tcaaagtata aatataagtt ggtatttgcc ctgaactgct tgcttatagt   3000
```

-continued

```
ggagattctg aactgagggt gttttcttct tctctccctt ttttagagca gaaggagaaa    3060
cgtgtgtgga gtttaaagcc atgttgattg cagtgggcat ccacttgctc ttgttgatgt    3120
ttgaagttct ggtctgtgac agaatcgaga gaggaagcca tttctggctc ctggtcttca    3180
tgccgctgtt ctttgtttcc ccggtgtctg ttgcagcttg cgtttggggc tttcgacatg    3240
acaggtcact agaggtgaga tttcatatat ttaagaatgt tttccacttt gggaggtcaa    3300
ggcaggtgga tcacttgagg tcaggagttt gagaccagcc tggccaacat ggtgaaaccc    3360
catctctact aataatacaa aaattagccg ggtgtggtgg catgcgccag taatcccagc    3420
ttctccggag gctgaggcgg gagaatctct tgaacccagg aggcggaggt tgcagtgagc    3480
caagattgaa ccattgcact ccagcctggg tgacagaatg aaactccgtc ttaaaaaaaa    3540 aaaaaagaa tgttttcaaa agtaaaatat tttgctcagt tattcagatg tcaatttctt    3600
accctttgtt aggaagagct tgatcattac caactctaca tcatgagaca acaaggcaac    3660
aaaagatgat ggaaataaca attttctctt cttcacttag aacactagct tttcacccag    3720
gacatcagcc ttctcccagc ttcacatcct gtatcaatca gacagaaaca gaactgatag    3780
gttagataca gatatatgta taagagagt taaggaactg gctcacatta ctgtggggct    3840
ggcaagtctg aaatctccag ggcaggtgaa caggctggag acctaggagg agttgacact    3900
gcagtcctgg cacagaattt tttcctctcc aggaaaccac agttttttgct tttaaggcct    3960 tcacctgatt gcatgaggcc cacccatgct atggagggta gtctccttta ttcaaagtca    4020
gtaccttcac tgcaacagca agcttagtgt ttgattaaat aactgggtac tatagcccag    4080
ccaagttgac actcaaaact gaccatctcc ccacctcaga ccccatgatt tagcacctcc    4140
cctgctgtct ggttagctta tcctgatgtg cccctgtgtt tgtttattca ttcaataaac    4200
atttatcaag tatttactag atgccaagcc ctttttccct aagcatagag gatatgcaga    4260
tgaataaaat accaggacta gtaataatag taatgaaagt aattgcagat aacgtttatt    4320
gagcacttac tgtgtgccag gcattgtgcg aggcacatta catgtggtag ttttcttact    4380
aactaactct gtgaggtagg tccagagaag ataagtcatt tgttcatggc cacatgtgaa    4440
ggggcaggac caggattccg tttgagtcag cccgactcta aagcccgggc ataactac    4500 ataactgcat agaagctgag ggcccaaagc tgaatactga tgggttgagg ggagaactag    4560
aggctgtaga tgcctggttt tgagccgtgt ggatgaagag tgaagggaga agactgcagt    4620
tggcttagga agtaaacata gcagctgtag ggtgggtcag gcatataagc ctagacccca    4680
ggtatgggcg tgaggggaag gtatgtagac agagggacgg tgatggagca aggccctgtg    4740
ggactcaggg agaatgggac ctagagcacc aggaagggtt tggccttgaa caaggggagc    4800
tattccctga ttttcatgct ggtggaaagg ccacagcatg ggtatagtgg taggtaggag    4860
tgagccgtgg agggagagta tctgatggtc cactttcacc ctccctacaa ttcccagttt    4920
atatcaggga cttgagcatc catggatttt ggtatccaca gggggtcctg gaaccaatcc    4980
cccacagata ctgagggaca actatacaag gactaggact gcattgggcc tgaattacag    5040
aaagtaagtc tttcatatat tcacactcta ggcattcctg cccttggaag aaacaacata    5100
ccaggagctg agctccctcc tcctgtgatg caagaacagt acctatgttg gtgaggggt    5160 ggtctggagt aggctcatac agagatggga aggaggagtt gagggtctgc caggaagccc    5220
tgtgttggga gggaagggat ggcattttg ggacacattg aagcctagag gcaggaaaca    5280
ctccatcagc tgagtggact gtggcgattc agatccgacg ggagcacaag gtggaaagga    5340
aggaactgtg ggagttgaga agagagggag cctctacaga gggattgggg caaatagggg    5400
```

```
ccacgtcctc agcccacaga gcatgtgctg aagtgcccca ggcacccagt gcactcaca    5460 gggcaccagg ggatagtgga cattttgagg aaaacagtaa tacctgacat tgttgggac    5520 accatacaaa ctactagctt gaaatagttt acaggtttat ttttaggcca cactgcattc    5580
ctttcagtga cgtcgtatct ttaagaagct gggttttcag cagttgctgt gaaaacaaaa    5640
aaggctaatg ctgtgtgaaa atccgggtga agaacaggta acgagtggga gcaccttgtc    5700
tgattccaag gcgtgggaaa tggtgagcta cctgacaggc acacgcatcc cactgggaat    5760
tagttttggt tatttaagaa taatattaac attttcttt agatttatat gaattatttt     5820
ttctagtggc tacttagaaa tacttactaa gttagatgta attacttaaa tcagtgcaac    5880
tgttggcatt cccagccaca ttagggattt cttttggcct agaggtctat ggaggaatta    5940
ctaaattccc catgtaccta tgtactgaga acttttggga agctctgggc ctggtcccag    6000
atttcaattt tgtgggcaag aatgtacttt accagagtga ggagcagcct gcagggcgtt    6060
tgggctggag gcgggaggtt agtaaggggt tgctgaagtg gtaggcggat ggtgccgaag    6120
aaggcctcac taggcagtca tcatcaggat aggaagtggg cacgggattc aggagaaatc    6180
tggactttac agtggacagg atgtggtgac tgaacgtgac agtgtgggaa aaagaatgca    6240
gggtgattcc cgggctcatg gcttgagaaa tgagaccact gttgtgcctc caagtgacat    6300
gggaggctat agaaagtgac atgggaggct atagaaagtg acatgggagg ccatagaaag    6360
tgacatggga ggccatagaa agtgacatgg gaggccatag aaagtgacaa gggaggccat    6420
agaaagtgac atgggaggcc atagtgacat gggaggccat agaaagtgac atgggaggct    6480
atagaaagtg acatgggagg ccatagaaag tgacatggga ggccatagaa agtgacatgg    6540
gaggccatag tgcatgggga ggccatagaa agtgacatgg gaggctatag aaagaggaga    6600
tacaaggttc taagtgcagg cgataatgat ctctatttgg gactggcttc atttgaggtg    6660
cctttaggag agccgagtgg cctatgcaca gctgggtctg ctatgcagca ggaaggctaa    6720
gttggagaca gatgtgagaa ctaaccatga aggaggtaat aatgcagacc aagggtctgg    6780
ttgaaatttc ttctccccca gtccagggtg cagcgggtga gtgaaaatat gtgtgtttgt    6840
gtgtctgtct tcctagtcgg gagagaagac tgagtttgtg gctctgcgga gcatcaccat    6900
ttaaggaggg ggaaaaggag acagaaggaa ttaccagaac actccagagg gctccaagac    6960
tgtatggtgg gatctagatg gccaggagga ggggagcaaa aaggaaagag tcatccacag    7020
tatcagtagg atgccagttg aagtgttttt gctgcctccc ggttatcggt gactttgatg    7080
aaagctgtct tctggtggtc atgggggtgg aggccagatc acaaggaagc tgggaatggt    7140
agatgagata gtaggggctt gcatattcat tactgtctcg cagagagaaa cctgaggcta    7200
agaggggtct tggatcaaag gatggggtgg gtttatctgg tttcgggggct tttgtttttta   7260 atgagaagga gtcatttctg tgctgctagg agggatcaat ggaataggtg gggttaaaga    7320
tacagtacgg aatctacagt tgatggcttg atgtgacaag gtcctcaagg agcctgaaag    7380 gaagggggtgg ggtccaaggg caaaaccgag gtatgagaag aaggatgcac aaggatggtt   7440
tcgagtagac agtattgttg gtagggacat gaaggaagtt tagtggtcta ttgcagctag    7500
cctgtgttcc cagtgaacct ggaaacaagg ttctcatctg tgctcaggcc tcaggccaga    7560
aagggcaagg cagcagaggg gcaaggcagc aggctgagcc ccatttcccc ttgccataat    7620
actgctgtgc ccctctggta ccgaaaatca ggagtttcca gtgcaatata atattataca    7680
agttacactg tattataatg tgtattgtct tttagtgtgt taaccaaatt actgcagtat    7740
taaatgcaaa ttatactttg tttaactgat tcttctcttc attttttagtt agaaatcctg   7800
```

```
tgttctgtca acattctcca gtttatattc attgccttaa gactggacaa gatcatccac   7860
tggccctggc ttgtatgtaa cttttaaaat ccttaaataa acttcttttt tattataaaa   7920
gtaattcata ttcactgtac aaagcttgga aaagacggac aagcagaagt aatagcctaa   7980
tagtcaccca taatcccacc atggggagat aacatggtta gtgtttttat gtctgtgttt   8040
tatacaaaca gtttggatat aactgtgtgc accattttgt atcctgattt ttttgtttta   8100
atgttgtatc ataaacattt tatcatgtta ataaaaggtc tttataaaca tgacttctaa   8160
agtttaattg atacaaaata ttcttcaagt gcatgtatca gaccatcctc ttatttctaa   8220
aatatggtat ttccattgtt gccagtgttg aatgatttta aatcatactg cagtatatat   8280
gtttatgcat taaaatttt gccttttgtt ttttggttgt tttcttagga aatagtccag    8340
aaatagtgtt actgagctag aggttgggaa ctatttgaga ttcctatata cgtatactgc   8400
actgccaact tgcttttcca aaagccatac ctggccaggc gcagtggctt acacttacag   8460
tcccagcact ttgggaggcc gaggtgagct gatcacttga gctcaggagt tcgagaccaa   8520
cctgtgcaat gtagcaagac cctgtctcaa agaaaaaaa aaaaaagcca tacccattta    8580
cactcttgct ggtggtggca tctatgtcat gcttctaaac tgtgacttca gttactgggc   8640
atttggttga aattaactgt gaataaatgg gtagatggat gcagagatag aaagataagt   8700
ggcaaggtag aaattagaga acacagtata gattccacta ttaaatgcat ggaaaaaaga   8760
tggagactaa aggcagaaga gttccattgc cactgggagg taaggtcatg ctagtgtttt   8820
tgttcggttt tattttctct gttgtttgat gtataatttt gcatacaata tattttatgt   8880
attaaatata gctacccttaa aaagtgaaaa agtatagtaa agaattggga gcagagaaga   8940
aatgaaggga acctaagtat actccatatt taaagatggg aataatcact tctgcccaaa   9000
gtctttgata aaacattcat aataaaaaat attcagtcac tcatcctaca acttcacagt   9060
gctgtatctg gagaatggtc attgggttca aaactgtttc tgttgtgacg tgaaggaaac   9120
atatctaaac aagaccaaat tttttcgtat aagatactgt cagggaaaaa aaagattagt   9180
aattttgaga gctttccaca aatgagaaga aagattttt ctgcccttca tcctctgtag    9240
atcccagttg atgaagcagt ctgagtacat gtttcccata gtgagcaaga gaaaacaagg   9300
aagcctattg agatctaaca ttccacccat gaagggaact tcagtaaaaa ggagaatctc   9360
atcacagaat ggggaacggg gaagaaaggc tgtgcataga ctctgcagag aaacctacaa   9420
tcaagaactg gtcaggagaa gtaaaattcg tatgccaact caaatcatag atctaaaaga   9480
aaatgtaaaa ctatagatct gttaggaaat aacataggac agaatctttg gggtttgcaa   9540
ttaggcagag agtacttaga aatggcactg ttaatatggt ccatacgaga gagaaatcat   9600
aaatttggac ttcctcaaaa ttaaaatgaa atgaagacag gccacagact gggagaaaat   9660
atttgcaaag cacacatcaa aacactgact tgcacccaga acatacagag aactcttaaa   9720
aactcaaaac tgcaaaaaga aacacctaaa aattggcaaa agagttgaca atttgcgaag   9780
gggatataca catggcgaaa aagcacagga aaagatgctc aacgccatta caggttaggg   9840
aagacaaact acaaccagga tgagggcccg aaacacatgg cttcagaatg gtgaaactca   9900
gcaacactga cgaggccacg tgcctgggag gatgcagagg aactgggaca ctccagtgtt   9960
actggcggga aggcaggtgg tacgggcact gtagaaaatg gtttggccat ctctgatgca  10020
gttaaaagcg cacttcccgt gggacttggc tgccccactc ctgggtataa gatttacccc  10080
cagagaagtg aaagcgcgca gccttgtaga aacccacaca ccagtgtttg tagcagtctt  10140
gtttgcattt tggatagcgg ccttgtttgg ttttcacaaa ccaccctcag cggacagtca  10200
```

```
gataaactgt aggcatccat acaatggaat accactcaga tctgagaggg aacgacctgt   10260
ggatacaggg agggaacaac ttggatgaat ctcattagag acattatgtg gatggcggga   10320
agccagtctc aacaggttac ttgtctcgcg atgccatcta cataaagttc cagcagagac   10380
aaaagtacag tgagagaaca gatcagtgtt tgccggggct aatggtgggg acggtgtgat   10440
agtgaaggga cagcacggag agttttgcag ggtgacagac ctcttctgca tcctgccaac   10500
ggctgtgtga atctacttgt gtgaagactc agggaactca caccaaagga agacggtcac   10560
ttttcctact gtatgataga taattaataa aaagggagaa cggaggagtg tcgtcccagg   10620
aggcagggca ggagggcgaa gacgtgtcac aggggagcct ggccaagtgg cgcccccgga   10680
actcgtcctc tgggcttgtg tgtggatgag acaaggtcta cctggtacga cagggacata   10740
ctgggaatgc gcccttgccg tggaggcggg gacccggcag cgctacgtat ccagcatcaa   10800
cctgtatcca gcatcaaccc gccaagttca ctaacttggt aggggtgagg ttagggatcc   10860
ttaggagccc aggcagccag actttctggg gagcccattc ccatttgtgt tgccaaagta   10920
cccccagcag gttgtgggaa tgttgcctgt gaagagagtc tgttggggtg agatcttgtg   10980
tgtgtgcaca gggtgacagt tgtgtcccat ttccgggaa gctgtgatgg cagcagaacc   11040
tagaggagcc tgagagagtg tgggagagtg ggcctctgga agagtagagg ctgcggagcc   11100
aggtgcaggg ctgtctgtca cccaaaggaa gagggactga tgactcactg agcgtgtgtg   11160
tccctggtg gcagcaggcc ccatagtgaa cataccatac cttttctgtc ctgagcgatg   11220
ctcccagcag tcctgggaga tggaacggtc cttattcggc tcacaggaag accgcctta   11280
actggacaga cacagcaagg tgctaaagat gccttccatc agaggccagg ttggaagctc   11340
taaagagact tctcttgctg ttctctcacc cacccccagg ttgtgtgtgt cccgctgtgg   11400
attctcatgt cctttctgtg cctggtggtc ctctactaca ttgtgtggtc cgtcttgttc   11460
ttgcgctcta tggatgtgat tgcggacagc gcaggacaca cataaccatg gccctgagct   11520
ggatgaccat cgtcgtgccc cttcttacat ttgaggtaag cgttccacgg gaagcctctt   11580
cagcccctga agcttgcgct tcccctgaca ggattctgca cccctagaaa ggcagcctct   11640
gtccctcgag ctcacagtga gcccactcca ggagagggga gagaacacag ccatctccga   11700
gagggagctt cggtgaaagg agagcatcct tcctttctct tgggggcagc acgtggggct   11760
ggcagggaga agagtgcacc ttttagcca tggtgcctct gtatggctcc agtttccact   11820
ctggggaaag cagagtggga tgtcagattt gtgtattgga gtcacgtgga gaattctaga   11880
atgggagctg ttgactcctt agaacaaaca cccggaggag tttgccataa aactgctggc   11940
actgggaact tttcaagtgg ataggctatt gccgagctct gaagagggac ataaaagctc   12000
atttcgagct ttccccaggg ataggtgtt tcctgccttt ttctggcggt gctgatgttc   12060
cctcttgtgg gagctcacgc gggggtgggg tggtggggag gaactgccta atgaagtctg   12120
gcttccgcct ctgcccattt tcggtgctgg catcaaccgg gactatgtct ctttctttag   12180
attctgctgg ttcacaaact ggatggccac aacgccttct cctgcatccc gatctttgtc   12240
cccctttggc tctcgttgat cacgctgatg gcaaccacat ttggacagaa gggaggaaac   12300
cactgtatgt actcagcatt tcagaagtcc ttggtgtgtg tctgggggggg gaccagggg   12360
tgggggggtg cggatagaag tctaggaagg gatgagtccc cgagggcccc aatttagaag   12420
cttgtgtggg aaagtgaggg ctgaggaaat tctgggacct tctaagggaa gggcatgccg   12480
taactctggt gttctgctgg cctgcaccgg gactttctc gcagtgcacg ctgccatttg   12540
aggtagaacc agacacggca ggcaacctct cagagatccc gttccctcct ctgcaaaatg   12600
```

-continued

```
gggatcaaga cagattcttc ccaggcccgg gagggtttga tggaaaatcc acatctccca   12660
cccaaacctg ggattcatcc taggtccctg ttggccgctc tgcctccccc atatccttgc   12720
tgccatcacc cgagtcttgc ctgtcttgcc ttgctaacac tctattcccc tccacctgct   12780
tgctgaggca gacacttcca aaacgatctc tgcagagggt gccttcctgg caaggctgtg   12840
ggctccatgg cacggaagcc cagagcattg cccttcggaa agccagtggg tttgggggca   12900
gggcctcact gcagcccagc agcccgggct gtgcttgctg tttgtgcctc tgcccctac    12960
cccgcacccg ggagcaggga gggcttgcac cgagctgaca ctccagtagc ctacagagag   13020
gagtagtggg actgggaaag tggctttaag gtggctccat gagttcaggc ccctcctgg    13080
ccaacccgtg catgactacc gccctcacgg attccagagg gtgacagaaa tcttgttctt   13140
gggtggcact gtcatccatg agtttatcct ggctggagaa gattagcgga agacaccgta   13200
gtctgcgcac cacagatatt ttgagactca ctggagcagt agttctcaaa tttgggcatc   13260
cagcagaatc ccaaaagggc caggaaaagg ggaccgctgg agcccaccct agcccgactc   13320
agtttctgga ggtctgggct ggggcccgag aatggcatcc ctaactaggc cccgtggacg   13380
ctgtccctgc cggtccggga accccactcc aagcaccaca gagctagcat ttgcacttct   13440
tccccatttt gggtactcaa gccctgttca ggctttgtga ctcaggagtc tggataaagt   13500
atgttatgac attgtaggag tgaaacttct tgttacggaa agaaagttaa caggaaggtc   13560
agttgagcct cgtgtgtgaa ataaaaaatt cttattttc agggtggttt ggtatccgca    13620
aagatttctg tcagtttctg cttgaaatct tcccatttct acgagaatat ggaaacattt   13680
cctatgatct ccatcacgaa gataatgaag aaaccgaaga gaccccagtt ccggagcccc   13740
ctaaaatcgc acccatgttt cgaaagaagg ccagggtggt cattacccag agccctggga   13800
agtatgtgct cccacctccc aaattaaata tcgaaatgcc agattagatg ccacttccgg   13860
ggacagagct taagtggact gggacgcact ctctccgcct tcctctgccc cctcgttcac   13920
cccgcagacc agaaccagta ctggagctgg gtctccaggt acgtccatct catgccttgt   13980
ttgcatccag cgcctatcag ccactcacca cgacgggacg cggaagtggc aggtgacggg   14040
ggtgtgtgcc agcagatgcg gatgccagga agagtgtgag aacaggggtg ggattaccgt   14100
ctgtctggga ggggctccag gtacccctct tccccgtcag acccactggg agatggctgc   14160
ttgccaggcc cccagaagga acatctgtct atacggtgct gaaatcccaa tcaaaagtat   14220
tgtttagaaa tgtatttctc cacagggctg acctcctgca gctcgctgag cactcccagg   14280
tcctcagcac tcccaggtcg tggctggggc agtcagtagg aactgtaact atgtctctga   14340
tgcaccacgt gtttagacac agcacagtcc ttttttctgt tcctactgtg gaagtagttt   14400
ctctttgggc atgctgacag cagttttttca tagcctcacg gatgagccct ttctacggga   14460
gtgactccat gcttgtatac agagtattta tacaaatgtt ttagcatctt catatgcggt   14520
gttaaccct agttctgtac agcatattct gttcaagtat ttttttacaa gcttgtgctg    14580
taggcacatg ccttctgctg cagaagtgga cgcccgtggc acactccccc ccccccccg    14640
tggggtgcca cgccttcatg ggacattgcc acttctgccc tggaactcgt gcaggtacgt   14700
agtagctgct actgccacaa cggcaacacc aagcaagaga tggtccatgc ttttctgacg   14760
ttctcagaat agtggctagc ttcaaacctg acaagcgctg cttgaagccg gaacactaga   14820
gaatgttgct gagagcagaa acggccacgc gggtcacgac tatgcgtggg aaagtctcaa   14880
gcttccctcc tgccagcaac aagaaggctt tggagtaggc atgatgtttt cacgtgtgcg   14940
tgccgtttct ccaagcactg caggttccac cgtgtgtcag aggctgcaag tttaacatcc   15000
```

```
tcctgcctga aaacaaatag gtcctttgct gaaaagaggg taaaaaaaga gctttgatct   15060
tctcagccag gagaagaggg tggtgttttc acgcgggcaa ctgctcgccg gcctacatgg   15120
ggttaattca agtctgctgc gagcacgact ccgcccttgg cactggcctc cagcaagccc   15180
tgttctcttt ggggtacagg ggaacgggat ggtttagact ttcctgctca gtgtgtaaaa   15240
aatgtagcta aagccactat ttttgctctc cttaagctgt tcaataaacc ggttcctcat   15300
tttacacgtg catgatgtgt atcttctttg ctggatgggc caggaaactg gagtggtcct   15360
ctcagccagc ctcagaggaa agaaatctct agctggcaca ggcagccagt gagtgaggct   15420
ggcggctgca ggggcacagc ctttagaatg agtccttcag tgcacaggtc ccagggtata   15480
cggggtagtg ggaggaagga ggggacgcct cgcagatgcc actgttggct gggctacacc   15540
ttgccacact tgttactgct taggaggctt tctggagtgt tccttgggtg ctacgacaat   15600
ctgcagcaga cactgtcctt tcaccgctcc tggtcctcgt ttgctcccca gtgatgtcaa   15660
cagctgagga ctgctcacgc tgcaacaaaa ggctctgcag tcgctgtcta gcttgcccta   15720
gtcgtctcta gagttctgcc tgaactgaaa ctcaagtggg gttcagctca tgacttgtgg   15780
caattgacca ggaaattcac cagttgctgt ggctggaagg attttcagtc ctgtgggttg   15840
taaccagagg ccacaggtgg attctgcctt aggctcatga gatttccgac ttgctgttga   15900
agaaaatgcc ttgtgaagtg acaacagtag ctctgaccca actgccggtg cctcgctagt   15960
tcctatacgt cccactggat cctcacagcc ccgggaagca ggtgctacta ctcttatccc   16020
cgggaggaga cagaggccga gagaggttaa gtgacgtgcc caagtcacac agctcggcag   16080
cggccgggtt gagcatcagc agtctgtttg cagacccctc actgtcaccc cctgagccag   16140
tgcgccttgg gccctgcggt caggatgtct caagcgtgga ggcatcaccg gttcgtggca   16200
gtctctggaa ggtcactgag ctctgtgccc agaatcgagt cgggggagtc tgtgcagagg   16260
tggccctgtg tgtggggaca gtgtgtgaca cagacactgc tttggatgga cacctctccc   16320
gtgacctcct agcatccaat cccaaaggaa caactgttgc agagatggac cgctggacac   16380
aaacccacgt gcgtttctct ggagacactg gccaaggaaa acaaaacatg ctcgaaggcc   16440
aacagctgca tgccccaccg cgatgtgacc gcagacaccc ggggtgtaga agggtctctg   16500
cctggtgggg ggacacgtgc aggccgagga gaggcaggaa ggaggctgcc tccgactccc   16560
cactggactg catggcgacg gcgtgtggtg gggcagtcag ctaagccatt tgcctaaggg   16620
gctgtcgggc atctgcgtgc tgggaccga cagtgtgggt gtgttaggag gatctgtatg   16680
gagcacattg ctgcctctgg ctaggacagg gtggaaaggg tggcgtggct acagcctgac   16740
ccatgggcac cgtcctaccc tttgttctgt gcttccgagt gtcagtcatg tgctggggtc   16800
tgtgggccca tgactcagac ggtgagctct gaccttcctg agccagggct ttgctgtagt   16860
tgtgcctggc tcaggagctc taggacaagg ggaccgctcc aggtctgcat ctacggtgtg   16920
gcagggcccc tcggcactct tgtgcactag tgtcatcttt cccattgaaa tgactgtgag   16980
gaccagaatg tgcacatgca gatgggcagc tacttgtctg ccttggccct ttattacaca   17040
acttgctggg ggtggagatg ccacccccg gcagtcagag ccccttatg atgtcatggg   17100 gctggttaca tgactgccaa ggggtgctgc tggccacact gcactagcaa gtttgccaga   17160
tggaggacaa gcgatcattg agtatggctc gctgtgaaga aagaaattcg agaggacagg   17220
atcatggctt ggaaagggtg cctttccctc cccagttgca gtcagagacc taccttcacc   17280
cagcagatcc ttcccctgcc tgggacgacc cggggtccac tggagcccct aacttggagc   17340
tgctgacaga agaaatcgct ttccaacctc tggccgagga agcttcgttc agaaggccgc   17400
```

| | |
|---|---|
| accctgacgg tgacgtcccg ccccagggag aagataatct cctctccctc cccttttccac | 17460 |
| agaaactgtg gagactggtc agcagcaacc agttttcgtc catctggtgg gatgacagtg | 17520 |
| gggcttgtag agtgatcaat caaaaactct ttgaaaagga gattctcaaa agggacgtcg | 17580 |
| cacacaaagt gtttgccaca acttcgataa agagcttctt ccgccagcta aacttgtatg | 17640 |
| gcttccgaaa acggcgtcaa tgcactttca ggaccttcac ccgcattttc tccgcaaaaa | 17700 |
| ggctggtctc catcttgaat aaggtaatga acgacaagcc tctggagggg ttaagtcggt | 17760 |
| gggctctggg gcctggtcgg gtggaagtcc caggactgcc tcctgggaag tgggcgacct | 17820 |
| caggcagggt gtggggccat cgctgtgggc ctgtgtcccc ctctgggtgg aggtgacatg | 17880 |
| aactaagagt gaatgtgggg agagggctga ggatggtgcg ggcccctctc gagtgtgtaa | 17940 |
| aatatcacag gtgccaagta gccgtatctg cgtgtcgtcc tccccggggc cagccatgtc | 18000 |
| atctggtggt tgctgtgtcc cctgactcc acagcacatt accctgtgag gtgagcaggc | 18060 |
| caggggagtc tggtatttgt accactgtca ccctagctgg tgtctggaga ggtgctcaag | 18120 |
| tggaagcact gaagggcgcc tggcgcagga ggtgcagatg ctcctgctgc ccttggtagg | 18180 |
| tgggcccctg gtgtggaaga gccagtaccc agggcctcca acccagccgg ggtgcattct | 18240 |
| gttgccagct gacactgcat gggggaggcc cagaatcttc ttccctcctg gtctgcaact | 18300 |
| tcaaagaccc tttccgccgg ccatggacac cctaatctgc cattgagg ctttttccaa | 18360 |
| gacggaaagg cccgccacaa cttggtaaac cttgacgatg tgaacgcgag tccccagctt | 18420 |
| cctttgggga ctgggacctt ttccagaaag gcctcctggg ccagtagagt tctcttgcac | 18480 |
| aggggcgtag atggttggta gttgtagtcc atccttgtga cttg | 18524 |

<210> SEQ ID NO 13
<211> LENGTH: 7695
<212> TYPE: DNA
<213> ORGANISM: Homo sapiens

<400> SEQUENCE: 13

| | |
|---|---|
| ggcccaggag gcctttctgg aaaaggtccc agtccccaaa ggaagctggg gactcgcgtt | 60 |
| cacatcgtca aggtttacca agttgtggcg ggcctttccg tcttggaaaa agcctcaaaa | 120 |
| tggcagatta gggtgtccat ggccggcgga aagggtcttt gaagttgcag accaggaggg | 180 |
| aagaagattc tgggcctccc ccatgcagtg tcagctggca acagaatgca ccccggctgg | 240 |
| gttggaggcc ctgggtactg gctcttccac accaggggcc cacctaccaa gggcagcagg | 300 |
| agcatctgca cctcctgcgc caggcgccct tcagtgcttc cacttgagca cctctccaga | 360 |
| caccagctag ggtgacagtg gtacaaatac cagactcccc tggcctgctc acctcacagg | 420 |
| gtaatgtgct gtggagtcag ggggacacag caaccaccag atgacatggc tggcccgggg | 480 |
| gaggacgaca cgcagatacg gctacttggc acctgtgata ttttacacac tcgagagggg | 540 |
| cccgcaccat cctcagccct ctccccacat tcactcttag ttcatgtcac ctccacccag | 600 |
| agggggacac aggcccacag cgatggcccc acccctgcc tgaggtcgcc cacttcccag | 660 |
| gaggcagtcc tgggacttcc acccgaccag gccccagagc ccaccgactt aaccccctcca | 720 |
| gaggcttgtc gttcattacc ttattcaaga tggagaccag cctttttgcg gagaaaatgc | 780 |
| gggtgaaggt cctgaaagtg cattgacgcc gttttcggaa gccatacaag tttagctggc | 840 |
| ggaagaagct ctttatcgaa gttgtggcaa acactttgtg tgcgacgtcc cttttgagaa | 900 |
| tctccttttc aaagagtttt tgattgatca ctctacaagc cccactgtca tcccaccaga | 960 |
| tggacgaaaa ctggttgctg ctgaccagtc tccacagttt ctgtggaaag gggagggaga | 1020 |

```
ggagattatc ttctccctgg ggcgggacgt caccgtcagg gtgcggcctt ctgaacgaag    1080
cttcctcggc cagaggttgg aaagcgattt cttctgtcag cagcctcaag ttagggctcc    1140
cagtggaccc cgggtcgtcc caggcagggg aaggatctgc tgggtgaagg taggtctctg    1200
actgcaactg gggagggaaa ggcacccttt ccaagccatg atcctgtcct ctcgaatttc    1260
tttcttcaca gcgagccata ctcaatgatc gcttgtcctc catctggcaa acttgctagt    1320
gcagtgtggc cagcagcacc ccttggcagt catgtaacca gccccatgac atcataaagg    1380
ggctctgact gccgggggt ggcatctcca cccccagcaa gttgtgtaat aaagggccaa     1440
ggcagacaag tagctgccca tctgcatgtg cacattctgg tcctcacagt catttcaatg    1500
ggaaagatga cactagtgca caagagtgcc gaggggccct gccacaccgt agatgcagac    1560
ctggagcggt ccccttgtcc tagagctcct gagccaggca caactacagc aaagccctgg    1620
ctcaggaagg tcagagctca ccgtctgagt catgggccca cagacccag cacatgactg      1680
acactcggaa gcacagaaca aagggtagga cggtgcccat gggtcaggct gtagccacgc    1740
caccctttcc accctgtcct agccagaggc agcaatgtgc tccatacaga tcctcctaac    1800
acacccacac tgtcggtccc cagcacgcag atgcccgaca gccccttagg caaatggctt    1860
agctgactgc cccaccacac gccgtcgcca tgcagtccag tggggagtcg gaggcagcct    1920
ccttcctgcc tctcctcggc ctgcacgtgt cccccacca gcagagacc cttctacacc      1980
ccgggtgtct gcggtcacat cgcggtgggg catgcagctg ttggccttcg agcatgtttt    2040
gttttccttg gccagtgtct ccagagaaac gcacgtgggg ttgtgtccag cggtccatct    2100
ctgcaacagt tgttcctttg ggattggatg ctaggaggtc acgggagagg tgtccatcca    2160
aagcagtgtc tgtgtcacac actgtcccca cacacagggc cacctctgca cagactcccc    2220
cgactcgatt ctgggcacag agctcagtga ccttccagag actgccacga accggtgatg    2280
cctccacgct tgagacatcc tgaccgcagg gcccaaggcg cactggctca ggggtgaca     2340
gtgagggtc tgcaaacaga ctgctgatgc tcaacccggc cgctgccgag ctgtgtgact      2400
tgggcacgtc acttaacctc tctcggcctc tgtctcctcc cggggataag agtagtagca    2460
cctgcttccc ggggctgtga ggatccagtg ggacgtatag gaactagcga ggcaccggca    2520
gttgggtcag agctactgtt gtcacttcac aaggcatttt cttcaacagc aagtcggaaa    2580
tctcatgagc ctaaggcaga atccaccgt ggcctctggt tacaacccac aggactgaaa      2640
atccttccag ccacagcaac tggtgaattt cctggtcaat tgccacaagt catgagctga    2700
accccacttg agtttcagtt caggcagaac tctagagacg actagggcaa gctagacagc    2760
gactgcagag ccttttgttg cagcgtgagc agtcctcagc tgttgacatc actggggagc    2820
aaacgaggac caggagcggt gaaaggacag tgtctgctgc agattgtcgt agcacccaag    2880
gaacactcca gaaagcctcc taagcagtaa caagtgtggc aaggtgtagc ccagccaaca    2940
gtggcatctg cgaggcgtcc cctccttcct cccactaccc cgtataccct gggacctgtg    3000
cactgaagga ctcattctaa aggctgtgcc cctgcagccg ccagcctcac tcactggctg    3060
cctgtgccag ctagagattt cttcctctg aggctggctg agaggaccac tccagtttcc      3120
tggcccatcc agcaaagaag atacacatca tgcacgtgta aaatgaggaa ccggtttatt    3180
gaacagctta aggagagcaa aaatagtggc tttagctaca ttttttacac actgagcagg    3240
aaagtctaaa ccatcccgtt ccctgtacc ccaaagagaa cagggcttgc tggaggccag      3300
tgccaagggc ggagtcgtgc tcgcagcaga cttgaattaa ccccatgtag gccgcgagc     3360
agttgcccgc gtgaaaacac caccctcttc tcctggctga aagatcaaa gctctttttt      3420
```

```
taccctctttt tcagcaaagg acctatttgt tttcaggcag gaggatgtta aacttgcagc    3480
ctctgacaca cggtggaacc tgcagtgctt ggagaaacgg cacgcacacg tgaaaacatc    3540
atgcctactc caaagccttc ttgttgctgg caggagggaa gcttgagact ttcccacgca    3600
tagtcgtgac ccgcgtggcc gtttctgctc tcagcaacat tctctagtgt tccggcttca    3660
agcagcgctt gtcaggtttg aagctagcca ctattctgag aacgtcagaa aagcatggac    3720
catctcttgc ttggtgttgc cgttgtgca gtagcagcta ctacgtacct gcacgagttc     3780
cagggcagaa gtggcaatgt cccatgaagg cgtggcaccc cacgggggggg gggggggagt   3840 gtgccacggg cgtccacttc tgcagcagaa ggcatgtgcc tacagcacaa gcttgtaaaa    3900
aaatacttga acagaatatg ctgtacagaa ctaggggtta acaccgcata tgaagatgct    3960
aaaacatttg tataaatact ctgtatacaa gcatggagtc actcccgtag aaagggctca    4020
tccgtgaggc tatgaaaaac tgctgtcagc atgcccaaag agaaactact tccacagtag    4080
gaacagaaaa aaggactgtg ctgtgtctaa acacgtggtg catcagagac atagttacag    4140
ttcctactga ctgccccagc cacgacctgg gagtgctgag gacctgggag tgctcagcga    4200
gctgcaggag gtcagccctg tggagaaata catttctaaa caatacttt gattgggatt      4260 tcagcaccgt atagacagat gttccttctg ggggcctggc aagcagccat ctcccagtgg    4320
gtctgacggg gaagagggggt acctggagcc cctcccagac agacggtaat cccacccctg   4380
ttctcacact cttcctggca tccgcatctg ctggcacaca ccccgtcac ctgccacttc      4440 cgcgtcccgt cgtggtgagt ggctgatagg cgctggatgc aaacaaggca tgagatggac    4500
gtacctggag acccagctcc agtactggtt ctggtctgcg gggtgaacga gggggcagag    4560
gaaggcggag agagtgcgtc ccagtccact taagctctgt ccccggaagt ggcatctaat    4620
ctggcatttc gatatttaat tgggaggtg ggagcacata cttcccaggg ctctgggtaa      4680 tgaccacccct ggccttcttt cgaaacatgg gtgcgatttt aggggggctcc ggaactgggg   4740 tctcttcggt ttcttcatta tcttcgtgat ggagatcata ggaaatgttt ccatattctc    4800
gtagaaatgg gaagatttca agcagaaact gacagaaatc tttgcggata ccaaaccacc    4860
ctgaaaaata agaattttt atttcacaca cgaggctcaa ctgaccttcc tgttaacttt      4920 cttccgtaa caagaagttt cactcctaca atgtcataac atactttatc cagactcctg      4980
agtcacaaag cctgaacagg gcttgagtac ccaaaatggg gaagaagtgc aaatgctagc    5040
tctgtggtgc ttggagtggg gttcccggac cggcagggac agcgtccacg gggcctagtt    5100
agggatgcca ttctcgggcc ccagcccaga cctccagaaa ctgagtcggg ctagggtggg    5160
ctccagcggt cccctttcc tggcccttt gggattctgc tggatgccca aatttgagaa       5220
ctactgctcc agtgagtctc aaaatatctg tggtgcgcag actacggtgt cttccgctaa    5280
tcttctccag ccaggataaa ctcatggatg acagtgccac ccaagaacaa gatttctgtc    5340
accctctgga atccgtgagg gcggtagtca tgcacgggtt ggccaggagg gggcctgaac    5400
tcatggagcc accttaaagc cactttccca gtcccactac tcctctctgt aggctactgg    5460
agtgtcagct cggtgcaagc cctccctgct cccgggtgcg gggtaggggg cagaggcaca    5520
aacagcaagc acagcccggg ctgctgggct gcagtgaggc cctgccccca aacccactgg    5580
ctttccgaag gcaatgctc tgggcttccg tgccatggag cccacagcct tgccaggaag     5640
gcaccctctg cagagatcgt tttggaagtg tctgcctcag caagcaggtg gaggggaata    5700
gagtgttagc aaggcaagac aggcaagact cgggtgatgg cagcaaggat atggggagg     5760 cagagcggcc aacagggacc taggatgaat cccaggtttg ggtgggagat gtggattttc    5820
```

```
catcaaaccc tcccgggcct gggaagaatc tgtcttgatc cccatttgc agaggaggga      5880 acgggatctc tgagaggttg cctgccgtgt ctggttctac ctcaaatggc agcgtgcact     5940
gcgagaaaag tcccggtgca ggccagcaga acaccagagt tacggcatgc ccttccctta    6000
gaaggtccca gaatttcctc agccctcact ttcccacaca agcttctaaa ttggggccct    6060
cggggactca tcccttccta gacttctatc cgccaccccc caccccctgg tccccccca    6120 gacacacacc aaggacttct gaaatgctga gtacatacag tggtttcctc ccttctgtcc    6180
aaatgtggtt gccatcagcg tgatcaacga gagccaaagg gggacaaaga tcgggatgca    6240
ggagaaggcg ttgtggccat ccagtttgtg aaccagcaga atctaaagaa agagacatag    6300
tcccggttga tgccagcacc gaaaatgggc agaggcggaa gccagacttc attaggcagt    6360
tcctccccac cacccaccc ccgcgtgagc tccacaaga gggaacatca gcaccgccag      6420
aaaaaggcag gaaaccacct atccctgggg aaagctcgaa atgagctttt atgtccctct    6480
tcagagctcg gcaatagcct atccacttga aaagttccca gtgccagcag ttttatggca    6540
aactcctccg ggtgtttgtt ctaaggagtc aacagctccc attctagaat tctccacgtg    6600
actccaatac acaaatctga catcccactc tgctttcccc agagtggaaa ctggagccat    6660
acagaggcac catggctaaa aaggtgcact cttctccctg ccagcccac gtgctgcccc     6720 caagagaaag gaaggatgct ctcctttcac cgaagctccc tctcggagat ggctgtgttc    6780
tctcccctct cctggagtgg gctcactgtg agctcgaggg acagaggctg cctttctagg    6840
ggtgcagaat cctgtcaggg gaagcgcaag cttcaggggc tgaagaggct tcccgtggaa    6900
cgcttacctc aaatgtaaga aggggcacga cgatggtcat ccagctcagg gccatggtta    6960
tgtgtgtcct gcgctgtccg caatcacatc catagagcgc aagaacaaga cggaccacac    7020
aatgtagtag aggaccacca ggcacagaaa ggacatgaga atccacagcg gacacacac    7080 aacctggggg tgggtgagag aacagcaaga gaagtctctt tagagcttcc aacctggcct    7140
ctgatggaag gcatctttag caccttgctg tgtctgtcca gttaaggcgg tccttcctgt   7200
gagccgaata aggaccgttc catctcccag gactgctggg agcatcgctc aggacagaaa    7260
aggtatggta tgttcactat ggggcctgct gccaccaggg gacacacacg ctcagtgagt    7320
catcagtccc tcttcctttg ggtgacagac agccctgcac ctggctccgc agcctctact    7380
cttccagagg cccactctcc cacactctct caggctcctc taggttctgc tgccatcaca    7440
gcttcccggg aaatgggaca caactgtcac cctgtgcaca cacacaagat ctcaccccaa    7500
cagactctct tcacaggcaa cattcccaca acctgctggg ggtactttgg caacacaaat    7560
gggaatgggc tccccagaaa gtctggctgc ctgggctcct aaggatccct aacctcaccc    7620
ctaccaagtt agtgaacttg gcgggttgat gctggataca ggttgatgct ggatacgtag    7680
cgctgccggg tgacc                                                      7695
```

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 14

```
gggcgaattg ggcccgacgt cgcatgctcc cggccgccat ggcggccgcg ggaattcgat      60
atcactagtg aattcgcggc cggcgattgg gcccgacgtc gcatgctccc ggccgccatg     120
```

```
gcggccgcgg gaattcgatt ccttaattaa gtcgactggg acccaaactt tggagtcgtt      180
gacagatgtg acaggtgaag cctgggatga catcgccaaa aatgcaacgt ctcactcatt      240
gtcactactc ccagggctca gtcgtcactg gggaaaatct ccagaaggta gcgcgggcca      300
aggtgacagg tgtctgccaa gatctgcccg ccagactccc gggcggcgcg ctccctccct      360
gcaggccttc agcccgtcag catccccttc ctcggggccc tgctcactcc cagcctccat      420
cccccctgcca tctcctccgc cggtcgcgtg cggacacaag gatggggacc tcccagcgag      480
gagcgctctg ggcggggctc cggacgcatg cgcggccctc gtacggaagc ccggaaggag      540
gggcaggggg cggtggctca ggtttctccg ggcggcggcg gcggcggcgg cggcgacggc      600
gacggcgacg gcagcgggga cggcagcagt agcgggagca gcagcgtgga cgcggctggc      660
gctggcgcca tgaacccgct gtaaggcgca ggctgtgcag cacggggtgc ggggaggag      720
gaggaggacg ccgcggtgaa gttctccgcc atgaacctga ggggcctctt ccaggacttc      780
aacccgaggt gaggcggcgt cgttggcgcc cccgggagtc cgcgctgcgg gctcgggcgc      840
gggctggtgt tcggctccgg ggaggcacgg cgggcgagat gctgcagccc gaggacccgg      900
gcgcctgccc gagcctccct gcgggtgcaa gcggtcccca ggcaaaacag tcggcctcgg      960
cgcccgcccg cttcctcctc ccgtgcccgg tgctttcagc ccctgcccgg ccacggccgg     1020
aagggccccgg ccgcgagccc cgtcctgccc caagggaacc ccattctttt ctgcttgctg     1080
tccctcattg gtgtcccaac ttcttcgtct cggttccatc ctcttctgcg ccgctgcggg     1140
ccctccattc tccgcgtcag ggccgtctca ctcgacccaa caccctacc cccaccccag     1200
ctgtttcctc cagttcctcg cagtccttgg ggttttcctt gggtttatgc ccatccctct     1260
cttgtttgct tctttgttga acggataccc gaaacactgt tgaatccttg gagtcagtgt     1320
cggggtatgg caataccttaa tataatgcat ttctgggtga gcctgatcat tttccatact     1380
cattttctca tcagtcttca ctacaagttt atttgcagga agtagatatt gctgtccttc     1440
ttttccagat ggggaacacc cagtggacag tgtggagaaa acactggcta agcactcaag     1500
cgcctgtcct tgcacttgcc cgactgtttt gtaactgttc tttacccag gctgtgagct     1560
ccctgaagct gagaccatct cctgctcatc tcagtgtccc cagcgcctcc cacccaccgt     1620
atctggcaca tagtaggcac atataaaatg tttgtggaac taaactgagc ccaaagactt     1680
ggattggaga cgaggccata tgtaactggg tgattctctg cccttctttg gcccttctgt     1740
aaaatgagga gttggcctaa ctgatctctt aaatgcacta ctctccgaaa ggagtatccg     1800
tttcccttat ttgccagttg ggaagacgtg ctcagtaaat atttgtgtgc tgtaacctat     1860
gttaggtgct ttagatgctg gcggtctcag catgggtga agaagggctt gtacacttaa      1920
gatgccttac agtactgtgc agtgctgtac tgcgggggcc aactctgggg acctatgcct     1980
tggctgcttg ttgaggatga aaggaagttt taggggagta tttgtatgtt gagggtgcag     2040
tctccctagg gatggtgaca ttttaacttg tgagtcattg tgactttgta tgtgccctta     2100
ttccactttg agttcatgtt ctggttagga gtgccagtgt ctctaacacg gtgcagacat     2160
tatcattgtt ggcttcgaag gcatagagga ggtaacagaa ctaactgcag tcccttcctc     2220
tgctgcatca gggggttaag attggtctgc agggtagtag ggttggtgct gtggctggac     2280
aagccctgta tgtcttctat ttggagatgg tgataagaaa gttaagtaaa aactgaattg     2340
ttttgtgccc ttgggcaact cacttatcta ttgttttatc tgtagaatga gtataatctc     2400
tcagtggggg agggaggcca attaaggatt gattacaaag tgccttacaa atagaaagct     2460
acagtgactt gtttgcaagg tgacagagaa ttcagaagcc tcaagaaact gccttaagtg     2520
```

```
atcaaacagg ctaacggagt tgccaaagca aaatagtgct gcactgatac tacctttaac    2580
cgttttttcc tttagcccct ttccccccaa aaaattagt atatgaaatt acagtgaaat    2640
acctggtatc taagcagatt tatagtaatt ctcaacatat tcatcaatct cttaattcta    2700
cctgcattaa aatgtatttc tacctgaaaa gtttaaaggt cttttatact gtgccatttt    2760
cctgattcat tgttgccaga ggtagtgagt tccttaattt tacagatatt tcaagaggac    2820
attggccagg tattattggt aaatcagatt tgttttttta gctggtagtg tttcacctct    2880
cctgagcact cctagttttt gacagtgtgc tttagtctcc ttccatgctg aggaaggcct    2940
tctctatagg agaaagaaaa ctgaggggtg tacacaggaa gttaccttat gctggggact    3000
caaaccttga tgctactgct ttgctccctg cctctatttt tgaaccaatt caacatctcc    3060
ctcctacccc aggaccttgt cacacactgt tctctttacc aggaatgttt ccctctcttt    3120
tcctctcctc cagacctagt gaactcctat ttatcctcac ttggcacttg ctaagggaag    3180
cattcctgac ttccctgacc agatttactg ctccctgttt ctacagttcc tgtagtattt    3240
actactcctc catcatagtg catatttgta cccttgtgtc tgtctggatg cttatttgat    3300
taatacctgc ctcccccact aaactttaag ctccatgggg tcaaggccgt gactgtgtca    3360
gtatcgtagc ctgcatactt ggaatagtac ctggctcaat aaatatttgt ggagtaaata    3420
actgaataac tctccagagc ctataagata aatctagagc tgctgctttc aatcactgct    3480
ttcctggtgg tctgtggcct ggttctcttt cttctcacac tcttcccacc ttcagagtgc    3540
agccattgct ttggagagat gggagagaac atggcactaa gcagaatat ggctatattt    3600 actttgaaga gcatgtcttt gtcatagaaa tagtcactgt catggtttgg tgggtcccaa    3660
ggcatgggtc atggctccag atccccttc cagccttttg gatcttggta agtctgaacc    3720
cactgctgcg ttgcaaggc tctggaaact atagtgacag agaatgattc acaagtgtca    3780
acactcagat gtacagggct gccagctgac ccactctacc tatttccatc tggcactgaa    3840
ctggttgatc atgaacttct tttcataatt gctttttagt tatgcaggtt aagacatgcc    3900
gaaacagatg taccggaccc acaaacaagt ccttccttga atgcctgagg cttcctaaca    3960
gtgaaagagc cctgttctta gagtaggcaa actgattctg aggcattgta ggtggtaggg    4020
atctggtagt aggtagcatt aggtgggctc ccggcactca ccatggagcc ttgaaatttt    4080
ctgctacttt gggggagttg ctggttcaga gaaggcccctt ccaccctggt agccatgtgg    4140
cactggaagg ctgtgaaaac tctgctgggc cttcttagtc atctgttgtg agctcctgat    4200
gggagtgtgg tgtatccctc aggtgtgcta gactggaaca aaggctgaga agtgttgctc    4260 tggggggttcc aacttgtggg catggggtac tgatgagatc agtagtgttt ggagacttct    4320
gtatgctcca tcttcagaag acattctgga gtccatataa gttatcttgt ctcttgtttg    4380
aagcaggaaa aaggaatgcg attgctggta atatagttca ctaaagtcag ctacctggcc    4440
tctaacagtt atttgcaaag tatattataa cattgattcc tcaaacatct agattcctat    4500
ctcgtgccaa gtgatgtact aggtgctcta agtacaaaaa taaggaata tagtcctcct    4560 ctcaatgcgt aagcctagtg gaagaagcag aaatgaaagg gaataagaa ttcaatagag    4620 tatgaggcat tacagtgaaa gaaccaaat gtcttagaag tacaaatggc agagctacta    4680
attctgtctc gagcaggcag ggaagagtct atagtgaaa tgacttttga gctagatttt    4740
gaattgagct agtcttttga gccagacttt tgagctagaa ttgtagggtt gtcatcagac    4800
cagagagtag gaagggtacc ttgtgaggaa gagagagaga gatcagattg ttactgtgtc    4860
tatgtagaaa aggaagacat aagaaactcc attttgatct gtactaagaa aaattgtttc    4920
```

```
tgctttgaga tgctgttaac ctgtaactttt agtcccaacc ctgtgctcac agaaacctgt    4980
gctgtaatga atcaaggttt aatggattta gggctgtgca ggatgtacct tgttaacaat    5040
atgtttgcag gcagtatgct tggtaaaagt catcgccatt ctccattctc gattaaccag    5100
ggacacagtg cactgcggaa ggccgcaggg acatctgccc aagaaagcct gggtattgtc    5160
caaggtttcc ccccactgag acagcctgag atatggcctt gtgggaaagg aaagacctta    5220
ccacccccca gcccgacacc cgtaaagtgt ctgtgctgag gaggagtagt gaaagagcgg    5280
ggcctctttg cagttgagat aagaggaagg cttctgtctc ctgctcatcc ctgggaatgg    5340
aatgtctctg tgtaaagctg accattccca ttcgttctat tctgagatag gagaaaacca    5400
ccctgtggct ggaggcgaag tatgctggca gcaatactgc tctgttactc tttgctacac    5460
tgagttgttt gggtaaagag aaacataaat ctagcctgcg tgcacatcca ggcacagtac    5520
ctttccttga acttattcat gatacagatt cctttgctca cgtttccctg ctgaccttct    5580
ccccacctgt tgccctgcta cactcccctc gctaagatag taaaaataat gatcagtaaa    5640
tactgaggta actcagaggc tagcgctggt gcgggtcctc cgtatgctga gtgccggtcc    5700
cctgggccca ctgttctttc tctatacttt gtttctgtgt cttatttctt ttctcagtct    5760
cgtcccacct gacgagaaat acccacaggt gtggaggggc tggccccttt cagtatctca    5820
gaagggacaa agtacacaaa ggcatggggt catgatagtg cctggtatgt tcaggtagtg    5880
aagaggtcca tgtggtatga gcactgcaga tgatatgtgt cgtatgaatt aaaaatacat    5940
agttactgca aatagttttt acaggttatt gttttttaaga aagcagtatc taatgcacga    6000
gtgtactgtc agtactgtca atgaactact taccactcaa gtgactgctt acgcgtcgaa    6060
tcactagtga attcgcggcc gcctgcaggt cgaccatatg ggagagctcc caacgcgttg    6120
gatgcatagc ttgagtattc tatagtgtca cctaaatagc ttggcgtaat catggtcata    6180
gctgtttcct gtgtgaaatt gttatccgct cacaattcca cacaacatac gagccggaag    6240
cataaagtgt aaagcctggg gtgcctaatg agtgagctaa ctcacattaa ttgcgttgcg    6300
ctcactgccc gctttccagt cgggaaacct gtcgtgccag ctgcattaat gaatcggcca    6360
acgcgcgggg agaggcggtt tgcgtattgg gcgctcttcc gcttcctcgc tcactgactc    6420
gctgcgctcg tcgttcggc tgcggcgagc ggtatcagct cactcaaagg cggtaatacg    6480
gttatccaca gaatcagggg ataacgcagg aaagaacatg tgagcaaaag gccagcaaaa    6540
ggccaggaac cgtaaaaagg ccgcgttgct ggcgtttttc cataggctcc gcccccctga    6600
cgagcatcac aaaaatcgac gctcaagtca gaggtggcga aacccgacag gactataaag    6660
ataccaggcg tttccccctg gaagctccct cgtgcgctct cctgttccga cccctgccgct    6720 taccggatac ctgtccgcct ttctcccttc gggaagcgtg cgctttctc atagctcacg    6780 ctgtaggtat ctcagttcgg tgtaggtcgt tcgctccaag ctgggctgtg tgcacgaacc    6840
ccccgttcag cccgaccgct cgccttatc cggtaactat cgtcttgagt ccaacccggt    6900
aagacacgac ttatcgccac tggcagcagc cactggtaac aggattagca gagcgaggta    6960
tgtaggcggt gctacagagt tcttgaagtg gtggcctaac tacggctaca ctagaagaac    7020
agtatttggt atctgcgctc tgctgaagcc agttaccttc ggaaaaagag ttggtagctc    7080
ttgatccggc aaacaaacca ccgctggtag cggtggtttt tttgtttgca agcagcagat    7140
tacgcgcaga aaaaaaggat ctcaagaaga tcctttgatc ttttctacgg ggtctgacgc    7200
tcagtggaac gaaaactcac gttaagggat tttggtcatg agattatcaa aaaggatctt    7260
cacctagatc cttttaaatt aaaaatgaag ttttaaatca atctaaagta tatatgagta    7320
```

```
aacttggtct gacagttacc aatgcttaat cagtgaggca cctatctcag cgatctgtct    7380
atttcgttca tccatagttg cctgactccc cgtcgtgtag ataactacga tacgggaggg    7440
cttaccatct ggccccagtg ctgcaatgat accgcgagac ccacgctcac cggctccaga    7500
tttatcagca ataaaccagc cagccggaag ggccgagcgc agaagtggtc ctgcaacttt    7560
atccgcctcc atccagtcta ttaattgttg ccgggaagct agagtaagta gttcgccagt    7620
taatagtttg cgcaacgttg ttgccattgc tacaggcatc gtggtgtcac gctcgtcgtt    7680
tggtatggct tcattcagct ccggttccca acgatcaagg cgagttacat gatccccat     7740 gttgtgcaaa aaagcggtta gctccttcgg tcctccgatc gttgtcagaa gtaagttggc    7800
cgcagtgtta tcactcatgg ttatggcagc actgcataat tctcttactg tcatgccatc    7860
cgtaagatgc ttttctgtga ctggtgagta ctcaaccaag tcattctgag aatagtgtat    7920
gcggcgaccg agttgctctt gcccggcgtc aatacgggat aataccgcgc cacatagcag    7980
aactttaaaa gtgctcatca ttggaaaacg ttcttcgggg cgaaaactct caaggatctt    8040
accgctgttg agatccagtt cgatgtaacc cactcgtgca cccaactgat cttcagcatc    8100
ttttactttc accagcgttt ctgggtgagc aaaaacagga aggcaaaatg ccgcaaaaaa    8160
gggaataagg gcgacacgga aatgttgaat actcatactc ttcctttttc aatattattg    8220
aagcatttat cagggttatt gtctcatgag cggatacata tttgaatgta tttagaaaaa    8280
taaacaaata ggggttccgc gcacatttcc ccgaaaagtg ccacctgatg cggtgtgaaa    8340
taccgcacag atgcgtaagg agaaaatacc gcatcaggaa attgtaagcg ttaatatttt    8400
gttaaaattc gcgttaaatt tttgttaaat cagctcattt tttaaccaat aggccgaaat    8460
cggcaaaatc ccttataaat caaaagaata ccgagata gggttgagtg ttgttccagt     8520
ttggaacaag agtccactat taaagaacgt ggactccaac gtcaaagggc gaaaaaccgt    8580
ctatcagggc gatggcccac tacgtgaacc atcaccctaa tcaagttttt tggggtcgag    8640
gtgccgtaaa gcactaaatc ggaaccctaa agggagcccc cgatttagag cttgacgggg    8700
aaagccggcg aacgtggcga gaaggaagg gaagaaagcg aaaggagcgg cgctagggc     8760 gctggcaagt gtagcggtca cgctgcgcgt aaccaccaca cccgccgcgc ttaatgcgcc    8820
gctacagggc gcgtccattc gccattcagg ctgcgcaact gttgggaagg gcgatcggtg    8880
cgggcctctt cgctattacg ccagctggcg aaagggggat gtgctgcaag gcgattaagt    8940
tgggtaacgc cagggttttc ccagtcacga cgttgtaaaa cgacggccag tgaattgtaa    9000
tacgactcac tata                                                     9014
```

<210> SEQ ID NO 15
<211> LENGTH: 5954
<212> TYPE: DNA
<213> ORGANISM: Homo sapiens

<400> SEQUENCE: 15

```
ggccgcggga attcgattcc ttaattaagt cgactgggac ccaaactttg gagtcgttga      60
cagatgtgac aggtgaagcc tgggatgaca tcgccaaaaa tgcaacgtct cactcattgt     120
cactactccc agggctcagt cgtcactggg aaaatctcc agaaggtagc gcgggccaag      180
gtgacaggtg tctgccaaga tctgcccgcc agactcccgg gcggcgcgct ccctccctgc    240
aggccttcag cccgtcagca tcccttcct cggggccctg ctcactccca gcctccatcc     300
ccctgccatc tcctccgccg gtcgcgtgcg gacacaagga tggggacctc ccagcgagga    360
gcgctctggg cggggctccg gacgcatgcg cggccctcgt acggaagccc ggaaggaggg    420
```

```
gcaggggcg gtggctcagg tttctccggg cggcggcggc ggcggcggcg gcgacggcga    480
cggcgacggc agcggggacg gcagcagtag cgggagcagc agcgtggacg cggctggcgc    540
tggcgccatg aacccgctgt aaggcgcagg ctgtgcagca cggggtgcgg gggaggagga    600
ggaggacgcc gcggtgaagt tctccgccat gaacctgagg ggcctcttcc aggacttcaa    660
cccgaggtga ggcggcgtcg ttggcgcccc cgggagtccg cgctgcgggc tcggcgcgg     720
gctggtgttc ggctccgggg aggcacggcg ggcgagatgc tgcagcccga ggacccgggc    780
gcctgcccga gcctcctgc gggtgcaagc ggtccccagg caaaacagtc ggcctcggcg     840
cccgcccgct tcctcctccc gtgccgggtg ctttcagccc ctgccggcc acggccggaa     900
gggcccggcc gcgagccccg tcctgcccca agggaacccc attcttttct gcttgctgtc    960
cctcattggt gtcccaactt cttcgtctcg gttccatcct cttctgcgcc gctgcgggcc   1020
ctccattctc cgcgtcaggg ccgtctcact cgacccaaca ccctaccc cacccagct      1080
gtttcctcca gttcctcgca gtccttgggg ttttccttgg gttatgccc atccctctct    1140
tgtttgcttc tttgttgaac ggatacctga acactgttg aatccttgga gtcagtgtcg    1200
gggtatggca ataccttata taatgcattt ctgggtgagc ctgatcattt tccatactca    1260
ttttctcatc agtcttcact acaagtttat ttgcaggaag tagatattgc tgtccttctt    1320
ttccagatgg ggaacaccca gtggacagtg tggagaaaac actggctaag cactcaagcg    1380
cctgtccttg cacttgcccg actgttttgt aactgttctt taccccaggc tgtgagctcc    1440
ctgaagctga gaccatctcc tgctcatctc agtgtcccca gcgcctccca cccaccgtat    1500
ctggcacata gtaggcacat ataaaatgtt tgtggaacta aactgagccc aaagacttgg    1560
attggagacg aggccatatg taactgggtg attctctgcc cttctttggc ccttctgtaa    1620
aatgaggagt tggcctaact gatctcttaa atgcactact ctccgaaagg agtatccgtt    1680
tcccttattt gccagttggg aagacgtgct cagtaaatat ttgtgtgctg taacctatgt    1740
taggtgcttt agatgctggc ggtctcagca tggggtgaag aagggcttgt acacttaaga    1800
tgccttacag tactgtgcag tgctgtactg cgggggccaa ctctggggac ctatgccttg    1860
gctgcttgtt gaggatgaaa ggaagtttta ggggagtatt tgtatgttga gggtgcagtc    1920
tccctaggga tggtgacatt ttaacttgtg agtcattgtg actttgtatg tgcccttatt    1980
ccactttgag ttcatgttct ggttaggagt gccagtgtct ctaacacggt gcagacatta    2040
tcattgttgg cttcgaaggc atagaggagg taacagaact aactgcagtc ccttcctctg    2100
ctgcatcagg gggttaagat tggtctgcag ggtagtaggg ttggtgctgt ggctggacaa    2160
gccctgtatg tcttctattt ggagatggtg ataagaaagt taagtaaaaa ctgaattgtt    2220
ttgtgcccctt gggcaactca cttatctatt gtttatctg tagaatgagt ataatctctc    2280
agtggggtag ggaggccaat taaggattga ttacaaagtg ccttacaaat agaaagctac    2340
agtgacttgt ttgcaaggtg acagagaatt cagaagcctc aagaaactgc cttaagtgat    2400
caaacaggct aacggagttg ccaaagcaaa atagtgctgc actgatacta cctttaaccg    2460
tttttttcctt tagccccttttt ccccccaaaa aaattagtat atgaaattac agtgaaatac    2520
ctggtatcta agcagattta tagtaattct caacatattc atcaatctct taattctacc    2580
tgcattaaaa tgtatttcta cctgaaaagt ttaaaggtct tttatactgt gccattttcc    2640
tgattcattg ttgccagagg tagtgagttc cttaattta cagatatttc aagaggacat    2700
tggccaggta ttattggtaa atcagatttg ttttttttagc tggtagtgtt tcacctctcc    2760
tgagcactcc tagttttga cagtgtgctt tagtctcctt ccatgctgag gaaggccttc    2820
```

```
tctataggag aaagaaaact gaggggtgta cacaggaagt taccttatgc tggggactca    2880
aaccttgatg ctactgcttt gctccctgcc tctatttttg aaccaattca acatctccct    2940
cctaccccag gaccttgtca cacactgttc tctttaccag gaatgtttcc ctctcttttc    3000
ctctcctcca gacctagtga actcctattt atcctcactt ggcacttgct aagggaagca    3060
ttcctgactt ccctgaccag atttactgct ccctgtttct acagttcctg tagtatttac    3120
tactcctcca tcatagtgca tatttgtacc cttgtgtctg tctggatgct tatttgatta    3180
atacctgcct cccccactaa actttaagct ccatgggtc aaggccgtga ctgtgtcagt     3240
atcgtagcct gcatacttgg aatagtacct ggctcaataa atatttgtgg agtaaataac    3300
tgaataactc tccagagcct ataagataaa tctagagctg ctgctttcaa tcactgcttt    3360
cctggtggtc tgtggcctgg ttctctttct tctcacactc ttcccacctt cagagtgcag    3420
ccattgcttt ggagagatgg gagagaacat ggcactaagg cagaatatgg ctatatttac    3480
tttgaagagc atgtctttgt catagaaata gtcactgtca tggtttggtg ggtcccaagg    3540
catgggtcat ggctccagat ccccttccca gccttttgga tcttggtaag tctgaaccca    3600
ctgctgcgtt ggcaaggctc tggaaactat agtgacagag aatgattcac aagtgtcaac    3660
actcagatgt acagggctgc cagctgaccc actctaccta tttccatctg cactgaact    3720 ggttgatcat gaacttcttt tcataattgc tttttagtta tgcaggttaa gacatgccga    3780
aacagatgta ccggacccac aaacaagtcc ttccttgaat gcctgaggct tcctaacagt    3840
gaaagagccc tgttcttaga gtaggcaaac tgattctgag gcattgtagg tggtagggat    3900
ctggtagtag gtagcattag gtgggctccc ggcactcacc atggagcctt gaaattttct    3960
gctactttgg gggagttgct ggttcagaga aggcccttcc accctggtag ccatgtggca    4020
ctggaaggct gtgaaaactc tgctgggcct tcttagtcat ctgttgtgag ctcctgatgg    4080
gagtgtggtg tatccctcag gtgtgctaga ctggaacaaa ggctgagaag tgttgctctg    4140
ggggttccaa cttgtgggca tggggtactg atgagatcag tagtgtttgg agacttctgt    4200
atgctccatc ttcagaagac attctggagt ccatataagt tatcttgtct cttgtttgaa    4260
gcaggaaaaa ggaatgcgat tgctggtaat atagttcact aaagtcagct acctggcctc    4320
taacagttat ttgcaaagta tattataaca ttgattcctc aaacatctag attcctatct    4380
cgtgccaagt gatgtactag gtgctctaag tacaaaaata aaggaatata gtcctcctct    4440
caatgcgtaa gcctagtgga agaagcagaa atgaaaggga aataagaatt caatagagta    4500
tgaggcatta cagtgaaaga aaccaaatgt cttagaagta caaatggcag agctactaat    4560
tctgtctcga gcaggcaggg aagagtctat agtggaaatg acttttgagc tagattttga    4620
attgagctag tcttttgagc cagacttttg agctagaatt gtagggttgt catcagacca    4680
gagagtagga agggtacctt gtgaggaaga gagagagaga tcagattgtt actgtgtcta    4740
tgtagaaaag gaagacataa gaaactccat tttgatctgt actaagaaaa attgtttctg    4800
ctttgagatg ctgttaacct gtaactttag tcccaaccct gtgctcacag aaacctgtgc    4860
tgtaatgaat caaggtttaa tggatttagg gctgtgcagg atgtaccttg ttaacaatat    4920
gtttgcaggc agtatgcttg gtaaaagtca tcgccattct ccattctcga ttaaccaggg    4980
acacagtgca ctgcggaagg ccgcagggac atctgcccaa gaaagcctgg gtattgtcca    5040
aggtttcccc ccactgagac agcctgagat atggccttgt gggaaaggaa agaccttacc    5100
accccccagc ccgacacccg taaagtgtct gtgctgagga ggagtagtga aagagcgggg    5160
cctctttgca gttgagataa gaggaaggct tctgtctcct gctcatccct gggaatggaa    5220
```

| | |
|---|---|
| tgtctctgtg taaagctgac cattcccatt cgttctattc tgagatagga gaaaaccacc | 5280 |
| ctgtggctgg aggcgaagta tgctggcagc aatactgctc tgttactctt tgctacactg | 5340 |
| agttgtttgg gtaaagagaa acataaatct agcctgcgtg cacatccagg cacagtacct | 5400 |
| ttccttgaac ttattcatga tacagattcc tttgctcacg tttccctgct gaccttctcc | 5460 |
| ccacctgttg ccctgctaca ctcccctcgc taagatagta aaaataatga tcagtaaata | 5520 |
| ctgaggtaac tcagaggcta cgctggtgc gggtcctccg tatgctgagt gccggtcccc | 5580 |
| tgggcccact gttctttctc tatactttgt ttctgtgtct tatttctttt ctcagtctcg | 5640 |
| tcccacctga cgagaaatac ccacaggtgt ggaggggctg gccccttca gtatctcaga | 5700 |
| agggacaaag tacacaaagg catggggtca tgatagtgcc tggtatgttc aggtagtgaa | 5760 |
| gaggtccatg tggtatgagc actgcagatg atatgtgtcg tatgaattaa aaatacatag | 5820 |
| ttactgcaaa tagttttac aggttattgt ttttaagaaa gcagtatcta atgcacgagt | 5880 |
| gtactgtcag tactgtcaat gaactactta ccactcaagt gactgcttac gcgtcgaatc | 5940 |
| actagtgaat tcgc | 5954 |

<210> SEQ ID NO 16
<211> LENGTH: 30756
<212> TYPE: DNA
<213> ORGANISM: Homo sapiens
<220> FEATURE:
<221> NAME/KEY: modified_base
<222> LOCATION: (5934)
<223> OTHER INFORMATION: a, c, g, t, unknown or other

<400> SEQUENCE: 16

| | |
|---|---|
| gtacggaagc ccggaaggag gggcagggg cggtggctca ggtttctccg ggcggcggcg | 60 |
| gcggcggcgg cggcgacggc gacggcgacg gcagcgggga cggcagcagt agcgggagca | 120 |
| gcagcgtgga cgcggctggc gctggcgcca tgaacccgct gtaaggcgca ggctgtgcag | 180 |
| cacggggtgc gggggaggag gaggaggacg ccgcggtgaa gttctccgcc atgaacctga | 240 |
| ggggcctctt ccaggacttc aacccgaggt gaggcggcgt cgttggcgcc ccgggagtc | 300 |
| cgcgctgcgg gctcgggcgc gggctggtgt tcggctccgg ggaggcacgg cgggcgagat | 360 |
| gctgcagccc gaggacccgg gcgcctgccc gagcctccct gcgggtgcaa gcggtcccca | 420 |
| ggcaaaacag tcggcctcgg cgcccgcccg cttcctcctc ccgtgccccgg tgctttcagc | 480 |
| ccctgcccgg ccacggccgg aagggcccgg ccgcgagccc cgtcctgccc caagggaacc | 540 |
| ccattctttt ctgcttgctg tccctcattg gtgtcccaac ttcttcgtct cggttccatc | 600 |
| ctcttctgcg ccgctgcggg ccctccattc tccgcgtcag ggccgtctca ctcgacccaa | 660 |
| caccccctacc cccacccag ctgtttcctc cagttcctcg cagtccttgg ggttttcctt | 720 |
| gggtttatgc ccatccctct cttgtttgct tctttgttga acggatacct gaaacactgt | 780 |
| tgaatccttg gagtcagtgt cggggtatgg caataccttg tataatgcat ttctgggtga | 840 |
| gcctgatcat tttccatact cattttctca tcagtcttca ctacaagttt atttgcagga | 900 |
| agtagatatt gctgtccttc ttttccagat ggggaacacc cagtggacag tgtggagaaa | 960 |
| acactggcta agcactcaag cgcctgtcct tgcacttgcc cgactgtttt gtaactgttc | 1020 |
| tttaccccag gctgtgagct ccctgaagct gagaccatct cctgctcatc tcagtgtccc | 1080 |
| cagcgcctcc cacccaccgt atctggcaca tagtaggcac atataaaatg tttgtggaac | 1140 |
| taaactgagc ccaaagactt ggattggaga cgaggccata tgtaactggg tgattctctg | 1200 |
| cccttctttg gcccttctgt aaaatgagga gttggcctaa ctgatctctt aaatgcacta | 1260 |

```
ctctccgaaa ggagtatccg tttcccttat ttgccagttg ggaagacgtg ctcagtaaat    1320
atttgtgtgc tgtaacctat gttaggtgct ttagatgctg gcggtctcag catggggtga    1380
agaagggctt gtacacttaa gatgccttac agtactgtgc agtgctgtac tgcggggggcc    1440 aactctgggg acctatgcct tggctgcttg ttgaggatga aaggaagttt taggggagta    1500
tttgtatgtt gagggtgcag tctccctagg gatggtgaca ttttaacttg tgagtcattg    1560
tgactttgta tgtgcccttta ttccactttg agttcatgtt ctggttagga gtgccagtgt    1620
ctctaacacg gtgcagacat tatcattgtt ggcttcgaag gcatagagga ggtaacagaa    1680
ctaactgcag tcccttcctc tgctgcatca gggggtaag attggtctgc agggtagtag    1740
ggttggtgct gtggctggac aagccctgta tgtcttctat ttggagatgg tgataagaaa    1800
gttaagtaaa aactgaattg tttttgtgccc ttgggcaact cacttatcta ttgttttatc    1860
tgtagaatga gtataatctc tcagtggggt agggaggcca attaaggatt gattacaaag    1920
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgtttttttcc tttagccctt ttcccccccaa aaaaattagt    2100 atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccattttt cctgattcat tgttgccaga ggtagtgagt tccttaattt    2280
tacagatatt tcaagaggac attggccagg tattattggt aaatcagatt tgttttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctctttacc    2580
aggaatgttt ccctctcttt tcctctcctc cagacctagt gaactcctat ttatcctcac    2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atccccttt cagccttttg    3180 gatcttggta agtctgaacc cactgctgcg ttggcaaggc tctggaaact atagtgacag    3240
agaatgattc acaagtgtca acactcagat gtacagggct gccagctgac ccactctacc    3300
tatttccatc tggcactgaa ctggttgatc atgaacttct tttcataatt gcttttagt    3360 tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt ggggagttg ctggttcaga gaaggccctt    3600
ccaccctggt agccatgtgg cactggaagg ctgtgaaaac tctgctgggc cttcttagtc    3660
```

```
atctgttgtg agctcctgat gggagtgtgg tgtatccctc aggtgtgcta gactggaaca    3720
aaggctgaga agtgttgctc tgggggttcc aacttgtggg catggggtac tgatgagatc    3780
agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
taaaggaata tagtcctcct ctcaatgcgt aagcctagtg aagaagcag  aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200
tgacttttga gctagatttt gaattgagct agtcttttga gccagacttt tgagctagaa    4260
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggtttcc ccccactgag acagcctgag atatggcctt    4680
gtgggaaagg aaagacctta ccaccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac cttccttga  acttattcat gatacagatt cctttgctca    5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat cccacaggt  gtggaggggc    5280
tggccccttt cagtatctca gaagggacaa agtacacaaa ggcatggggt catgatagtg    5340
cctggtatgt tcaggtagtg aagaggtcca tgtggtatga gcactgcaga tgatatgtgt    5400
cgtatgaatt aaaaatacat agttactgca aatagttttt acaggttatt gttttttaaga    5460
aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca aacgggccct ctagacgcgt tgacattgat tattgactag ttattaatag    5640
taatcaatta cggggtcatt agttcatagc ccatgatatc atatggagtt ccgcgttaca    5700
taacttacgg taaatggccc gcctggctga ccgcccaacg acccccgccc attgacgtca    5760
ataatgacgt atgttcccat agtaacgcca atagggactt tccattgacg tcaatgggtg    5820
gagtatttac ggtaaactgc ccacttggca gtacatcaag tgtatcatat gccaagtacg    5880
cccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
```

```
aagtctccac cccattgacg tcaatgggag tttgttttgg caccaaaatc aacgggactt    6120
tccaaaatgt cgtaacaact ccgccccatt gacgcaaatg gcggtaggc gtgtacggtg     6180 ggaggtctat ataagcagag ctctctggct aactagagaa ccctgctta ctggcttatc    6240 gagatatctg cagaattcat ctgtcgactg ctaccggcag cgcgcagcgg caagaagtgt    6300
ctgggctggg acggacagga gaggctgtcg ccatcggcgt cctgtgcccc tctgctccgg    6360 cacgccctg tcgcagtgcc cgcgctttcc ccggcgcctg cacgcggcgc gcctgggtaa     6420
catgcttggg gtcctggtcc ttggcgcgct ggccctggcc ggcctggggt tcccgcacc    6480 cgcagagccg cagccgggtg gcagccagtg cgtcgagcac gactgcttcg cgctctaccc    6540
gggccccgcg accttcctca atgccagtca gatctgcgac ggactgcggg gccacctaat    6600
gacagtgcgc tcctcggtgg ctgccgatgt catttccttg ctactgaacg gcgacggcgg    6660
cgttggccgc cggcgcctct ggatcggcct gcagctgcca cccggctgcg gcgaccccaa    6720
gcgcctcggg ccctgcgcg gcttccagtg ggttacggga gacaacaaca ccagctatag     6780
caggtgggca cggctcgacc tcaatggggc tccctctgc ggcccgttgt gcgtcgctgt     6840
ctccgctgct gaggccactg tgcccagcga gccgatctgg gaggagcagc agtgcgaagt    6900
gaaggccgat ggcttcctct gcgagttcca cttcccagcc acctgcaggc cactggctgt    6960
ggagcccggc gccgcggctg ccgccgtctc gatcacctac ggcaccccgt tcgcggcccg    7020
cggagcggac ttccaggcgc tgccggtggg cagctccgcc gcggtggctc ccctcggctt    7080
acagctaatg tgcaccgcgc cgcccggagc ggtccagggg cactgggcca gggaggcgcc    7140
gggcgcttgg gactgcagcg tggagaacgg cggctgcgag cacgcgtgca atgcgatccc    7200
tggggctccc cgctgccagt gcccagccgg cgccgccctg caggcagacg ggcgctcctg    7260
caccgcatcc gcgacgcagt cctgcaacga cctctgcgag cacttctgcg ttcccaaccc    7320
cgaccagccg ggctcctact cgtgcatgtg cgagaccggc taccgctgg cggccgacca    7380 acaccggtgc gaggacgtgg atgactgcat actggagccc agtccgtgtc cgcagcgctg    7440
tgtcaacaca cagggtggct tcgagtgcca ctgctaccct aactacgacc tggtggacgg    7500
cgagtgtgtg gagcccgtgg acccgtgctt cagagccaac tgcgagtacc agtgccagcc    7560
cctgaaccaa actagctacc tctgcgtctg cgccgagggc ttcgcgccca ttccccacga    7620
gccgcacagg tgccagatgt tttgcaacca gactgcctgt ccagccgact gcgacccaa    7680 cacccaggct agctgtgagt gccctgaagg ctacatcctg gacgacggtt tcatctgcac    7740
ggacatcgac gagtgcgaaa acggcggctt ctgctccggg gtgtgccaca acctccccgg    7800
taccttcgag tgcatctgcg ggcccgactc ggcccttgcc cgccacattg caccgactg    7860 tgactccggc aaggtggacg gtggcgacag cggctctggc gagcccccgc ccagcccgac    7920
gcccggctcc accttgactc ctccggccgt ggggctcgtg cattcgggct tgctcatagg    7980
catctccatc gcgagcctgt gcctggtggt ggcgcttttg gcgctcctct gccacctgcg    8040
caagaagcag ggcgccgcca gggccaagat ggagtacaag tgcgcggccc cttccaagga    8100
ggtagtgctg cagcacgtgc ggaccgagcg gacgccgcag agactctgag cggcctccgt    8160
ccaggagcct ggctccgtcc aggagcctgt gcctcctcac ccccagcttt gctaccaaag    8220
caccttagct ggcattacag ctggagaaga ccctccccgc acccccaag ctgttttctt     8280 ctattccatg gctaactggc gaggggtga ttagagggag gagaatgagc ctcggcctct     8340
tccgtgacgt cactggacca ctgggcaatg atggcaattt tgtaacgaag acacagactg    8400
cgatttgtcc caggtcctca ctaccgggcg caggagggtg agcgttattg gtcggcagcc    8460
```

```
ttctgggcag accttgacct cgtgggctag ggatgactaa aatatttatt ttttttaagt    8520
atttaggttt ttgtttgttt cctttgttct tacctgtatg tctccagtat ccactttgca    8580
cagctctccg gtctctctct ctctacaaac tcccacttgt catgtgacag gtaaactatc    8640
ttggtgaatt ttttttttcct agccctctca catttatgaa gcaagcccca cttattcccc    8700
attcttccta gttttctcct cccaggaact gggccaactc acctgagtca ccctacctgt    8760
gcctgaccct acttcttttg ctcttagctg tctgctcaga cagaacccct acatgaaaca    8820
gaaacaaaaa cactaaaaat aaaaatggcc atttgctttt tcaccagatt tgctaattta    8880
tcctgaaatt tcagattccc agagcaaaat aattttaaac aaaggttgag atgtaaaagg    8940
tattaaattg atgttgctgg actgtcatag aaattacacc caagaggta tttatcttta     9000
cttttaaaca gtgagcctga attttgttgc tgttttgatt tgtactgaaa aatggtaatt    9060
gttgctaatc ttcttatgca atttcctttt ttgttattat tacttatttt tgacagtgtt    9120
gaaaatgttc agaaggttgc tctagattga gagaagagac aaaaccctcc caggagacag    9180
ttcaagaaag cttcaaactg catgattcat gccaattagc aattgactgt cactgttcct    9240
tgtcactggt agaccaaaat aaaaccagct ctactggtct tgtggaattg ggagcttggg    9300
aatggatcct ggaggatgcc caattagggc ctagccttaa tcaggtcctc agagaatttc    9360
taccatttca gagaggcctt ttggaatgtg gcccctgaac aagaattgga agctgccctg    9420
cccatgggag ctggttagaa atgcagaatc ctaggctcca ccccatccag ttcatgagaa    9480
tctatattta acaagatctg caggggggtgt gtctgctcag taatttgagg acaaccattc    9540
cagactgctt ccaatttttct ggaatacatg aaatatagat cagttataag tagcaggcca    9600
agtcaggccc ttattttcaa gaaactgagg aattttcttt gtgtagcttt gctctttggt    9660
agaaaaggct aggtacacag ctctagacac tgccacacag ggtctgcaag gtctttggtt    9720
cagctaagct aggaatgaaa tcctgcttca gtgtatggaa ataaatgtat catagaaatg    9780
taacttttgt aagacaaagg ttttcctctt ctattttgta aactcaaaat atttgtacat    9840
agttatttat ttattggaga taatctagaa cacaggcaaa atccttgctt atgacatcac    9900
ttgtacaaaa taaacaaata acaatgtgaa aaaaaaaaa aaaaaaaaaa aaaaaaaaa     9960
aaaaaaaagg tagcagtcga cagatgaatt ccaccacact ggactagtgg atccgagctc   10020
ggtaccaagc ttaagtttgg gctgcaggaa ttctgatggc tctcaaaatt cctgcctcct   10080
ttagggataa aagactttaa gactttttaa caaaaaagaa aaagaaaaaa aaaattcctg   10140
cctcctggtg tacacacaca gaagggttcc ctccccttga atgtgaccag gatctgtgaa   10200
aataacggga tagccgctcc tgtgattagg ttatgtggta gactagagca agattctcct   10260
gctggttttg aagaagtcag ctgccatgtt gtgagactgt catgggctag gcatgagcc    10320
tttaaatatc tgggagcaac ccctggccag cagccagtga gaaacgggc cctcagtcct    10380
acaatcacaa ggaactaaat tctgccaaca acctgaagga actttgaaga ggatcatgag   10440
tcccttgatt cagcttgatg agcccctgag cagaggatac agctaacttg tactagggaa   10500
gtataaaaaa catgcatggg aatgatatat atcaactta aggataattg tcatacttct    10560
gggaatgaag ggaaagaaat ggggctttag ttgtattatg atctttaatt tctcaaaaaa   10620
aataagatca gaagcaaata tggcaaaatg ttaatacttt tgtgggtacg taggtattca   10680
gcataccctt ttttctgagt tcaaaatatt ttataattaa aatgaaatgc aggccaggca   10740
cagtggctca tgcctataat accagcactt tgcgaggccg aggtggggagg atggcttgag   10800
gccagaccag cctggccaac atggcaaaac cccatctcta cttaaaaaaa aaaaaactat   10860
```

```
atatatatat atgtgtgtgt gtgtgtatat atatatatgt atatatattt atatatgtgt   10920
gtatatatat atatgtatat atatttatat atgtgtgtgt atatatatat atacacacac   10980
acacatatat acatacatac atacacacac acacacacac aattagccag gcatggtggc   11040
gcacacctgt agtcccagct acttgggagg ctgagacatg agaattgctt gaacctggga   11100
ggcagagtag ttagtgagct gagatcatac cactgcactc cagcctggtg acagagtgag   11160
actctgtctt aaaaaaaata aaaattaaaa ttaaatgcaa aaggtccaag tgaattgaag   11220
aggaaagggg tatcaaggaa ggttttgtgg aggtgacgtt tgagctgggt cttaaatgac   11280
ttaaacatgg gataagaagg gagggaataa ggacatttca ggtacgagaa ataaggagca   11340
aacagtggaa acaacctaac gtctgtcaac cagtgaatgg ataacaaaaa tgtaattcag   11400
atggtatcca acttacgatg gttcaacatg agattttttct gactttagga tagatttatc   11460
aaagtagtaa atccattttc aacttatgat attttcaact tcagatgggt ttatcaggac   11520
acagttgagg aacacctgtc tatccataca atttggcaat aaaaaggaaa tgagtgcaga   11580
tatactccac aacatgaatg aaccttgaaa acattaagtg agagaagcca gatacaaaag   11640
gccacatatt gtatgattct atttatacaa aatgtccaga ataggcaaat cttatagaca   11700
gcaagtaggt agatgatcag tttgctaggt gctgggggaa ggggaaatgg ggagtgatgg   11760
ctaaggggat tgggtttctt tgtggggcaa tgaaaatgtt ttaaaattga gcgtgataat   11820
gattgcacaa tgctgcatat atatataatc tatagattat atatatataa agagaggctg   11880
ttagacagtg ataagtgata tatatatata tatacataga gagagagaga gagagagaga   11940
gaggctgtta gtgataagtg atcaggaaaa taaaagtatt gaggaggaat acgaagttga   12000
cggtgtgaaa acatgagatt ttatataggaa tggccaggga aggccttaat gagaaagtga   12060
cttatgagta aaaacaaggg atcctaaacc ttagcatgca tcagaatcac tcggaaactt   12120
gttaaagcat agcttgctgg gcctcatcac agatattttg attcggtagg ttcttgtctg   12180
atattaatac ttttggtcta gggaaccaca ttttgagaac cactgagcta aaggaagtaa   12240
aggtttccct tagtttacta gctggtaaca ctggcccagg aggcctttct ggaaaaggtc   12300
ccagtcccca aaggaagctg gggactcgcg ttcacatcgt caaggtttac caagttgtgg   12360
cgggcctttc cgtcttggaa aaagcctcaa aatggcagat tagggtgtcc atggccggcg   12420
gaaagggtct ttgaagttgc agaccaggag ggaagaagat tctgggcctc ccccatgcag   12480
tgtcagctgg caacagaatg caccccggct gggttggagg ccctgggtac tggctcttcc   12540
acaccagggg cccacctacc aagggcagca ggagcatctg cacctcctgc gccaggcgcc   12600
cttcagtgct tccacttgag cacctctcca gacaccagct agggtgacag tggtacaaat   12660
accagactcc cctggcctgc tcacctcaca gggtaatgtg ctgtggagtc aggggacac    12720
agcaaccacc agatgacatg gctggccccg gggaggacga cacgcagata cggctacttg   12780
gcacctgtga tattttacac actcgagagg ggcccgcacc atcctcagcc ctctccccac   12840
attcactctt agttcatgtc acctccaccc agagggggac acaggcccac agcgatggcc   12900
ccacaccctg cctgaggtcg cccacttccc aggaggcagt cctgggactt ccacccgacc   12960
aggccccaga gcccaccgac ttaacccctc cagaggcttg tcgttcatta ccttattcaa   13020
gatggagacc agccttttttg cggagaaaat gcgggtgaag gtcctgaaag tgcattgacg   13080
ccgttttcgg aagccataca agtttagctg gcggaagaag ctctttatcg aagttgtggc   13140
aaacactttg tgtgcgacgt ccctttttgag aatctccttt tcaaagagtt tttgattgat   13200
cactctacaa gccccactgt catcccacca gatggacgaa aactggttgc tgctgaccag   13260
```

```
tctccacagt ttctgtggaa aggggaggga gaggagatta tcttctccct ggggcgggac   13320
gtcaccgtca gggtgcggcc ttctgaacga agcttcctcg gccagaggtt ggaaagcgat   13380
ttcttctgtc agcagcctca agttaggct cccagtggac cccgggtcgt cccaggcagg    13440
ggaaggatct gctgggtgaa ggtaggtctc tgactgcaac tggggaggga aaggcaccct   13500
ttccaagcca tgatcctgtc ctctcgaatt tctttcttca cagcgagcca tactcaatga   13560
tcgcttgtcc tccatctggc aaacttgcta gtgcagtgtg gccagcagca cccttggca    13620 gtcatgtaac cagccccatg acatcataaa ggggctctga ctgccggggg gtggcatctc   13680
cacccccagc aagttgtgta ataaagggcc aaggcagaca agtagctgcc catctgcatg   13740
tgcacattct ggtcctcaca gtcatttcaa tgggaaagat gacactagtg cacaagagtg   13800
ccgaggggcc ctgccacacc gtagatgcag acctggagcg gtccccttgt cctagagctc   13860
ctgagccagg cacaactaca gcaaagccct ggctcaggaa ggtcagagct caccgtctga   13920
gtcatgggcc cacagacccc agcacatgac tgacactcgg aagcacagaa caaagggtag   13980
gacggtgccc atgggtcagg ctgtagccac gccacccttt ccaccctgtc ctagccagag   14040
gcagcaatgt gctccataca gatcctccta acacacccac actgtcggtc cccagcacgc   14100
agatgcccga cagccccttg ggcaaatggc ttagctgact gccccaccac acgccgtcgc   14160
catgcagtcc agtggggagt cggaggcagc ctccttcctg cctctcctcg gcctgcacgt   14220 gtcccccac caggcagaga cccttctaca ccccgggtgt ctgcggtcac atcgcggtgg    14280
ggcatgcagc tgttggcctt cgagcatgtt ttgttttcct tggccagtgt ctccagagaa   14340
acgcacgtgg gtttgtgtcc agcggtccat ctctgcaaca gttgttcctt tgggattgga   14400
tgctaggagg tcacgggaga ggtgtccatc caaagcagtg tctgtgtcac acactgtccc   14460
cacacacagg gccacctctg cacagactcc cccgactcga ttctgggcac agagctcagt   14520
gaccttccag agactgccac gaaccggtga tgcctccacg cttgagacat cctgaccgca   14580
gggcccaagg cgcactggct caggggtga cagtgagggg tctgcaaaca gactgctgat    14640
gctcaacccg gccgctgccg agctgtgtga cttgggcacg tcacttaacc tctctcggcc   14700
tctgtctcct cccggggata agagtagtag cacctgcttc ccggggctgt gaggatccag   14760
tgggacgtat aggaactagc gaggcaccgg cagttgggtc agagctactg ttgtcacttc   14820
acaaggcatt ttcttcaaca gcaagtcgga aatctcatga gcctaaggca gaatccacct   14880
gtggcctctg gttacaaccc acaggactga aaatccttcc agccacagca actggtgaat   14940
ttcctggtca attgccacaa gtcatgagct gaacccccact tgagtttcag ttcaggcaga   15000
actctagaga cgactagggc aagctagaca gcgactgcag agccttttgt tgcagcgtga   15060
gcagtcctca gctgttgaca tcactgggga gcaaacgagg accaggagcg gtgaaaggac   15120
agtgtctgct gcagattgtc gtagcaccca aggaacactc cagaaagcct cctaagcagt   15180
aacaagtgtg gcaaggtgta gcccagccaa cagtggcatc tgcgaggcgt ccctccttc    15240 ctcccactac cccgtatacc ctgggacctg tgcactgaag gactcattct aaaggctgtg   15300
cccctgcagc cgccagcctc actcactggc tgcctgtgcc agctagagat ttctttcctc   15360
tgaggctggc tgagaggacc actccagttt cctggcccat ccagcaaaga agatacacat   15420
catgcacgtg taaaatgagg aaccggttta ttgaacagct taaggagagc aaaaatagtg   15480
gctttagcta catttttac acactgagca ggaaagtcta aaccatcccg ttcccctgta   15540
ccccaaagag aacagggctt gctggaggcc agtgccaagg gcggagtcgt gctcgcagca   15600
gacttgaatt aaccccatgt aggccggcga gcagttgccc gcgtgaaaac accaccctct   15660
```

```
tctcctggct gagaagatca aagctctttt tttaccctct tttcagcaaa ggacctattt   15720
gttttcaggc aggaggatgt taaacttgca gcctctgaca cacggtggaa cctgcagtgc   15780
ttggagaaac ggcacgcaca cgtgaaaaca tcatgcctac tccaaagcct tcttgttgct   15840
ggcaggaggg aagcttgaga ctttcccacg catagtcgtg acccgcgtgg ccgtttctgc   15900
tctcagcaac attctctagt gttccggctt caagcagcgc ttgtcaggtt tgaagctagc   15960
cactattctg agaacgtcag aaaagcatgg accatctctt gcttggtgtt gccgttgtgg   16020
cagtagcagc tactacgtac ctgcacgagt tccagggcag aagtggcaat gtcccatgaa   16080
ggcgtggcac cccacggggg gggggggggga gtgtgccacg ggcgtccact tctgcagcag   16140
aaggcatgtg cctacagcac aagcttgtaa aaaatactt gaacagaata tgctgtacag   16200
aactaggggt taacaccgca tatgaagatg ctaaaacatt tgtataaata ctctgtatac   16260
aagcatggag tcactcccgt agaaagggct catccgtgag gctatgaaaa actgctgtca   16320
gcatgcccaa agagaaacta cttccacagt aggaacagaa aaaaggactg tgctgtgtct   16380
aaacacgtgg tgcatcagag acatagttac agttcctact gactgcccca gccacgacct   16440
gggagtgctg aggacctggg agtgctcagc gagctgcagg aggtcagccc tgtggagaaa   16500
tacatttcta aacaatactt ttgattggga tttcagcacc gtatagacag atgttccttc   16560
tgggggcctg gcaagcagcc atctcccagt gggtctgacg gggaagaggg gtacctggag   16620
cccctcccag acagacggta atcccacccc tgttctcaca ctcttcctgg catccgcatc   16680
tgctggcaca cacccccgtc acctgccact tccgcgtccc gtcgtggtga gtggctgata   16740
ggcgctggat gcaaacaagg catgagatgg acgtacctgg agacccagct ccagtactgg   16800
ttctggtctg cggggtgaac gagggggcag aggaaggcgg agagagtgcg tcccagtcca   16860
cttaagctct gtccccggaa gtggcatcta atctggcatt tcgatattta atttgggagg   16920
tgggagcaca tacttcccag ggctctgggt aatgaccacc ctggccttct ttcgaaacat   16980
gggtgcgatt ttaggggggct ccggaactgg ggtctcttcg gtttcttcat tatcttcgtg   17040
atggagatca taggaaatgt ttccatattc tcgtagaaat gggaagattt caagcagaaa   17100
ctgacagaaa tctttgcgga taccaaacca ccctgaaaaa taagaatttt ttatttcaca   17160
cacgaggctc aactgacctt cctgttaact ttctttccgt aacaagaagt ttcactccta   17220
caatgtcata acatacttta tccagactcc tgagtcacaa agcctgaaca gggcttgagt   17280
acccaaaatg gggaagaagt gcaaatgcta gctctgtggt gcttggagtg gggttccccgg   17340 accggcaggg acagcgtcca cggggcctag ttagggatgc cattctcggg ccccagccca   17400
gacctccaga aactgagtcg ggctagggtg ggctccagcg gtcccctttt cctggccctt   17460
ttgggattct gctggatgcc caaatttgag aactactgct ccagtgagtc tcaaaatatc   17520
tgtggtgcgc agactacggt gtcttccgct aatcttctcc agccaggata aactcatgga   17580
tgacagtgcc acccaagaac aagatttctg tcaccctctg gaatccgtga gggcggtagt   17640
catgcacggg ttggccagga gggggcctga actcatggag ccaccttaaa gccactttcc   17700
cagtcccact actcctctct gtaggctact ggagtgtcag ctcggtgcaa gccctccctg   17760
ctcccgggtg cggggtaggg ggcagaggca caaacagcaa gcacagcccg ggctgctggg   17820
ctgcagtgag gccctgcccc caaacccact ggctttccga agggcaatgc tctgggcttc   17880
cgtgccatgg agcccacagc cttgccagga aggcaccctc tgcagagatc gttttggaag   17940
tgtctgcctc agcaagcagg tggaggggaa tagagtgtta gcaaggcaag acaggcaaga   18000
ctcgggtgat ggcagcaagg atatggggga ggcagagcgg ccaacaggga cctaggatga   18060
```

```
atcccaggtt tgggtgggag atgtggattt tccatcaaac cctcccgggc ctgggaagaa    18120
tctgtcttga tccccatttt gcagaggagg gaacgggatc tctgagaggt tgcctgccgt    18180
gtctggttct acctcaaatg gcagcgtgca ctgcgagaaa agtcccggtg caggccagca    18240
gaacaccaga gttacggcat gcccttccct tagaaggtcc cagaatttcc tcagccctca    18300
cttccccaca caagcttcta aattggggcc ctcggggact catcccttcc tagacttcta    18360
tccgccaccc cccacccccct ggtccccccc cagacacaca ccaaggactt ctgaaatgct    18420
gagtacatac agtggtttcc tcccttctgt ccaaatgtgg ttgccatcag cgtgatcaac    18480
gagagccaaa gggggacaaa gatcgggatg caggagaagg cgttgtggcc atccagtttg    18540
tgaaccagca gaatctaaag aaagagacat agtcccggtt gatgccagca ccgaaaatgg    18600
gcagaggcgg aagccagact tcattaggca gttcctcccc accacccccac cccgcgtga    18660
gctcccacaa gagggaacat cagcaccgcc agaaaaaggc aggaaaccac ctatccctgg    18720
ggaaagctcg aaatgagctt ttatgtccct cttcagagct cggcaatagc ctatccactt    18780
gaaaagttcc cagtgccagc agttttatgg caaactcctc cgggtgtttg ttctaaggag    18840
tcaacagctc ccattctaga attctccacg tgactccaat acacaaatct gacatcccac    18900
tctgcttcc ccagagtgga aactggagcc atacagaggc accatggcta aaaaggtgca    18960
ctcttctccc tgccagcccc acgtgctgcc cccaagagaa aggaaggatg ctctcctttc    19020
accgaagctc cctctcggag atggctgtgt tctctcccct ctcctggagt gggctcactg    19080
tgagctcgag ggacagaggc tgcctttcta ggggtgcaga atcctgtcag gggaagcgca    19140
agcttcaggg gctgaagagg cttcccgtgg aacgcttacc tcaaatgtaa aaggggcac    19200
gacgatggtc atccagctca gggccatggt tatgtgtgtc ctgcgctgtc cgcaatcaca    19260
tccatagagc gcaagaacaa gacggaccac acaatgtagt agaggaccac caggcacaga    19320
aaggacatga gaatccacag cgggacacac acaacctggg ggtgggtgag agaacagcaa    19380
gagaagtctc tttagagctt ccaacctggc ctctgatgga aggcatcttt agcaccttgc    19440
tgtgtctgtc cagttaaggc ggtccttcct gtgagccgaa taaggaccgt tccatctccc    19500
aggactgctg ggagcatcgc tcaggacaga aaaggtatgg tatgttcact atggggcctg    19560
ctgccaccag gggacacaca cgctcagtga gtcatcagtc cctcttcctt tgggtgacag    19620
acagccctgc acctggctcc gcagcctcta ctcttccaga ggcccactct cccacactct    19680
ctcaggctcc tctaggttct gctgccatca cagcttcccg ggaaatggga cacaactgtc    19740
accctgtgca cacacacaag atctcacccc aacagactct cttcacaggc aacattccca    19800
caacctgctg ggggtacttt ggcaacacaa atgggaatgg gctccccaga aagtctggct    19860
gcctgggctc ctaaggatcc ctaacctcac ccctaccaag ttagtgaact tggcgggttg    19920
atgctggata caggttgatg ctggatacgt agcgctgccg ggtcgtgacc cctaaggaat    19980
tatccaaact cttgttttta gatgctttat tatatcaaac tctcctttaa acaagtggcc    20040
catctgctgg gatttggaag cctgtaatac tgaaattttc atcataatgg aaattttaaa    20100
aacagaattt gacccacctg tttttaaaac actttcatta cttaacaaga ggtctaatct    20160
tgggcaagtc ttgaaatttc tctggcctta gtttcccatg tgttaaatga aacttgaagc    20220
agttggtctc ttatagtctc ctgactctaa cattctaaga attatatttg tacaataact    20280
caaaaatcac ataatttaat ttaccatatg gactccaaaa tatattttct cattaggcta    20340
aacttgatct gcattttctg gatgtgtcca tattcttgga ctacactaaa acatgatacc    20400
aatgcttcct ctcaccataa accctcactt cgctttctac atttaagaat tttatagctg    20460
```

```
gaagagtcct taacagaaaa taccatctaa taattacccc tcaaaatcga gaaagtccta      20520
tctgttctta tgctagttat aagaatgagg cagcatttca cataatggtt ataaacactg      20580
ccacaagaag attcatgatg tgttgtttat ctgtagctct catcatactc tgtcatataa      20640
ctatagcatt aagattttaa tgttctatat attcttctaa gacagtgttt accagagtaa      20700
ggcacaaaag atccactggt ttgcaagaaa gattagaact tttaaatttt ttacctcacc      20760
ttgtttaatc tatattttttg tatgtatttt gtaacatata tattattatt accataaatc      20820
atatataatt taaaatgcat atattagggg taaatgctca ggaaactttt tataaattgg      20880
gcatgcaaat acaagtttga agactcactg ttctaggtat taaaagtaaa gttataacca      20940
agtaaagctt ccacctttttc atgtctcaaa gcagtttatt gttggaggta agatctctta     21000
gaagcctaaa caggtccaag tacagaatga agtaaggcta gcccataact tgtggcaagc      21060
aattcatact atttctctca tgctgagctc tcctcagtga agcagctact atagacaact      21120
gcagccattt ggtagcctat tttacaggca ggaaaaaaat tactttttat tcaaagtgga      21180
actcaggaca tggggagaaa atgaatacaa aaaatagggt caatccaaag gcacacagca      21240
aatgagtaac acagttatgt tttttttccca tttgtatgag gtcccagtaa attctaagta      21300
aactgcaaat ttaataatac actaaaaaag ccatgcaatt gttcaaatga atcccagcat      21360
ggtacaagga gtacagacac tagagtctaa aaaacaaaag aatgccatta ttgagttttt      21420
gaattatatc aagtagttac atctctactt aataaatgag aaaaacgagg ataagaggcc      21480
atttgataaa atgaaaatag ccaagaagtg gtattagaga cttgaataca ggtattcggg      21540
tccaaagttc atctgctcaa atactaactg gggaaaagag ggaaaaatat ttatatacat      21600
atatatctgc acacaaaaat acccccaaaa gacaaaatga ggccaggcag ggtggctcac      21660
acccgtaatc ccggtacttt gggaggctga ggcaggtgga tacctgagat caggagttgg      21720
agatcagcct ggtcaacatg gtgaaaccct gtctctacta agataaaaaa aattagccag      21780
gcatggtggc gtgcgcctgt aatcccagct acttgggagt ctgaggcagg agaatcactt      21840
gaactgggaa gggagggttg cagtgagcca agatcgtact actgcactcc agcctgggca      21900
gcagagtgag actccatcac aaaaataaat aaataaataa aatacaatga aacagaaagt      21960
tcaaataatc ccataatctt accaccaaga aataactttc actcgttata cttattgatt      22020
tttccataat aaatgtactt tactgtgact atcatgaaaa gaaagttatt ttagaaacag      22080
agaactgttt cagatcaaat ctatgtagta gaacagagcc attaggtggg aaagacgaga      22140
tcaaactaaa tctcagaagg cctaaaaggc taggtccatt ccagcactaa aaactgacca      22200
gacaagtaat ggcttcaaca gcttctaaat atggacaaag catgctgaaa gggaaggaca      22260
ggtctaacag tggtatatga aatgaacagg aggggcaaag ctcatttctc ctctgaagtt      22320
ttccaaagat gctgaggagg acattagttt gacatgaccc tgatatggga caagataatt      22380
tcacagaagt tttacatgtt aaagtttttct tatagatact cattcaagta agcaatgaac      22440
actaaaatct aaagaaagaa aagagcttta gagtcaggtc tgtattcaaa ttcaagctct      22500
accacttact ggttctgtga ctttgggcaa gtcttttaac cttattaagt cttaatttcc      22560
tgatttgtaa aatggggata tcgtctccct cacaggattg ttgtgaaact tttatgagat      22620
taatgccttt atatttggca tagtgtaagt aaacaataac tggcagcttc aaaaaaaaaa      22680
agcagtagca ttccatcatt tattattggt tactctcaaa aagttttttca atgtactaga      22740 agataaaatat tcaaataccct taatatctcc attattttca ggtaaacagc atgctcctga      22800
acaaccaatg ggtcaacaaa taaattaaaa gggaaatcta aaaacatctt gatattaaac      22860
```

```
tacatggaag cacaatatac caaaaccaat ggttcacact aggagaattt taaggtacaa  22920
gaaaactctt tgagatttct taaaataata gtatgtctga atttattgag tgatttacca  22980
gaaactgttg taagagctct acttgcatta tagcacttaa tcctcttaac tctatggctg  23040
ctattatcaa cctcacccta atcacatatg ggacacagag aggttaagta acttgcccaa  23100
ggtcagagtt aggaagtact aagccatgct ttgaatcagt tgtcaggctc cggaactcac  23160
actttcagcc actacataat actgctttgc tatcttttag gaaactatgt gagtctacct  23220
cacatagact cacataggtt tgtttttttt ttttttttaa aggctatctt ttcccccatc  23280
aatgttttt gaaggatccc aaattagagt cccacagagg cagacagcag tacttgacaa  23340
tatggacatt taaggttaat gttggattct actgtctttt tactacatga cctagggaac  23400
gataattaac ctagactgct tccaagggtt aaataaccca tttagttata ctatgtaaat  23460
tatctcttag tgattgattg aaagcacact gttactaatt gactcggtat gaagtgcttt  23520
tttttcttcc ctttcaagat acatacctt ccagttaaag ttgagagatc atctccacca  23580
attactttta tgtcccctgt tgactggtca ttctagttaa aaaaaaaaa aactatatat  23640
atatatatct acacacacat atgtatatgt atatccttat gtacacacac aaacttcaaa  23700
ttaaatgaga actagaagat ttgagaagtt agctagctaa tatccatagc attatgatat  23760
tctaaatgat atgaattata agaattaggt ttcctgaaat gaatgactag aaaactttca  23820
agtagagatt agtaaaaatt aaaaagtcct aatcggccat tactgatttg atgttttaa  23880
gagtcctaaa aaatgggtta catccatttt taagtgggta gtattataac agccacccat  23940
cttcaatcac agtgatttct gaattgtgag ggaagttatt agcatgacag gtgtctggtt  24000
ctggccctgt acgattccca tgagtcaagc aaattgtaag ggctggtcta tatcacaccc  24060
aaccccaagg atatgtccct caaaagtcta gcccaggccc cgtcatcttc agcatcatct  24120
gggaaaccag gtctgattag tagtccttta aggaatacct cttaggctcc cattttactg  24180
ctatcacaga atccaataaa acccttacag gagattcaat gggaaatgct caacacccac  24240
tgtagttggt ggtgacaatg accataattt ggctgtgctg gattcaggac agaaaatttg  24300
ggtgaaagag caggtgaaca aaagagcttc gacttgccct agcagagagc aagccatacc  24360
ataccacaaa gccacagcaa ttacaacggt gcagtaccag cacagtaaat gaacaaagta  24420
gagcccagaa acagacccag aactatatga ggatttagta tacaataaag atggtatttc  24480
gagtcagtag ggaaaagatg aattattcaa taaatgatgt ttggccaact agtaacccat  24540
ttgggaaaaa ataaaagtat ggtccctacc tcacagcata cacaaaaata aattccagac  24600
ggattaaaat ctaaatgtaa aaaataaagc cataagtgga ctggaagaaa atagagaatt  24660
tttttaaca tccgtagaaa gggtaaaaac ccaggcatga catgaaccaa aactgaagag  24720
gttctgtaac aaataccccc ttttatatat tgggctccaa caataagaac ccataggaaa  24780
atggagaatg aacacaaata gacaatttat agaagagaag gttataaggt gtaaaattat  24840
atctatctga gaaacaaaca ctaaaacaat gtgattctac tgttctccca cccatactgg  24900
caaaacttaa gcctgataat atgctgaggg gaaataagca ctcttgttgg tgagagtatt  24960
aattggcata gcttcttttg aaaatgacat agcaatacct gttaaaattg caaacatgca  25020
tgtcacttaa tccagtaatc ccacttctgg gaatcaatgc tacaaaaaca ctgacaagta  25080
tacaaagata cattcaagag tgttcactgg gccgggtgcg gtggcttcat gcctgtaatc  25140
ccagggaggc agaggcaaga cgatcgcttg accccaggag ttcaaggcca gcccgagaaa  25200
cacagcaaga ccctgtctct ctttttttta tttaaaaaat aaatgttcac tgtatcagtt  25260
```

```
gttcacaaaa acaaaccaac atgtccatta acagggaacc atttaaatta atcaagttca   25320
tctacacaat gtaataccat gcaactatta aaaagcaccct gataatccaa agcacactga   25380
gacagaataa tgctattaaa aacaccaagt agtggaacac tgtgttgcct atgacaccat   25440
ttttattcaa catttaaaca aatttgtaac agcaattaca tgagtagtga caatggcgtt   25500
tatgagactt ttcacttta tgtgcttcta tttttgttat gcttctatat atacatccat   25560
ttattatgga gtgttacttt caaaaatcac aaatgggcca gtattatttg gtgttgcaag   25620
gtgagcatat gacttctgat atcaacctt gcatattact tctcaattta gggaaattac   25680
agacatccct tattctaact aacttaaaac ccagcatttc aaacatacag aattgatggg   25740 gaaaaaaag aaagaagaaa gaaagaaaag gcaacaagct tcagatgaca gtgactcaca   25800
tcaaattatt tataaaatct gttaaatagt gccatcttct ggagatacct ggtattacag   25860
tccaactcca gttgatgtct ttacagagac aagaggaata aaggaaaaaa tattcaagaa   25920
ctgaaaagta tggagtcatg gaaaaattgc tgtgatccaa aggctacggt gataggacaa   25980
gaaacaagag aactccaagc agtaagacac tgctgttcta ttagcatcca aacctccata   26040
ctcctgtttg ccccaaggct tttttaaaaa atagagacag gatctcacta ttttgctcag   26100
gctggtcttg aactcctgga ctcaagctat cctcctgcct cggcctccta aagtgccgag   26160
attacaggct tgagtcacca tacctggcta tttatttttt cttaactctc ttgcctggcc   26220
tatagccacc atggaagcta ataagaata ttaatttaag agtaatggta tagttcacta   26280
cattggaata caggtataag tgcctacatt gtacatgaat ggcatacatg gatcaattac   26340
cccacctggg tggccaaagg aactgcgcga acctccctcc ttggctgtct ggaacaagct   26400
tcccactaga tcccttact gagtgcctcc ctcatcttta attatggtta agtctaggat   26460
aacaggactg gcaaaggtga ggggaaagct tcctccagag ttgctctacc ctctcctcta   26520
ccgtcctatc tcctcactcc tctcagccaa ggagtccaat ctgtcctgaa ctcagagcgt   26580
cactgtcaac tacataaaat tgccagagaa gctctttggg actacaaaca catcccctta   26640
atgtctttat ttctatttg tctacctctt cagtctaggt gaaaaaatag gaaggataat   26700
agggaagaac tttgtttatg cctacttatc cgccccctagg aattttgaaa acctctaggt   26760
agcaataaga actgcagcat ggtatagaaa aagaggagga aagctgtata gaaatgcata   26820
ataaatgggc aggaaaagaa ctgcttggaa caaacaggga ggttgaacta taaggagaga   26880
aagcagagag gctaatcaac aaggctgggt tcccaagagg gcatgatgag actattacta   26940
aggtaggaat tactaagggc tccatgtccc cttagtggct tagtactatg tagcttgctt   27000
tctgcagtga acttcagacc cttcttttag gatcctagaa tggactttt tttttttatcg   27060 gaaaacagtc attctctcaa cattcaagca ggccccaagt ctaccacact caatcacatt   27120
ttctcttcat atcataatct ctcaaccatt ctctgtcctt ttaactgttt ttctataccc   27180
tgatcaaatg ccaacaaaag tgagaatgtt agaatcatgt atttttagag gtagactgta   27240
tctcagataa aaaaaaggg cagatattcc attttccaaa atatgtatgc agaaaaaata   27300
agtatgaaag gacatatgct caggtaacaa gttaatttgt ttacttgtat tttatgaatt   27360
ccctaaaacc tacgtcaccc gccccgttcc cacgccccgc gccacgtcac aaactccacc   27420
ccctcattat catattggct tcaatccaaa ataaggtata ttattgatga tgttaattaa   27480
catgcatgga tccatatgcg gtgtgaaata ccgcacagat gcgtaaggag aaaataccgc   27540
atcaggcgct cttccgcttc ctcgctcact gactcgctgc gctcggtcgt tcggctgcgg   27600
cgagcggtat cagctcactc aaaggcggta atacggttat ccacagaatc agggggataac   27660
```

```
gcaggaaaga acatgtgagc aaaaggccag caaaaggcca ggaaccgtaa aaaggccgcg   27720
ttgctggcgt ttttccatag gctccgcccc cctgacgagc atcacaaaaa tcgacgctca   27780
agtcagaggt ggcgaaaccc gacaggacta taaagatacc aggcgtttcc ccctggaagc   27840
tccctcgtgc gctctcctgt tccgaccctg ccgcttaccg gatacctgtc cgcctttctc   27900
ccttcgggaa gcgtggcgct ttctcatagc tcacgctgta ggtatctcag ttcggtgtag   27960
gtcgttcgct ccaagctggg ctgtgtgcac gaaccccccg ttcagcccga ccgctgcgcc   28020
ttatccggta actatcgtct tgagtccaac ccggtaagac acgacttatc gccactggca   28080
gcagccactg gtaacaggat tagcagagcg aggtatgtag gcggtgctac agagttcttg   28140
aagtggtggc ctaactacgg ctacactaga aggacagtat ttggtatctg cgctctgctg   28200
aagccagtta ccttcggaaa aagagttggt agctcttgat ccggcaaaca aaccaccgct   28260
ggtagcggtg gttttttttgt ttgcaagcag cagattacgc gcagaaaaaa aggatctcaa   28320
gaagatcctt tgatcttttc tacggggtct gacgctcagt ggaacgaaaa ctcacgttaa   28380
gggattttgg tcatgagatt atcaaaaagg atcttcacct agatcctttt aaattaaaaa   28440
tgaagtttta aatcaatcta agtatatat gagtaaactt ggtctgacag ttaccaatgc   28500
ttaatcagtg aggcacctat ctcagcgatc tgtctatttc gttcatccat agttgcctga   28560
ctccccgtcg tgtagataac tacgatacgg gagggcttac catctggccc cagtgctgca   28620
atgataccgc gagacccacg ctcaccggct ccagatttat cagcaataaa ccagccagcc   28680
ggaagggccg agcgcagaag tggtcctgca actttatccg cctccatcca gtctattaat   28740
tgttgccggg aagctagagt aagtagttcg ccagttaata gtttgcgcaa cgttgttgcc   28800
attgctgcag ccatgagatt atcaaaaagg atcttcacct agatcctttt cacgtagaaa   28860
gccagtccgc agaaacggtg ctgaccccgg atgaatgtca gctactgggc tatctggaca   28920
agggaaaacg caagcgcaaa gagaaagcag gtagcttgca gtgggcttac atggcgatag   28980
ctagactggg cggttttatg gacagcaagc gaaccggaat tgccagctgg ggcgccctct   29040
ggtaaggttg ggaagccctg caaagtaaac tggatggctt tcttgccgcc aaggatctga   29100
tggcgcaggg gatcaagctc tgatcaagag acaggatgag gatcgtttcg catgattgaa   29160
caagatggat tgcacgcagg ttctccggcc gcttgggtgg agaggctatt cggctatgac   29220
tgggcacaac agacaatcgg ctgctctgat gccgccgtgt tccggctgtc agcgcagggg   29280
cgcccggttc tttttgtcaa gaccgacctg tccggtgccc tgaatgaact gcaagacgag   29340
gcagcgcggc tatcgtggct ggccacgacg ggcgttcctt gcgcagctgt gctcgacgtt   29400
gtcactgaag cgggaaggga ctggctgcta ttgggcgaag tgccggggca ggatctcctg   29460
tcatctcacc ttgctcctgc cgagaaagta tccatcatgg ctgatgcaat gcggcggctg   29520
catacgcttg atccggctac ctgcccattc gaccaccaag cgaaacatcg catcgagcga   29580
gcacgtactc ggatggaagc cggtcttgtc gatcaggatg atctggacga agagcatcag   29640
gggctcgcgc cagccgaact gttcgccagg ctcaaggcga gcatgcccga cggcgaggat   29700
ctcgtcgtga cccatggcga tgcctgcttg ccgaatatca tggtggaaaa tggccgcttt   29760
tctggattca tcgactgtgg ccggctgggt gtggcggacc gctatcagga catagcgttg   29820
gctacccgtg atattgctga agagcttggc ggcgaatggg ctgaccgctt cctcgtgctt   29880
tacggtatcg ccgctcccga ttcgcagcgc atcgccttct atcgccttct tgacgagttc   29940
ttctgaattt tgttaaaatt tttgttaaat cagctcattt tttaaccaat aggccgaaat   30000
cggcaaaatc ccttataaat caaaagaata gaccgagata gggttgagtg ttgttccagt   30060
```

```
ttggaacaag agtccactat taaagaacgt ggactccaac gtcaaagggc gaaaaaccgt    30120
ctatcagggc gatggcccac tacgtgaacc atcaccctaa tcaagttttt tggggtcgag    30180
gtgccgtaaa gcactaaatc ggaaccctaa agggagcccc cgatttagag cttgacgggg    30240
aaagccggcg aacgtggcga gaaaggaagg gaagaaagcg aaaggagcgg gcgctagggc    30300
gctggcaagt gtagcggtca cgctgcgcgt aaccaccaca cccgccgcgc ttaatgcgcc    30360
gctacagggc gcgtccattc gccattcagg atcgaattaa ttcttaatta acatcatcaa    30420
taatatacct tattttggat tgaagccaat atgataatga gggggtggag tttgtgacgt    30480 ggcgcgggc gtgggaacgg ggcgggtgac gtagtagtgt ggcggaagtg tgatgttgca    30540
agtgtggcgg aacacatgta agcgacggat gtggcaaaag tgacgttttt ggtgtgcgcc    30600
ggtgtacaca ggaagtgaca attttcgcgc ggttttaggc ggatgttgta gtaaatttgg    30660
gcgtaaccga gtaagatttg gccattttcg cgggaaaact gaataagagg aagtgaaatc    30720
tgaataattt tgtgttactc atagcgcgta atactg                             30756
```

EX VIVO AND IN VIVO EXPRESSION OF THE THROMBOMODULIN GENE FOR THE TREATMENT OF CARDIOVASCULAR AND PERIPHERAL VASCULAR DISEASES

This application is a continuation-in-part application of U.S. Ser. No. 10/725,013, (now U.S. Pat. No. 7,179,459) filed Dec. 2, 2003 which claims priority from U.S. Provisional Application Ser. No. 60/430,099 filed Dec. 2, 2002. The entirety of all of the aforementioned applications is incorporated herein by reference.

FIELD

The present invention is directed to methods and compositions for the treatment of cardiovascular and peripheral vascular diseases, and in particular, is directed to methods and compositions for ex vivo and in vivo expression of the thrombomodulin gene using gutless adenovirus vector.

BACKGROUND

Atherosclerosis is one of the chief causes of morbidity and mortality in the United States and many other countries of the world. (Zuckerbraun et al., *Arch Surg.* 137:854-861 [2002]; Kibbe et al., *Circ Res.* 86:829-33 [2000]). This process can result in limiting the flow of blood to the heart, kidneys and the peripheral vessels, to name a few. Current approaches to the treatment of lesions in the arteries include coronary artery by-pass graft (CABG) surgery and angioplasty with or without the placement of a stent. The latter may serve as a vehicle for drug delivery, as is currently being tested in clinical trials. A number of pharmacological agents that affect platelet function or provide anticoagulant properties have so far failed to reduce re-occlusion or intimal hyperplasia. (Kibbe et al., *Circ Res.* 86:829-33 [2000]).

Cardiovascular diseases, however, are the result of complex pathophysiologic processes that involve the expression of many proteins and molecules that can adversely affect the grafted vessel (Shears et al., *J. Am Coll Surg.,* 187(3):295-306 [1998]; Ross et al., *Nature,* 362:801-9 [1993]). Approximately 15-30% of patients receiving vein grafts for coronary or peripheral vascular disease require follow-up treatment, either in the form of angioplasty or new grafts.

Thrombomodulin (TM) is an integral membrane glycoprotein expressed on the surface of endothelial cells (Sadler et al., *Trhomb Haemost.,* 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., *Faseb J.,* 9:946-55 [1995]). The latter two proteins are essential for the function of two of the coagulation proteases, namely factors IXa and Xa. TM thus plays an active role in blood clot formation in vivo and can function as a direct or indirect anticoagulant.

There are several other proteins or enzymes that have shown to reduce the process of intimal hyperplasia, whose evolution is the cause of late graft failure. For instance, Nitric oxide synthase, an enzyme expressed by endothelial cells has been shown in animal models to inhibit intimal hyperplasia, especially the inducible enzyme (iNOS) (Salmaa et al., *Lancet,* 353:1729-34 [1999]; Palmer et al., *Nature,* 327:524-26 [1987]; Kubes et al., *PNAS USA.,* 88:4651-5 [1991]).

Animal studies shown that cytoxic gene transfection utilizing the Herpes Simplex Virus thymydine kinase gene delivered via an adenoviral vector was able to inhibit intimal hyperplasia (Steg et al., *Circulation,* 96:408-11 [1997]). Vascular endothelial growth factor (VEGF), basic fibroblast growth factor (bFGF) and platelet derived growth factor (PDGF) have all been shown to promote reendothelization and enhance the healing of vascular injury and help limit intimal hyperplasia. (Ban Bellle et al., *Biochem Biophs Res Commun.,* 235:311-16 [1997]; Salyapongse et al., *Tissue Engineering* 26(4):663-76 [1999]).

A gene therapy approach is currently under clinical investigation. It involves the injection, directly into heart muscles, of an adenoviral vector delivery system containing the gene for the expression of vascular endothelial growth factor (VEGF). This is being tested in patients whose coronary vessels are not amenable to standard grafting procedures. However, some recent adverse clinical events demonstrated that injection of large quantities of adenovirus vectors is associated with significant risks. Accordingly, there still exists a need for a method to effectively introduce therapeutic genes, such as TM, into vascular tissues.

SUMMARY

One aspect of the present invention relates to methods for treating a vascular disease in a mammal. In one embodiment, the method comprises the steps of: infecting a segment of blood vessel in vitro using a gutless adenoviral vector comprising a polynucleotide encoding a thrombomodulin protein or its variant, and grafting the virus-treated blood vessel in the mammal, wherein the thrombomodulin protein or its variant is expressed in a amount sufficient to reduce re-occlusion or intimal hyperplasia in the grafted blood vessel, and wherein the gutless adenoviral vector comprises the nucleotide sequence of SEQ ID NO:13 or SEQ ID NO:15.

In another embodiment, the method comprises the steps of: evacuating a clot from a blood vessel in the mammal, isolating a segment of the blood vessel around the evacuation site, and infecting the segment of blood vessel in vivo using a gutless adenoviral vector comprising a polynucleotide encoding a thrombomodulin protein or its variant, wherein the thrombomodulin protein or its variant is expressed in a amount sufficient to reduce re-occlusion or intimal hyperplasia in the infected blood vessel, and wherein said gutless adenoviral vector comprises the nucleotide sequence of SEQ ID NO:13 or SEQ ID NO:15.

In another embodiment, the method comprises the step of administering a therapeutically effective amount of a gutless adenovirus vector into a segment of a blood vessel in vivo using a stent, wherein the gutless adenovirus vector comprises the nucleotide sequence of SEQ ID NO:13 or SEQ ID NO:15, and is capable of expressing a thrombomodulin protein or a variant of the thrombomodulin protein.

In another embodiment, the method comprises the step of administering intravenously an effective amount of a gutless adenoviral vector comprising a polynucleotide encoding a thrombomodulin protein or its variant, wherein the gutless adenoviral vector comprises the nucleotide sequence of SEQ ID NO:13 or SEQ ID NO:15.

Another aspect of the present invention pertains to a gutless adenovirus vector comprising the nucleotide sequence of SEQ ID NO:13 or SEQ ID NO:15.

Another aspect of the present invention pertains to a gutless adenovirus vector comprising a polynucleotide encoding a thrombomodulin protein having the amino acid sequence of SEQ ID NO:2, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a vascular disease, comprising the gutless adenovirus vector described above and a pharmaceutically acceptable carrier.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
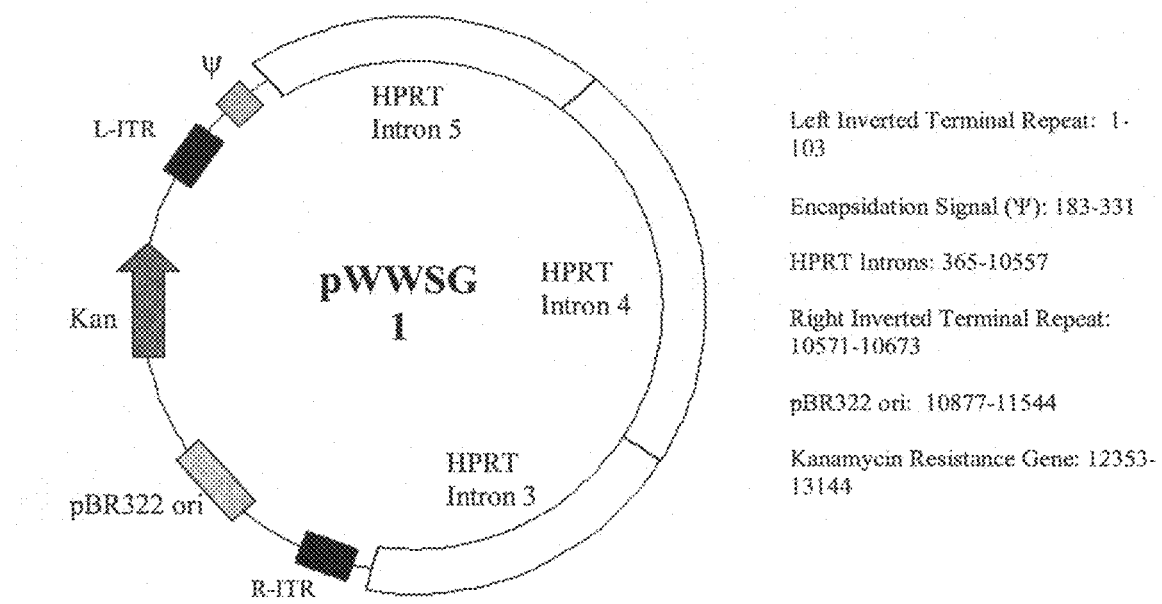
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating vascular diseases using gene delivery technologies. One aspect of the present invention relates to a method for treating a vascular disease by introducing a DNA sequence encoding a TM protein or its variant into a segment of a blood vessel in vitro using a gutless adenovirus vector and grafting the virus-treated vessel in a patient affected by a vascular disease. The virus-mediated TM expression reduces re-occlusion and intimal hyperplasia in the grafted vessel. This ex vivo approach eliminates the need to inject a large quantity of virus into a patient and hence significantly reduces the viral-related toxicity.

In one embodiment, the method is used for a coronary artery bypass. In another embodiment, the method is used for the treatment of peripheral vascular diseases. In yet another embodiment, the method is used for the maintenance of vein access in renal dialysis patients.

Another object of the present invention is to provide a method to deliver a gutless adenovirus vector carrying a DNA sequence encoding a TM protein or its variant using a stent. The viral vector is embedded in the stent and is released only at a treatment site. Since the viral infection is restricted at the treatment site and the surrounding area, only a small amount of the virus is needed and the virus-related toxicity is reduced.

Yet another object of the present invention pertains to a gutless adenovirus carrying a TM gene. In one embodiment, the gutless adenovirus, which contains a regulatory element operably linked to a DNA sequence encoding a TM protein or its variant and a polyA sequence, is produced using a novel shuttle vector containing a pBR322 replication origin, a selection marker, an adenovirus left inverted terminal repeat, an adenovirus encapsidation signal, a stuffer sequence, and an adenovirus left inverted terminal repeat.

In one embodiment, the regulatory element is a constitutive promoter such a CMV promoter and RSV promoter. In another embodiment, the regulatory element is an inducible promoter.

The forth object of the present invention is to provide a pharmaceutical composition which comprises an effective amount of gutless adenovirus carrying a TM gene of the present invention and a pharmaceutically acceptable carrier. Such compositions may be liquids or lyophilized or otherwise dried formulations and may further include diluents of various buffer content, (e.g., Tris-HC1, acetate, phosphate) pH and ionic strength, additives such as albumin and gelatin to prevent absorption to surfaces, detergents (e.g., Tween 20, Tween 80, Pluronic F68, bile acid salts), solubilizing agents (e.g., glycerol, polyethylene glycerol); anti-oxidants (e.g., ascorbic acid, sodium metabisulfite), and preservatives (e.g. Thimerosal, benzyl alcohol, parabens).

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles including "naked" expression vectors, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a, DNA regulatory sequence that is sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, muscle creatine kinase (MCK) promoter, myosin promoter, (α-actin promoter) and the like.

The term "transduction" denotes the delivery of a DNA molecule to a recipient cell either in vivo or in vitro, via a replication-defective viral vector, such as via a recombinant adenovirus.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *PNAS USA* 46:453 (1960) and Doty et al., *PNAS USA* 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "Tm." The Tm. of a particular nucleic acid duplex under specified conditions is the temperature at which on average half of the base pairs have disassociated. The equation for calculating the Tm. of nucleic acids is well known in the art.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data bands, or in a Southern hybridization experiment under, for example, stringent conditions as defined for that particular system. Suitable conditions include those characterized by a hybridization buffer comprising 0.9M sodium citrate ("SSC") buffer at a temperature of about 37° C. and washing in SSC buffer at a temperature of about 37° C.; and preferably in a hybridization buffer comprising 20% formamide in 0.9M SSC buffer at a temperature of about 42° C. and washing in 0.2×SSC buffer at about 42° C. Stringency conditions can be further varied by modifying the temperature and/or salt content of the buffer, or by modifying the length of the hybridization probe as is known to those of skill in the art. Defining appropriate hybridization conditions is within the skill of the art. See e.g., Sambrook, J. Fritsch, E. J., & Maniatis, T. (1989) *Molecular Cloning: A Laboratory Manual* (Cold Spring Harbor Lab. Press, Plainview, N.Y.).

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

The term "thrombomodulin variant" is a polypeptide that differs from a native thrombomodulin polypeptide in one or more substitutions, deletions, additions and/or insertions, such that the bioactivity of the native thrombomodulin polypeptide is not substantially diminished or enhanced. In other words, the bioactivity of a thrombomodulin variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a thrombomodulin variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

Thrombomodulin variants preferably exhibit at least about 70%, more preferably at least about 90% and most preferably at least about 95% sequence homology to the original thrombomodulin polypeptide.

A thrombomodulin variant also includes a thrombomodulin polypeptides that is modified from the original thrombomodulin polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Adenovirus Vectors

The genome of an adenovirus can be manipulated such that it encodes and expresses a gene product of interest but is inactivated in terms of its ability to replicate in a normal lyric viral life cycle (Curie D T, *Ann NY Acad Sci* 886, 158-171 [1991]). Suitable adenoidal vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells and muscle cells. Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoidal genome for foreign DNA is large (up to 8 kilobases) relative to other gene delivery vectors (Haj-Ahmand et al. *J. Virol.* 57, 267-273 [1986]). Most replication-defective adenoidal vectors currently in use are deleted for all or parts of the viral E1 and E3 genes but retain as much as 80% of the adenoidal genetic material. Adenoidal vectors deleted for all viral coding regions are also described by Kochanek et al. and Chamberlain et al. (U.S. Pat. Nos. 5,985,846 and 6,083,750).

Adenovirus vectors have been successfully tested in a number of animal models (Ragot et al. *Nature* 361, 647-650 [1993]; Howell et al. *Hum Gene Ther* 9, 629-634 [1998]). Nonetheless, the toxicity and immunogenicity remain major hurdles to overcome before the adenovirus vectors can be safely used in humans.

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The so-called "gutless" rAd vectors contain a minimal amount of adenovirus DNA and are incapable of expressing any adenovirus antigens (hence the term "gutless"). The gutless rAd vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., *J. Virol.* 70:8944-8960 (1996).

The "inverted terminal repeats (ITRs) of adenovirus" are short elements located at the 5' and 3' termini of the linear adenoviral genome, respectively and are required for replication of the viral DNA. The left ITR is located between 1-130 bp in the Ad genome (also referred to as 0-0.5 mu). The right ITR is located from about 3,7500 bp to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward.

The "encapsidation signal of adenovirus" or "adenovirus packaging sequence" refers to the ψ sequence which comprises five (AI-AV) packaging signals and is required for encapsidation of the mature linear genome; the packaging signals are located from about 194 to 358 bp in the Ad genome (about 0.5-1.0 mµ).

One aspect of the present invention relates to a viral backbone shuttle vector for the construction of gutless rAd vectors. In one embodiment, the viral backbone shuttle vector of the present invention contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb. (SEQ ID NO: 1).

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may encode protein, or contain regulatory sites, including but not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human, etc., origin. Specific examples of promoters are the promoters of the genes PGK, TK, GH, α-EF1, APO, CMV, RSV etc. or artificial promoters, such as those for p53, E2F or cAMP.

In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1.

One aspect of the present invention relates to a gutless adenoviral vector that carries a DNA sequence encoding a native TM protein or a variant of a TM protein. In one embodiment, the native TM protein is a human TM protein having the amino acid sequence recited in SEQ ID NO:2. Another aspect of the present invention also relates to a gutless adenoviral vector that carries other transgenes. These transgenes may include, but are not limited to, those coding for cytokines such as IL-1, IL-2, IL-3, IL-4, IL-5, IL-6, IL-7, IL-8, IL-9, IL-10, IL-11, IL-12, IL-13, IL-14, IL-15, IL-16, IL-17 and other interleukins; hematopoetic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2, KGF, myotrophin, NGF, OSM, PDGF, somatotrophin, TGF-β, TGF-α and VEGF; antiviral cytokines such as interferons, antiviral proteins induced by interferons, TNF-α, and TNF-β; amyloid protein and amyloid precursor protein; anti-angiogenic proteins such as angiostatin, endostatin, METH-1 and METH-2; clotting factors such as Factor IX, Factor VIII, and others in the clotting cascade; collagens; cyclins and cyclin inhibitors, such as cyclin dependent kinases, cyclin D1, cyclin E, WAF1, cdk4 inhibitor, and MTS1; cystic fibrosis transmembrane conductance regulator gene (CFTR); enzymes such as cathepsin K, cytochrome p-450 and other cytochromes, farnesyl transferase, glutathione-s transferases, heparanase, HMG CoA synthetase, n-acetyltransferase, phenylalanine hydroxylase, phosphodiesterase, ras carboxyl-terminal protease, telomerase and TNF converting enzyme; glycoproteins such as cadherins, e.g., N-cadherin and E-cadherin; cell adhesion molecules; selectins; transmembrane glycoproteins such as CD40; heat shock proteins; hormones such as 5-α reductase, atrial natriuretic factor, calcitonin, corticotrophin releasing factor, diuretic hormones, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, and thyroid stimulating hormone; proteins involved in immune responses, including antibodies, CTLA4, hemagglutinin, MHC proteins, VLA-4, and kallikrein-kininogen-kinin system; ligands such as CD4; oncogene products such as sis, hst, protein tyrosine kinase receptors, ras, abl, mos, myc, fos, jun, H-ras, ki-ras, c-fns, bcl-2, L-myc, c-myc, gip, gsp, and HER-2; receptors such as bombesin receptor, estrogen receptor, GABA receptors, growth factor receptors including EGFR, PDGFR, FGFR, and NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb.

In one embodiment, the DNA sequence is controlled by a regulatory element. In on embodiment, the regulatory element is a constitutive promoter such as the CMV promoter or RSV promoter. In another embodiment, the DNA sequence is controlled by a regulatable expression system. Systems to regulate expression of therapeutic genes have been developed and incorporated into the current viral gene delivery vectors. These systems are briefly described below:

Tet-onloff system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP 16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the drosophila steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

Ex Vivo and In Vivo Thrombomodulin Gene Transfer

The instant invention uses a gutless adenovirus vector to express a native thrombomodulin protein or a variant of the thrombomodulin protein at a vessel graft or angioplasty site to prevent or reduce re-occlusion and intimal hyperplasia. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]).

In one embodiment, the in vivo expression of thrombomodulin or a thrombomodulin variant is used for the treatment of atherosclerotic cardiovascular disease (CVD). Though venous grafts can be used for bypass surgeries, the veins eventually, become occluded by thrombosis resulting the recurrence of the diseases. In this embodiment, TM gene delivery is used in coronary artery bypass grafting, and vascular graft prostheses to block thrombosis. Specifically, TM gene is introduced into a segment of blood vessel in vitro using a gene transfer vector.

TM gene delivery can be also used for the reduction of no-intima formation, for the prevention of atherosclerosis; for the prevention of myocardial infarction and for the inhibition of fibrinolysis in hemophilic plasma. TM gene transfer at the site of thrombus formation is potent approach to reverse these vascular diseases.

In another embodiment, in vivo TM expression is achieved by embedding a gene transfer vector in a stent which is placed at the treatment site following percutaneous transluminal coronary angioplasty, peripheral artery angioplasty, thrombectomy, or an intravascular stenting procedure.

In another embodiment, the in vivo expression of thrombomodulin, or a thrombomodulin variant is used for the treatment of end stage renal failure (ESRD). ESRD patients often exhibit decreased antithrombotic activity due to low TM levels. In such patients, enhanced in vivo TM gene expression can be potentially very useful.

In another embodiment, the in vivo TM expression is achieved by administering a gene transfer vector to a mammal intravenously (i.v.), intramuscularly (i.m.), intraperitoneally (i.p.) or subcutaneously. For adenoviral and AAV vectors, intravenous administration often lead to viral infection of hepatocytes and transgene expression in the liver.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At bp 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRL/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence. The new plasmid is designated as pShuttle-ITR-HPRT (SEQ ID NO:1)

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette. The intermediate vector used was pcDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV. pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The human TM cDNA (SEQ ID NO:5) was obtained from Dr. Sadler (Dittman et al., *Biochemistry*, 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at bp 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                              (SEQ ID NO:8)
    5'-gtaacactgg cccaggaggc ctttctggtg acccc-3'

(SEQ ID NO:9)
    3'-tgacc gggtcctccg gaaagaccac tggggatt-5'
```

Creation of pTMadap-stuffer1

Based on the published sequence HSU71148 of the human X chromosome region q28 the following PCR primers were synthesized:

```
                                             (SEQ ID NO:10)
    Forward:  5' TAGTTCCTTCTGCCTGGAATAC 3'

(SEQ ID NO:11)
    Reverse:  5' CAAGTCACAAGGATGGACTACA 3'
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 bp was inserted into the BsteII and SfiI sites of pTMadap, resulting in pTMadap-stuffer 1.

2(a)-4 Creation of pTMadap-stuffer1-short

To reduce the size of the stuffer 1 fragment in pTMadap-stuffer1, pTMadap-stuffer1 was digested with SanDI and BstEII and the resulting DNA ends were modified by a fill-in reaction with Klenow. Re-ligation resulted in the 25207 bp vector pTMadap-stuffer1-short. The sequence of stuffer1-short fragment is shown in SEQ ID NO:13.

2(a)-5 Creation of pTMadap-stuffer1-short-stuffer2

The plasmid p2-2 (SEQ ID NO: 14, obtained from GenBank) was cut with NotI and the resulting fragment of approximately 5954 bp (stuffer 2, SEQ ID NO: 15) was inserted into the NotI site of pTMadap-stuffer1 short, resulting in pTMadap-stuffer1-short-stuffer2.

2(a)-6 Removal of PacI Site from pTMadap-stuffer1short-stuffer2

Figure 2:
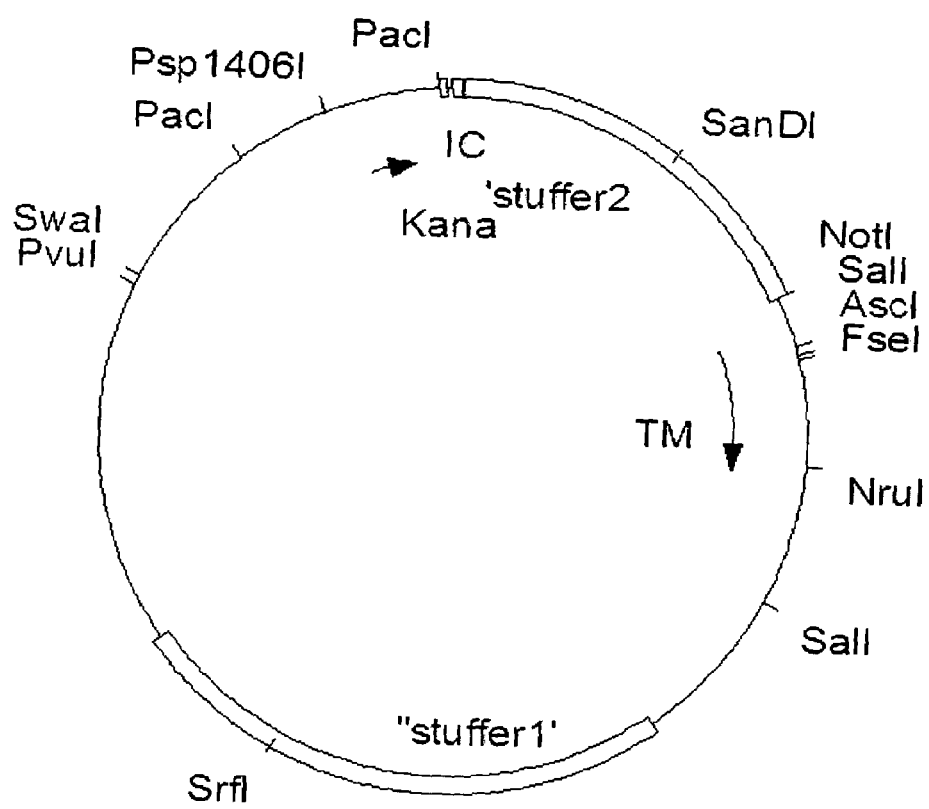
FIG. 2 is a schematic drawing of an embodiment of the full length backbone vector pTM-final.

Plasmid pTMadap-stuffer1-short-stuffer2 was cut with AclI and BsiW1. The resulting 28790 bp fragment was isolated from gel. pShuttle-ITR-HPRT (SEQ ID NO:1) was cut with AclI and Acc65I. The resulting 1966 bp fragment was ligated into the isolated 28790 bp fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

EXAMPLE 3

Preparation of Gutless Adenovirus Carrying Human Thrombomodulin Gene (Gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 µg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy*, 3(5):809-815 [2001]; Umana et al., *Nature Biotechnology*, 19:582-585 [2001]).

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETOH. Cotton swabs (one swab for each tube) were used to completely dry out the tube, and two tubes were used per sample.

14. Preparation of the first gradient: 2.5 mL CsCl—Density 1.25, and 2.5 mL CsCl—Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/ml. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris—pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5 10, and 15 µg/ml. (BSA is fine). Sample cuvettes were prepared using 1-10 µl of sample, depending on estimate of titer. (Sample OD must be within the linear range of the standard line.) OD was taken at 595 λ and formula of the line was calculated from standards. The protein concentration of the samples was calculated using this formula. The following formula was used to convert protein concentration to titer: $[12.956+224.15 \, (\mu g/ml)] \times 10^8$.

EXAMPLE 4

Figure 3:
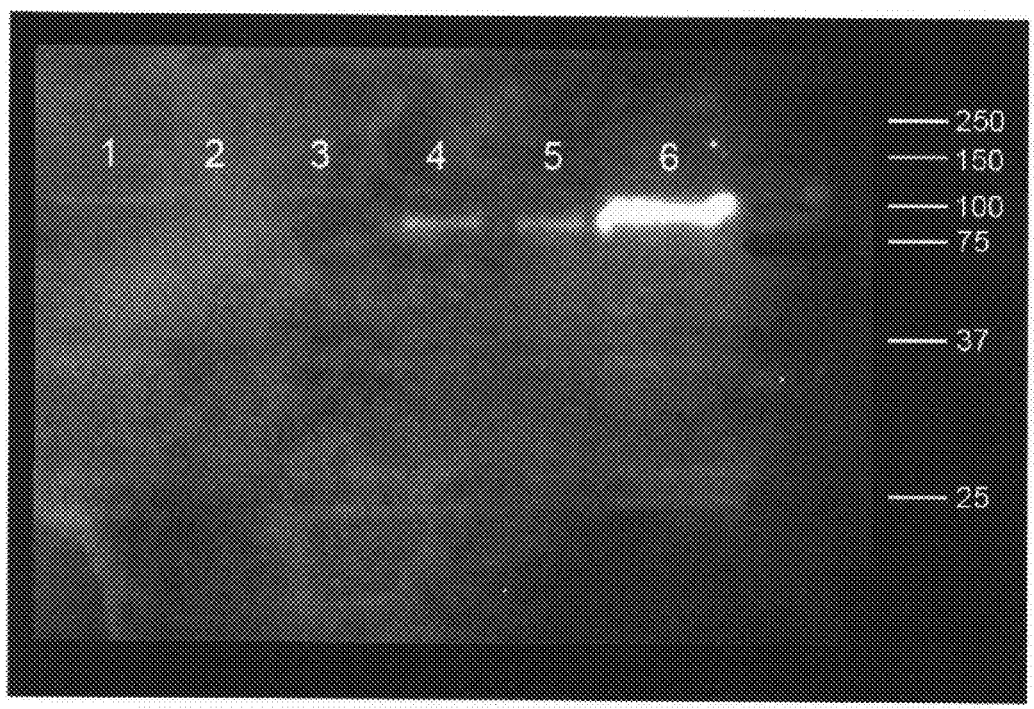
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-final HEK 293 cells were cultured in a 6 well cluster and transfected with 1 µg of pTM-final. After 24 hours, the cells were washed with PBS and lysed in 125 µl RIPA buffer with protease inbitors Protein samples (16 µl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 µl Igepal ca-630, 50 mg sodium deoxycholate, 500 µl 20% SDS, 10 mM β-mercapto ethanol, and 1 ml 10×PBS, and add water to a final volume of 10 ml at room temperature. A cocktail of protease inhibitors containing 11.5 µl PMSF (from 34.8 mg/ml in isopropanol, 64 µl Benzamidine (from 15.6 mg/ml stock), 100 µl sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(B) Expression of hTM in P2 Lysate of 293FLP Cells

Figure 4:
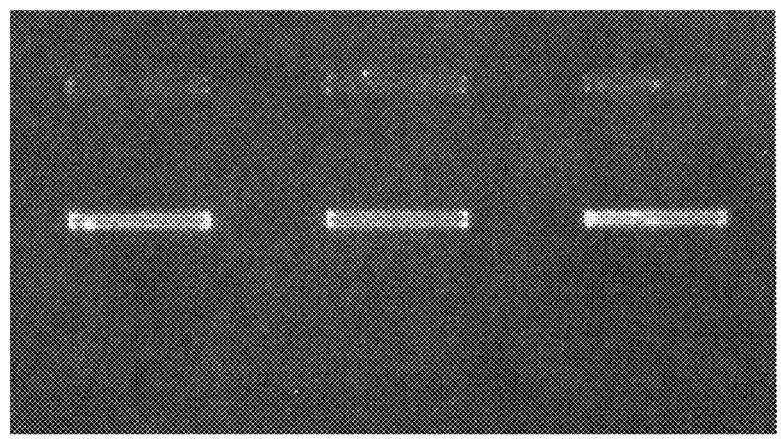
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250 µl RIPA buffer. 7 ul of 5× loading buffer was added to 35 µl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11, 5 µl PMSF (from 34, 8 mg/ml in isopropanol, 64 µl Benzamidine (from 15, 6 mg/ml sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
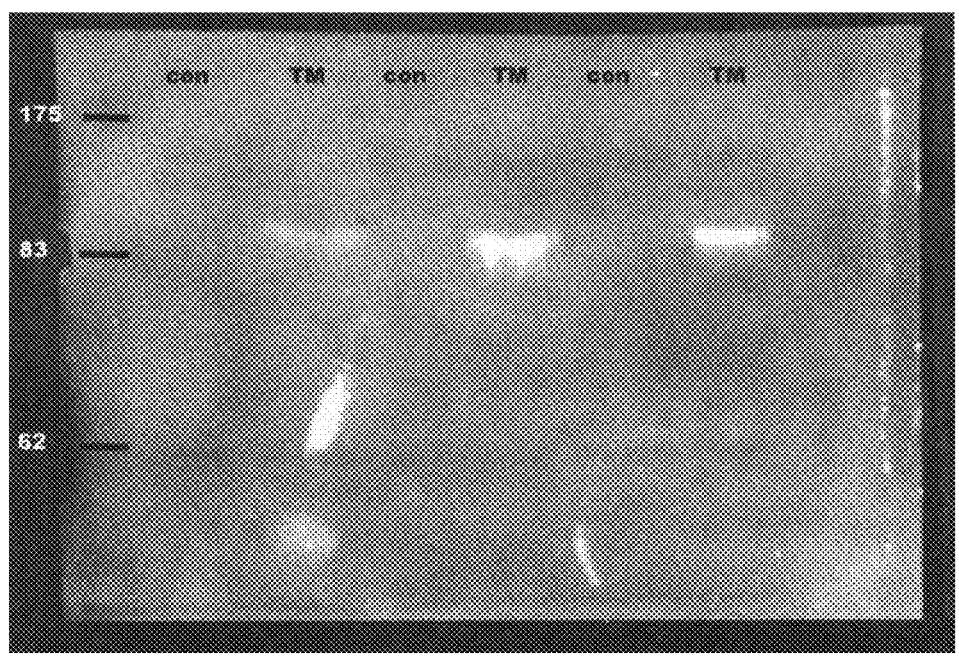
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 µg of PacI digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/ thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
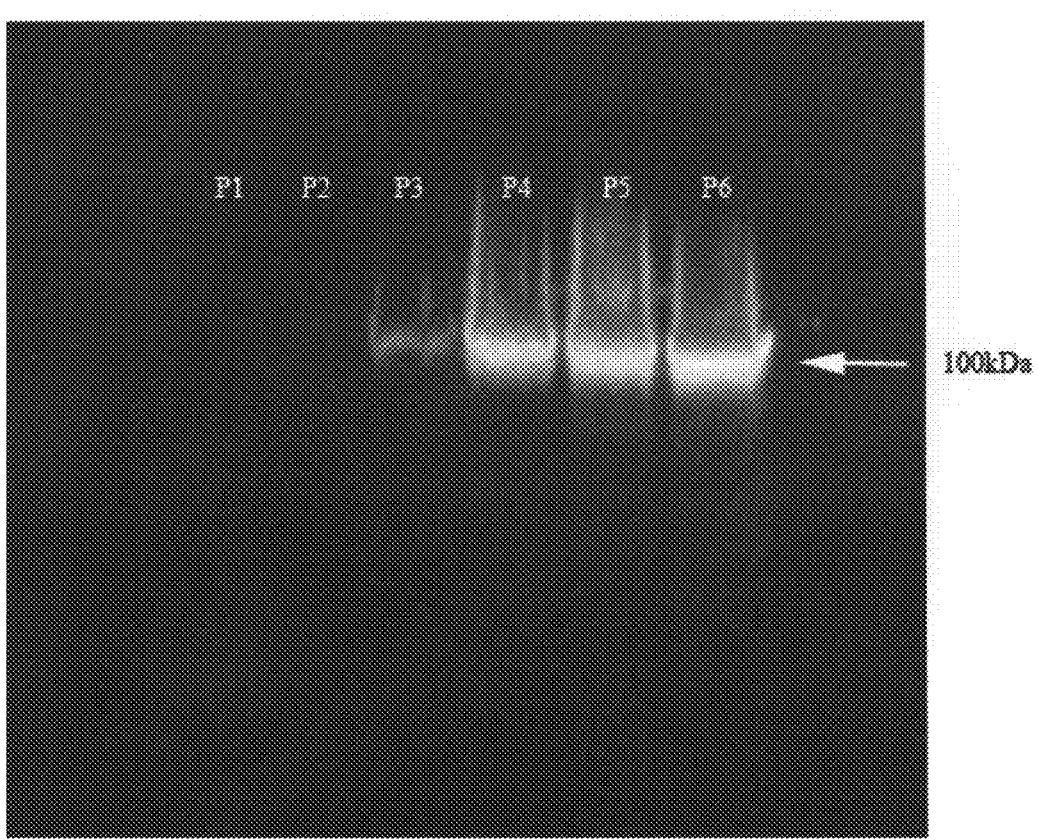
FIG. 6 is a picture of a Western bolt showing TM expression in CRE cells at passage number 1-6 (P1-P6).

HEK 293 cells were cultured in a 6 well cluster and transfected with 200 µl of TM gutless virus of passage 1-6. After 24 hours, the cells were washed with PBS and lysed in 125 µl RIPA buffer. Protein samples (16 µl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293 CRE cells.

The RIPA buffer (10 ml) was prepared as follows: 100 µl Igepal ca-630, 50 mg sodium deoxycholate, 500 µl 20% SDS, 10 mM β-mercapto ethanol, 1 ml 10×PBS, add water to make up 10 ml. Immediately before use, the following protease inhibitors were added to the RIPA buffer: 115 µl PMSF (from 34, 8 mg/ml in isopropanol), 64 µl Benzamidine (from 15,6 mg/ml stock), 100 µl sodium orthovanadate (100 mM), 5 µl pepstatin (from 1 mg/ml stock), 1 µl leupeptin (from 5 mg/ml stock), 1 µl aprotin (from 5 mg/ml stock).

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Treatment for Renal Disease

In this application, the vein in the kidney is treated following evacuation of the clot. A catheter is inserted in the kidney vein and both the proximal and distal balloons are inflated to isolate the vein segment to be transfected. The segment is evacuated of all blood, rinsed with physiologic saline; it is then filled with the CVDS described above, under pressure. The isolated vein segment is exposed to the CVDS for a period of 10 to 45 minutes, depending upon the desired transfection efficiency.

EXAMPLE 9

In Vivo Treatment with Virus Containing Stent

In this application, a virus-coated stent is placed at a treatment site after angioplasty. The virus is a gutless adenovirus carrying a polynucleotide encoding a thrombomodulin protein or a variant of a thrombomodulin protein. Alternatively, the virus may be embedded in the stent and is releases gradually through a time-releasing mechanism well-known to one skilled in the art.

EXAMPLE 10

In Vivo Expression of Transgene by Intravenous Infusion of Viral Vectors

Figure 7:
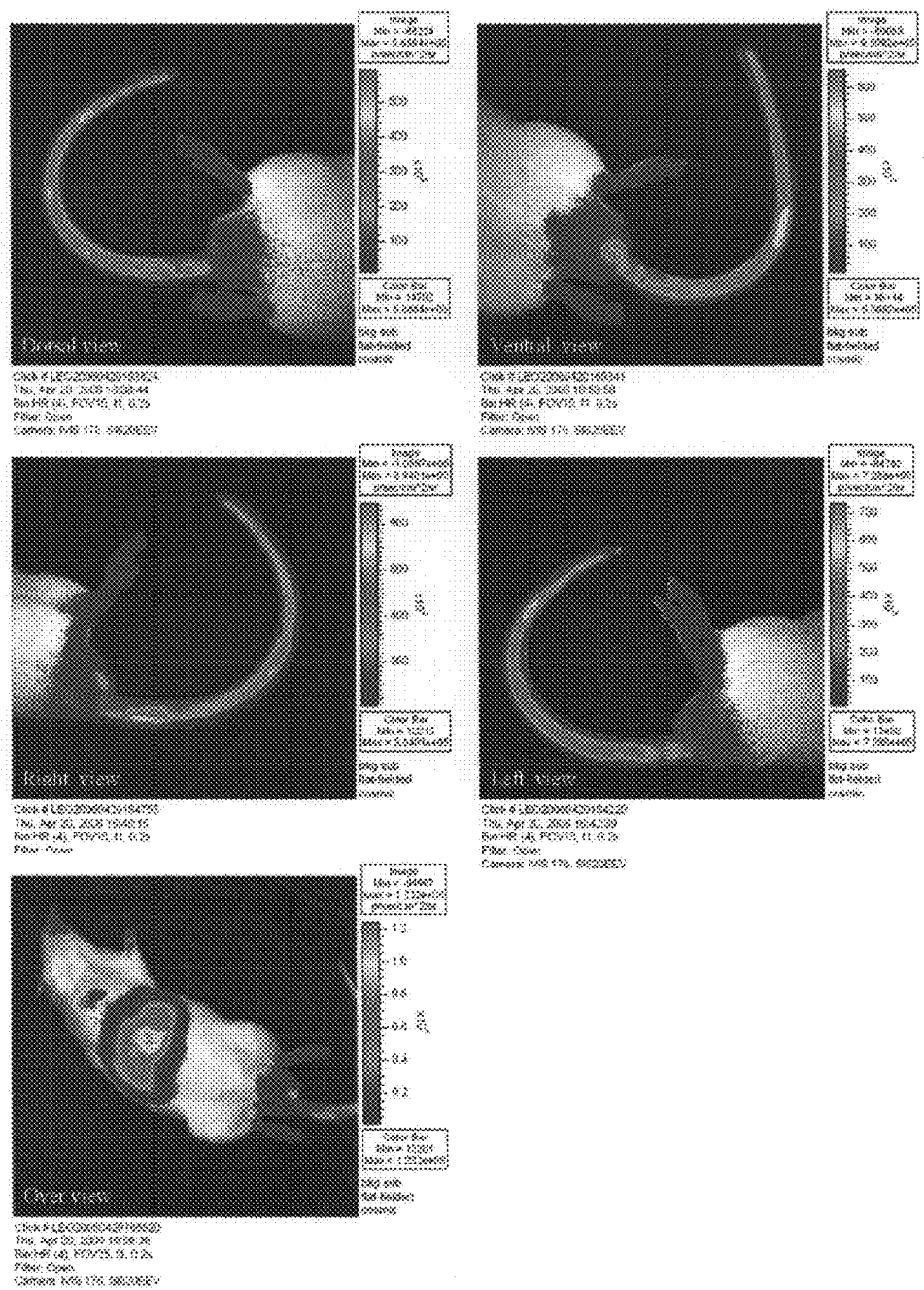
FIG. 7 is a composite of images showing gutless adenovirus-mediated luciferase expression in rat tail vein.

In one experiment, the tail vein of experimental rats was flushed with a solution containing a gutless adenoviral vector carrying a luciferase transgene. As shown in FIG. 7, the expression of luciferase was still very strong in the tail vein eight days after viral infection.

In another experiment, experimental rats were injected intravenously with the gutless TM viruses at doses ranging from $1 \times 10^8$ to $3 \times 10^{11}$ particles/rat. TM expression in liver will be analyzed by the rate of blood coagulation (APTT) and by Western blot of liver biopsy samples.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

```
SEQ ID NO:1 (pShuttle-ITR/HPRT)
CATCATCAATAATATACCTTATTTTGGATTGAAGCCAATATGATAATGAG
GGGGTGGAGTTTGTGACGTGGCGCGGGGCGTGGGAACGGGGCGGGTGACG
TAGTAGTGTGGCGGAAGTGTGATGTTGCAAGTGTGGCGGAACACATGTAA
GCGACGGATGTGGCAAAAGTGACGTTTTTGGTGTGCGCCGGTGTACACAG
GAAGTGACAATTTTCGCGCGGTTTTAGGCGGATGTTGTAGTAAATTTGGG
CGTAACCGAGTAAGATTTGGCCATTTTGGCGGGAAAACTGAATAAGAGGA
AGTGAAATCTGAATAATTTTGTGTTACTCATAGGGCGTAATACTGGTACC
GCGGCCGCCTCGAGTCTAGAACTAGTGGATCCCCCGGGCTGCAGGAATTC
TGATGGCTCTCAAAATTCCTGCCTGCTTTAGGGATAAAAGACTTTAAGAC
TTTTTAACAAAAAAGAAAAAGAAAAAAAAAATTCCTGGCTCCTGGTGTAC
ACACACAGAAGGGTTCCCTCCCCTTGAATGTGACCAGGATCTGTGAAAAT
AACGGGATAGCCGGTCCTGTGATTAGGTTATGTGGTAGACTAGAGCAAGA
TTCTCCTGCTGGTTTTGAAGAAGTCAGCTGCCATGTTGTGAGACTGTCAT
GGGCTAGGGCATGAGCCTTTAAATATCTGGGAGCAACCCCTGGCCAGCAG
CCAGTGAGAAAACGGGCCCTCAGTCCTACAATCACAAGGAACTAAATTCT
GCCAACAACCTGAAGGAACTTTGAAGAGGATCATGAGTCCCTTGATTCAG
CTTGATGAGCCCCTGAGCAGAGGATACAGCTAACTTGTACTAGGGAAGTA
TAAAAAACATGCATGGGAATGATATATATCAACTTTAAGGATAATTGTCA
TACTTCTGGGAATGAAGGGAAAGAAATGGGGCTTTAGTTGTATTATGATC
TTTAATTTCTCAAAAAAAATAAGATCAGAAGCAAATATGGCAAAATGTTA
ATACTTTTGTGGGTACGTAGGTATTCAGCATACCCTTTTTTCTGAGTTCA
AAATATTTTATAATTAAAATGAAATGCAGGCCAGGCACAGTGGCTCATGC
CTATAATACCAGCACTTTGCGAGGCCGAGGTGGGAGGATGGCTTGAGGCC
AGACCAGCCTGGCCAACATGGCAAAACCCCATCTCTACTTTAAAAAAAAA
AAACTATATATATATATGTGTGTGTGTGTATATATATATATGTATA
TATATTTATATATGTGTGTATATATATATATGTATATATATTTATATATG
TGTGTGTATATATATATAGACACACACACATATATACATACATACATA
CACACACACACACACAATTAGCCAGGCATGGTGGCGCACACCTGTAGT
CCCAGCTACTTGGGAGGCTGAGACATGAGAATTGCTTGAACCTGGGAGGC
AGAGTAGTTAGTGAGCTGAGATCATACCACTGCACTCCAGCCTGGTGACA
GAGTGAGACTCTGTCTTAAAAAAAATAAAAATTAAAATTAAATGCAAAAG
GTCCAAGTGAATTGAAGAGGAAAGGGGTATCAAGGAAGGTTTTGTGGAGG
TGACGTTTGAGCTGGGTCTTAAATGACTTAAACATGGGATAAGAAGGGAG
GGAATAAGGACATTTCAGGTACGAGAAATAAGGAGCAAACAGTGGAAACA
ACCTAACGTGTGTCAACCAGTGAATGGATAACAAAAATGTAATTCAGATG
GTATCCAACTTACGATGGTTCAACATGAGATTTTTCTGACTTTAGGATAG
ATTTATCAAAGTAGTAAATCCATTTTCAACTTATGATATTTTCAACTTCA
GATGGGTTTATCAGGACACAGTTGAGGAACACCTGTCTATCCATACAATT
TGGCAATAAAAAGGAAATGAGTGCAGATATACTGCACAACATGAATGAAG
CTTGAAACATTAAGTGAGAGAAGCCAGATACAAAAGGCCACATATTGTA
TGATTCTATTTATACAAAATGTCCAGAATAGGCAAATCTTATAGACAGCA
AGTAGGTAGATGATCAGTTTGCTAGGTGCTGGGGGAAGGGGAAATGGGGA
GTGATGGCTAAGGGGATTGGGTTTCTTTGTGGGGCAATGAAAATGTTTTA
AAATTGAGCGTGATAATGATTGCACAATGCTGCATATATATATAATCTAT
AGATTATATATATAAAGAGAGGCTGTTAGACAGTGATAAGTGATATAT
ATATATATATACATAGAGAGAGAGAGAGAGAGAGAGGCTGTTAGTG
ATAAGTGATCAGGAAAATAAAAGTATTGAGGAGGAATACGAAGTTGACGG
TGTGAAAACATGAGATTTTATATAGGATGGCCAGGGAAGGCCTTAATGAG
AAAGTGACTTATGAGTAAAAACAAGGGATCCTAAACCTTAGCATGCATCA
GAATCACTGGGAAACTTGTTAAAGCATAGCTTGCTGGGCCTCATCACAGA
TATTTTGATTCGGTAGGTTCTTGTGTGATATTAATACTTTTGGTCTAGGG
AACCACATTTTGAGAACCACTGAGCTAAAGGAAGTAAAGGTTTCCCTTAG
TTTACTAGCTGGTAACCCTAGGAAACTGCTTAGCCTCTCGGTGCTAAGAT
ACAAAATACTTTAGCACATAATAACACATGGAAAATAGTGTATAAATTAT
AAATATTATTTTTTATGTACCAAATATTACATAAGACAAAATCTAAGCAA
GATATATATATATAGATAAAATAAGATATATATGTATATATTATAT
ATAGATAAATAGAGAGAGAGAGTTATGTTTAGAAAGAAAATACTTCAAAC
TAAAAAAAGAGAGGTAGGAAGTATACCATTCCATTATTGGTAAAAACAAA
TTACTAAGTAGTCTTTACAAAAAACCAATCTCACTCCTTTAGAACACAAG
CCCACCATTAAAACTGATGCAGAGGAATTTGTCTGCCTGGCTTACCTTTA
GGATGGTGCATACTAAGTTAGAAAAGTCATAAATGTTATATTAAAAGTAA
ATGTGAACTTACTTCCACAATCAAGACATTCTAGAAGAAAAAGAGAAATG
AAAATCAGTACAATGAATAAAACGGTATTTCCAATTATAAGTCAAATCAC
ATCATAACAACCCTAAGGAATTATCCAAACTCTTGTTTTTAGATGCTTTA
TTATATCAAACTCTCCTTTAAACAAGTGGCCCATCTGCTGGGATTTGGAA
GCCTGTAATACTGAAATTTTCATCATAATGGAAATTTTAAAAACAGAATT
TGACCCACCTGTTTTTAAAACACTTTCATTACTTAACAAGAGGTCTAATC
TTGGGCAAGTCTTGAAATTTCTCTGGCCTTAGTTTGCCATGTGTTAAATG
AAACTTGAAGCAGTTGGTCTCTTATAGTCTCCTGACTCTAACATTCTAAG
```

-continued

```
AATTATATTTGTACAATAACTCAAAAATCAGATAATTTAATTTACCATAT
GGACTCCAAAATATATTTTCTCATTAGGCTAAACTTGATGTGCATTTTCT
GGATGTGTCCATATTCTTGGACTACACTAAAAGATGATACCAATGGTTCC
TCTCACCATAAACCGTCACTTCGCTTTCTACATTTAAGAATTTTATAGCT
GGAAGAGTCCTTAACAGAAAATACCATCTAATAATTACCCCTCAAAATCG
AGAAAGTCCTATCTGTTCTTATGCTAGTTATAAGAATGAGGCAGCATTTC
ACATAATGGTTATAAACACTGCCACAAGAAGATTCATGATGTGTTGTTTA
TCTGTAGCTCTCATCATACTGTGTCATATAACTATAGCATTAAGATTTTA
ATGTTCTATATATTCTTCTAAGACAGTGTTTACCAGAGTAAGGCACAAAA
GATCCACTGGTTTGCAAGAAAGATTAGAACTTTTAAATTTTTTACCTCAC
CTTGTTTAATCTATATTTTTGTATGTATTTTGTAACATATATATTATTAT
TACCATAAATCATATATAATTTAAAATGCATATATTAGGGGTAAATGCTC
AGGAAACTTTTTATAAATTGGGCATGCAAATACAAGTTTGAAGACTCACT
GTTCTAGGTATTAAAAGTAAAGTTATAACCAAGTAAAGCTTCCACCTTTT
CATGTCTCAAAGCAGTTTATTGTTGGAGGTAAGATCTCTTAGAAGCCTAA
ACAGGTCCAAGTACAGAATGAAGTAAGGCTAGCCCATAACTTGTGGCAAG
CAATTCATACTATTTCTCTCATGCTGAGGTGTCCTCAGTGAAGCAGCTAC
TATAGACAACTGCAGCCTATTGGTAGCCTATTTTACAGGCAGGAAAAAAA
TTACTTTTTATTGAAAGTGGAAGTCAGGACATGGGGAGAAAATGAATACA
AAAAATAGGGTCAATCCAAAGGCACACAGCAAATGAGTAACACAGTTATG
TTTTTTTCCCATTTGTATGAGGTCGCAGTAAATTCTAAGTAAACTGCAAA
TTTAATAATACACTAAAAAAGCCATGCAATTGTTCAAATGAATCCCAGCA
TGGTACAAGGAGTACAGACACTAGAGTCTAAAAAACAAAAGAATGCCATT
ATTGAGTTTTTGAATTATATCAAGTAGTTACATCTCTACTTAATAAATGA
GAAAAACGAGGATAAGAGGCCATTTGATAAAATGAAAATAGCCAAGAAGT
GGTATTAGAGACTTGAATACAGGTATTCGCGTCCAAAGTTCATCTGCTCA
AATACTAACTGGGGAAAAGAGGGAAAAATATTTCTATATACATATATATCTG
CACACAAAAATACCCCCAAAAGACAAAATGAGGCCAGGCAGGGTGGCTCA
CACCCGTAATCCCGGTACTTTGGGAGGCTGAGGCAGGTGGATACCTGAGA
TCAGGAGTTGGAGATCAGCCTGGTCAACATGGTGAAACCCTGTCTGTACT
AAAGATAAAAAAATTAGCCAGGCATGGTGGCGTGCGCCTGTAATCCCAGC
TACTTGGGAGTCTGAGGCAGGAGAATCACTTGAACTGGGAAGGGGAGGTT
GCAGTGAGCCAAGATCGTACTACTGCACTGCAGCCTGGGCAGCAGAGTGA
GACTCCATCACAAAAATAAATAAATAAATAAATACAATAGACAGAAAG
TTCAAATAATCCCATAATCTTACCAGCAAGAAATAACTTTCACTCGTTAT
ACTTATTGATTTTCGATAATAAATGTACTTTACTGTGACTATCATGAAA
AGAAAGTTATTTTAGAAACAGAGAACTGTTTCAGATCAAATCTATGTAGT
AGAACAGAGCCATTAGGTGGGAAAGACGAGATCAAACTAAATGTCAGAG
GCCTAAAAGGCTAGGTCCATTCCAGCACTAAAAACTGACCAGACAAGTAA
TGGCTTCAACAGCTTCTAAATATGGACAAAGCATGCTGAAAGGGAAGGAC
AGGTCTAACAGTGGTATATGAAATGAACAGGAGGGGCAAAGCTCATTTCT
CCCTCTGAAGTTTTCGAAAGATGCTGAGGAGGACATTAGTTTGACATGACC
CTGATATGGGACAAGATAATTTCACAGAAGTTTTACATGTTAAAGTTTTC
TTATAGATACTCATTCAAGTAAGCAATGAACACTAAAATCTAAAGAAAGA
AAAGAGCTTTAGAGTCAGGTCTGTATTCAAATTCAAGCTCTACCACTTAC
TGGTTCTGTGACTTTGGGCAAGTCTTTAACCTTATTAAGTCTTAATTTC
CTGATTTGTAAAATGGGGATATCGTCTCCCTCACAGGAGTTGTTGTGAAAC
TTTTATGAGATTAATGCCTTTATATTTGGCATAGTGTAAGTAAACAATAA
CTGGCAGCTTCAAAAAAAAAAAAGCAGTAGCATTCCATCATTTATTATTGG
TTACTCTCAAAAAGTTTTTCAATGTACTAGAAGATAAATATTCAAATACC
TTAATATCTCCATTATTTTCAGGTAAACAGCATGCTCCTGAACACCAAT
GGGTCAACAAATAAATTAAAAGGGAAATCTAAAAACATCTTGATATTAAA
CTACATGGAAGCACAATATACCAAAACCAATGGTTCACACTAGGAGAATT
TTAAGGTACAAGAAAACTCTTTGAGATTTCTTAAAATAATAGTATGTCTG
AATTTATTGAGTGATTTACCAGAAACTGTTGTAAGAGCTCTACTTGCATT
ATAGCACTTAATCCTCTTAACTCTATGGCTGCTATTATCAACCTCACCCT
AATCACATATGGGACACAGAGAGGTTAAGTAACTTGCCCAAGGTCAGAGT
TAGGAAGTACTAAGCCATGCTTTGAATCAGTTGTCAGGCTCCGGAACTCA
CACTTTCAGCCACTACATAATACTGCTTTGCTATCTTTTAGGAACATATG
TGAGTCTACCTCACATAGACTCACATAGGTTTGTTTTTTTTTTTTTTTTA
AAGGCTATCTTTTCCCCCATCAATGTTTTTTGAAGGATCCCAAATTAGAG
TCCCACAGAGGCAGACAGCAGTACTTGACAATATGGACATTTAAGGTTAA
TGTTGGATTCTACTGTCTTTTTACTACATGACTACTAGGGAACGATAATTAA
CCTAGACTGCTTCCAAGGGTTAAATAACCCATTTAGTTATACATATGTAAA
TTATCTCTTAGTGATTGATTGAAAGCACACTGTTACTAATTGACTCGGTA
TGAAGTGCTTTTTTTCTTCCCTTTCAAGATACATACCTTTCCAGTTAAA
GTTGAGAGATCATCTCCACCAATTACTTTTATGTCCCCTGTTGACTGGTC
ATTCTAGTTAAAAAAAAAACATATATATATATATATATCTACACACACA
TATGTATATGTATATCCTTATGTACACACACAAACTTCAAATTAAATGAG
AACTAGAAGATTTGACAAGTTAGCTAGCTAATATCCATAGCATTATGATA
TTCTAAATGATATGAATTATAAAGATTAGGTTTCCTGAAATGAATGACTA
GAAAACTTTCAAGTAGAGATTAGTAAAAATTAAAAAGTCCTAATCGGCCA
TTACTGATTTGATGTTTTAAGAGTCCTAAAAAATGGGTTACATCCATTT
TTAAGTCGGTAGTATTATAACAGCCACCCATCTTCAATCACAGTGATTTC
TGAATTGTGAGGGAAGTTATTACATGACAGGTGTCTGGTTCTGGCCCTG
TACGATTCCCATGAGTCAAGCAAATTGTAAGGGCTGGTCTATATCACACC
CAACCCCAAGGATATGTCCCTCAAAAGTCTAGCCCAGGCCCCGTCATCTT
CAGCATCATCTGGGAAACCAGGTCTGATTAGTAGTCCTTTAAGGAATACC
TCTTAGGCTCCCATTTTACTGCTATCACAGAATCCAATAAAACCCTTACA
GGAGATTCAATGGGAAATGCTCAACACCCACTGTAGTTGGTGGTGACAAT

GACCATAATTTGGCTGTGCTGGATTCAGGACAGAAAATTTGGGTGAAAGA
GCAGGTGAACAAAAGAGCTTCGACTTGCCCTAGCAGAGAGCAAGCCATAC
CATAGCACAAAGCCACAGCAATTACAACGGTGCACTACCAGCACAGTAAA
TGAACAAAGTAGAGCCCAGAAACAGACCCAGAACTATATGAGGATTTAGT
ATACAATAAAGATGGTATTTCGAGTCAGTAGGGAAAAGATGAATTATTCA
ATAAATGATGTTTGGCCAACTAGTAACCCATTTGGGAAAAAATAAAAGTA
TGGTCCCTACCTCACAGCATACACAAAAATAAATTCCAGACGGATTAAAA
TCTAAATGTAAAAAATAAAGCCATAAGTGGACTGGAAGAAAATAGACAAT
TTTTTTTAACATCCGTAGAAAGGGTAAAAACCCAGGCATGACATGAACCA
AAACTGAAGAGGTTCTGTAACAAATACCCCCTTTTATATATTGGGCTCCA
ACAATAAGAACCCATAGGAAAATGGAGAATGAACACAAATAGACAATTTA
TAGAAGAGAAGGTTATAAGGTCTAAAATTATATCTATCTGAGAAACAAAC
ACTAAAACAATGTGATTCTACTGTTCTCCCACCCATACTGGCAAAACTTA
AGCCTGATAATATGCTGAGGGGAAATAAGCACTCTTGTTGGTGAGAGTAT
TAATTGGCATAGCTTCTTTTGAAAATGACATAGCAATACCTGTTAAAATT
GCAAACATGCATGTCACTTAATCCAGTAATCCCACTTCTGGGAATCAATG
CTACAAAAACACTGACAAGTATACAAAGATACATTCAAGAGTGTTCACTG
GGCCGGGTGCGGTGGCTTCATGCCTGTAATCCCAGGGAGGCAGAGGCAAG
ACGATCGCTTGACCCCAGGAGTTCAAGGCCAGCCCGAGAAACACAGCAAG
ACCCTGTCTCTCTTTTTTTTATTTAAAAAATAAATGTTCACTGTATCAGT
TGTTCACAAAAACAAACCAACATGTCCATTAACAGGGAACCATTTAAATT
AATCAAGTTCATCTACACAATGTAATACCATGCAACTATTAAAAAGCACC
TGATAATCCAAAGCACACTGAGACAGAATAATGCTATTAAAAACACCAAG
TAGTGGAACACTGTGTTGCCTATGACACCATTTTTATTCAACATTTAAAC
AAATTTGTAACAGCAATTACATGAGTAGTGACAATGGCGTTTATGAGACT
TTTCACTTTTTATGTGCTTCTATTTTTGTTATGCTTCTATATATACATCCA
TTTATTATGGAGTGTTACTTTCAAAAATCACAAATTGGGCCAGTATTATTT
GGTGTTGCAAGGTGAGCATATGACTTCTGATATCAACCTTTGCATATTAC
TTCTCAATTTTAGGGAAATTACAGACATCCCTTATTCTAACTAACTTAAAA
CCCAGCATTTCAAACATACAGAATTGATGGGAAAAAAAAGAAAGAAAGAA
AGAAAAAAAAGCAACAAGCTTCAGATGACAGTGACTCACATCAAATTAT
TTATAAAATCTGTTAAATAGTGCCATCTTCTGGAGATACCTGGTATTACA
GTCCAACTCCAGTTGATGTCTTTACAGAGACAAGAGGAATAAAGGAAAAA
ATATTCAACAACTGAAAAGTATGGAGTCATGGAAAAATTGCTGTGATCCA
AAGGCTACGGTGATAGGACAAGAAACAAGAAGGAACTCCAAGCAGTAAGACA
CTGCTGTTCTATTAGCATCCAAACCTCCATACTCCTGTTTGCCCCAAGGC
TTTTTTAAAAAATAGAGACAGGATCTCACTATTTTGCTCAGGCTGGTCTT
GAACTCCTGGACTCAAGCTATCGTCCTGCGTCGGCCTCCTAAAGTGCCGA
GATTACAGGCTTGAGTCACCATACCTGGCTATTTATTTTTTCTTAACTCT
CTTGGCTGGCCTATAGCCACCATGGAAGCTAATAAAGAATATTAATTTAA
GAGTAATGGTATAGTTCACTACATTGGAATACAGGTATAAGTGCCTACAT
TGTACATGAATGGCATAGATGGATCAATTACCCCCACCTGGGTGGCCAAGA
GAACTGCGCGAACCTCCCTCCTTGGCTGTCTGGAACAAGCTTCGCACTAG
ATCCCTTTACTGAGTGCCTCCCTCATCTTTAATTATGGTTAAGTCTAGGA
TAACAGGACTGGCAAAGGTGAGGGGAAAGCTTCCTCCAGAGTTGCTCTAC
CCTCTCCTCTACCGTCCTATCTCCTCACTCTGTCAGCCAAGGAGTCCAA
TCTGTCCTGAACTCAGAGCGTCACTGTCAACTACATAAAATTGCCAGAGA
AGCTCTTTGGGACTACAAACACATACCCTTAATGTCTTTATTTCTATTTT
GTCTACCTCTTCAGTCTAGGTGAAAAAATAGGAAGGATAATAGGGAAGAA
CTTTGTTTATGCCTACTTATCCGCCCCTAGGAATTTTGAAAACCTCTAGG
TAGCAATAAGAACTGCAGCATGGTATAGAAAAAGAGGAGGAAAGCTGTAT
AGAAATGCATAATAAATGGGCAGGAAAAGAACTGCTTGGAACAAACAGGG
AGGTTGAACTATAAGGAGAGAAAGCAGAGAGGCTAATCAACAAGGCTGGG
TTCCCAAGAGGGCATGATGAGACTATTACTAAGGTAGGAATTACTAAGGG
CTCCATGTCCCCTTAGTGGCTTAGTACTATGTAGCTTGCTTTCTGCAGTG
AACTTCAGACCCTTCTTTTAGGATCCTAGAATGGACTTTTTTTTTTTATC
GGAAAACAGTCATTCTCTCAACATTCAAGCAGGGCCCAAGTCTACCACAC
TCAATCACATTTTCTCTTCATATCATAATCTCTCAACCATTCTCTGTGCT
TTTAACTGTTTTTCTACCTCGATCAAATGCCAACAAAAGTAAGAAATGT
TAGAATCATGTATTTTTAGAGGTAGACTGTATCTCAGATAAAAAAAAGG
GCAGATATTCCATTTTCCAAAATATGTATGCAGAAAAAATAAGTATGAAA
GGACATATGCTCAGGTAACAAGTTAATTTGTTTACTTGTATTTTATGAAT
TCCCTAAAACCTACGTCACCCGCCCCGTTCCCACGCCCCGCGCCACGTCA
CAAACTCCACCCCCTCCATTATCATATTGGCTTCAATCCAAAATAAGGTAT
ATTATTGATGATGTTAATTAACATGCATGGATCCATATGCGGTGTGAAAT
ACCGCACAGATGCGTAAGGAGAAAATACCGCATCAGGCGCTCTTCGGCTT
CCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAA
CGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAG
CATCACAAAATCGACGCTCAAGTCAGAGGTGGCGAAACCCGACAGGACT
ATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGA
CACGACTTATCGCCACTGGCAGCAGCCACTGGTAACAGGATTAGCAGAGC
GAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTT
ACCTTCGGAAAAAGAGTTGGTAGCTCTTGATCCGGCAAACAAACCACCGC
```

-continued
```
TGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTGAG
TGGAACGAAAACTCACGTTAAGGGATTTTGGTGATGAGATTATCAAAAAG
GATCTTCACCTAGATCCTTTTAAATTAAAAATGAAGTTTTAAATCAATCT
AAAGTATATATGAGTAAACTTGGTCTGACAGTTACCAATGCTTAATCAGT
GAGGCACCTATCTCAGCGATCTGTCTATTTCGTTCATCCATAGTTGCCTG
ACTCCCGTCGTGTAGATAACTACGATACGGGAGGGCTTACCATCTGGCC
CCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAG
TAAGTAGTTCGCCAGTTAATAGTTTGCGCAACGTTGTTGCCATTGGTGCA
GCCATGAGATTATCAAAAAGGATCTTCACCTAGATCCTTTTCACGTAGAA
AGCCAGTCCGCAGAAACCGTGCTGACCCCGGATGAATGTCAGCTACTGGG
CTATCTGGACAAGGGAAAACGCAAGCGCAAAGAGAAAGCAGGTAGCTTGC
AGTGGGCTTACATGGCGATAGCTAGACTGGGCGGTTTTATGGACAGCAAG
CGAACCGGAATTGCCAGCTGGGGCGCCCTCTGGTAAGGTTGGGAAGCCCT
GCAAAGTAAACTGGATGCTTTCTTGCCGCCAAGGATCTGATGGCGCAGG
GGATCAAGCTCTGATCAAGAGACAGGATGAGGATCGTTTCGCATGATTGA
ACAAGATGGATTGCACGCAGGTTCTCCGGCCGCTTGGGTGGAGAGGCTAT
TCGGCTATGACTGGGCACAACAGACAATCGGCTGCTGTGATGCCGCCGTG
TTCCGGCTGTCAGCGCAGGGGCGCCCGGTTCTTTTTGTCAAGACCGACCT
GTCCGGTGCCCTGAATGAACTGCAAGACGAGGCAGCGCGGCTATCGTGGC
TGGCCACGACGGGCGTTCCTTGCGCAGCTGTGCTCGACGTTGTCACTGAA
GCGGGAAGGGACTGGCTGGTATTGGGCGAAGTGCCGGGGCAGGATCTCCT
GTCATCTCACCTTGCTCCTGCCGAGAAAGTATCCATCATGGCTGATGCAA
TGCGGCGGCTGCATACGCTTGATCCGGCTACCTGCCCATTCGACCACCAA
GCGAAACATCGCATCGAGCGAGCACGTACTCGGATGGAAGCCGGTCTTGT
CGATCAGGATGATCTGGACGAAGAGCATCAGGGGCTCGCGCCAGCCGAAC
TGTTCGCCAGGCTCAAGGCGAGCATGCCCGACGGGGAGGATCTCGTCGTG
ACCCATGGCGATGCCTGCTTGCCGAATATCATGGTGGAAAATGGCCGCTT
TTCTGGATTCATCGACTGTGGCCGGCTGGGTGTGGCGGACCGCTATCAGG
ACATAGCGTTGGCTACCCGTGATATTGCTGAAGAGCTTGGCGGCGAATGG
GGTGACCGCTTCGTCGTGCTTTACGGTATCGCCGCTCCCGATTCGCAGCG
CATCGCCTTCTATCGCCTTCTTGACGAGTTCTTCTGAATTTTGTTAAAAT
TTTGTTAAATCAGCTCATTTTTTAACCAATAGGCCGAAATCGGCAAAAT
CCCTTATAAATCAAAAGAATAGACCGAGATAGGGTTGAGTGTTGTTCCAG
TTTGGAACAAGAGTCCACTATTAAAGAACGTGGACTCCAACGTCAAAGGG
CGAAAAACCGTGTATCAGGGCGATGGCCCACTACGTGAACCATCACCCTA
ATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCG
AGAAAGGAAGGGAAGAAAGCGAAAGGAGGGGGCGCTAGGGCGCTGGCAAG
TGTAGCGGTCACGCTGCGCGTAACCACCACACCCGCCGCGCTTAATGCGC
CGCTACAGGGCGCGTCCATTCGCCATTCAGGATCGAATTAATTCTTAATT
AA SEQ ID NO:2 (human TM amino acid sequence)
MLGVLVLGALALAGLGFPAPAEPQPGGSQCVEHDCFALYPGPATFLNASQ
ICDGLRGHLMTVRSSVAADVISLLLNGDGGVGRRRLWTGLQLPPGCGDPK
RLGPLRGFQWVTGDNNTSYSRWARLDLNGAPLCGPLCVAVSAAEATVPSE
PIWEEQQCEVKADGFLCEFHFPATCRPLAVEPGAAAAAVSITYGTPPAAR
GADFQALPVGSSAAVAPLGLQLMCTAPPGAVQGHWAREAPGAWDCSVENG
GCEHACNAIPGAPRCQCPAGAALQADGRSCTASATQSCNDLCEHFCVPNP
DQPGSYSCMCETGYRLAADQHRCEDVDDCILEPSPCPQRCVNTQGGFECH
CYPNYDLVDGECVEPVDPCFRANCEYQCQPLNQTSYLCVCAEGFAPIPHE
PHRCQMFCNQTACPADCDPNTQASCECPEGYILDDGFICTDIDECENGGF
CSGVCHNLPGTFECICGPDSALARHIGTDCDSGKVDGDSGSGEPPPSPT
PGSTLTPPAVGLVHSGLLIGISIASLCLVVALLALLCHLRKKQGAARAKM
EYKCAAPSKEVVLQHV RTERTPQRL SEQ ID NO:3 (human TM nucleotide sequence)
atgcttggg tcctggtcc ttggcgcgct ggccctggcc
ggcctggggt tccccgcacc cgcagagccg cagccgggtg
gcagccagtg cgtcgagcac gactgcttcg cgctctaccc
gggccccgcg accttcctca atgccagtca gatctgcgac
ggactgcggg gccacctaat gacagtgcgc tcctcggtgg
ctgccgatgt catttccttg ctactgaacg gcgacggcgg
cgttggccgc cggcgcctct ggatcggcct gcagttgcca
cccggctgcg gcgaccccaa gcgcctcggg ccctgcgcg
gcttccagtg ggttacggga gacaacaaca ccagctatag
caggtgggca cggctcgacc tcaatgggc tcccctctgc
ggcccgtttgt gcgtcgctgt ctccgctgct gaggccactg
tgcccagcga gccgatctgg gaggagcagc agtgcgaagt
gaaggccgat ggcttcctct gcgagttcca cttcccaggc
acctgcaggc cactggctgt ggagcccggc gccgcggctg
cgcgcgtctc gatacctac ggcacccgt tcgcggccg
cggagcgac ttccaggcgc tgccggtggg cagctccgcc
gcggtggctc cctcggctt acagctaatg tgcaccgcgc
cgcccggagc ggtccagggg cactgggcca gggaggcgcc
gggcgcttgg gactgcagcg tggagaacgg cggctgcgag
cacgcgtgca atgcgatccc tgggctccc cgctgccagt
```
```
gcccagccgg cgccgccctg caggcagacg ggcgctcctg
caccgcatcc gcgacgcagt cctgcaacga cctctgcgag
cacttctgcg ttcccaaccc cgaccagccg ggctcctact
cgtgcatgtg cgagaccggc taccggctgg cggccgacca
acaccggtgc gaggacgtgg atgactgcat actggagccc
agtccgtgc cgcagcgctg tgtcaacaca cagggtggct
tcgagtgcca ctgctaccct aactacgacc tggtggacgg
cgagtgtgtg gagcccgtgg acccgtgctt cagagccaac
tgcgagtacc agtgccagcc cctgaaccaa actagctacc
tctgcgtctg cgccgagggc ttcgcgccca ttcccacga
gccgcacagg tgccagatgt tttgcaacca gactgcctgt
ccagccgact gcgaccccaa cacccaggct agctgtgagt
gcctgaaggc ctacatcctg gacgacggtt tcatctgcac
ggacatcgac gagtgcgaaa acggcggctt ctgctccggg
gtgtgccaca acctccccgg taccttcgag tgcatctgcg
ggcccgactc ggcccttgcc cgccacattg gcaccgactg
tgactccggc aaggtggacg gtgcgacag cggctctggc
gagccccgc ccagcccgac gcccggctcc accttgactc
ctccggccgt ggggctcgtg cattcgggct tgctcatagg
catctccatc gcgagcctgt gcctggtggt ggcgcttttg
gcgctcctct gccaccctgcg caagaagcag ggcgccgcca
gggccaagat ggagtacaag tgcgcggccc cttccaagga
ggtagtgctg cagcacgtgc ggaccgagcg gacgccgcag
agactc SEQ ID NO:4 (CMV promoter)
TCTAGACGCGTTGACATTGATTATTGACTAGTTATTAATAGTAATCAATT
ACGGGGTCATTAGTTCATAGCCCATATATGGAGTTCCGCGTTAC
ATAACTTACGGTAAATGGCCCGCCTGGCTGACCGCCCAACGACCCCCGCC
CATTGACGTCAATAATGACGTATGTTCCCATAGTAACGCCAATAGGGACT
TTCCATTGACGTCAATGGGTGGAGTATTTACGGTAAACTGCCCACTTGGC
AGTACATCAAGTGTATCATATGCCAAGTACGCCCCCCTATTGACGTCAAT
GACGGTAAATGGCCCGCCTGGCATTATGCCCAGTNCATGACCTTATGGGA
CTTTCCTACTTGGCAGACATCTACGTATTAGTCATCGCTATTACCATGGT
GATGCGGTTTTGGCAGTACATCAATGGGCGTGGATAGCGGTTTGACTCAC
GGGGATTTCCAAGTCTCCACCCCATTGACGTCAATGGGAGTTTGTTTTG
GCACCAAAATCAACGGGACTTTCCAAAATGTCGTAACAACTCCGCCCCAT
TGACGCAAATGGGCGGTAGGCGTGTACGGTGGGAGGTCTATATAAGCAGA
GCTCTCTGGCTAACTAGAGAACCCGCTGCTTACTGGCTTATCGAGATATC SEQ ID NO:5 (hTM cDNA)
GGCAGCGCGCAGCGGCAAGAAGTGTCTGGGCTGGGACGGACAGGAGAGGC
TGTCGCCATCGGCTCCTGTGCCCCTCTGCTCCGGCACGGCCCTGTCGCA
GTGCCCGCGCTTTCCCGGCGCCTGCACGCGGCGCGCCTGGGTAACATGC
TTGGGGTCCTGGTCCTTGGCGCGCTGGCCCTGGCCGGCCTGGGGTTCCCC
GCACCCGCAGAGCCGCAGCCGGGTGGCAGCCAGTGCGTCGAGCACGAGTG
CTTCGCGCTCTACCCGGGCCCCGCCACCTTCCTCAATGCCAGTCAGATCT
GCGACGGACTGCGGGGCCACCTAATGACAGTGCGCTCCTCGGTGGCTGCC
GATGTCATTTCCTTGCTACTGAACGGCGACGGCGGCGTTGGCCGCCGGCG
CCTCTGGATCGGCCTGCAGCTGCCCACCCGGCTGCGGCGACCCCAAGCGC
TCGGGCCCCTCCGCGGCTTCCAGTGGGTTACGGGAGACAACAACACCAGC
TATAGCAGGTGGGCACGGCTCCACCTCAATGGGGCTCCCCTCTGCGGGCCC
GTTGTGCGTCGCTGTCTCCGCTGCTGAGGCCACTGTGCCCAGCGAGCCGA
TCTGGGAGGAGCAGCAGTGCGAAGTGAAGGCCGATGGCTTCCTCTGCGAG
TTCCACTTCCCAGCCACCTGCAGGCCACTGGCTGTGGAGCCCGGCGCCGC
GGCTGCCGCCGTCTCGATCACCTACGGCACCCCGTTCGCGGCCCGGGGAG
CGGACTTCCAGGCGCTGCCGGTGGGCAGCTCCGCCGCGGTGGCTCCCCTC
GCCTTACAGCTAATGTGCACCGCGCCGCCCGGAGCGGTCCAGGGGCACTG
GGCCAGGGAGGCGCCCGGTTGCAGCGTGGAGAACGGCGGCTGCGAGCACG
CGTGCAATGCGATCCCTGGGCTCCCCGCTGCCAGTGCCCAGCCGGCGCCGCCCTGCAGGCAGACGGGCGCTCCTGCACCGCATCCGCGAC
GGAGTCCTGCAACGACCTCTGCGAGCACTTCTGCGTTCCCAACCCCGACC
AGCCGGGCTCCTACTCGTGCATGTGCGAGACCGGCTACCGGCTGGCCGCC
GACCAACACCGGTGCGAGGACGTGGATGACTGCATACTGGAGCCCAGTCC
GTGTCCGCAGCGCTGTGTCAACACACAGGGTGGCTTCGAGTGCCACTGCT
ACCCTAACTACGACCTGGTGGACGGCGAGTGTGTGGAGCCCGTGGACCCG
TGCTTCAGAGCCAACTGCGAGTACCAGTGCCAGCCCCTGAACCAAACTAG
CTACCTCTGCGTCTGCGCCGAGGGCTTCGCGCCCATTCCCCACGAGCCGC
ACAGGTGCCAGATGTTTTGCAACCAGACTGCCTGTCCAGCCGACTGCGAC
CCCAACACCCAGGCTAGCTGTGAGTGCCCTGAAGCCTACATCCTGGACGA
CGGTTTCATCTGCACAGACATCGACGAGTGCGAAAACGGCGGCTTCTGCT
CCGGGGTGTGCCACAACCTCCCCGGTACCTTCGAGTGCATCTGCGGGCCC
GACTCGGCCCTTGCCCGCCACATTGGCACCGACTGTGACTCCGGCAAGGT
GGACGGTGGCGACAGCGGCTCTGGCGAGCCCCCGCCCAGCCCGACGGCCG
GCTCCACCCTGACTCCTCCGGCCGTGGGGCTCGTGCATTCGGGCTTGCTC
ATAGGCATCTCCATCGCGAGCCTGTGCCTGGTGGTGGCGCTTTTGGCGCT
CCTCTGCCACCTGCGCAAGAAGCAGGGCGCCGCCAGGGCCAAGATGGAGT
ACAAGTGCGCGGCCCCGTTCGAAGGAGGTAGTGCTGCAGCACGTGCGGACC
GAGCGGACGCCGCAGAGACTCTGAGCGGCCTCCGTCCAGGAGCCTGGCTC
CGTCCAGGAGCCTGTGCCTCCTCACCCCCAGCTTTGCTACCAAAGCACCT
```

-continued
TAGCTGGCATTACAGCTGGAGAGAGACCCTCCCCGCACCCCCCAAGCTGTT
TTCTTCTATTCCATGGCTAACTGGCGAGGGGGTGATTAGAGGGAGGAGAA
TGAGCCTCGGCCTCTTCCGTGACGTCACTGGACCACTGGGCAATGATGGC
AATTTTGTAACGAAGACACAGACTGCGATTTGTCCCAGCTCCTCACTACC
GGGCGCAGGAGGGTGAGCGTTATTGGTCGGCAGCCTTCTGGGCAGACCTT
GACCTCGTGGGGTAGGGATGACTAAAATATTTATTTTTTTTAAGTATTTA
GGTTTTTGTTTGTTTCCTTTGTTCTTACCTGTATGTCTCCAGTATCCACT
TTGCACAGCTCTCCGGTCTCTCTCTCTACAAACTCCCACTTGTCATGT
GACAGGTAAACTATCTTGGTGAATTTTTTTTTCCTAGCCCTCTCACATTT
ATGAAGCAAGCCCCACTTATTCCCCATTCTTCCTAGTTTTCTCCTCCCAG
GAACTGGGCGAACTCACCTGAGTCACCCTAGCTGTGCCTGACCCTACTTC
TTTTGCTCTTAGCTGTCTGCTCAGACAGAACCCCTACATGAAACAGAAAC
AAAAACACTAAAAATAAAAATGGCCATTTGCTTTTTCACCAGATTTGCTA
ATTTATGCTGAAATTTCAGATTCCCAGAGCAAAATAATTTTAAACAAAGG
TTGAGATGTAAAAGGTATTAAATTGATGTTGCTGGACTGTCATAGAAATT
ACACCCAAAGAGGTATTTATCTTTACTTTTAAACAGTGAGCCTGAATTTT
GTTGCTGTTTTGATTTGTACTGAAAAATGGTAATTGTTGCTAATCTTCTT
ATGCAATTTCCTTTTTTGTTATTATTACTTATTTTTGACAGTGTTGAAAA
TGTTCAGAAGGTTGCTCTAGATTGAGAGAAGAGACAAACACCTCCCAGGA
GACAGTTCAAGAAAGCTTCAAACTGCATGATTCATGCCAATTAGCAATTG
ACTGTCACTGTTCCTTGTCACTGGTAGACCAAAATAAAACCAGCTCTACT
GGTCTTGTGGAATTGGGAGCTTGGGAATGGATCCTGGAGGATGCCCAATT
AGGGCCTAGCCTTAATCAGGTCCTCAGAGAATTTCTACCATTTCAGAGAG
GGCTTTTGGAATGTGGCCCCTGAACAAGAATTGGAAGCTGCCCTGCCCAT
GGGAGCTGGTTAGAAATGCAGAATCCTAGGCTCCACCCCATCCAGTTCAT
GAGAATCTATATTTAACAAGATCTGCAGGGGGTGTGTCTGCTCAGTAATT
TGAGGACAACCATTCCAGACTGCTTCCAATTTTCTGGAATACATGAAATA
TAGATCAGTTATAAGTAGCAGGCCAAGTCAGGCCCTTATTTTCAAGAAAC
TGAGGAATTTTCTTTGTGTAGCTTTGCTCTTTGGTAGAAAAGGGTAGGTA
CACAGCTCTAGACACTGCCACACAGGGTCTGCAAGGTCTTTGGTTCAGCT
AAGCTAGGAATGAAATCCTGCTTCAGTGTATGGAAATAAATGTATCATAG
AAATGTAACTTTTGTAAGACAAAGGTTTTCCTCTTCTATTTTGTAAACTC
AAAATATTTGTACATAGTTATTTATTTATTGGAGATAATCTAGAACACAG
GCAAAATCCTTGCTTATGACATCACTTGTACAAAATAAACAAATAACAAT
GTGAAAAAAAAAAAAAAAAAAAAAAAAAAAAAAAAAAAAAA SEQ ID NO:6 (CMV-hTM expression cassette)
GTTTAAACGGGCCCTCTAGACGCGTTGACATTGATTATTGACTAGTTATT
AATAGTAATCAATTACGGGGTCATTAGTTCATAGCCCATGATATGATATG
GAGTTCCGCGTTACATAACTTACGGTAAATGGCCCGCCTGGCTGACCGCC
CAACGACCCCCGCCCATTGACGTCAATAATGACGTATGTTCCCATAGTAA
CGCCAATAGGGACTTTCCATTGACGTCAATGGGTGGAGTATTTACGGTAA
ACTGCCCACTTGGCAGTACATCAAGTGTATCATATGCCAAGTACGCCCCC
CTATTGACGTCAATGACGGTAAATGGCCCGCCTGGCATTATGCCCAGTNC
ATGACCTTATGGGACTTTCCTACTTGGCAGACATCTACGTATTAGTCATC
GCTATTACCATGGTGATGCGGTTTTGGCAGTACATCAATGGGCGTGGATA
GCGGTTTGACTCACGGGGATTTTCCAAGTCTCCACCCCATTGACGTCAAT
GGGAGTTTGTTTTGGCACCAAAATCAACGGGACTTTCCAAAATGTCGTAA
CAACTCCGCCCCATTGACGCAAATGGGCGGTAGGCGTGTACGGTGGGAGG
TCTATATAAGCAGAGCTCTCTGGCTAACTAGAGAACCCGTGCTTACTGGC
TTATCGAGATATCTGCAGAATTCATCTGTCGACTGCTACCGGCAGCGGGC
AGCGGCAAGAAGTGTCTGGGCTGGACGGACAGGAGAGGCTGTCGCCATC
GGCGTCCTGTGCCCCTCTGGTCCGGCACGGCCCTGTCGGAGTGCCCGCGC
TTTCCCCGGCGCCTGCACGCGGCGCGCTGGGTAACATGCTTGGGGTCCT
GGTCCTTGGCGCGCTGGCCCTGGCCGGCCTGGGGTTCCCCGCACCCGCAG
AGCCGCAGCCGGGTGGCAGCCAGTGCGTCGAGCACGACTGCTTCGCGCTC
TACCCGGGCCCCGCGACCTTCCTCAATGCCAGTCAGATCTGCGACGGACT
GCGGGGCCACCTAATGACAGTGCGCTCCTCGGTGGCTGCCGATGTCATTT
CCTTGCTACTGAACGGCGACGGCGGCGTTGGCCGCCGGCGCCTCTGGATC
GGCGTGCAGCTGCCACCCGGCTGCGGCGACCGCAAGCGCCTCGGGCCCT
GCGCGGCTTCCAGTGGGTTACGGGAGACAACAACACCAGCTATAGCAGGT
CGGCACGGCTCGACCTCAATGGGGCTCCCCTCTGCGCCCGTTGTGCGTC
GCTGTCTCCGCTGCTGAGGCCACTGTGCCCAGCGAGCCGATCTGGGAGGA
GCAGCAGTGCGAAGTGAAGGCCGATGGCTTCCTCTGCGAGTTCCACTTCC
CAGCCACCTGCAGGCCACTGGCTGTGGAGCCCGGCCGCCGGCTGCCGC
GTCTCGATCACCTACGCACCCCGTTCGCGGCCCGCGGAGCGGACTTCCA
GGCGCTGCCGGTGGCGACCTCCGGGGTGGCTCCCCTCGGCTTACAGC
TAATGTGCACGCGCCGCCCGGAGCGGTCCAGGGGCACTGGGCAGGGAG
GCGCCGGGCGCTTGGGACTGCAGCGTGGAGAACGGCGGCTGCGAGCACGC
GTGCAATGCGATCCCTGGGGCTCCCCGCTGCCAGTGCCCAGCCGGCGCCG
CCCTGCAGGCAGACGGGCGCTCCTGCACCGATATCGATCCGCGACGCAGTCCTGC
AACGACCTCTGCGAGCACTTCTGCGTTCCCAACCCCGACCAGCCGGGCTC
CTACTCGTGCATGTGCGAGACCGGCTACCGGCTGGCGGCGGATCAACACC
GGTGCGAGGACGTGGATGACTGCATACTGGAGCCCAGTCCGTGTCCGCAG
CGCTGTGTCAACACAGGGTGGCTTCGAGTGCCACTGCTACCCTAACTA
CGACCTGGTGGACGGCGAGTGTGTGGAGCCCGTGGACCCGTGCTTCAGAG
CCAACTGCGAGTACCAGTGCCAGCCCCTGAACCAAACTAGCTACCTCTGC
GTCTGCGCCGAGGGCTTCGCGCCCATTCCCCACGAGCCGCACAGGTGCCA
GATGTTTTGCAACCAGACTGCCTGTCCAGCCGACTGCGACCCCAACACCC
AGGCTAGCTGTGAGTGCCCTGAAGGCTAGATCCTGGACGACGGTTTCATC -continued
TGCACGGACATCGACGAGTGCGAAAACGGCGGCTTCTGCTCCGGGGTGTG
CCACAACCTCGCCGGTACCTTCGAGTGCATCTGCGGGCCCGACTCGGCCC
TTGCCCGCCACATTGGCACCGACTGTGACTCCGGCAAGGTGGACGGTGGC
GACAGCGGCTCTGGCGAGCCCGCGCCCAGCCCGACGCCCGGCTCCACCTT
GACTCCTCCGGCCGTGGGGCTCGTGCATTCGGGCTTGCTCATAGGCATCT
CCATCGCGAGCCTGTGCCTGGTGGTGGCGCTTTTGGCGCTCCTCTGCCAC
GTGGGCAAGAAGCAGGGCGCCGCCAGGGCCAAGATGGAGTACAAGTGCGC
GGCCCCCTTCCAAGGAGGTAGTGCTGCAGCACGTGCGGACCGAGCGGACGC
CGCAGAGACTCTGACGGCCTCCGTCCAGGAGCCTGGCTCCGTCCAGGAG
CCTGTGCCTCCTCACCCCCAGCTTTGCTACCAAAGCACCTTAGCTGGCAT
TACAGCTGGAGAAGACCCTCCCCGCACCGGCCAAGCTGTTTTCTTCTATT
CCATGGCTAACTGGCGAGGGGGTGATTAGAGGGAGGAGAATGAGCCTCGG
CCTCTTCCGTGACGTCACTGGACCACTGGGCAATGATGGCAATTTTGTAA
CGAAGACACAGACTGCGATTTGTCCCAGGTCCTCACTACCGGGCGCAGGA
GGGTGAGCGTTATTGGTCGGCAGCCTTCTGGGCAGACCTTGACCTCGTGG
GCTAGGGATGACTAAAATATTTATTTTTTTTAAGTATTTAGGTTTTTGTT
TGTTTCCTTTGTTCTTACCTGTATGTCTCCAGTATCCACTTTGCACAGCT
CTCCGGTCTCTCTCTCTCTACAAACTCGCACTTGTCATGTGACAGGTAAA
CTATCTTGGTGAATTTTTTTTTCCTAGCCCTCTCACATTTATGAAGCAAG
CCCCACTTATTCCCCATTCTTCGTAGTTTTCTCCTCCCAGGAACTGGGCC
AACTCACCTGAGTCACCCTACCTGTGCCTGACCCTACTTCTTTTGCTCTT
AGCTGTCTGCTCAGACAGAACCCCTACATGAAACAGAAACAAAAACACTA
AAAATAAAAATGGCCATTTGCTTTTTCACCAGATTTGCTAATTTATCCTG
AAATTTCAGATTCCCAGAGCAAAATAATTTTAAACAAAGGTTGAGATGTA
AAAGGTATTAAATTGATGTTGCTGGACTGTCATAGAAATTACACGCAAAA
AGGTATTTATCTTTACTTTTAAACAGTGAGCCTGAATTTTGTTGCTGTTT
TGATTTGTACTGAAAAATGGTAATTGTTGCTAATCTTCTTATGCAATTTC
CTTTTTTGTTATTATTACTTATTTTTGACAGTGTTGAAAATGTTCAGAAG
GTTGCTCTAGATTGAGAGAAGAGACAAACACCTCCCAGGAGACAGTTCAA
GAAAGCTTCAAACTGCATGATTCATGCCAATTAGCAATTGACTGTCACTG
TTCCTTGTCACTGGTAGACCAAAATAAAACCAGCTCTACTGGTCTTGTGG
AATTGGGAGCTTGGGAATGGATCCTGGAGGATGCCCAATTAGGGCCTAGC
CTTAATCAGGTCCTCAGAGAATTTCTACCATTTCAGAGAGGCGTTTTGGA
ATGTGGCCCCTGAACAAGAATTGGAAGCTGCCCTGCCCATGGGAGCTGGT
TAGAAATGCAGAATCCTAGGCTCCACCCCATCCAGTTCATGAGAATCTAT
ATTTAACAAGATCTGCAGGGGGTGTGTCTGCTCAGTAATTTGAGGACAAC
CATTCCAGACTGCTTCCAATTTTCTGGAATACATGAAATATAGATCAGTT
ATAAGTAGCAGGCCAAGTCAGGCCCTTATTTTTCAAGAAACTGAGGAATTT
TCTTTGTGTAGCTTTGCTCTTTGGTAGAAAAGGGTAGGTACACAGCTCTA
GACACTGCCACACAGGGTCTGCAAGGTCTTTGGTTCAGCTAAGCTAGGAA
TGAAATCCTGCTTCAGTGTATGGAAATAAATGTATCATAGAAATGTAACT
TTTGTAAGACAAAGGTTTTCCTCTTCTATTTTGTAAACTCAAAATATTTG
TACATAGTTATTTATTTATTGGAGATAATCTAGAACACAGGCAAAATCCT
TGCTTATGACATCACTTGTACAAAATAAACAAATAACAATGTGAAAAAAA
AAAAAAAAAAAAAAAAAAAAAAAAAAAAAAGGTAGCAGTCGACAGAT
GAATTCCACCACACTGGACTAGTGGATCCGAGCTCGGTACCAAGCTTAAG
TTTAAAC SEQ ID NO:7 (pTMadap)
CATCATCAATAATATACCTTATTTTGGATTGAAGCCAATATGATAATGAG
GGGGTGGAGTTTGTGACGTGGCGCGGGGCGTGGGAACGGGGCGGGTGACG
TAGTAGTGTGGCGGAAGTGTGATGTTGCAAGTGTGGCGGAACACATGTAA
GCGACGGATGTGGCAAAAGTGACGTTTTTGGTGTGCGCCGGTGTACACAG
GAAGTGACAATTTTCGCGCGGTTTTAGGCGGATGTTGTAGTAAATTTGGG
CGTAACGAGTAAGATTTGGCCATTTTCGCGGGAAAACTGAATAAGAGA
AGTGAAATCTGAATAATTTTTGTGTTACTCATAGCGCGTAATACTGGTACC
GCGGCGGCCTCGAGTCTAGAACTAGTGGATCCCCAAACGGGCCCTCTAG
ACGCGTTGACATTGATTATTGACTAGTTATTAATAGTAATCAATTACGGG
GTCATTAGTTCATAGCCCATATATATGGAGTTCCGCGTTACATAACTTAC
GGTAAATGGCCCGCCTGGCTGACCGCCCAACGACCCCCGCCCATTG
ACGTCAATAATGACGTATGTTCCCATAGTAACGCCAATAGGGACTTTCCA
TTGACGTCAATGGGTGGAGTATTTACGGTAAACTGCCCACTTGGCAGTAC
ATCAAGTGTATCATATGCCAAGTACGCCCCCCTATTGACGTCAATGACGG
TAAATGGCCCGCCTGGCATTATGCCCAGTNCATGACCTTATGGGACTTTC
CTACTTGGCAGACATCTACGTATTAGTCATGGCTATTACCATGGTGATGC
GGTTTTGGCAGTACATCAATGGGCGTGGATAGCGGTTTGACTCACGGGGA
TTTTCCAAGTCTCCACCCCATTGACGTCAATGGGAGTTTGTTTTGGCACC
AAAATCAACGGGACTTTCCAAAATGTCGTAACAACTCCGCCCCATTGACG
CAAATGGGCGGTAGGCGTGTACGGTGGGAGGTCTATATAAGCAGAGCTCT
CTGGCTAACTAGAGAACCCTGCTTAGTGGCTTATCGAGATATCTGCAGA
ATTCATCTGTCGACTGCTACCGGCAGCGGGCAGCGGCAAGAAGTGTCTGG
GGTGGGACGGACAGGAGAGGCTGTCGCCATCGGCGTCCTGTGCCCCTCTG
CTCCGGCACGGCCCTGTGGCAGTGCCCGCGCTTTCCCGGCGCCTGCACG
CGGCGCGCCTGGGTAACATGCTTGGGGTCCTGGTCCTTGGCGCGCTGGCC
CTGGCCGGCCTGGGGTTCCCCGCACCCGCAGAGCCGCAGCCGGGTGGCAG
CCAGTGCGTCGAGCACGACTGCTTCGCGCTCTACCCGGGCCCCGCGACCT
TCCTCAATGGAGTCAGATCTGCGACGGACTGCGGGGCCACCTAATGACA
GTGCGCTCCTCGGTGGCTGCCGATGTCATTTCCTTGCTACTGAACGGCGA
CGGCGGCGTTGGCCGCCGGCGCCTCTGGATCGGCGTGCAGCTGCCACCCG
GCTGCGGCGACCCCAAGCGCCTCGGGCCCTGCGCGGCTTCCAGTGGGTT -continued

```
ACGGGAGACAACAACACCAGCTATAGCAGGTGGGCACGGCTCGACCTCAA
TGGGGCTCCCCTCTGCGGCCCGTTGTGCGTCGCTGTCTCCGCTGCTGAGG
CCACTGTGCCCAGCGAGCCGATCTGGGAGGAGCAGCAGTGCGAAGTGAAG
GCCGATGGCTTCCTCTGCGAGTTCCACTTCCCAGCCACCTGCAGGCCACT
GGCTGTGGAGCCCGGCGCCGCGGCTGCCGCCGTCTCGATCACCTACGGCA
CCCCGTTCGCGGCCCGCGGAGCGGACTTCCAGGCGCTGCCGGTGGGCAGC
TCCGCCGCGGTGGCTCCCCTCGGCTTACAGCTAATGTGCACCGCGCCGCC
CGGAGCGGTCCAGGGGCACTGGGCAGGGAGGCGCCGGGCGCTTGGGACT
GCAGCGTGGAGAACGGCGGCTGCAGCACGCGTGCAATGCGATCCCTGGG
GCTCCCCGCTGCCAGTGCCCAGCCGGCGCCGCCCTGCAGGCAGACGGGCG
CTCCTGCACCGCATCCGCGACGCAGTCCTGCAACGACCTCTGCGAGCACT
TCTGCGTTCCCAACCCCGACCAGCCGGGCTCCTACTCGTGCATGTGCGAG
ACCGGCTACCGGCTGGCGGCCGACCAACACCGGTGCGAGGACGTGGATGA
CTGCATACTGGAGCCCAGTCCGTGTCCGCAGCGCTGTGTCAACACACAGG
GTGGCTTCGAGTGCCACTGCTACCCTAACTACGACCTGGTGGACGGCGAG
TGTGTGGAGCCCGTGGACCCGTGCTTCAGAGCCAACTGCGAGTACCAGTG
CCAGCGCCTGAACCAAACTAGCTACCTCTGCGTCTGCGCCGAGGGCTTCG
CGCCCATTCCCCACGAGCCGCACAGGTGCCAGATGTTTTGCAACCAGACT
GCCTGTCCAGCCGACTGCGACCCCAACACCCAGGCTAGCTGTGAGTGCCC
TGAAGGCTACATCCTGGACGACGGTTTCATCTGCACGGACATCGACGAGT
GCGAAAACGGCGGGTTCTGCTCCGGGGTGTGCCACAACCTCCCCGGTACC
TTCGAGTGCATCTGCGGGCCCGACTCGGCCCTTGCCCGCCACATTGGCAC
CGACTGTGACTCCGGCAAGGTGGACGGTGGCGACAGCGGCTCTGGCGAGC
CCCGCCCAGCCCGACGCCCGGCTCCACCTTGACTCGTCCGGCCGTGGGG
CTCGTGCATTCGGGCTTGCTCAGGATCTCCATCGCGAGGCTGTGCCTT
GGTGGTGGCGCTTTTGGCGCTCCTCTGCCACCTGCGCAAGAAGCAGGGCG
CCGCCAGGGCCAAGATGGAGTACAAGTGCGCGGCCCCTTCCAAGGAGGTA
GTGCTGCAGCACGTGCGGACCGAGCGGACGCCGCAGAGACTCTGAGCGGC
CTCCGTCCAGGAGCCTGGCTCCGTCCAGGAGGCTGTGCCTCCTCACCCCC
AGCTTTGCTACCAAAGCACCTTAGCTGGCATTACAGCTGGAGAAGACCCT
CCCCGCACCCCCCAAGCTGTTTTCTTCTATTCCATGGCTAACTGGCGAGG
GGGTGATTAGGGGAGGAGAATGAGCCTCGGCCTCTTCCGTGACGTCACT
GGACCACTGGGCAATGATGGCAATTTTGTAACGAAGACACAGACTGCGAT
TTGCTCCCAGGTCCTCACTACCGGGCGCAGGAGGGTGAGCGTTATTGGTCG
GCAGCCTTCTGGGCAGACCTTGACCTCGTGGGCTAGGGATGACTAAAATA
TTTATTTTTTTAAGTATTTAGGTTTTGTTTGTTTCCTTTGTTCTTACC
TGTATGTCTCCAGTATCCACTTTGCACAGCTCTCCGGTCTCTCTCTCTCT
ACAAACTCCCACTTGCTCATGTGACAGGTAAACTATCTTGGTGAATTTTTT
TTTCCTAGCCCTCTCACATTTATGAAGCAAGCCCCACTTATTCCCCATTC
TTCCTAGTTTTCTCCTCCCAGGAACTGGGCCAACTCACCTGAGTCACCCT
ACCTGTGCCTGACCCTACTTCTTTTGCTCTTAGCTGTCTGCTCAGACAGA
ACCCCTACATGAACAGAAAGAAAAAGAACTATAAAAATAAAAATGGCCATTT
GCTTTTTCACCAGATTTGCTAATTTATCCTGAAATTTCAGATTCCCAGAG
CAAAATAATTTTAAACAAAGGTTGAGATGTAAAAGGTATTAAATTGATGT
TGCTGGACTGTCATAGAAATTACACCCAAAGAGGTATTTATCTTTACTTT
TAAACAGTGAGCCTGAATTTTGTTGCTGTTTTGATTTGTACTGAAAAATG
GTAATTGTTGCTAATCTTCTTATGCAATTTCCTTTTTTGTTATTATTACT
TATTTTTGACAGTGTTGAAAATGTTCAGAAGGTTGCTCTAGATTGAGAGA
AGAGACAAACACCTCCCAGGAGACAGTTCAAGAAAGCTTCAAACTGCATG
ATTCATGCCAATTAGCAATTGACTGTCACTGTTCCTTGTCACTGGTAGAC
CAAAATAAAACCAGCTCTACTGGTCTTGTGGAATTGCGAGCTTGGGAATG
GATCCTGGAGGATGCCCAATTAGGGCCTAGCCTTAATCAGGTCCTCAGAG
AATTTCTAGCATTTCAGAGAGGCCTTTTGGAATGTGGCCCCTGAACAAGA
ATTGGAAGCTGCCCTGCCCATGGGAGCTGGTTAGAAATGCAGAATCCTAG
GCTCCACCCCATCCAGTTCATGAGAATCTATATTTAACAAGATCTGCAGG
GGGTGTGTCTGCTCAGTAATTTGAGGACAACCATTCCAGACTGCTTCCAA
TTTTCTGGAATACATGAAATATAGATCAGTTATAAGTAGCAGGCCAAGTC
AGGCCCTTATTTTCAAGAAACTGAGGAATTTTCTTTGTGTAGCTTTGCTC
TTTGGTAGAAAAGGCTAGCTACACAGGTCTAGACACTGCCACAGCAGGGTC
TGCAAGGTCTTTGGTTCAGCTAAGCTAGGAATGAAATCCTGCTTCAGTGT
ATGGAAATAAATGTATCATAGAAATGTAACTTTTGTAAGACAAAGGTTTT
CCTCTTCTATTTTGTAAACTCAAAATATTTGTACATAGTTATTTATTTAT
TGGAGATAATCTAGAACACAGGCAAAATCCTTGCTTATGACATCACTTGT
ACAAAATAAAACAAATACAATGTGAAAAAAATAAAAAATGTAATTCAGATGG
AAAAAAAAAAAAAAGGTAGCAGTCGACAGATGAATTCCACCACACTGGAC
TAGTGGATCCGAGCTCGGTACCAAGCTTAAGTTTGGGCTGCAGGAATTCT
GATGGCTCTCAAAATTCCTGCCTCCTTTAGGGATAAAGACTTTAAGACT
TTTTAACAAAAAGAAAAGAAAAAAAAAATTCCTGCCTCCTGGTGTACA
CACACAGAAGGGTTCCCTCCCCTTGAATGTGACCAGGATCTGTGAAAATA
ACGGGATAGCGCTCGTGTGATTAGGTTATGTGGTAGACTAGAGCAAGAT
TCTCCTGCTGGTTTTGAAGAAGTCAGCTGCCATGTGTGAGACTGTCATG
GGCTAGGGCATGAGCCTTTAAATATCTGGGAGCAACCCTGGCCAGCAGC
CAGTGAGAAAACGGGCCCTCAGTCCTACAATCACAAGGAACTAAATTCTG
CCAACAACCTGAAGGAACTTTGAAGAGGATCATGAGTCCCTTGATTGAGC
TTGCTGATGAGCCCCTGACAGAGGATACAGCTAACTTGTACTAGGGAAGTAT
AAAAAACATGCATGGGAATGATATATATCAACCTTTAAGGATAATTGTCAT
ACTTCTGGGAATGAAGGGAAAGAAATGGGGCTTTAGTTGTATTATGATCT
TTAATTTCTCAAAAAAAATAAGATCAGAAGCAAATATGGCAAAATGTTAA
TACTTTTGTGGGTACGTAGGTATTCAGCATACCCTTTTTTCTGAGTTCAA
AATATTTTATAATTAAAATGAAATGCAGGCCAGGCACAGTGGCTCATGCC
TATAATACCAGCACTTTGCGAGGCCGAGGTGGGAGGATGGCTTGAGGCCA
GAGCAGCCTGGCCAACATGGCAAACCCCATCTCTACTTAAAAAAAAAAA
AACTATATATATATATATGTGTGTGTGTGTATATATATATATGTATAT
ATATTTATATATGTGTGTATATATATATATGTATATATATTTATATATGT
GTGTGTATATATATATACACACACACATATATACATACATACATACAC
ACACACACACACACACAATTAGCCAGGCATGGTGGCGCACACCTGTAGTC
CCAGCTACTTGGGAGGCTGAGACATGAGAATTGCTTGAACCTGGGAGGCA
GAGTAGTTAGTGAGCTGAGATCATACCACTGCACTCCAGCCTGGTGACAG
AGTGAGACTCTGTCTTAAAAAAAAAATAAAAATTAAATGCAAAAGG
TCCAAGTGAATTGAAGAGGAAAGGGGTATCAAGGAAGGTTTTGTGGAGGT
GACGTTTGAGCTGGGTCTTAAATGACTTAAACATGGGATAAGAAGGGAGG
GAATAAGGACATTTCAGGTACGAGAAATAAGGAGCAAACAGTGGAAACAA
CCTAACGTCTGTCAACCAGTGAATGGATAACAAAATGTAATTCAGATGG
TATCCAACTTACGATGGTTCAACATGAGATTTTCTGACTTTAGGATAGA
TTTATCAAAGTAGTAAATCCATTTTCAACTTATGATATTTTCAACTTCAG
ATGGGTTTATCAGGACACAGTTGAGGAACACCTGTCTATCCATACAATTT
GGCAATAAAAAGGAAATGAGTGCAGATATACTCCACAACATGAATGAACC
TTGAAAAACATTAAGTGAGGAAGCCAGATACAAAAGGCCACATATTGTAT
GATTCTATTTATACAAAATGTCCAGAATAGGCAAATCTTATAGACAGCAA
GTAGGTAGATGATCAGTTTGCTAGGTGCTGGGGGAAGGGGAAATGGGGAG
TGATGGCTAAGGGGATTGGGTTTCTTTGTGGGCAATGAAAATGTTTTAA
AATTGAGCGTGATAATGATTGCACAATGCTGCATATATATATAATCTATA
GATTATATATATAAAGAGAGGCTGTTAGACAGTGATAAGTGATATATA
TATATATATACATAGAGAGAGAGAGAGAGAGAGAGGCTGTTAGTGA
TAAGTGATCAGGAAAATAAAAGTATTGAGGAGGAATACGAAGTTGACGGT
GTGAAAACATGAGATTTTATATAGGATGGCCACGGAAGGCCTTAATGAGA
AAGTGACTTATGATAAAACAAGGGATCGTAAACCTTAGCATGCATCAG
AATCACTCGGAAACTTGTTAAAGCATAGCTTGCTGGGCCTCATCACAGAT
ATTTTGATTCGGTAGGTTCTTGTCTGATATTAATACTTTTGGTCTAGGGA
ACCACATTTTGAGAACCACTGAGCTAAGGAAGTAAAGGTTTCCCTTAGT
TTACTAGCTGGTAACACTGGCCCAGGAGGCCTTTCTGGTGACCCCTAAGG
AATTTATCGAAACTCTTGTTTTTAGATGCTTTATTTATATCAAACTCTCCTT
TAAACAAGTGGCCCATCTGCTGGGATTTGGAAGCCTGTAATACTGAAATT
TTCATCATAATGGAAATTTAAAAACAGAATTTGACCCACCTGTTTTTAA
AACACTTTCATTACTTAACAAGAGGTCTAATCTTGGGCAAGTCTTGAAAT
TTCTCTGGCCTTAGTTTCCCATGTGTTAAATGAAACTTGAAGCAGTTGGT
CTCTTATAGTCTCCTGACTCTAACATTCTAAGAATTATATTTGTACAATA
ACTCAAAAATCACATAATTTAATTTACCATATGGACTCCAAAATATATTT
TCTCATTAGGCTAAACTTGATCTGCATTTTCTGGATGTGTCGATATTCTT
GGACTACACTAAAACATGATACCAATGCTTCCTCTCACCATAAACCCTCA
CTTCGCTTTCTACATTTAAGAATTTTATAGCTGGAAGAGTCCTTAACAGA
AAATACCATCTAATTATTACCCCTCAAAATCGAGAAAGTCCTATCTGTTC
TTATGCTAGTTATAAGAATGAGGCAGCATTTCACATAATGGTTATAAACA
CTGCCACAAGAAGATTCATGATGTGTTGTTTATCTGTAGCTCTCATCATA
CTCTGTCATATAACTATAGCATTAAGATTTTAATGTTCTATATATTCTTC
TAAGACAGTGTTTACCAGGTAAGGACAAAAGATCCACTGGTTTGCAA
AAAGATTAGAACTTTTAAATTTTTACCTCACCTTGTTTAATCTATATTT
TTGTATGTATTTTGTAACATATATATTATTACCATAAATCATATATA
ATTTAAAATGCATATATTAGGGGTAAATGCTCAGGAAACTTTTTATAAAT
TGGGCATGCAAATACAAGTTTGAAGACTCACTGTTCTAGGTATTAAAAGT
AAAGTTATAACCAAGTAAAGCTTCCAGCTTTTCATGTCTCAAAGCAGTTT
ATTGTTGGAGGTAAGATCTCTTAGAAGCCTAAACAGGTCCAAGTACAGAA
TGAAGTAAGGCTAGCCCATAACTTGTGGCAAGCAATTCATACTATTTCTC
TCATGCTGAGCTCTCCTCAGTGAAGCAGCTACTATAGACAACTGCAGCCT
ATTGGTAGCCTATTTTACAGGCAGGAAAAAAATTACTTTTTATTCAAAGT
GGAACTCAGGACATGGGAGAAAATGAATACAAAAATAGGGTCAATCCA
AAGGCACACAGCAAATGAGTAACACAGTTATGTTTTTTTCCCATTTGTAT
GAGGTCCCAGTAAATTCTAAGTAAACTGCAAATTTAATAATACACTAAAA
AAGCCATGCAATTGTTCAAATGAATCCCAGCATGGTACAAGGAGTACAGA
CACTAGAGTCTAAAAACAAAAGAATGCCATTATTGAGTTTTTGAATTAT
ATCAAGTAGTTACATCTCTACTTAATAAATGAGAAAACGAGGATAAGAG
GCCATTTGATAAAATGAAAATAGCCAAGAAGTGGTATTAGAGACTTGAAT
ACAGGTATTCGGGTCCAAGTTCATCTGCTCAAATACTAACTGGGGAAAA
GAGGGAAAATATTTATATACATATATATCTGCACACAAAATACCCCCA
AAAGACAAATGAGGCCAGGCAGGTGGCTCACACCCGTAATCCCGGTAC
TTTGGGAGGCTGAGGCAGGTGGATACCTGAGATCAGGAGTTGGAGATCAG
CCTGGTCAACATGGTGAAACCCGTGTCTCTACTAAAGATAAAAAATTAGC
CAGGCATGGTGGCGTGCGCCTGTAATCCCAGCTACTTGGGAGTCTGAGGC
AGGAGAATCACTTGAACCTGGGAAGGGGAGGTTGCAGTGAGCCAAGATCGT
ACTACTGCACTCCAGCCTGGGCAGAGAGTGAGACTCCATCACAAAAATA
AATAAATAAATAAAATAAAACAATGAAACAGAAGTTCAAATAATCCCATAAT
CTTACCAGCAAGAAATAACTTTCACTCGTTATACTTATTGATTTTTCCAT
AATAAATGTACTTTACTGTGACTATCATGAAAAGAAAGTTATTTTAGAAA
CAGAGAACTGTTTCAGATCAAATCTATGTAGTAGAACAGAGCCATTAGGT
GGGAAAGACAGATCAAACTAAATCTCAGAAGGCCTAAAAGGCTAGGTCC
ATTCCAGCACTAAAAACTGACCAGACAAGTAATGCCTTCAACAGCTTCTA
AATATGGACAAAGCATGCTGAAAGGGAAGGACAGGTCTAACAGTGGTATA
TGAAATGAACAGGAGGGGCAAAGCTCATTTCTCCTCTGAAGTTTTCCAAA
GATGCTGAGGAGGACATTAGTTTGACATGACCCTGATATGGGACAAGATA
ATTTCACAGAAGTTTTACATGTTAAAGTTTTCTTATAGATACTTCATTCAA
```

```
GTAAGCAATGAACACTAAAATCTAAAGAAAGAAAAGAGCTTTAGAGTCAG
GTCTGTATTCAAATTCAAGCTCTACCACTTACTGGTTCTGTGACTTTGGG
CAAGTCTTTTAACCTTATTAAGTCTTAATTTCCTGATTTGTAAAATGGGG
ATATCGTCTCCCTCACAGGATTGTTGTGAAACTTTTATGAGATTAATGCC
TTTATATTTGGCATAGTGTAAAGTAACAATAACTGGCAGCTTCAAAAAAA
AAAAGCAGTAGCATTCCATCATTTATTATTGGTTACTCTCAAAAAGTTTT
TCAATGTACTAGAAGATAAATATTCAAATACCTTAATATCTCCATTATTT
TCAGGTAAACAGCATGCTCCTGAACAACCAATGGGTCAACAAATAAATTA
AAAGGGAAATCTAAAAACATCTTGATATTAAACTACATGGAAGCACAATA
TACCAAAACCAATGGTTCACACTAGGAGAATTTTAAGGTACAAGAAACT
CTTTGAGATTCTTAAAATAATAGTATGTCTGAATTTATTGAGTGATTTA
CCAGAAACTGTTGTAAGAGCTCTACTTGCATTATAGCACTTAATCCTCTT
AACTCTATGGCTGCTATTATCAACCTCACCCTAATCACATATGGGACACA
GAGAGGTTAAGTAACTTGCCCAAGGTCAGAGTTAGGAAGTACTAAGCGAT
GCTTTGAATCAGTTGTCAGGCTCCGGAACTCACACTTTCAGCCACTACAT
AATACTGCTTTGCTATCTTTTAGGAAACTATGTGAGTCTACCTCACATAG
ACTCACATAGGTTTGTTTTTTTTTTTTTTAAAGGCTATCTTTTCCCCC
ATCAATGTTTTTTGAAGGATCCCAAATTAGAGTCCCACACAGAGGCAGACAG
CAGTACTTGACAATATGGACATTTAAGGTTAATGTTGGATTCTACTGTCT
TTTTACTACATGACCTAGGGAACGATAATTAACCTAGACTGCTTCCAAGG
GTTAAATAACCCATTTAGTTATACTATGTAAATTATCTCTTAGTGATTGA
TTGAAAGCACACTGTTACTAATTGACTCGGTATGAAGTGCTTTTTTTTCT
TCCCTTTCAAGATACATACCTTTCCAGTTAAAGTTGAGAGATCATCTCCA
CCAATTACTTTTATGTCCCCTGTTGACTGGTCATTCTAGTTAAAAAAAAA
AAAAACTATATATATATATATCTACACACACATATGTATATGTATATCCT
TATGTACACACAAACTTCAAATTAAATAGAGAACTAGAAGATTTGAGAA
GTTAGCTAGCTAATATCCATAGCATTATGATATTCTAAATGATATGAATT
ATAAGAATTAGGTTTCCTGAAATGAATGACTAGAAAACTTTCAAGTAGAG
ATTAGTAAAAATTAAAAAGTCCTAATCGGCCATTACTGATTTGATGTTT
TAAGAGTCCTAAAAAATGGGTTACATCCATTTTTAAGTGGGTAGTATTAT
AACAGCCACCCATCTTCAATCACAGTGATTTCTGAATTGTGAGGGAAGTT
ATTAGCATGACAGGTGTCTGGTTCTGGCCCTGTACGATTCCCATGAGTCA
AGCAAATTGTAAGGGCTGGTCTATATCACACCCAACCCCAAGGATATGTC
CCTCAAAAGTCTAGCCCAGCCCCGTCATCTTCAGCATCATCTGGGAAAC
CAGGTCTGATTAGTAGTCCTTTAAGGAATACCTCTTAGGCTCCCATTTTA
CTGCTATCACAGAATCCAATAAAACCCTTACAGGAGATTCAATGGGAAAT
GCTCAACACCCACTGTAGTTGGTGGTGACAATGACCATAATTTGGCTGTG
CTGGATTCAGGACAGAAAATTTGGGTGAAAGACCAGGTGACAAAAGAGC
TTCGACTTGCCCTAGCAGAGAGCAAGCCATACCATACCACAAAGCCACAG
CAATTACAACGGTGCAGTACCAGCACAGTAAATGAACAAGTAGAGCCCA
GAAACAGACCCAGAACTATATGAGGATTTAGTATACAATAAAGATGGTAT
TTCAGCTGAGGATGGAAAAGATGAATTATTCAATAAATGATGTTTGGCCA
ACTAGTAACCCATTTGGGAAAAAATAAAAGTATGGTCCCTACCTCACAGC
ATACACAAAAATAAATTCCAGACGGATTAAAATCTAAATGTAAAAAATAA
AGCCATAAGTGGACTGGAAGAAAATAGAGAATTTTTTTAACATCCGTAG
AAAGGGTAAAAACCCAGGCATGACATGAACCAAAACTGAAGAGGTTCTGT
AACAAATACCCCCTTTTATATATTGGGCTCCAACAATAAGAACCCATAGG
AAAATGGAGAATGAACACAAATAGACAATTTATAGAAGAGAAGGTTATAA
GGTGTAAAATTATATCTATCTGAGAAACAAACACTAAAACAATGTGATTC
TACTGTTCTCCCACCCATACTGGCAAAACTTAAGCCTGATAATATGCTGA
GGGGAAATAAGCACTCTTGTTGGTGAGAGTATTAATTGGCATAGCTTCTT
TTGAAAATGACATAGCAATACCTGTTAAAATTGCAAACATGCATGTCACT
TAATCCAGTAATCCCACTTCTGGGAATCAATGCTACAAAAACACTGACAA
GTATACAAAGATACATTCAAGAGTGTTCACTGGGCCGGGTGCGGTGGCTT
CATGCCTGTAATCCCAGGGAGGCAAGAGGCAAGACGATGCGCTTGACCCCAG
GAGTTCAAGGCCAGCCCGAGAAACACAGCAAGACCCTGTCTCTCTTTTT
TTATTTAAAAAATAAATGTTCACTGTATCAGTTGTTCACAAAAACAAACC
AACATGTCCATTAACAGGGAACCATTTAAATTAATCAAGTTCATGTACAC
AATGTATACCATCCAACTATTAAAAAGCACCTGATAATCCAAAGCACAC
TGAGACAGAATAATGCTATTAAAAACACCAGTAGTGAACACTGTGTTG
CCTATGACACCATTTTATTCAACATTTAAACAAATTTGTAACAGCAATT
ACATGAGTAGTGACAATGGCGTTTATGAGACTTTTCACTTTTATGTGGTT
CTATTTTTGTTATGCTTCTATATATACATCCATTTATTATGGAGTGTTAC
TTTCAAAAATCACAAATGGGCCAGTATTTATTTGGTGTTGCAAGGTGAGCA
TATGACTTCTGATATCAACCTTTGCATATTAGTTCTCAATTTAGGGAAAT
TACAGACATCCCTTATTCTAACTAACTTAAAACCCAGCATTTCAAACATA
CAGAATTGATGGGGAAAAAAAGAAGAAGAAAGAAGAAAAAGGGCAACAA
GCTTCAGATGACAGTGACTCACATCAAATTATTATAAAAATCTGTTAAAT
AGTGCCATCTTCTGGAGATACCTGGTATTACAGTCCAACTCCAGTTGATG
TCTTTACAGAGACAAGAGGAATAAAGGAAAAAATATTCAAGAACTGAAAA
GTATGGAGTCATGGAAAAATTGCTGTGATCCAAAGGCTACGATGATAGGA
CAAGAAACAAGAAGACTCCAAGCAGTAAGACACTGCTGTTCTATTAGCAT
CCAAACCTCCATACTCCTGTTTGCCCCAAGGCTTTTTAAAAAATAGAGA
CAGGATCTCACTATTTTGCTCAGGCTGGTCTTGAACTCCTGGACTCAAGC
TATCCTCCTGCCTCGGCCTCCTAAAGTGCGGAGATTACAGGCGTTGAGTCA
CCATACCTGGCTATTTATTTTTTCTTAACTCTCTTGCCTGGCCTATAGCC
ACCATGGAAGCTAATTAAAGACAATATAATTTAAGAGTAATGGTATAGTTCA
CTACATTGGAATACAGGTATAAGTGCCTACATTGTACATGAATGGCATAC
ATGGATCAATTACCCCACCTGGGTGGGCAAAGGAACTGCGCGAACCTCCC
TGCTTGGCTGTCTGGAACAAGCTTCCCACTAGATCCCTTTAGTGAGTGCC
TCCCTCATCTTTAATTATGGTTAAGTCTAGGATAACAGGACTGGCAAAGG
TGAGGGGAAAGCTTCCTCCAGAGTTGCTCTACCCTCTCCTCTACCGTCCT
ATCTCCTCACTCCTCTCAGCCAAGGAGTCCAATCTGTCGTGAACTCAGAG
CGTCACTGTCAACTACATAAAATTGCCAGAGAAGCTCTTTGGGACTACAA
ACACATACCCTTAATGTCTTTATTTCTATTTTGTCTACCTCTTCAGTCTA
GGTGAAAAATAGGAAGGATAATAGGGAAGAACTTTGTTTATGCCTACTT
ATCCGCCCCTAGGAATTTTGAAAACCTCTAGGTAGCAATAAGAACTGCAG
CATGGTATAGAAAAGAGGAGGAAAGCTGTATAGAAATGCATAATAAATG
GGCAGGAAAAGAACTGCTTGGAACAACACAGGGAGGTTGAACTATAAGGAG
AGAAAGCAGAGAGGCTAATCAACAAGGCTGGGTTCCCAAGAGGGGCATGAT
GAGACTATTACTAAGGTAGGAATTACTAAGGGCTCCATGTCCCGTTAGTG
GCTTAGTACTATGTAGCTTGCTTTCTGCAGTGAACTTCAGACCCTTCTTT
TAGGATCCTAGAATGGACTTTTTTTTTTTATCGGAAAACAGTCATTCTCT
GAACATTCAAGCAGGCCCCAAGTCTACCACACTCAATCACATTTTCTCTT
CATATCATAATCTCTCAACCATTCTCTGTCCTTTTAACTGTTTTTCTATA
CCCTGATCAAATGCCAACAAAAGTGAGAATGTTAGAATCATGTATTTTA
GAGGTAGACTGTATCTCAGATAAAAAAAAAGGCAGATATTCCATTTTCC
AAAATATGTATGCAGAAAAATAAGTATGAAAGGACATATGCTCAGGTAA
CAAGTTAATTTGTTTACTTGTATTTTATGAATTCCCTAAAACCTACGTCA
CCCGCCCCGTTCGCACGCCCCGCGCCACGTCACAAACTCCACCCCCTCAT
TATCATATTGGCTTCAATCCAAAATAAGGTATATTATTGATGATGTTAAT
TAACATGCATGGATCCATATGCGGTGTGAAATACCGCACAGATGCGTAAG
GAGAAAATACCGGATCAGGCGCTCTTCCGCTTCCTCGCTCACTGACTCGC
TGCGCTCGGTCGTTCGGCTGCGGCGAGCGGTATCAGCTCACTCAAAGGCG
GTAATACGGTTATCCACAGAATCAGGGGATAACGCAGGAAAGAACATGTG
AGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGC
TCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCG
GTAACTATCGTCTTGAGTCCAACCCGGTAAGACACGACTTATCGCCACTG
GCAGCAGCCACTGGTAACAGGATTAGCAGAGCGAGGTATGTAGGCGGTGC
TACAGAGTTCTTGAAGTGGTGGCCTAACTACGGCTACACTAGAAGGACAG
TATTTGGTATCTGCGCTCTGCTGAAGCCAGTTAGCTTCGGAAAAAGAGTT
GGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATC
CTTTGATCTTTTCTACGGGGTCTGACGCTCAGTGGAACGAAAACTCACGT
TAAGGGATTTTGGTCATGAGATTATCAAAAGGATCTTCACCTAGATCCT
TTTAAATTAAAAATGAAGTTTTAAATCAATCTAAAGTATATATGAGTAAA
CTTGGTCTGACAGTTACCAATGCTTAATCAGTGAGGCACCTATCTCAGCG
ATCTGTCTATTTCGTTCATCCATAGTTGCCTGACTCCCCGTCGTGTAGAT
AACTACGATACGGGAGGGCTTACCATCTGGCCCCAGTGCTGCAATGATAC
CGCGAGACCCACGCTCACCGGCTCCAGATTTATCAGCAATAAACCAGCCA
GCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTA
ATAGTTTGCGCAACGTTGTTGCCATTGCTGCAGCCATGAGATTATCAAAA
AGGATCTTCACCTAGATCCTTTTCACGTAGAAAGCCAGTCCGCAGAAACG
GTGCTGACCCCGGATGAATGTCAGCTACTGGGCTATCTGGACAAGGGAAA
ACGCAAGCGCAAAGAGAAAGCAGGTAGCTTGCAGTGGGCTTACATGGCGA
TAGCTAGACTGGGCGGTTTTATGGACAGCAAGCGAACCGGAATTGCCAGC
TGGGGCGCCCTCTGGTAAGGTTGGGAAGCCCTGCAAAGTAAACTGGATGG
CTTTCTTGCCGCCAAGGATCTGATGGCGCAGGGGATCAAGCTCTGATCAA
GAGACAGGATGAGGATCGTTTCGCATGATTGAACAAGATGGATTGCACGC
AGGTTCTCCGGCCGCTTGGGTGGAGAGGCTATTCGGCTATGACTGGGCAC
AACAGACAATCGGCTGCTCTGATGCCGCCGTGTTCCGGCTGTCAGCGCAG
GGGCGCCCGGTTCTTTTTGTCAAGACCGACCTGTCCGGTGCCCTGAATGA
ACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTG
CTATTGGGCGAAGTGCCGGGGCAGGATCTCCTGTCATCTCACCTTGCTCC
TGCCGAGAAAGTATCCATCATGGCTGATGCAATGCGGCGGCTGCATACGC
TTGATCCGGCTACCTGCCCATTCGACCACCAAGCGAAACATCGCATCGAG
CGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGG
CGAGCATGCCCGACGGCGAGGATCTCGTCGTGACCCATGGCGATGCCTGC
TTGCCGAATATCATGGTGGAAAATGGCCGCTTTTCTGGATTCATCGACTG
TGGCCGGCTGGGTGTGGCGGACCGCTATCAGGACATAGCGTTGGCTACCC
GTGATATTGCTGAAGAGCTTGGCGGCGAATGGGCTGACCGCTTCCTCGTG
CTTTACGGTATGGCCGCTCCCGATTCGCAGCGCATCGCCTTCTATCGCCT
TCTTGACGAGTTCTTCTGAATTTTGTTAAAATTTTGTTAAATCAGCTCA
TTTTTTAACCAATAGGCCGAAATCGGCAAAATCCCTTATAAATCAAAAGA
ATAGACCGAGATAGGGTTGAGTGTTGTTCCAGTTTGGAACAAGAGTCCAC
TATTAAAGAACGTGGACTCCAACGTCAAAGGGCGAAAAACCGTCTATCAG
GGCGATGGCCCACTACGTGAACCATCACCCTAATCAAGTTTTTTGGGGTC
GAGGTGCCGTAAAGCACTAAATCGGAACCCTAAAGGGAGCCCCCGATTTA
GAGCTTGACGGGGAAAGCCGGCGAACGTGGCGAGAAAGGAAGGGAAGAAA
GCGAAAGGAGCGGGCGCTAGGGCGCTGGCAAGTGTAGCGGTCACGCTGCG
CGTAACCACCACACCCGCCGCGCTTAATGCGCCGCTACAGGGCGCGTCCA
TTCGCCATTCAGGATCGAATTAATTCTTAATTAA
```

-continued

SEQ ID NO:8 (BstII linker)
5'-gtaacactgg cccaggaggc ctttctggtg acccc-3'

SEQ ID NO:9 (SfiI linker)
3'-tgacc gggtcctccg gaaagaccac tggggatt-5'

SEQ ID NO:10 (Forward PCR primer)
5' TAGTTCCTTCTGCCTGGAATAC 3'

SEQ ID NO:11 (Reverse PCR primer)
5' CAAGTCACAAGGATGGACTACA 3'

SEQ ID NO:12 (Stuffer 1)
TAGTTCCTTCTGCCTGGAATACTTCCTCATCTCACTTGCTTTCCTGCCTG
GCAGCTTCCTACTTGCCCTCTCGAACCAGCTCTAGGGTCACCACATCTCT
GCTTCTGAGTGCCTCCTCAGACACAGTCTGTATTTCCTCTTCCAAGCTCT
CATCACAAACATTGTGCTGTATTATATGTTTCTGTGTGGTCTTCCTTCTA
TGAGGAAGCCTTGGAAAGCAGGAGACTTATTTTAGTCTTCTTTATGTTTC
TTTTATTCCCAACACATTATGTCTGCCCCATAGACCTTTTCAATAAATGA
TTATTGAGTTAGTGACTCCTTTTACATGCTGACAAATGTGGCTCTTATTA
CTCCCCATTTCAGTATCACATATTTGTAAAAGTGAATCCTTCTTAATCGT
TTTACTTTTCTCCTAGTAAATTCCTCATCTATGCCTGTCTGCTGCTGTTC
TCTGTGCTGCTGGCCCTTCGTTTGGATGGCATCATACAGTGGAGTTACTG
GGCTGTCTTTGCTCCAATATGCTGTGGAAGTTAATGGTCATTGTTGGAG
CCTCAGTTGGAACTGGAGTCTGGGCACGAAATCCTCAATATCGGTAATAC
TGCTTTATACAACCCATTGGTCTGTAGCATGAGGGAGCAATATCTTGACT
TTTGTCACTTTTGATGAAGTAAGGACCATTTTATTTTCTACCTATCTGGG
GTCTTAGAACTATAGTATAAGCTAACAGATCTCTTCTGTGTTTTTGAAAA
TTTAGTCTTTGGTATGTATTTTCTTACAAAAGCAGTGCCATTTGGGGGTA
AGTTGCCAGCCAGCTCACAGATGCCTATATAATCCAAAATGCACCCAAAA
TACAGAACTGGTATGCCATACTAGACTAAGCAGCATGAAACCAGCCTGTT
TTTAGGAAAAGACACTCATATTATGTTTGGTCATGAAAGATCTTTCTCCA
ATACAGTTTTGGAACTGGGGCTCCCCTTGTCCCACCCTGCTAGTCCCAGA
CCTTTAGGACTATTAGCAGTGTAGGGGAGGTGGGTTGACCAGGAGACCAT
GAGTCCCTGAGACAGCAGCTGGGGAATGAGGAAAGTCAAAGATTGGATGC
CGAGAAGGAAAGCAGAGCCTTTGGGGCAGGGGAGAGGGGTACCCTTTAC
CGTTTCCAACTCTTGCCCTCCCTGCTCTTGGATGCCTCCGCTGGCCCAAA
TTCCTGGGAGTTGCTCACGCCAGCATGCAACCTGCTTGTTGCTGGGACCT
GCGAGAGTCTTTCCCTTCTCTGCCACAGAGACTGTAACTACATAAAGGGA
AAAAGGGGGACTTAAGACTGGGAGGCTATTATGAACCTCCACTGGGAAAA
TGAGGAGTACAGGAATTCCCAGAAGGCAGCTGCTCATGTGGGAAAAGTGT
AAAGTTGAAACTACCGCACCTTTTTTTTTTTTTTTTTTTTTTTTTTTTTT
TTGAGACAGAGTTTCGCTCTTGTTGCCCAGGCTGGAGTGCAATGGTGTGA
TCTCGGCCCACTGCAGCCTCCACATCCCGGGTTCAAGTGATTCTCCTGCC
TCGGCCTCCTGAGTAGCTGGGATTACAGGCACCTGCCACCATGCCCAGCT
AATTTTTTGTATTTTTAGTAGAGATAGGGTTTGACCATGCCAGGCTAGTT
TTGAACTCCTGACATCAGGTGATCCACCCGCCTTGGCCTCCTGAAGTGCT
GGGATTACAGGTGTGAGCCACCACGTCCGGCGACTACATCAACTTTTTAA
ATTTTTGTTTACTAAATATGAAAATGATTCAGATTGTGTAAATTACATAT
CACATACATGTCTAAGAACTGTAAAACAGTTACACAGAGAGCCTTGGCAG
GTGAGGGACATTCATGTATAGCTGTTTCAGAGTTCTTAGATTTTTTTGA
AAGATTGATGACCTGTGTGGCTGTATGTGTTTTATTTTTTTATGAGATAT
TTTCAGATATCTAATATTAATTGCTTCTCAAAGAATGCAAAGTTAAATAA
ACATTTAGCTTCTACTAATTGATATTTAGAATATATTCAAACTTCTCTTT
GTTGGTCTTATTTAAGATGTTTTGAGCAAGGAAAGGAATTGTGTATGTGG
GGTTGAATGTAAGGAATGTACAGGCGTGGTCATTCTCATGTTAACATTAA
CCAGTGGAACATGGTTGGGTCCTACAGGAATAACCTCTGATAGCATTTTC
TCTATGATCTAACTTCCGGTGTATTTGTCACCGACAATACATGATTATCA
TAAATGTTCATCTGTATTTTGAATAAACATTGTAGGCCTTTCAGATGCAT
TATAGAGGCTTTTCCTGATTAGGGGCCTTACCATTGGTCAATTGTAGATC
TGTTAAGGTTATTGTGGATGATACTTAGCTAATTAAACTGATTTTGTTTG
AGAACAGTTTTAACTCTTGTTCTTCTTTCTCTTTCATGTGCAGGTGTTAA
TTTATCTTAATGGAATAGAAAGGAAAATGAAAATCATTTATACGTTTTAT
TTGCATTTAAAAATAGCACCTAACAATAGTTACTACTATCTTGAAATATA
ACTGGCAGTTGTTCATAGAACTAGAGTTATTTTTATAATATTGTGTGAAG
GGTGGTTTACATGGTTTCTTGAAAAATGAGGATCATGACTTAAGGGGT
ATTTGCCTGGTTTTAGCAGCAGAAGCAAATCAGCTTGAATAATCTTGGAA
GTAACTCTTGTTGTTGAATTTAAAGATGTGAACAGAAGTGTTTATGTACA
TTGTCAGGGAAATAAGAACTGGCTATTACTTTTGAGAATATCCTTATACG
GTTAAAACATTAAATTCTGGTTTGGGTTGTAATGTTGATTTTGTATTATGT
AGTAGTTCTTCGATGTTTCAGAGATTGCCTACGAAAGCTTAGGTTTAAGT
TAGCTTTCTAGCTGATTTCCCTTTGCTTTTGTCAAATTTTCAAGTAAAAT
TCAAAGTATAAATATAAGTTGGTATTTGCCCTGAAGTGGTTGCTTATAGT
GGAGATTCTGAACTGAGGGTGTTTTCTTCTTCTCCCTTTTTTAGAGCA
GAAGGAGAAACGTGTGTGGAGTTTAAAGCCCATGTTGTCAGTGGGCAT
CCACTTGCTCTTGTTGATGTTTGAAGTTCTGGTCTGTGACAGAATCGAGA
GAGGAAGCCATTTCTGGCTCCTGGTCTTCATGCCGCTGTTCTTTGTTTCC
CCGGTGTCTGTTGCAGCTTGCGTTTGGGCTTTCGACATGAGAGGTCACT
AGAGGTGAGATTTCATATATTTAAGAATGTTTTCCACTTTGGGAGGTCAA -continued GGCAGGTGGATCACTTGAGGTCAGGAGTTTGAGACCAGCCTGGCGAACAT
GGTGAAACCCCATCTCTACTAATAATACAAAAATTAGCCGGGTGTGGTGG
CATGCGCCAGTAATCCCAGCTTCTCCGGAGGCTGAGGCGGGAGAATCTCT
TGAACCCAGGAGGCGGAGGTTGCAGTGAGCCAAGATTGAACCATTGCACT
CCAGCCTGGGTGACAGAATGAAACTCCGTCTTAAAAAAAAAAAAAAGAA
TGTTTTCAAAAGTAAAATATTTTGCTCAGTTATTCAGATGTCAATTTCTT
ACCCTTTGTTAGGAAGAGCTTGATCATTACCAACTCTACATCATGAGACA
ACAAGGCAACAAAAGATGATGGAAATAACAATTTTTCTTTCTTCACTTAG
AACACTAGCTTTTCACCCAGGACATCAGCCTTCTCCCAGCTTCACATCCT
GTATCAATCAGACAGAAACAGAACTGATAGGTTAGATACAGATATATGTA
TAAAGAGAGTTAAGGAACTGGCTCACATTACTGTGGGCTGGCAAGTCTG
AAATCTCCAGGGCAGGTGAACAGGCTGGAGACCTAGGAGGAGTTGACACT
GCAGTCCTGGCACAGAATTTTTCCTCTCCAGGAAACCACAGTTTTTGCT
TTTAAGGCCTTCACCTGATTGCATGAGGCCCACCCATGCTATGGAGGGTA
GTCTCCTTTATTCAAAGTCAGTACCTTCACTGCAACAGCAAGCTTAGTGT
TTGATTAAATAACTGGGTACTATAGCCCAGCCAAGTTGACACTCAAAACT
GACCATCTCCCCACCTCAGACCCCCATGATTTAGCACCTCCCCCTGCTGT
GGTTAGGTTATCCTGATGTGCCCCTGTGTTTGTTTATTCATTCAATAAAC
ATTTATCAAGTATTTACTAGATGCCAAGCCCTTTTTCCCTAAGCATAGAG
GATATGCAGATGAATAAAATACCAGGACTAGTAATAATAGTAATGAAAGT
AATTGCAGATAACGTTTATTGAGCATTCTACTGTGTGCCAGGCATTGTGCG
AGGCACATTACATGTGGTAGTTTTCTTACTAACTAACTCTGTGAGGTAGG
TCCAGAGAAGATAAGTCATTTGTTCATGGCCACATGTGAAGGGGCAGGAC
CAGGATTCCGTTTGAGTCAGCCCGACTCTAAAGCCCGGGCACATAACTAC
ATAATGCATAGAAGCTGAGGGCCCAAAGCTGAATACTGATGGGTTGAGG
GGAGAACTAGAGGCTGTAGATGCCTGGTTTTGAGCCGTGTGGATGAAGAG
TGAAGGGAGAAGATGCAGTTGGCTTAGGAAGTAAACATAGCAGCTGTAG
GGTGGGTCAGGCATATAAGCCTAGACCCCAGGTATGGGCGTGAGGGGAAG
GTATGTAGACAGAGGGACGGTGATGGAGCAAGGCCCTGTGGGACTCAGGG
AGAATAGGACCTAGAGCACCAGGAAGGGTTTGGCCTTGAACAGGGGAGC
TATTCCCTGATTTTCATGCTGGTGGAAAGGCCACAGCATGGGTATAGTGG
TAGGTAGGAGTGAGCCGTGGAGGGAGAGTATCTGATGGTCCACTTTCACC
CTCCCTACAATTCCCAGTTTATATCAGGGACTTGAGCATCCATGGATTTT
GGTATCCACAGGGGTCCTGGAACCAATCCCCCACAGATACTGAGGGACA
ACTATACAAGGACTAGGACTGCATTGGGCCTGAATTACAAAGTAAGTC
TTTCATATATTCACACTCTAGGCATTCCTGCCCTTGGAAGAAACAACATA
CCAGGAGCTGAGCTCCCTCCTCCTGTGATGCAAGAACAGTACCTATGTTG
GTGAGGGGGTGGTCTGGAGTAGGCTCATACAGAGATGGGAAGGAGGAGTT
GAGGGTTGCCAGGAGACCCTGTGTTGGGAGGGAAAGGGATGGCATTTTTG
GGACACATTGAAGCCTAGAGGCAGGAAACACTCCATCAGCTGAGTGGACT
GTGGCGATTCAGATCCGACGGGAGCACAAGGTGGAAAGGAAGGAACTGTG
GGAGTTGAGAGAGGAGGAGCCTCTACAGAGGGATTGGGGCAAATAGGGG
CCACGTCCTCAGCCCCACAGAGCATGCTGCTGAAGTGCCCCAGGCACCCCAG
TGCACTCACAGGGCACCAGGGGATAGTGGACATTTTGAGGAAAACAGTAA
TACCTGACATTTGTTGGGACACCATACAAACTACTAGCTTGAAATAGTTT
ACAGGTTTATTTTTAGGCCACACTGCATTCCTTTCAGTGACGTCGTATCT
TTAAGAAGCTGGGTTTTCAGCAGTTGCTGTGAAAACAAAAAAGGCTAATG
CTGTGTGAAAATCCGGGTGAAGAACAGGTAACGAGTGGGAGCACCTTGTC
TGATTCCAAGGCGTGGGAAATGGTGAGCTACCTGACAGGCACACGCATCC
CACTGGGAATTAGTTTTGGTTATTTAAGAATAATAATTAACATTTTTCTTT
AGATTTATATGAATTATTTTTTCTAGTGGCTACTTAGAAATACTTACTAA
GTTAGATGTAATTACTTAAATCAGTGCAACTGTTGGCATTCCCAGCCACA
TTAGGGATTCTTTTGGCCTAGAGGTCTATGGAGGAATTACTAAATTCCC
CATGTACCTATGTACTGAGAACTTTTGGGAAGCTCTGGGCCTGGTCCCAG
ATTTCAATTTTGTGGGCAAGAATGTTTTACCAGAGTGAGGAGCAGCCT
GCAGGGCGTTTGGGCTGGAGGCGGGAGGTTAGTAAGGGGTTGCTGAAGTG
GTAGGCGGATGGTGCCGAAGAAGGCCTCACTAGGCAGTCATCATCAGGAT
AGGAAGTGGGCACGGGATTCAGGAGAAATCTGGACTTTACAGTGGACAGG
ATGTGGTGACTGAACGTGACAGTGGGGAAAAGAATGCAGGGTGATTCC
CGGGCTCATGCTTGAGAAATGAGCCACTGTTGTGCCTCCAAGTGACAT
GGGAACTGTATAGAAAGTGACATGGGAGGCTATAGAAAGTGACATGGGAGG
CCATAGAAAGTGACATGGGAGGCCATAGAAAGTGACATGGGAGCCATAGTGACAT
GGGAGGCCAAGGGAGGCCATAGAAAGTGACATGGGAGCCCATAGTGACAT
GGGAGGCCATAGAAGTGACATGGGAGGCCATAGAAAGTGACATGGGAGG
CCATAGAAAGTGACATGGGAGGCCATAGAAAGTGACATGGGAGGCCATAG
TGACATGGGAGGCCATAGAAAGTGACATGGGAGGCTATAGAAAGAGGAGA
TACAAGGTTCTAAGGTCAGGCGATAATGATCTCTATTTGGGACTGGCTTC
ATTTGAGGTGCCTTTAGGAGAGCCGAGTGGCCTATGCACAGCTGGGTCTG
CTATGCAGCAGGAAGGCTAAGTTGGACAGATGTGAGAACTAACGATGA
AGGAGGTAATAATGCAGACCAAGGGTCTGGTTGAAATTTCTTCTCCCCCA
GTCCAGGGTGCAGCGGGTGAGTGAAAATATGTGTGTTTGTGTCTGTCT
TCCTAGTCGGGAGGAAGAACTGAGTTTGTGGCTCTGCGGAGCATCACCAT
TTAAGGAGGGGAGAAAGGAGAGAAGGAATTACCAGAACACTCCAGAGG
GCTCCAAGACTGTATGGTGGGATCTAGATGGCCAGGAGGAGGGGAGCAAA
AAGGAAAGAGTCATCCACAGTATCAGTAGGATGCCAGTTGAAGTGTTTTT
GCTGCCTCCCGGTTATCGGTGACTTTGATGAAAGCTGTCTTCTGGTGGTC
ATGGGGTGGAGGCCAGATCACAAGGAAGCTGGGAATGGTAGATGAGATA
GTAGGGGCTTGCATATTCATTACTGTCTGGCAGAGAGAAACCTGAGGCTA
AGAGGGGTCTTGGATCAAAGGATGGGTGGGTTTATCTGGTTTCGGGGCT
TTTGTTTTTAATGAGAAGGAGTCATTTCTGTGCTGCTAGGAGGGATCAAT -continued

```
GGAATAGGTGGGGTTAAAGATACAGTACGGAATCTACAGTTGATGGCTTG
ATGTGACAAGGTCCTCAAGGAGCCTGAAAGGAAGGGGTGGGGTCCAAGGG
CAAAACCGAGGTATGAGAAGAAGGATGCACAAGGATGGTTTCGAGTAGAC
AGTATTGTTGGTAGGGACATGAAGGAAGTTTAGTGGTCTATTGCAGCTAG
CCTGTGTTCCCAGTGAACCTGGAAACAAGGTTCTCATCTGTGCTCAGGG
TCAGGCCAGAAAGGGCAAGGCAGCAGAGGGGCAAGGCAGCAGGCTGAGCC
CCATTTCCCCTTGCCATAATACTGCTGTGCCCCTCTGGTACCGAAAATCA
GGAGTTTCCAGTGCAATATAATATTATACAAGTTACACTGTATTATAATG
TGTATTGTCTTTTAGTGTGTTAACCAAATTACTGCAGTATTAAATGCAAA
TTATACTTTGTTTAACTGATTCTTCTCTTCATTTTTAGTTAGAAATCCTG
TGTTCTGTCAACATTCTCCAGTTTATATTCATTGCCTTAAGACTGGACAA
GATCATCCACTGGCCCTGGCTTGTATGTAACTTTTAAAATGCTTAAATAA
ACTTCTTTTTATTATAAAAGTAATTCATATTCACTGTACAAAGCTTGGA
AAAGACGGACAAGCAGAAGTAATAGCCTAATAGTCACCCATAATCCCACC
ATGGGGAGATAACATGGTTAGTGTTTTTATGTCTGTGTTTATAGAAACA
GTTTGGATATAACTGTGTGCACGATTTGTATCCTGATTTTTTGTTTTA
ATGTTGTATCATAAACATTTATCATGTTAATAAAAGGTCTTTATAAACA
TGACTTCTAAAGTTTAATTGATACAAAATATTCTTCAAGTGCATGTATCA
GACCATCCTCTTATTTCTAAAATATGGTATTTCCATTGTTGCCAGTGTTG
AATGATTTTAAATCATACTGCAGTATATATGTTTATGCATTAAAATTTTT
GCCTTTTGTTTTTGGTTGTTTTCTTAGGAAATAGTCCAGAAATAGTGTT
ACTGAGCTAGAGGTTGGGAACTATTTGAGATTCCTATATACGTATACTGC
ACTGCCAACTTGCTTTTCCAAAAGCCATACCTGGCCAGGCGCAGTGCTT
ACACTTACAGTCCCAGCACTTTGGGAGGCCGAGGTGAGCTGATCACTTGA
GCTCAGGAGTTGGAGACCAACCTGTGCAATGTAGCAGAGCCCTGTCTCAA
AGAAAAAAAAAAAAAAGCCATACCCATTTACACTCTTGGTGGCTGGCA
TCTATGTCATGCTTCTAAACTGTGACTTCAGTTACTGGGCATTTGGTTGA
AATTAACTGTGAATAAATGGGTAGATGGATGCAGAGATAGAAAGATAAGT
GGCAAGGTAGAAATTAGAGAACACAGTATAGATTCCACTATTAAATGCAT
GGAAAAAAGATGGAGACTAAAGGCAGAAGAGTTCCATTGCCACTGGGAGG
TAAGGTCATGCTAGTGTTTTTGTTCGGTTTTATTTTCTCTGTTGTTTGAT
GTATAATTTTGCATACAATATATTTTATGTATTAAATATAGCTACCCTTA
AAAAGTGAAAAGTATAGTAAAGAATTGGGAGCAGAGAAGAAATGAAGGGA
ACCTAAGTATACTCCATATTTAAAGATGGAATAATCACTTCTGCCCAAA
GTCTTTGATAAAACATTCATAATAAAAAATATTCAGTCACTCATCCTACA
ACTTCACAGTGCTGTATCTGGAGAATGGTCATTGGGTTCAAAACTGTTTC
TGTTGTGACGTGAAGGAAACATATCTAAACAAGACCAAATTTTTTCGTAT
AAGATACTCTCAGGGAAAAAAAAGATTAGTAATTTTGAGAGCTTTCCAA
AATGAGAAGAAAGATTTTTCTGCCCTTCATCCTCTGTAGATCCCAGTTG
ATGAAGCAGTCTGAGTACATGTTTCCCATAGTGAGCAAGAGAAAACAAGG
AAGCCTATTGAGATCTAACATTCCACCCATGAAGGGAACTTCAGTAAAAA
GGAGAATCTCATCACAGAATGGGGAACGGGGAAGAAAGGCTGTGCATAGA
CTCTGCAGAGAAACCTACAATCAAGACTGGTCAGGAGAAGTAAAATTCG
TATGCCAACTCAAATCATAGATCTAAAAGAAAATGTAAAACTATAGATCT
GTTAGGAAATAACATAGGACAGAATCTTTGGGGTTTGCAATTAGGCAGAG
AGTACTTAGAAATGGCACTGTTAATATGGTCCATACAGAGAGAAATCAT
AAATTTGGACTTCCTCAAAATTAAAATGAAATGAAGACAGGCCACAGACT
GGGAGAAAATATTTGCAAAGCACACATCAAAACACTGACTTGCACCCAGA
ACATACAGAACTCTTAAAAACTCAAAACTGCAAAAAGAAACACCTAAA
AATTGGCAAAAGAGTTGACAATTTGCGAAGGGGATATACACATGGCGAAA
AGCACAGGAAAAGATGCTCAACGCCATTACAGGTTAGGGAAGACAAACT
ACAACCAGGATGAGGGCCCGAAACACATGGCTTCAGAATGGTGAAACTCA
GCAACACTGACGAGGCCACGTGCCTGGGAGGATGCAGAGGAACTGGGACA
CTCCAGTGTTACTGGCGGGAAGGCAGGTGGTACGGGCACTGTAGAAAATG
GTTTGGCCATCTCTGATGCAGTTAAAAGCGCACTTCCCGTGGCAGCTTGGC
TGCCCCACTCCTGGGTATAAGATTTACCCCCAGAGAATGAAAGCGCGCA
GCCTTGTAGAAACCCACACACCAGTGTTTGTAGCAGTCTTGTTTGCATTT
TGGATAGCGGCCTTGTTTGGTTTTCACAAACCACCCTCAGCGGACAGTCA
GATAAACTGTAGGCATCCATACAATGGAAATTACCACTCAGATCTGAGGG
AACGACCTGTGGATACAGGGAGGGAACAACTTGGATGAATCTCATTAGAG
ACATTATGTGGATGGCGGGAAGCCAGTCTCAACAGGTTACTTGTCTCGCG
ATGCCATCTACATAAAGTTCCAGCAGAGACAAAAGTACAGTGAGAGAACA
GATCAGTGTTTGCCGGGGCTAATGGTGGGGACGGTGGATAGCTCACGGATGAAGGGA
CAGCACGGAGAGTTTTGCAGGGTGACAGACCTCTTCTGCATCCTGCCAAC
GGCTGTGTGAATCTACTTGTGTGAAGACTCAGGGAACTCACACCAAAGGA
AGACGGTCACTTTTCCTACTGTATGATAGATAATTAATAAAAAGGGAGAA
CGGAGGAGTGCGTCCCAGGAGGCAGGGCAGGAGGGCGAGACGTGTCAC
AGGGGAGCCTGGCCAAGTGGCGCCCCCGGGAACTCGTCCTCTGGGCTTGTG
TGTGGATGAGACAAGGTCTACCTGGTACGACAGGGACATACTGGGAATGC
GCCCTTGGCGTGGAGGCGGGGACCCGGCAGCGCTACGTATCCAGCATCAA
CCTGTATCCAGCATCAACCCGCCAAGTTCACTAACTTGGTAGGGGTGAGG
TTAGGGATCCTTAGGAGCCCAGGCAGCCAGACTTTCTGGGGAGCCCATTC
CCATTTGTGTTGCCAAAGTACCCCAGCAGGTTGTGGGAATGTTGCCTGT
GAAGAGAGTCTGTTGGGGTGAGATCTTGTGTGTGTGCACAGGGTGACAGT
TGTGTCCCATTTCCCGGCTGTGATGGCAGCAGAACCTAGAGGAGCC
TGAGAGAGTGTGGGAGAGTGGGCCTCTGGAAGAGTAGAGGCTGCGGACC
AGGTGCAGGGCTGTCTGTCACCCAAAGGAAGAGGGAGTGATGACTCACTG
AGCGTGTGTGTCCCTGGTGGCAGCAGGCCCCATAGTGAACATACCCATAC
CTTTTCTGTCCTGAGCGATGCTCCCAGCAGTCCTGGGAGATGGAACGGTC
CTTATTCGGCTCACAGGAAGGACCGCCTTAACTGGACAGACACAGCAGG
```

-continued

```
TGCTAAAGATGCCTTCCATCAGAGGCCAGGTTGGAAGCTCTAAAGAGACT
TCTCTTGCTGTTCTCTCACCCACCCCCAGGTTGTGTGTGTGCCGCTGTGG
ATTCTCATGTCCTTTCTGTGCCTGGTGGTCCTCTACTACATTGTGTGGTC
CGTCTTGTTCTTGCGGTCTATGGATGTGATTGCGGACAGCGCAGGACACA
CATAACCATGGCCCTGAGCTGGATGACCATCGTCGTGCCCCTTCTTACAT
TTGAGGTAAGCGTTCCACGGGAAGCCTCTTCAGCCCCTGAAGCTTGCGCT
TCCCCTGACAGGATTCTGCACCCCTAGAAAGGCAGCCTCTGTGCCTCGAG
CTCACAGTGAGCCCACTGCAGGAGAGGGGAGAGAACACAGCCATCTCCGA
GAGGGAGCTTCGGTGAAAGGAGAGCATCCTTCCTTTCTCTTGGGGGCAGG
ACGTGGGGCTGGCAGGGAGAAGAGTGCACCTTTTTAGCCATGGTGCCTCT
GTATGGCTCGAGTTTCCACTCTGGGGAAAGCAGAGTGGGATGTCAGATTT
GTGTATTGGAGTCACGTGGAGAATTGTAGAATGGGAGCTGTTGACTCCTT
AGAACAAACACCCGGAGGAGTTTGCCATAAAACTGCTGGCACTGGGAACT
TTTCAAGTGGATAGGCTATTGCCGAGCTCTGAAGAGGGACATAAAAGCTC
ATTTCGAGCTTTCCGCAGGGATAGGTGGTTTCCTGCCTTTTTCTGGCGGT
GCTGATGTTCCCTCTTGTGGGAGCTCACGCGGGGTGGGTGGTGGGGAG
GAACTGCCTAATGAAGTCTGGCTTCCGGCTCTGCCCATTTTCGGTGCTGG
CATCAACCGGGACTATGTCTCTTTCTTTAGATTCTGCTGGTTCACAAACT
GGATGGCCACAACGCCTTCTCCTGCATCCCGATCTTTGTCCCCCTTTGGC
TCTCGTTGATCACGGTGATGGCAACCACATTTGGACAGAAGGGAGGAAAC
CACTGTATGTACTCAGCATTTCAGAAGTCCTTGGTGTGTCTGGGGGGG
GACCAGGGGGTGGGGGTGGCGGATAGAAGTCTAGGAAGGGATGAGTCCC
CGAGGGCCCCAATTTAGAAGCTTGTGTGGGAAAGTGAGGGCTGAGGAAAT
TCTGGGACCTTCTAAGGGAAGGGCATGCCGTAACTCTGGTGTTCTGCTGG
CCTGCACCGGGACTTTTCTCGCAGTGCACGCTGCCATTTGAGGTAGAACT
AGACACGGCAGGCAACCTCTCAGAGATCCCGTTCCCTCCTCTGCAAAATG
GGGATCAAGACAGATTCTTCCCAGGCCCGGGAGGGTTTGATGGAAAATCC
ACATCTCCCACCCAAACCTGGGATTCATCCTAGGTCCCTGTTGGCCGCTC
TGCCTCCCCCATATCCTTGCTGCCATCACCCGAGTCTTGCCTGTCTTGCC
TTGCTAACACTCTATTCCCCTCCACCTGCTTGCTGAGGCAGACACTTCCA
AAACGATCTCTGCAGAGGGTGCCTTCCTGGCAAGGCTGTGGGCTCCATGG
CACGGAAGCCCAGAGCATTGCCCTTCGGAAAGCCAGTGGGTTTGGGGGCA
GGGCCTCACTGCAGCCCAGCAGCCCGGGCTGTGCTTGCTGTTTGTGCCTC
TGCCCCCTACCCCGCACCCGGGAGCAGGGAGGGCTTGCACCGAGCTGACA
CTCCAGTACTACAGAGGAGTAGTGGGACTGGGAAAGTGGCTTTAAG
GTGGCTCCATGAGTTCAGGCCCCCTCCTGGCCAACCCGTGCATGACTACG
GCCCTCACGGATTCCAGAGGGTGACAGAAATCTTGTTCTTGGGTGGCACT
GTCATCCATGGTTTATCCTGGCTGGAGAAGATTAGCGGAAGACAGCGTA
GTCTGCGCACCACAGATATTTTGAGACTCACTGGAGTAGTTCTCAAA
TTTGGGCATCCAGCAGAATCCCAAAAGGGCCAGGAAAAGGGGACCGCTGG
AGCCCACCCTAGCCCGACTCAGTTTCTGGAGGTCTGGGCTGGGGCCCGAG
AATGGCATCCCTAACTAGGCCCCGTGGACGCTGTCCCTGCCGGTCCGGAG
ACCCCAGTCCAAGCACCACAGAGCTAGCATTTGCACTTCTTCCCCATTTT
GGGTACTCAAGCCCTGTTCAGGCTTTGTGACTCAGGAGTCTGGATAAAGT
ATGTTATGACATTGTAGGAGTGAAACTTCTTGTTACGGAAAGAAAGTTAA
CAGGAAGGTCAGTTCAGCCTCGTGTGTGAAATAAAAAATTCTTATTTTTC
AGGGTGGTTTGGTATCCGCAAAGATTTCTGTCAGTTTCTGCTTGAAATCT
TCCCATTTCTACGAGAATATGGAAACATTTCCTATGATCTCCATCACGAA
GATAATGAAGAAACCGAAGAGACCCCAGTTCCGGAGCCCCCTAAAATCGC
ACCCATGTTTCGAAAGAAGGCCAGGGTGGTCATTACCCAGAGCCCTGGAA
AGTATGTGCTCCCACCTCCCAAATTAAATATCGAAATGCCAGATTAGATG
CGACTTCCGGGGACAGAGCTTAAGTGGACTGGGACGCACTCTCTCCGCCT
TCCTCTGCCCCCTCGTTCACCCCGCAGACCAGAACCAGTACTGGAGCTGG
GTCTCCAGGTACGTCCATCTCATGCCTTGTTTGCATCCAGCGCCTATCAG
CCCACTCACCACGACGGGACGCGGAAGTGGCAGGTGACGGGGTGTGTGCC
AGCAGATGCGGATGCCAGGAAGAGTGTGAGAACAGGGGTGGGATTACCGT
CTGTCTGGGAGGGGCTCCAGGTACCCCTCTTCCCCGTCAGACCCACTGGG
AGATGGCTGCTTGCCAGGCCCCCAGAAGGAACATCTGTCTATACGGTGCT
GAAATCCCAATCAAAAGTATTGTTTAGAAATGTATTTCTCCACAGGGCTG
ACCTCCTGCCAGCTCGCTGAGCACTCCCAGGTCCTCAGCACTCCCAGGTG
TGGCTGGGGCAGTCAGTAGGAACTGTAACTATGTCTCTGATGCACCACGT
GTTTAGACACAGCACAGTCCTTTTTTCTGTTCCTACTGTGGAAGTAGTTT
CTCTTTGGGCATGCTGACAGCAGTTTTTCATAGCCTCACGGATGAGCCCT
TTCTACGGGAGTGACTCCATGCTTGTATACAGAGTATTTATACAAATGTT
TTAGCATCTTCATATGCGGTGTTAACCCGTAGTTCTGTACAGCATATTCT
GTTCAAGTATTTTTTACAAGCTTGTGCTGTAGGCACATGCCTTCTGCTG
CAGAAGTGGACGCCCGTGGCACACTCTCCCCCCCCCCCCCGTGGGGGTGCCA
CGCCTTCATGCGACATTGCCACTTCTGCCCTGGAACTCGTGCAGGTACGT
AGTAGCTGCTACTGCCAGAACGGCAACACCAAGCAAGAGGATGGTCCATGC
TTTTTCTGACGTTCTCAGAATAGTGGCTAGCTTCAAACCTGACAAGCGCTG
CTTGAAGCCGGAACACTAGAGAAGTTGCTGAGAGCAGAAACGGCCACGC
GGGTCACGACTATGCGTGGGAAAGTCTCAAGCTTCCCTCCTGCCGCAAC
AAGAAGGCTTTGGAGTAGGCATGATGTTTTCACGTGTGCGTGCCGTTTCT
CCAAGCACTGCAGGTTCCACCGTGTGTCAGAGGCTGCAAGTTTAACATCC
TCCTGCCTGAAAACAAATAGGTCCTTTGCTGAAAAGAGGGTAAAAAAAGA
GCTTTGATCTTCTCAGCCAGGAGAAAGGGTGGTGTTTTCACGCGGGCAA
CTGCTCGCCGGCCTACATGGGGTTAATTCAAGTCTGCTGCGAGCACGACT
CCGCCCTTGGCACTGGCCTCCAGCAAGCCCTGTTCTCTTTGGGGTACAGG
GGAACGGGATGGTTTAGACTTTCCTGCTCAGTGTGTAAAAAATGTAGCTA
AAGCCACTATTTTTGCTCTCCTTAAGCTGTTCAATAAACCGGTTCCTCAT
```

-continued

TTTACACGTGCATGATGTGTATCTTCTTTGCTGGATGGGCCAGGAAACTG
GAGTGGTCCTCTCAGCCAGCCTCAGAGGAAAGAAATCTCTAGCTGGCACA
GGCAGCCAGTGAGTGAGGCTGGCGGCTGCAGGGGCACAGCCTTTAGAATG
AGTCCTTCAGTGCACAGGTCCCAGGGTATACGGGGTAGTGGGAGGAAGGA
GGGGACGCCTCGGAGATGCCACTTGGCTGGGCTACACCTTGCCACACT
TGTTACTGCTTAGGAGGCTTTGTGGAGTGTTCCTTGGGTGCTACGACAAT
CTGCAGCAGACACTGTCCTTTCACCGCTCCTGGTCCTCGTTTGCTCCCCA
GTGATGTCAACAGCTGAGGACTGCTCACGCTGCAACAAAAGGCTCTGCAG
TCGCTGTCTAGCTTGCCCTAGTCGTCTCTAGAGTTCTGCCTGAACTGAAA
CTCAAGTGGGGTTCAGCTCATGACTTGTGGCAATTGACCAGGAAATTCAC
CAGTTGCTGTGGCTGGAAGGATTTTCAGTCCTGTGGGTTGTAACCAGAGG
CCACAGGTGGATTCTGCCTTAGGCTCATGAGATTTCCGACTTGCTGTTGA
AGAAAATGCCTTGTGAAGTGACAACAGTAGCTCTGACCCAACTGCCGGTG
CCTCGCTAGTTCCTATACGTCCCACTGGATCCTCACAGCCCCGGGAAGCA
GGTGCTACTACTCTTATCCCCGGGAGGAGACAGAGGCCGAGAGAGGTTAA
GTGACGTGCCCAAGTCACACAGCTCGGCAGCGGCCGGGTTGAGCATCAGC
AGTCTGTTTGCAGACCCCTCACTGTCACCCCCTGAGCCAGTGCGCTTGG
GCCCTGCGGTCAGGATGTCTCAAGCGTGGAGGCATCACCGGTTCGTGGCA
GTCTCTGGAAGGTCACTGAGCTCTGTGCCCAGAATCGAGTCGGGGAGTC
TGTGCAGAGGTGGCCCTGTGTGTGGGGACAGTGTGTGACACAGACACTGC
TTTGGATGGACACCTCTCCCGTGACCTCCTAGCATCCAATCCCAAAGGAA
CAACTGTTGCAGAGATGGACCGCTGGACACAAACCCACGTGCGTTTCTCT
GGAGACACTGGCCAAGGAAAACAAAACATGCTCGAAGGCCAACAGCTGCA
TGCCCCACCGCGATGTGACCGCAGACACCCGGGGTGTAGAAGGGTCTCTG
CCTGGTGGGGGGACACGTGCAGGCCGAGGAGAGGGAGGGAAGGAGGCTGCC
TCCGACTCCCCAGTGGACTGCATGGCGACGGCTGTGGTGGGGCAGTCAG
CTAAGCCATTTGCCTAAGGGGCTGTGGGGCATCTGCGTGCTGGGGACCGA
CAGTGTGGGTGTGTTAGGAGGATCTGTATGGAGCACATTGCTGCCTCTGG
GTAGGACAGGGTGGAAAGGGTGGCGTGGCTACAGCCTGACCCATGGGCAC
CGTCTACCGTTTGTTCTGTGCTTCCGAGTGTCAGTCATGTGCTGGGGTC
TGTGGGCCCATGACTCAGACGGTGAGCTCTGACCTTCCTGAGCCAGGGCT
TTGCTGTAGTTGTGCCTGGCTGAGGAGCTCTAGGACAAGGGGACCGCTCC
AGGTCTGCATCTACGGTGTGGCAGGGCCCCTCGGCACTCTTGTGCACTAG
TGTCATCTTTCCCATTGAAATGACTGTGAGGACCAGAATGTGCACATCG
GATGGGCAGCTACTTGTCTGCCTTGGCCCTTTATTACACAACTTGCTGGG
GGTGGAGATGCCACCCCCCGGCAGTGAGAGCCCCTTTATGATGTCATGGG
GCTGGTTACATGACTGCCAAGGGGTGCTGCTGGCCACACTGCACTAGCAA
GTTTGCCAGATGGAGGACAAGCGATCATTGAGTATGGCTCGCTGTGAAGA
AAGAAATTCGAGAGGACAGGATCATGGCTTGGAAAGGGTGCGTTTCCCTC
CCCAGTTGCAGTCAGAGACCTACCTTCACCCAGCAGATCCTTCCCTGCC
TGGGACGACGCGGGGTCCACTGGGAGCCCTAAGTTGAGGCTGCTGACAGA
AGAAATCGCTTTCAACCTCTGGCCGAGGAAGCTTCAGTTCAGAAGGCCTGC
ACCCTGACGGTGACGTCCCGCCCAGGGAGAAGATAATCTCCTCTCCCTC
CCCTTTCCACAGAAACTGTGGAGACTGGTCAGCAGCAACCAGTTTTCGTC
CATGTGGTGGGATGACAGTGGGGCTTGTAGAGTGATCAATCAAAAACTCT
TTGAAAAGGAGATTCTCAAAAGGGACGTCGCAGACAAAGATGTTTGCCAA
ACTTCTGATAAAGAGCTTCTTCCGCGAGCTAAACTTGTATGGCTTCCGAAA
ACGGCGTCAATGCACTTTCAGGACCTTCACCCGCATTTTCTCCGCAAAAA
GGCTGGTCTCCATCTTGAATAAGGTAATGAACGACAAGCCTCTGGAGGGG
TTAAGTCGGTGGCTCTGGGGCCTGGTCGGGGTGGAAGTCCCAGGACTGCC
TCCTGGGAAGTGGGCGAGCTCAGGCAGGGTGTGGGGCCATCGCTGTGGGC
CTGTGTCCCCCTCTGGGTGGAGGTGACATGAACTAAGAGTGAATGTGGGG
AGAGGGCTGAGGATGGTGCGGGCCCCTCTCGAGTGTGTAAAATATCACAG
GTGCCAAGTAGCCGTATCTGCGTGTCGTCCTCCCCGGGGCCAGCCATGTC
ATCTGGTGGTTGCTGTGTCCCCCTGACTCCACAGCACATTACCCTGTGAG
GTGAGCAGGCCAGGGGAGTCTGGTATTTGTACCACTGTCACCCTAGCTGG
TGTCTGGAGAGGTGCTCAAGTGGAAGCACTGAAGGGCGCCTGGCGCAGGA
GGTGCAGATGCTCCTGCTGCCCTTGGTAGGTGGGCCCCTGGTGTGGAAGA
GCCAGTACCCAGGGCCTCCAACCCAGCCAGGGGTCTTCTGTTGCCAGCT
GACACTGCATGGGGAGGCCCAGAATCTTCTTCCCTCCTGGTCTGCAACT
TCAAAGACCCTTTCCGCCGGCCATGGACACCCTAATCTGCCATTTTGAGG
CTTTTTCCAAGACGGAAAGGCCCGCCACAACTTGGTAAACCTTGACGATG
TGAACGCGAGTCCCCAGCTTCCTTTGGGGACTGGGACCTTTTCCAGAAAG
GCCTCCTGGGCCAGTAGAGTTCTCTTGCACAGGGGCGTAGATGGTTGGTA
GTTGTAGTCCATCCTTGTGACTTG

SEQ ID NO:13 (Stuffer 1-Short)
GGGCCCAGGAGGCCTTTCTGGAAAAGGTCCCAGTCCCCAAAGGAAGCTGGG
GACTCGCGTTCACATCGTCAAGGTTTACCAAGTTGTGGCGGGCCTTTCCG
TGTTGGAAAAAGCCTCAAAATGGCAGATTAGGGTGTCCATGGCCGGCGGA
AAGGGTCTTTGAAGTTGCAGCAGGAGGGAAAGAGGATTGTGGGCCTCCC
CCATGCAGTGTCAGCTGGCAACAGAATGCACCCCGGCTGGGTTGGAGGCC
CTGGGTACTGGCTCTTCCACACCAGGGGCCCACCTACCAAGGGCAGCAGG
AGCATCTGCACCTCCTGCGCCAGGCGCCCTTCAGTGCTTCCACTTGAGCA
CCCTCTCCAGACACCAGCTAGGGTGACAGTGGTACAAATACCAGACTCCC
TGGCCTGCTCACCTCACAGGGTAATGTGCTGTGGAGTCAGGGGACACAG
CAACCACCAGATGACATGGCTGCCCCGGGAGGACGACGAGATACG
GCTACTTGGCACCTGTGATATTTACACACTCGAGAGGGGCCCGCAGCAT
CCTCAGCCCTCTCCCCACATTCACTCTTAGTTCATGTCACCTCCACCCAG
AGGGGGACACAGGCCCACAGCGATGGCCCCACACCCTGCCTGAGGTCGCC -continued CACTTCCCAGGAGGCAGTCCTGGGACTTCCACCCGACCAGGCCCCAGAGC
CCACCGACTTAACCCCTCAGAGGCTTGTCGTTCATTACCTTATTCAAGA
TGGAGACCAGCCTTTTTGCGGAGAAAATGCGGGTGAAGGTCCTGAAAGTG
CATTGACGCCGTTTTCGGAAGCCATACAAGTTTAGCTGGCGGAAGAAGCT
CTTTATCGAAGTTGTGCAAAGACTTTGTGTGCGACGTCCCTTTTGAGAA
TCTCCTTTTCAAAGAGTTTTTGATTGATCACTCTACAAGCCCCACTGTCA
TCCCACCAGATGGACGAAAACTGGTTGCTGCTGACCAGTCTCCACAGTTT
CTGTGGAAAGGGGAGGGAGAGGAGATTATCTTCTCCCTGGGGCGGGACGT
CACCGTCAGGGTGCGGCCTTCTGAACGAAGCTTCCTCGGCCAGAGGTTGG
AAAGCGATTTCTTCTGTCAGCAGCCTCAAGTTAGGGCTCCCAGTGGACCC
CGGGTCGTGCCAGGCAGGGGAAGGATCTGCTGGGTGAAGGTAGGTCTCTG
ACTGCAACTGGGGAGGGAAAGGCACCCTTTCCAAGCCATGATCCTGTCCT
CTCGAATTTCTTTCTTCACAGCGAGCCATACTCAATGATCGCTTGTCCTC
CATCTGGCAAACTTGCTAGTGCAGTGTGGCGAGCAGCACCCCTTGGCAGT
CATGTAACCAGCCCCATGACATCATAAAGGGGCTCTGACTGCCGGGGGT
GGCATCTCCACCCCCAGCAAGTTGTGTAATAAAGGGCGAAGGCAGACAAG
TAGCTGCCCATCTGCATGTGGACATTCTGGTCCTCACAGTCATTTCAATG
GGAAAGATGACACTAGTGCACAAGAGTGCCGAGGGGCCCTGCCACACCGT
AGATGCAGACCTGGAGCGGTCCCCTTGTCCTAGAGCTCCTGAGCCAGGCA
CAACTACAGCAAAGCCCTGGCTCAGGAAGGTCAGAGCTGACCGTCTGAGT
CATGGGCCCACAGACCCCAGCACATGACTGACACTCGGAAGCACAGAACA
AAGGGTAGGACGGTGCCCATGGGTCAGGCTGTAGCCACGGCACCGTTTCC
ACCCTGTCCTAGCCAGAGGCAGCAATGTGCTCCATACAGATCCTCCTAAC
ACACCGACACTGTCGGTCCCCAGCACGCAGATGCCCGACAGCCCCTTAGG
CAAATGCTTAGCTGACTGCCCCACCACACGCGGTCGCCATGCAGTCCAG
TGGGGAGTCGGAGGCAGCCTGCTTCCTGCCTCTCCTCGGCCTGCACGTGT
CCCCCCACCAGGCAGAGACCCTTCTACACCCCGGGTGTCTGCGGTCACAT
CGCGGTGGGGCATGCAGCTGTTGGCCTTCGAGCATGTTTTGTTTTCCTTG
GCCAGTGTCTCCAGAGAATCGCACGTGGGTTTGTGTCCAGCGGTCCATCT
CTGCAACAGTTGTTCCTTTGGGATTGGATGCTAGGAGGTCACGGGAGAGG
TGTCCATCCAAAGCAGTGTCTGTGTCACACTGTTCCCCACACAGAGGGC
CACCTCTGCACAGACTCCCCGGACTCGATTCGGGCACAGAGGTCAGTGA
CCTTCCAGAGACTGCCACGAACCGGTGATGCCTCCACGCTTGAGACATCC
TGACCGCAGGGCCCAAGGCGCACTGGCTCAGGGGGTGACAGTGAGGGGTC
TGCAAACAGACTGCTGATGCTCAACCCGGCCGCTGCCGAGCTGTGTGACT
TGGGCACGTCACTTAACCTCTCTCGGCCTCTGTCTCCTCCCGGGGATAAG
AGTAGTAGCACCTGCTTCCCGGGGCTGTGAGGATCCAGTGGGACGTATAG
GAACTAGGGAGGCACCGGCAGTTGGGTCAGAGCTACTGTTGTCACTTCAC
AAGGCATTTTCTTCAACAGCAAGTCGGAAATCTCATGAGCCTAAGGCAGA
ATCCACCTGTGGCCTCTGGTTACAACCCACAGGACTGAAAATCGTTCCAG
CCACAGCAACTGGTGAATTTGCTGGTCAATTGCCAGAAGTCATGAGCTGA
ACCGCACTTGAGTTTCAGTTCAGGCAGAACTCTAGAGACGACTAGGGCAA
GCTAGACAGCGACTGCAGAGCCTTTTGTTGCAGCGTGAGCAGTCCTCAGC
TGTTGACATCACTGGGGAGCAAACAGGACCAGGAGCGGTGAAAGGACAG
TGTCTGCTGCAGATTGTCGTAGCACCCAAGGAACACTCCAGAAAGCCTCC
TAAGCAGTAACAAGTGACCAAGGTGTAGCCCAGCCAACAGTGGCATCTG
CGAGGCGTCCCCTCCTTCCTCCCACTACCCCGTATACCCTGGGACCTGTG
CACTGAAGGACTCATTCTAAAGGCTGTGCCCCTGCAGCCGCCAGCCTGAC
TCACTGGCTGCCTGTGCCAGCTAGAGATTTCTTTCCTCTGAGGCTGGCTG
AGAGGACCACTCCAGTTTCCTGGCCCATCCAGCAAAGAAGATACACATCA
TGCACGTGTAAAATGAGGAACCGGTTTATTGAACAGCTTAAGGAGAGCAA
AAATAGTGGCTTTAGCTACATTTTTTACACACTGAGCAGGAAAGTCTAAA
CCATCCCGTTCCCCTGTACCCCAAAGAGAACAGGGCTTGCTGGAGGCCAG
TGCCAAGGGCGGAGTCGTGCTCGCAGCAGACTTGAATTAACCCCATGTAG
GCCGGCGAGCAGTTGCCCGTGGTGAAAACACCCACCCTCTTCTCCTGGCGA
GAAGATCAAAGCTCTTTTTTTTACCCTCTTTTCAGCAAAGGACCTATTTGT
TTTCAGGCAGGAGGATGTTAAACTTGCAGCCTCTGACACACGGTGGAACC
TGCAGTGCTTGGAGAAACGGCACGCACACGTGAAAACATCATGCCTACTC
CAAAGCCTTCTTGTTGCTGGCAGGAGGGAAGCTTGAGCTTTCCCACGCA
TAGTCGTGACCCGCGTGGCCGTTTCTGCTCTCAGCAACATTCTCTAGTGT
TCCGGCTTCAAGCAGCGCTTGTCAGGTTTGAAGCTAGCCACTATTCTGAG
AACGTCAGAAAAGCATGGACCATCTCTTGCTTGGTGTTGCCGTTGTGGCA
GTAGCAGCTACTACGTACCTGCACGAGTTCCAGGGCAGAAGTGGCAATGT
CCCATGAAGGCGTGCACCCACGGGGGGGGGGGGGAGTGTGCCACGGG
CGTCCACTTCTGCAGCAGAAGGCATGTGCCTACAGCAAGCTTGTAAAA
AATACTTGAACAGAATATGCTGTACAGAACTAGGGGTTAACACCGCATA
TGAAGATGCTAAAACATTTGTATAAATACTCTGATACAAGCATGGAGTC
ACTCCCGTAGAAAGGGCTCATCCGTGAGGCTATGAAAAACTGCTGTCAGC
ATGCCCAAAGAGAAACTACTTCCACAGTAGGAACAGAAAAAAGGACTGTG
CTGTGTCTAAACACGTGGTGCATCAGAGACATAGTTACAGTTCCTACTGA
CTGCCCCACCACGACCTGGGAGTGCTGAGGACCTGGGAGTGCTCAGCGA
GCTGCAGGAGGTCAGCCCTGTGGAGAAATACATTTCTAAACAATACTTTT
GATTGGGATTTCAGCACCGTATAGACAGATGTTCCTTCTGGGGGCCTGGC
AAGCAGCCATCTCCCAGTGGGTCTGACGGGGAAGAGGGGTACCTGGAGCC
CCTCCCAGACAGACGGTAATCCCACCCCTGTTCTCACACCTCTTCCTGGCA
TCCGCATCTGCTGGCACACACCCCGTCACCTGCCACTTCCGCGTCCCGT
CGTGGTGAGTGGCTGATAGGCGCTGGATGCAAACAAGGCATGAGATGGCA
GTACCTGGAGACCCAGCTCCAGTACTGGTTCTGGTCTGCGGGTGAACGA
GGGGGCAGAGGAAGGCGGAGAGAGTGCGTCCCAGTCCACTTAAGCTCTGT
CCCCCGGAAGTGGCATCTAATCTGGCATTTCGATATTTAATTTGGGAGGTG -continued
GGAGCACATACTTCCCAGGGCTCTGGGTAATGACCACCCTGGCCTTCTTT
CGAAACATGGGTGCGATTTTAGGGGGCTCCGGAACTGGGGTCTCTTCGGT
TTCTTCATTATCTTCGTGATGGAGATCATAGGAAATGTTTCCATATTCTC
GTAGAAATGGGAAGATTTCAAGCAGAAACTGACAGAAATCTTTGCGGATA
CCAAACCACCCTGAAAAATAAGAATTTTTTATTTCACACACGAGGCTCAA
CTGACCTTCCTGTTAACTTTCTTTCCGTAACAAGAAGTTTCACTCCTACA
ATGTCATAACATACTTTATCCAGATCCTGAGTCACAAAGCCTGAACAGG
GCTTGAGTACCCAAAATGGGGAAGAAGTGCAAATGCTAGCTCTGTGGTGC
TTGGAGTGGGGTTCCCGGACCGGCAGGGACAGCGTCCACGGGGCCTAGTT
AGGGATGCCATTCTCGGGCCCCAGCCCAGACCTCCAGAAACTGAGTCGGG
CTAGGGTGGGCTCCAGCGGTCCCCTTTTCCTGGCCCTTTTGGGATTCTGC
TGGATGCCCAAATTTGAGAACTACTGCTCCAGTGAGTCTCAAAATATCTG
TGGTGCGCAGACTACGGTGTCTTCCGCTAATCTTCTCCAGCCAGGATAAA
CTCATGGATGACAGTGCCACCCAAGAACAAGATTTCTGTCACCCTCTGGA
ATCCGTGAGGGCGGTAGTCATGCACGGGTTGGCCAGGAGGGGCCTGAAC
TCATGGAGCCACCTTAAAGCCACTTTCCCAGTCCCACTACTCCTCTCTGT
AGGCTACTGGAGTGTCAGCTCGGTGCAAGCCCTCCCTGCTCCCGGGTGCG
GGGTAGGGGGCAGAGGCACAAACAGCAAGCACAGCCCGGGCTGCTGGGCT
GCAGTGAGGCCCTGCCCCCAAACCCACTGGCTTTCCGAAGGGCAATGCTC
TGGGCTTCCGTGCCATGGAGCCCACAGCCTTGCCAGGAAGGCACCCTCTG
CAGAGATCGTTTTGGAAGTGTCTGCCTCAGCAAGCAGGTGGAGGGGAATA
GAGTGTTAGCAAGGCAAGACAGGCAAGACTCGGGTGATGGCAGCAAGGAT
ATGGGGGAGGCAGAGCGGCCAACAGGGACCTAGGATGAATCCCAGGTTTG
GGTGGGAGATGTGGATTTTCCATCAAACCCTCCCGGGCCTGGGAAGAATC
TGTCTTGATCCCCATTTTGCAGAGGAGGGAACGGGATCTCTGAGAGGTTG
CCTGCCGTGTCTGGTTCTACCTCAAATGGCAGCGTGCACTGCGAGAAAAG
TCCCGGTGCAGGCGAGCAGAACACCAGAGTTACGGCATGCCCTTCCCTTA
GAAGGTCCCAGAATTTCCTCAGCCCTCAGTTTCCCACACAAGCTTCTAAA
TTGGGGCCCTCGGGGACTCATCCCTTCCTAGACTTCTATCCGCCACCCCC
CACCGCCTGGTCCCCCCCAGACACACACCAAGGACTTCTGAAATGCTGA
GTACATACAGTGGTTTCCTCCCTTCTGTCCAAATGTGGTTGCCATCAGCG
TGATCAACGAGAGCCAAAGGGGGACAAAGATCGGGATGCAGGAGAAGGCG
TTGTGGCCATCCAGTTTGTGAACCAGCAGAATCTAAAGAAAGAGACATAG
TCCCGGTTGATGCCAGCACCGAAAATGGGCAGAGGCGGAAGCCAGACTTC
ATTAGGCAGTTCCTCCCCACCACCCCACCCCCGCGTGAGCTCCCACAAGA
GGGAACATCAGCACCGCCAGAAAAGGCAGGAAACCACCTATCCCTGGGG
AAAGCTCGAAATGAGCTTTTATGTCCCTCTTCAGAGCTCGGCAATAGCCT
ATCCACTTGAAAAGTTCCCAGTGCCAGCAGTTTTATGGCAAACTCCTCCG
GGTGTTTGTTCTAAGGAGTCAACAGCTCCCATTCTAGAATTCTCCACGTG
ACTCCAATACACAAATCTGACATCCCACTCTGCTTTCCCCAGAGTGGAAA
CTGGAGCCATACAGAGGCACCATGGCTAAAAAGGTGCACTCTTCTCCCTG
CCAGCCCGACGTGCTGCCCCCAAGAGAAAGGAAGGATGCTCCTCCTTTCAC
CGAAGCTCCCTCTCGGACATGGCTGTGTTCTCTCCCCTCTCCTGGAGTGG
GCTCACTGTGAGCTCGAGGGACAGAGGCTGCCTTTCTAGGGGTGCAGAAT
CCTGTCAGGGGAAGCGCAAGCTTCAGGGGCTGAAGAGGCTTCCCGTGGAA
CGCTTACCTCAAATGTAAGAAGGGGCACGACGATGGTCATCCAGCTCAGG
GCCATGGTTATGTGTGTCCTGCGCGTGTCCGCAATCACATCCATAGAGCGC
AAGAACAAGACGGACCACACAATGTAGTAGAGGACCACCAGGCACAGAAA
GGACATGAGAATCCACAGCGGGACACACACAAACCTGGGGGTGGGTGAGAG
AACAGCAAGAGAAGTCTCTTTAGAGCTTCCAACCTGGCCTCTGATGGAAG
GCATCTTTAGCCACTTGCTGTGTCTGTCCAGTTAAGGCGGTCCTTCCTGT
GAGCCGAATAAGGACCGTTCCATCTCCCAGGACTGCTGGGAGCATCGCTC
AGGACAGAAAAGGTATGGTATGTTCACTATGGGCCTGCTGCCACCAGGG
GACACACACGCTCAGTGAGTCATCAGTCCCTCTTCCTTTGGGTGACAGAC
AGCCCTGCACCTGGCTCCGCAGCCTCTACTCTTCGTGCCATCACACCTCTCC
CACACTCTCTCAGGCTCCTCTAGGTTCTGCTGCCATCACAGCTTCCCGGG
AAATGGGACACAACTGTCACCCTGTGCACACACAAGATCTCACCCCAA
CAGACTCTCTTCACAGGCAACATTCCCACAACCTGCTGGGGGTACTTTGG
CAACACAAATGGAGATGGCTCCCCAGAAGTCTGGCTGCCTGGGCTCCT
AAGGATCCCTAACCTCACCCCTACCAAGTTAGTGAACTTGGCGGGTTGAT
GCTGGATACAGGTTGATGCTGGATACGTAGCGCTGCCGGGTGACC SEQ ID NO:14 (p2-2)
GGGCGAATTGGGCCCGACGTCGCATGCTCCCGGCCGCCATGGCGGCCGCG
GGAATTCGATATCACTAGTGAATTCGCGGCCGCCGATTGGGCCGGACGTC
GCATGCTCCCGGCCGCCATGGCGGCCGCGGGAATTCGATTCCTTAATTAA
GTCGACTGGGACCCAAACTTTGGAGTCGTTGACAGATGTGAGAGGTGAAG
CCTGGGATGACATCGCCAAAAATGCAACGTCTCACTCATTGTCACTACTC
CCAGGGCTCAGTCGTCACTGGGGAAAATCTCCAGAAGGTAGCGCGGGCCA
AGGTGACAGGTGTCTGCCAAGATCTGCCCGCCAGACTCCCGGGCGGCGCG
CTCCCTCCCTGCAGGCCTTCAGGCCGTCAGCATCCCCTTCCTCGGGGGCC
TGCTCACTCCCAGCCTCCATCCGCCTGCCATCTCCTCCGCCGGTCGCGTG
CGGACACAAGGATGGGGACCTCCCAGCGAGGAGCGCTCTGGGCGGGGCTC
CGGACGCATGCGCGGCCCTCGTACGGAAGCCCGGAAGGAGGGGCAGGGGG
CGGTGGCTCAGGTTTCTCCGGGCGCGGCGGGGGCGGCGGCGGCGACGGC
GACGGCGACGGCAGCGGCGGGGACGGCAGCAGTAGCGGGACGGCAGCGTGGA
CGCGGCTGGCGCTGGCGCCATGAACCCGCTGTAAGGCGCAGGCTGTGCAG
CACGGGGTGCGGGGAGGAGGAGGAGGACGCGGCGGTGAAGTTCTCCGCC
ATGAACGTGAGGGGCCTCTTCCAGGACTTCAACCCGAGGTGAGGCGGCGT
CGTTGGGGCCCCCGGGAGTCCGCGCTGCGGGCTCGGGCGCGGGCTGGTGT -continued
TCGGCTCCGGGGAGGCACGGCGGGCGAGATGGTGCAGCCCGAGGACCCGG
GCGCCTGCCCGAGCCTCCCTGCGGGTGCAAGCGGTCCCCAGGCAAAACAG
TCGGCCTCGGCGCCCGCCCGCTTCCTCCTCCCGTGCCCGGTGCTTTCAGC
CCCTGCCCGGCCACGGCCGGAAGGGCCCGGCCGCGAGCCCCGTCCTGCCC
CAAGGGAACCCATTCTTTTCTGCTTGCTGTCCCTCATTGGTGTCCCAAC
TTCTTCGTCTCGGTTCCATCCTCTTCTGCGCCGCTGCGGGGCCTCCATTC
TCCGCGTCAGGGCCGTCTCACTCGACCCAACACCCCTACCCCCACCCCAG
CTGTTTCCTCCAGTTCCTCGCAGTCCTTGGGGTTTTCCTTGGGTTTATGC
CCATCCCTCTCTTGTTTGCTTCTTTGTTGAACGGATACCTGAAACACTGT
TGAATCCTTGGAGTCAGTGTCGGGGTATGGCAATACCTTATATAATGCAT
TTCTGGGTGAGCCTGATCATTTTCCATACTCATTTTCTCATCAGTCTTCA
CTACAAGTTTATTTGCAGGAAGTAGATATTGCTGTCCTTCTTTTCCAGAT
GGGGAACACCCAGTGGACAGTGTGGAGAAAACATGGCTAAGCACTCAAG
CGCCTGTCCTTGCACTTGCCCGACTGTTTTGTAACTGTTCTTTACCCCAG
GCTGTGAGCTCCCTGAAGCTGAGACCATCTCCTGCTCATCTCAGTGTCCC
CAGCGCCTCCCACCCACCGTATCTGGCACATAGTAGGCAGATATAAAATG
TTTGTGGAACTAAACTGAGCCCAAAGACTTGGATTGGAGACGAGGCCATA
TGTAACTGGGTGATTCTCTGCCCTTCTTTGGCCCTTCTGTAAAATGAGGA
GTTGGCCTAACTGATCTCTTAAATGCACTACTCTCCAAAGGAGTATCCG
TTTCCCTTATTTGCCAGTTGGGAAGACGTGCTCAGTAAATATTTGTGTGC
TGTAACCTATGTTAGGTGCTTTAGATGCTGGCGGTCTCAGCATGGGGTGA
AGAAGGGCTTGTACACTTAAGATGCCTTACAGTACTGTGCAGTGCTGTAC
TGCGGGGCCAACTCTGGGGACCTATGCCTTGGCTGGTTGTTGAGGATGA
AAGGAAGTTTTAGGGGAGTATTTGTATGTTGAGGGTGCAGTCTCCCTAGG
GATGGTGACATTTTAACTTGTGAGTCATTGTGACTTTGTATGTGCCCTTA
TTCCACTTTGAGTTCATGTTCTGGTTAGGGATGCCAGTGTCTCTAACACG
GTGCAGACATTATCATTGTTGGGTTCGAAGGCATAGAGGAGGTAACAGAA
CTAACTGCAGTCCCTTCCTCTGCTGCATCAGGGGGTTAAGATTGGTCTGC
AGGGTAGTAGGGTTGGTGCTGTGGCTGGACAAGCCCTGTATGTCTTCTAT
TTGGAGATGGTGATAAGAAAGTTAAGTAAAAACTGAATTGTTTTGTGCCC
TTGGGCAACTCACTTATCTATTGTTTTATCTGTAGAATGAGTATAATCTC
TCAGTGGGGTAGGGAGGCCAATTAAGGATTGATTACAAAGTGCCTTACAA
ATAGAAAGCTACAGTGACTTGTTTGCAAGGTGACAGAGAATTCAGAAGCC
TCAAGAACTGCCTTAAGTGATCAAACAGGCTAACGGAGTTGCCAAAGCC
AAATAGTGCTGCACTGATACTACCTTTAACCGTTTTTTCCTTTAGCCCTT
TTCCCCCCAAAAAATTAGTATATCAAATTACAGTGAAATACCTGGTATC
TAAGCAGATTTATAGTAATTCTCAACATATTCATCAATCTCTTAATTCTA
CCTGCATTAAAATGTATTTCTACCTGAAAAGTTTAAAGGTCTTTTATACT
GTGCCATTTTCCTGATTCATTGTTGCCAGAGGTAGTGAGTTCCTTAATTT
TACAGATATTTCAAGAGGACATTGGCCAGGTATTATTGGTAAATCAGATT
TGTTTTTTTAGCTGGTAGTGTTTCACCTCTCCTGAGCACTCCTAGTTTTT
GACAGTGTGCTTTAGTCTCCTTCCATGCTGAGGAAGGCCTTTCTCTATAGG
AGAAAGAAAACTTGAGGGGTGTACACAGGAAGTTACCTTATGCTGGGGACT
CAAACCTTGATGCTACTGCTTTGCTCCCTGCCTCTATTTTGAACCAATT
CAACATCTCCCTCCTACCCCAGGACCTTGTCACACACTGTTCTCTTTACC
AGGAATGTTTCCCTCTCTTTTCCTCTCCTCCAGACCTAGTGAACTCCTAT
TTATCCTCACTTGGCACTTGCTAAGGGAAGCATTCCTGACTTCCCTGACC
AGATTTACTGCTCCCTGTTTCTACAGTTCCTGTAGTATTTACTACTCCTC
CATCATAGTGCATATTTGTACCCTTGTGTCTGTCTGGATGCTTATTTGAT
TAATACCTGCCTCCCCCACTAAACTTTAAGCTCCATGGGGTCAAGGCCGT
GACTGTGTCAGTATCGTAGCCTGCATACTTGGAATAGTACCTGGCTCAAT
AAATATTTGTGGAGTAAATAACTGAATAACTCTCCAGACCTATAAGATA
AATCTAGAGCTGCTGCTTTCAATCACTGCTTTCCTGGTGGTCTGTGGCCT
GGTTCTCTTTCTTCTCACACTCTTTCCCACCTTCAGAGTGCAGCCATTGCT
TTGGAGAGATGGGAGAGAACATGGCACTAAGGCAGAATATGGCTATATTT
ACTTTGAAGACATGTCTTTGTCATAGAAATAGTCACTGTCATGTTTGG
TGGGTCCCAAGGCATGGGTCATGGCTCCAGATCCCCTTTCCAGCCTTTTG
GATCTTGGTAAGTCTGAACCCACTGCTGCGTTGGCAAGGCTCTGGAAACT
ATAGTGACAGAGAATGATTCACAAGTGTCAACACTCAGATGTACAGGGCT
GCCAGCTGACCCACTCTACCTATTTCATCTGGCACTGAACTGGTTGATC
ATGAACTTCTTTTCATAATTGCTTTTTAGTTATGCAGGTTAAGACATGCC
GAAACAGATGTACCGGACCCACAAACAAGTCCTTCCTTGAATGCCTGAGG
CTTCCTAACAGTGAAAGAGCCCTGTTCTTAGAGTAGGCAAACTGATTCTG
AGGCATTGTAGGTGGTAGGGATCTGGTATTGGTAGGCATTAGGTGGGCTC
CCGGCACTCACCATGGAGCCTTGAAATTTCTGCTACTTTGGGGGAGTTG
CTGGTTCAGAGAAGGCCCTTCCACCCTGGTAGCCATGTGGCACTGGAAGG
CTGTGAAAACTCTGCTGGCCTTCTTAGTCATCTGTTGTGAGCTCCTGAT
GGGAGTGTGGTGTATCCCTCAGGTGTGCTAGACTGGAACAAAGGCTGAGA
AGTGTTGCTCTGGGGGTTCCAACTTGTGGGCATGGGGTACTGATGAGATC
AGTAGTGTTGGAGACTTCTGTATGCTCGATCTTCAGAAGACATTCTGGA
GTCCATATAAGTTATCTTGTCTCTTGTTTGAAGCAGGAAAAAGGAATGCG
ATTGCTGGTAATATAGTTCACTAAAGTCAGCTACCTGGCCTCTAACAGTT
ATTTGCAAAGTATATTATAACATTGATTCCTCAAACATCTAGATTCCTAT
CTCGTGCCAAGTGATGTACTAGGTGCTCTAAGTACAAAAATAAAGGAATA
TAGTCCTCCTCTCAATGCGTAAGCCTAGTGGAAGAAGCAGAAATGAAAGG
GAAATAAGAATTCAATAGAGTATGAGGCATTACAGTGAAAGAAACCAAAT
GTCTTAGAAGTACAAATGGCAGAGCTACTAATTCTGTCTCGAGCAGGCAG
GGAAGAGTCTATAGTGGAAATGACTTTTGAGCTAGATTTTGAATTGAGCT
AGTCTTTTGAGCCAGACTTTTGAGCTAGAATTGTAGGGTTGTCATCAGAC
CAGAGAGTAGGAAGGGTACCTTGTGAGGAAGAGAGAGAGAGATCAGATTG

```
TTACTGTGTCTATGTAGAAAAGGAAGACATAAGAAACTGCATTTTGATCT
GTACTAAGAAAAATTGTTTCTGCTTTGAGATGCTGTTAACCTGTAACTTT
AGTCCCAACCCTGTGGTCACAGAAACCTGTGCTGTAATGAATCAAGGTTT
AATGGATTTAGGGCTGTGCAGGATGTACCTTGTTAACAATATGTTTCAG
GCAGTATGCTTGGTAAAAGTCATCGCCATTGTCCATTCTCGATTAACCAG
GGACACAGTGCACTGCGGAAGGCCGCAGGGACATCTGCCCAAGAAAGCGT
GGGTATTGTCCAAGGTTTCCCCCCACTGAGACAGCCTGAGATATGGCCTT
GTGGGAAAGGAAAGACCTTACCACCCCCCAGCCCGACACCCGTAAAGTGT
CTGTGCTGAGGAGGAGTAGTGAAAGAGCGGGGCCTCTTTGCAGTTGAGAT
AAGAGGAAGGCTTCTGTCTCCTGCTCATCCCTGGGAATGGAATGTCTCTG
TGTAAAGCTGACCATTCCCATTCGTTCTATTCTGAGATAGGAGAAAACGA
CCCTGTGGCTGGAGGCGAAGTATGCTGGCAGCAATACTGCTCTGTTACTC
TTTGCTACACTGAGTTGTTTGGGTAAAGAGAAACATAAATCTAGCCTGCG
TGCACATCCAGGCACAGTACGTTTCCTTGAACTTATTCATGATACAGATT
CCTTTGCTCACGTTTCCCTGCTGACCTTCTCCCCACCTGTTGCCCTGCTA
CACTCCCCTCGCTAAGATAGTAAAAATAATGATCAGTAAATACTGAGGTA
ACTCAGAGGCTAGCGCTGGTGCGGGTCCTCCGTATGCTGAGTGCCGGTCC
CCTGGGCCCACTGTTCTTTCTCTATACTTTGTTTCTGTGTCTTATTTCTT
TTCTCAGTCTCGTCCCACCTGACGAGAAATACCCACAGGTGTGGAGGGGC
TGGCCCCTTTCAGTATCTCAGAAGGGACAAAGTACACAAAGGCATGGGGT
CATGATATGCCTGGTATGTTCAGGTAGTGAAGAGGTCCATGTGGTATGA
GCACTGCAGATGATATGTGTCGTATGAATTAAAAATACATAGTTACTGCA
AATAGTTTTTACAGGTTATTGTTTTTAAGAAAGCAGTATCTAATGCACGA
GTGTACTGTCAGTACTGTCAATGAACTACTTACCACTCAAGTGACTGGTT
ACGCGTCGAATCACTAGTGAATTCGCGGCCGCCTGCAGGTCGACGATATG
GGAGAGCTCCCAACGCGTTGGATGCATAGCTTGAGTATTCTATAGTGTCA
CCTAAATAGCTTGGCTAATCATGGTCATAGCTGTTTCCTGTGTGAAATT
GTTATCCGCTCACAATTCCACACAACATACGAGCCGGAAGCATAAAGTGT
AAAGCCTGGGGTGCCTAATGAGTGAGCTAACTCACATTAATTGCGTTGCG
CTCACTGCCCGCTTTCCAGTCGGGAAACCTGTCGTGCCAGGTGCATTAAT
GAATCGGCCAACGCGCGGGGAGAGGCGGTTTGCGTATTGGGCGCTCTTCC
GGTTCCTCGCTCACTGACTCGGTGCGCTCGGTCGTTCGGCTGCGGCGAGC
GGTATCAGCTCACTCAAAGGCGGTAATACGGTTATCCACAGAATCAGGGG
ATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAG
GACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTC
GGGAAGCGTGGCGCTTTCTCATAGCTCAGGCTGTAGGTATCTCAGTTCGG
TGTAGGTCGTTCGCTCCAAGCTGGGCTGTGTGCACGAACCCCCCGTTCAG
GCCGACCGCTGCGCCTTATCCGGTAACTATCGTCTTGAGTCCAACCCGGT
AAGACACGACTTATCGCCACTGGCAGCAGCCACTGGTAACAGGATTAGCA
GAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCC
AGTTACCTTCGGAAAAGAGTTGGTAGCTCTTGATCCGGCAAACAAACCA
CCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGC
TCAGTGGAACGAAAACTCACGTTAAGGGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACGGACGCTCACCGGCTCCAGA
TTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGG
TACAGGCATCGTGGTGTCACGCTCGTCGTTTGGTATGGCTTCATTCAGCT
CCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTG
TCATGCCATCCGTAAGATGCTTTTCTGTGACTGGTGAGTACTCAACCAAG
TCATTCTGAGAATAGTGTATGCGGCGACCGAGTTGCTCTTGCCCGGCGTC
AATACGGATATAACCGCGCCACATAGCAGAACTTTAAAAGTGCTCATCA
TTGGAAAACGTTCTTCGGGGCGAAAACTCTCAAGGATCTTACCGCTGTTG
AGATCCAGTTCGATGTAACCCACTCGTGCACCCAACTGATCTTCAGCATC
TTTTACTTTCACCAGCGTTTCTGGGTGAGCAAAAACAGGAAGGCAAAATG
CCGCAAAAAAGGGAATAAGGGCGACACGGAAATGTTGAATACTCATACTC
TTCCTTTTTCAATATTATTGAAGCATTTATCAGGGTTATTGTCTCATGAG
CGGATACATATTTGAATGTATTTAGAAAAATAAACAAATAGGGGTTCCGC
GCACATTTCCCCGAAAAGTGCCACCTGATGCGGTGTGAAATACCGCACAG
ATGCGTAAGGAGAAAATACCGCATCAGGAAATTGTAAGCGTTAATATTTT
GTTAAAATTCGCGTTAAATTTTTGTTAAATCAGCTCATTTTTTAACCAAT
AGGCCGAAATCGGCAAAATCCCTTATAAATCAAAAGAATAGACCGAGATA
GGGTTGAGTGTTGTTCCAGTTTGGAACAAGAGTCCACTATTAAAGAACGT
GGACTCCAACGTCAAAGGGCGAAAAACGCTATCAGGGCGATGGCCCACTA
CGTGAACCATCACCCTAATCAAGTTTTTTGGGGTGGAGGTGCCGTAAA
GCACTAAATCGGAACCCTAAAGGGAGCCCCCGATTTAGAGCTTGACGGGG
AAAGCCGGCGAACGTGGCGAGAAAGGAAGGGAAGAAAGCGAAAGGAGCGG
GGGCTAGGGCGCTGGCAAGTGTAGCGGTCACGCTGCGCGTAACCACCACA
CCCGCCGCGCTTAATGCGCCGCTACAGGGCGCGTCCATTGGCCATTCAGG

CTGCGCAACTGTTGGGAAGGGCGATCGGTGCGGGCCTCTTCGCTATTACG
CCAGCTGGCGAAAGGGGGATGTGCTGCAAGGCGATTAAGTTGGGTAACGC
CAGGGTTTTCCCAGTCACGACGTTGTAAAACGACGGCCAGTGAATTGTAA
TACGACTCACTATA

NEED SEQ ID NO:15 (Stuffer 2)
GGCCGCGGGAATTCGATTCCTTAATTAAGTCGACTGGGACCCAAACTTTG
GAGTCGTTGACAGATGTGACAGGTGAAGCCTGGGATGACATCGCCAAAAA
TGCAACGTCTCACTCATTGTCACTACTCCCAGGGCTCAGTCGTCACTGGG
GAAAATCTCCAGAAGGTAGCGCGGGCCAAGGTGACAGGTGTCTGCCAAGA
TCTGCCCGCCAGACTCCGGGGCGGGGCGCTCCCTCCCTGCAGGCCTTCAG
CCCGTCAGCATCCCCTTGCTGGGGGCCCTGCTCACTCCCAGCCTCCATCG
CCCTGCCATCTCCTCCGCCGGTCGGGTGCGGAGACAAGGATGGGGACCTC
CCAGCGAGGAGCGCTCTGGGGGGGGCCTCGGGACGCATGCGCGGCCCTCGT
ACGGAAGCCCGGAAGGAGGGGCAGGGGGCGGTGGCTCAGGTTTCTGCGGG
CGGCGGCGGCGGCGGCGGCGACGGCGACGGCGACGGCAGCGGGGACG
GCAGCAGTAGCGGGAGCAGCAGCGTGGACGCGGCTGGCGCTGGCGCCATG
AACCCGCTGTAAGGCGCAGGCTGTGCAGCACGGGGTGGCGGTGGAGGAGGA
GGAGGACGCCGCGGTGAAGTTCTCCGCCATGAACCTGAGGGGCCTCTTCC
AGGACTTCAACCCGAGGTGAGGCGGCGTCGTTGGCGCCCCCGGGAGTCCG
CGCTGCCGGCGCTCGGGCGCGGGCTGGTTCGGCTCCGGGGAGGCACGGCG
GGCGAGATGCTGCAGCCCGAGGACCCGGGCGCTGCCGGAGCCTCCCTGC
GGGTGCAAGCGGTCCCCAGGCAAAACAGTCGGCCTCGGCGGCCGCCCGCT
TCCTCCTCCCGTGCCCGGTGCTTTCAGCCCCTGCCCGGCCACGGCCGGAA
GGGGCCGGCCGCGAGCCCCGTCCTGGCCCAAGGGAACCCCATTCTTTTCT
GCTTGCTGTCCCTCATTGGTGTCCCAACTTCTTCGTCTCGGTTCCCATCCT
CTTCTGCGCCGCTGCGGGCCTCCATTCTCCGCTCAGGGCGTCTCACT
CGACCCAACACCCCTACCCCCACCCCAGCTGTTTCCTCCAGTTCCTCGCA
GTCCTTGGGGTTTTCCTTGGGTTTATGCCCATCCCTCTCTTGTTTGCTTC
TTTGTTGAACGGATACCTGAAACACTGTTGAATCCTTGGAGTCAGTGTCG
GGGTATGGCAATACCTTATATAATGCATTTCTGGGTGAGCCTGATCATTT
TCCATACTCATTTTCTCATCAGTCTTCACTACAAGTTTATTGCAGGAAG
TAGATATTGCTGTCCTTCTTTTCCAGATGGGGAACACCCAGTGGACAGTG
TGGAGAAACACTGGCTAAGCCTGCCAGCGCCTGTCCTTGCACTTGCCCG
ACTGTTTTGTAACTGTTCTTTACCCCAGGCTGTGAGCTCCCTGAAGCTGA
GACCATCTCCTGCTCATCTCAGTGTCCCAGCGCCTCCCACCCACCGTAT
CTGGCACATAGTAGGCACATATAAAATGTTTGTGGAACTAAACTGAGCCC
AAAGCTTGGATTGGAGACGAGGCCATATGTAACTGGGTGATTCTCTGCC
CTTCTTTGGCCCTTCTGTAAAATGAGGAGTTGGCCTAACTGATCTCTTAA
ATGCACTACTCTCCGAAACGAGTATCCGTTTCCCTTATTTGCCAGTTGGG
AAGACGTGCTCAGTAAATATTTGTGTGCTGTAACCTATGTTAGGTGCTTT
AGATGCTGGCTCAGCATGGGGTGAAGAAGGGCTTGTACACTTAAGA
TGCCTTACAGTACTGTGCAGTGCTGTACTGGGGGCCAACTCTGGGGAC
CTATGCCTTGGCTGCTTGTTGAGGATGAAAGGAAGTTTTAGGGGAGTATT
TGTATGTTGACGGTGCAGTCTCCCTAGGGATGGTGACATTTTAACTTGTG
AGTCATTGCTGTTCTGTATGTGCCCTTATTCCACTTTGAGTTCATGTTCT
GGTTAGGAGTGCCAGTGTCTCTAACACGGTGCAGACATTATCATTGTTGG
CTTCGAAGGCATAGAGGAGGTAACAGAACTAACTGCAGTCCCTTCCTCTG
CTGCATCAGGGGGTTAAGATTGGTCTGCAGGGTAGTAGGGTTGGTGCTGT
GGCTGGACAAGCCCTGTATTCTTATTTGGAGATGGTGATAAGAAAGT
TAAGTAAAAACTGAATTGTTTTTGTGCCCTTGGGCAACTCACTTATCTATT
GTTTTATCTGTAGAATGAGTATAATCTCAGTGGGGTAGGGAGGCCAAT
TAAGGATTGATTACAAAGTGCCTTACAAATAGAAAGCTACAGTGACTTGT
TTGCAAGGTGACAGAGAATTCAGAAGCCTCAAGAAACTGCCTTAAGTGAT
CAAACAGGCTAACGAAGTTGCCAAAGCAAAATAGTGCTGCACTGATACTA
CCTTTAACCGTTTTTTCCTTTAGCCCTTTTCCCCCAAAAAAATTAGTAT
ATGAAATTACAGTGAAATACCTGGTATCTAAGCAGATTTATAGTAATTCT
CAACATATTCATCAATCTCTTAATTCTACCTGCATTAAAATGTATTTCTA
CCTGAAAAGTTTAAAGGTCTTTTAACTGTGCCATTTTCCTGATTCATTG
TTGCCAGAGGTAGTCAGTTCCTTAATTTTACAGATATTTCAAGAGGACAT
TGGCCAGGTATTATTGGTAAATCAGATTTGTTTTTTTAGCTGGTAGTGTT
TCACCTCTCCTGAGCACTCCTAGTTTTTGACAGTGTGCTTTAGTCTCCTT
CCATGCTGAGGAAGGCCTTCTCTATAGGAGAAAGAAAACTGAGGGTGTA
CACAGGAAGTTACCTTATGCTGGGGAGTCAAACCTTGATGCTACTGCTTT
GCTCCCTGCCTCTATTTTGAACCAATTCAACATCTCCCTCCTACCCCAG
GACCTTGTCACACACTGTTCTCTTTACCAGGAATGTTTCCCTCTCTTTTC
CTCTCCTCCAGACCTAGTGACTCCTATTTATCCTCACTTGGCACTTGCT
AAGGGAAGCATTCCTGACTTCCCTGACCCAGATTTACTGCTCCCTGTTTCT
ACAGTTCCTGTAGTATTTACTACTCCTCCATCATAGTGCATATTTGTACC
CTTGTGTCTGTCTGGATGCTTATTTGATTAATACCTGCCTCCCCCACTAA
ACTTAAGCTCCATGGGGTCAAGGCCGTGCTGTGTCAGTATCGTAGCCT
GCATACTTGGAATAGTACCTGGCTCAATAAATATTTGTGGAGTAAATAAC
TGAATAACTCTCCAGAGCCTATAAGATAAATCTAGAGCTGCTGCTTTCAA
TCACTGCTTTCCTGGTGGTCTGTGGCCTGGTTCTCTTTCTTCTCACACTC
TTCCCACCTTCAGATGCAGCCATTTGTTTGGAGAGTGGGAGAGAACAT
GGCACTAAGGCAGAATATGCTATATTTACTTTGAAGACATGTCTTTGT
CATAGAAATAGTCACTGTCATGGTTTGGTGGGTCCCAAGGCATGGGTCAT
GGCTCCAGATCCCCTTTCCAGCCTTTTGGATGTTGGTAAGTCTGAACCCA
CTGCTGCGTTGGCAAGGCTCTGGAAACTATAGTGACAGAGAATGATTCAC
AAGTGTCAACACTCAGATGTACAGGGCTGCGAGCTGACCCACTCTACCTA
```

TTTCCATCTGGCACTGAACTGGTTGATCATGAAGTTCTTTTCATAATTGC
TTTTTAGTTATGCAGGTTAAGACATGCCGAAACAGATGTACCGGACCCAC
AAACAAGTCCTTCCTTGAATGCCTGAGGCTTCCTAACAGTGAAAGAGCCC
TGTTCTTAGAGTAGGCAAACTGATTCTGAGGCATTGTAGGTGGTAGGGAT
CTGGTAGTAGGTAGCATTAGGTGGGCTGCCGGCACTCAACATGGAGCCTT
GAAATTTTCTGCTACTTTGGGGGAGTTGCTGGTTCAGAGAAGGCCCTTCC
ACCCTGGTAGCCATGTGGCACTGGAAGGCTGTGAAAACTCTGCTGGGCCT
TCTTAGTCATCTGTTGTGAGCTCCTGATGGGAGTGTGGTGTATCCCTCAG
GTGTGCTAGACTGGAACAAAGGCTGAGAAGTGTTGCTCTGGGGGTTCCAA
CTTGTGGGCATGGGGTACTGATGAGATCAGTAGTGTTTGGAGACTTCTGT
ATGCTCCATCTTCAGAAGACATTCTGGAGTCCATATAAGTTATCTTGTCT
CTTGTTTGGCAAAGGAAAAAGGAATGCGATTGCTGGTAATATAGTTCACT
AAGTCAGCTACCTGGCCTCTAACAGTTATTTGCAAAGTATATTATAAACA
TTGATTCCTCAAACATCTAGATTCCTATGTCGTGCCAAGTGATGTACTAG
GTGCTCTAAGTAGAAAAATAAAGGAATATAGTCCTCCTCTCAATGCGTAA
GCCTAGTGGAAGAAGCAGAAATGAAAGGGAAATAAGAATTCAATAGAGTA
TGAGGCATTACAGTGAAAGAAACCAAATGTCTTAGAAGTACAAATGGCAG
AGCTACTAATTCTGTCTCGAGCAGGCAGGGAAGAGTCTATAGTGGAAATG
ACTTTTGAGCTAGATTTTGAATTGAGCTAGTCTTTTGAGCCAGACTTTTG
AGCTAGAATTGTAGGGTTGTCATCAGACGAGAGAGTAGGAAGGGTACCTT
GTGAGGAAGAGAGAGAGAGATCAGATTGTTACTGTGTCTATGTAGAAAAG
GAAGACATAAGAAACTCGATTTTGATCTGTACTAAGAAAAATTGTTTCTG
CTTTGAGATGCTGTTAACCTGTAACTTTAGTCCCAACCCTGTGCTCACAG
AAACCTGTGCTGTAATGAATCAAGGTTTAATGGATTTAGGGCTGTGCAGG
ATGTACCTTGTTAACAATATGTTTGCAGGCAGTATGCTTGGTAAAAGTCA
TCGCCATTCTCCATTCTCGATTAACCAGGGACACAGTGCACTGCGGAAGG
CCGCAGGGACATCTGCCCAAGAAAGCCTGGGTATTGTCAAGGTTTCCCC
CCAGTGAGACAGCCTGAGATATGGGCTTGTGGGAAAGGAAAGACCTTACC
ACCCCCCAGCCCGACACCCGTAAAGTGTCTGTCGTGAGGAGGAGTAGTGA
AAGAGCGGGGCCTCTTTGCAGTTGAGATAAGAGGAAGGCTTCTGTCTCCT
GCTCATCCCTGGGAATGAATGTCTCTGTGTAAAGCTGACCATTCCCATT
CGTTCTATTCTGAGATAGGAGAAAACCACCCTGTGGCTGGAGGCGAAGTA
TGCTGGCAGCAATACTGCTCTGTTACTCTTTGCTACACTGAGTTGTTTGG
GTAAAGAGAAACATAAATCTAGCCTGCGTGCACCCTGCCAGGCACAGTACCT
TTCCTTGAACTTATTCATGATACAGATTCCTTTGCTCACGTTTCCCTGCT
GACCTTCTCCCCACCTGTTGCCCTGCTACACTCCCCTCGCTAAGATAGTA
AAAATAATGATCAGTAAATACTGAGGTAACTCAGAGGCTAGCGCTGGTGC
GGGTCCTCCGTATGCTGAGTGCCGGTCCCCTGGGCCCACTGTTCTTTCTC
TATACTTTCTTTCTGTGTCTTATTTCTTTCTCAGTCTCGTCCCACCTGA
CGAGAAATACCCACAGGTGTGGAGGGGCTGGCCCCTTTCAGTATCTCAGA
AGGGACAAAGTACACAAAGGCATGGGTCATGATAGTGCCTGGTATGTTC
AGGTAGTGAAGAGGTCCAGTGGTATGAGCACTGCAGGATGATTTATTGT
TATGAATTAAAAATACATAGTTACTGCAAATAGTTTTTTACAGGTTATTGT
TTTTAAGAAAGCAGTATCTAATGCACGAGTGTACTGTCAGTACTGTCAAT
GAACTACTTACCACTCAAGTGACTGCTTACGCGTCGAATCACTAGTGAAT
TCGC

SEQ ID NO:16 (pTM-final)
GTACGGAAGCCCGGAAGGAGGGGCAGGGGGCGGTGGCTCAGGTTTCTCCG
GGCGGCGGCGGCGGCGGCGACGGCGACGGCGACGGCAGCGGGGA
CGGCAGCAGTAGCGGGAGCAGCAGCGGTGGACGCGGCTGGCGCTGGCGCCA
TGAACCCGCTGTAAGGCGCAGGCTGTGCAGCACGGGGTGCGGGGAGGAG
GAGGAGGACGCCGCGGTGAAGTTCTCCGCCATGAACCTGAGGGGCCTCTT
CCAGGACTTCAACCCGAGGTGAGGCGGCGTCGTTGGCGCCCCCGGGAGTC
CGCGCTGCGGGCTCGGGCGCGGGCTGGTGTTCGGCTCCGGGGAGGCACGG
CGGGCGAGATGCTGCAGCCCGAGGACCCGGGCGCCTGCCCGAGCCTCCCT
GCGGGTGCAAGCGGTCCCCAGGCAAACAGTCGGCCTCGGCGCCCGCCCG
CTTCCTCCTCCCGTGCCCGGTGCTTTCAGCCCCTGCCCGGCCACGGCCGG
AAGGGCCCGGCCGCGAGCCCCGTCTGCCCCAAGGGAACCCCATTCTTTT
CTGCTTGCTGTCCCTCATTGGTGTCCCAACTTCTTCGTCTCGGTTCCATC
CTCTTCTGCCGCTGCGGGCCCTCCATTCTCCGCGTCAGGGCCGTCTCA
CTCGACCCAACACCCCTACCCCCACCCCAGCTGTTTCCTCCAGTTCCTCG
CAGTCCTTGGGGTTTTCCTTGGGTTTATGCCCATCCCTCTGTTGTTGCT
TCTTTGTTGAACGGATACTGAAACACTGTTGAATCCTTGGAGTCAGTGT
CGGGGTATGGCAATACCTTATATAATGCATTTCTGGGTGAGCCTGATCAT
TTTCCATACTCATTTTCTCATCAGTCTTCACTACAAGTTTATTTGCAGGA
AGTAGATATTGCTGTCCTTCTTTTCCAGATGGGAAGACTAAACTGGACAG
TGTGAGAAAACACTGGCTAAGCACTCAAGCGCCTGTCCTTGCACTTGCC
CGACTGTTTTGTAACTGTTCTTTACCCCAGGCTGTGAGCTCCCTGAAGCT
GAGACCATCTCCTGCTCATCTCAGTGTCCCCAGCGCCTCCCACCCACCGT
ATCTGGCACATAGGACATATAAAATGTTTGTGGAACTAAACTGAGC
CCAAAGACTTGGATTGGAGACGAGGCCATATGTAACTGGGTGATTCTCTG
CCCTTCTTTGGCCCTTCTGTAAAATGAGGAGTTGGCCTAACTGATCTCTT
AAATGCACTACTCTCCGAAAGGAGTATCCGTTTCCCTTATTTGCCAGTTG
GGAAGACGTGCTCAGTAAATATTTGTGCTGTAACCTATGTTAGGTGCT
TTAGATGCTGGCGGTCTCAGCATGGGGTGAAGAAGGGCTTGTACACTTAA
GATGCCTACAGTACTGTCAGTGCTGTACTGCGGGGCCAACTCTGGG
ACCTATGCCTTGGCTGCTTGTTGAGGATGAAAGGAAGTTTTAGGGGAGTA
TTTGTATGTTGAGGGTGCAGTCTCCCTAGGGATGGTGACATTTTAACTTG
TGAGTCATTGTGACTTTGTATGTGCCCTTATTCCACTTTGAGTTCATGTT CTGGTTAGGAGTGCCAGTGTCTCTAACACGGTGCAGACATTATCATTGTT
GGCTTCGAAGGCATAGAGGAGGTAACAGAACTAACTGCAGTCCCTTCCTC
TGCTGCATCAGGGGGTTAAGATTGGTCTGCAGGGTAGTAGGGTTGGTGCT
GTGGCTGGACAAGCCCTGTATGTCTTCTATTTGGAGATGGTGATAAGAAA
GTTAAGTAAAAACTGAATTGTTTTGTGCCCTTGGGCAACTCACTTATCTA
TTGTTTTATCTGTAGAATGAGTATAATCTCTCAGTGGGGTAGGGAGGCCA
ATTAAGGATTGATTACAAAGTGCCTTACAAATAGAAAGCTACAGTGACTT
GTTTGCAAGGTGACAGAGAATTCAGAAGCCTCAAGAAACTGCCTTAAGTG
ATCAAACAGGCTAAGGGAGTTGCCAAAGCAAAATAGTGCTGCACTGATAC
TACCCTTTAACCGTTTTTTCCTTTAGCCCTTTTGCCCGCAAAAAAATTAGT
ATATGAAATTACAGTGAAATACCTGGTATCTAAGCAGATTTATAGTAATT
CTCAACATATTCATCAATCTCTTAATTCTAGCTGCATTAAAATGTATTTC
TACCTGAAAAGTTTAAAGGTCTTTTATACTGTGCCATTTTCCTGATTCAT
TGTTGCCAGAGGTAGTGAGTTCCTTAATTTTACAGATATTTCAAGAGGAC
ATTGGCCAGGTATTATTGGTAAATCAGATTTGTTTTTTTAGCTGGTAGTG
TTTCACCTCTCCTGAGCACTCCTAGTTTTTGACAGTGTGCTTTAGTCTGC
TTCCATGCTGAGGAAGGCCTTCTCTATAGGAGAAGAAAGAAACTGAGGGGTG
TACACAGGAAGTTACCTTATGCTGGGGAATCAAAGCTTGATGCTACTGCT
TTGCTCCCTGCCTCTATTTTTGAACCAATTCAACATCTCCCTCCTAGCCC
AGGACCTTGTCACACACTGTTCTCTTTACCAGGAATGTTTCCCTCTCTTT
TCGTCTCCTCCAGAGCTAGTGAACTCCTATTTATCCTCACTTGGCACTTG
CTAAGGGAAGCATTCCTGACTTCCCTGACCAGATTTACTGCTGCCTGTTT
CTACAGTTCCTGTAGTATTTACTACTCCTCCATGATAGTGCATATTTGTA
CCCTTGTGTCTGTCTGGATGCTTATTTGATTAATACCTGCCTCCCCCACT
AAACTTTAAGCTCCATGGGGTCAAGGCCGTGACTGTGTCAGTATCGTAGC
CTGCATACTTGGATATGACCTGGCTCAATAAATATTTGTGGAGTAAATA
ACTGAATAACTCTCCAGAGCCTATAAGATAAATCTAGAGCTGCTGCTTTC
AATCACTGCTTTCCTGGTGGTCTGTGGCCTGGTTCTCTTTCTTCTCAGAC
TCTTCCCACCTTCAGAGTGCAGCCATTGCTTTGGAGAGATGGGAGAGAAC
ATGGCACTAAGGCAGAATATGGCTATATTTACTTTGAAGACATGTCTTT
GTCATAGAAATAGTCACTGTCATGGTTTGGTGGGTGCCAAGGCATGGGTC
ATGGCTCCAGATCCCCTTTCCAGCCTTTTGGATCTTGGTAAGTCTGAACC
CACTGCTGGGTTGGCAAGGCTCTGGAAACATATAGTGACAGAGAATGATTC
ACAAGTGTCAACACTCAGATGTACAGGCTGCCAGCTGACCCACTCTACC
TATTTCCATCTGGCACTGAACTGGTTGATCATGAACTTCTTTTCATAATT
GCTTTTTAGTTATGCAGGTTAAGACATGCCGAAACAGATGTACCGGACCC
ACAAACAAGTCCTTCCTTGAATGCCTGAGGCTTCCTAACAGTGAAAGAGC
CGTGTTCTTAGAGTAGGCAAACTGATTCTGAGGCATTGTAGGTGGTAGGG
ATCTGGTAGTAGGTAGCATTAGGTGGGCTGCCGGCACTCAACATGGAGCC
TTGAAATTTTCTGCTACTTTGGGGGAGTTGCTGGTTCAGAGAAGGCCCTT
CCACCCTGGTAGCCATGTGGGACTGGAAGGCTGTGAAAACTCTGCTGGGC
CTTCTTAGTCATCTGTTGTGAGCTCCTGATGGGAGTGTGGTGTATCCCTC
AGGTGTGCTAGACTGGAACAAAGGCTGAGAAGTGTTGCTCTGGGGGTTCC
AACTTGTGGGCATGGGGTACTGATGAGATCAGTAGTGTTTGGAGACTTCT
GTATGCTCCATCTTCAGAAGACATTCTGGAGTCCATATAAGTTATGTTGT
CTCTTGTTTGAAGCAGGAAAAAGGAATGCGATTGCTGGTAATATAGTTCA
CTAAAGTCAGCTACCTGGCCTCTAACAGTTATTTGCAAAGTATATTATAA
CATTGATTCCTCAAACATCTAGATTCCTATCTCGTGCCAAGTGATGTACT
AGGTGCTCTAAGTACAAAATAAAGGAATATAGTCGTCCTCTCAATGCGT
AAGCCTAGTGGAAGAAGCAGAAATGAAAGGGAAATAAGAATTCAATAGAG
TATGAGGCATTACAGTGAAAGAAAGAAACCAAATGTCTTAGAAGTACAAATGGC
AGAGCTACTAATTCTGTCTCGAGCAGGCAGGGAAGAGTCTATAGTGGAAA
TGACTTTTGAGCTAGATTTTGAATTGAGCTAGTCTTTTGAGCCAGACTTT
TGAGCTAGAATTGTAGGGTTGTCATCAGACCAGAGAGTAGGAAGGGTACC
TTGTGAGGAAGAGAGAGAGAGATCAGATTGTTACTGTGTCTATGTAGAAA
AGGAAGACATAAGAAACTCCATTTTGATCTGTACTAAGAAAAATTGTTTC
TGCTTTGAGATGCTGTTAACCTGTAACTTTAGTCCCAACCCTGTGCTCAC
AGAAACCTGTGCTGTAATGAATCAAGGTTTAATGGATTTAGGGCTGTGCA
GGATGTACCTTGTTAACAATATGTTTGCAGGCAGTATGCTTGGTAAAAGT
CATCGCCATTCTCCATTCTCGATTAACCAGGGACACAGTGCACTGCGGAA
GGCCGCAGGGACATCTGCCCAAGAAAGCCTGGGTATTGTCAAGGTTTCC
CCCCACTGAGACAGCCTGAGATATGGGCTTGTGGGAAAGGAAAGACCTTA
CCACCCCCCAGCCCGACACCCGTAAAGTGTCTGTGCTGAGGAGGAAGTAG
TGAAAGAGCGGGGCCTCTTTGCAGTTGAGATAAGAGGAAGGCTTCTGTCTC
CTGCTCATCCCTGGGAATGAATGTCTCTGTGTAAAGCTGACCATTCCCA
TTGGTTCTATTCTGAGATAGGAGAAAACCACCCTGTGGCTGGAGGCGAAG
TATGCTGGCAGCAATACTGCTCTGTTACTCTTTGCTACACTGAGTTGTTT
GGGTAAAGAGAAACATAAATCTAGCCTGCGTGCACCCTGCCAGGCACAGTA
CCTTTCCTTGAACTTATTCATGATACAGATTCCTTTGCTCACGTTTCCTG
CTGACCTTCTCCCCACCTGTTGCCCTGCTACACTCCCCTCGCTAAGATAG
TAAAAATAATGATCAGTAAATACTGAGGTAACTCAGAGGCTAGCGCTGGT
GCGGGTCCTCCGTATGCTGAGTGCCGGTCCCCTGGGCCCACTGTTCTTTC
TCTATACTTTGTTTCTGTGTCTTATTTCTTTTCTCAGTCTCGTCCCACCT
GACGAGAAATACCCACAGGTGTGGAGGGGCTGGCCCCTTTCAGTATCTCA
GAAGGGACAAAGTACACAAAGGCATGGGTCATGATAGTGCCTGGTATGT
TCAGGTAGTGAAGAGGTCCATGGTATGAGCACTGCAGATGATTTGT
CGTATGAATTAAAAATACATAGTTACTGCAAATAGTTTTTACAGGTTATT
GTTTTTAAGAAAGCAGTATCTAATGCACGAGTGTACTGTCAGTACTGTCA
ATGAACTACTTACCACTCAAGTGACTGCTTACGCGTCGAATCACTAGTGA
ATTCGCGGCCGCCTCGAGTCTAGAACTAGTGGATCCCCCAAACGGGCCCT

```
CTAGACGCGTTGACATTCATTATTGACTAGTTATTAATAGTAATCAATTA
CGGGGTCATTAGTTCATAGCCCATGATATCATATGGAGTTCCGCGTTACA
TAACTTACGGTAAATGGCCCGCCTGGCTGACCGCCCAACGACCCCCGCCC
ATTGACGTGAATAATGACGTATGTTCCCATAGTAACGCCAATAGGGACTT
TCCATTGACGTCAATGGGTGGAGTATTTACGGTAAACTGCCCACTTGGCA
GTACATCAAGTGTATCATATGCCAAGTACGCCCCCCTATTGACGTCAATG
ACGGTAAATGGCCCGCCTGGCATTATGCCCAGTNCATGACCTTATGGGAC
TTTCCTACTTGGCAGACATCTACGTATTAGTCATCGCTATTACCATGGTG
ATGCGGTTTTGGCAGTACATCAATGGGCGTGGATAGCGGTTTGACTCACG
GGGATTTTCCAAGTCTCGACCCCATTGACGTCAATGGGAGTTTGTTTTGG
CACCAAAATCAACGGGACTTTCCAAAATGTCGTAACAACTCCGCCCCATT
GACGCAAATGGGCGGTAGGCGTGTACGGTGGGAGGTCTATATAAGCAGAG
CTCTCTGGCTAACTAGAGAACCCACTGCTTACTGGCTTATCGAGATATCTG
CAGAATTCATCTGTCGACTGCTACCGGCAGCGCGCAGCGGCAAGAAGTGT
CTGGGCTGGACGGACAGGAGAGGCTGTCGCCATCGGCGTCCTGTGCCCC
TCTGCTCCGGCACGGCCCTGTCGCAGTGCCCGCGCTTTCCCCGGCGCCTG
CACGCGGCGCGCCTGGGTAACATGCTTGGGGTCCTGGTCCTTGGCGGCT
GGCCCTGGCCGGCCTGGGGTTCCCCGCACCCGCCAGAGCCGCAGCCGGGTG
GCAGCCAGTGCGTCGAGCACGACTGCTTCGCGCTCTACCCGCGCCCCGCG
ACCTTCCTCAATGCCAGTCAGATCTGCGACGGACTGCGGGGCCACCTAAT
GACAGTGCGCTCCTCGGTGGCTGCCGATGTCATTTCCTTGCTACTGACG
GCGACGGCGGCGTTGGCCGCCGGCGCCTCTGGATCGGCCTGCAGCTGCCA
CCCGGCTGCGGCGACCCCAAGCGCCTCGGGCCCCTGCGCGGCTTCCAGTG
GGTTACGGGAGACAACAACACCAGCTATAGCAGGTGGGCACGGCTCGACC
TCAATGGGCTCCCCTCTGCGGCCCGTTGTGCGTCGCTGTCTCCGCTGCT
GAGGCCACTGTGCCCAGCGAGCGCGATCTGGGAGGAGCAGCAGTGCGAAGT
GAAGGCCGATGGCTTCCTCTGCGAGTTCCACTTCCCAGCCACCTGCAGGC
CACTGGCTGTGGAGCCCGGCGCCGCGGCTGCCGCCGTCTCGATCACCTAC
GGCACCCCGTTCGCGGCCCGCGGGAGCGGACTTCCAGGCGCTGCCGGTGGG
CAGCTCCGCCGCGGTGGCTCCGCTCGGCTTACAGCTAATGTGCACCGCAC
CGCCCGGAGCGGTCCAGGGGCACTGGGCCAGGGAGGCGCCGGGCGCTTGG
GACTGCAGCGTGGAGAACGGCGGCTGCGAGCACGCGTGCAATGCGATCCC
TGGGGCTCCCCGCTGCCAGTGCCCAGCCGGCGCCGCCCTGCAGGCAGACG
GGCGCTGCTGCACCGCATCCGCGACGCAGTCCTGCAACGACCCTCTGCAG
CACTTCTGCGTTCCCAACCCCGACCAGCCGGGCTCCTACTCGTCATGTG
CGAGACCGGCTACCGGCTGGCGGCCGACCAACACCGGTGCGAGGACGTGG
ATGACTGCATACTGGAGCCCAGTCCGTGTCCGCAGCGCTGTGTCAACACA
CAGGGTGGCTTCGAGTGCCACTGCTACCCTAACTACGACCTGGTGGACGG
CGAGTGTGTGGAGCCCGTGGACCCGTGCTTCAGAGCCAACTGCGAGTACC
AGTGCCAGCCCCTGAACCAAACTAGCTACCTCTGCGTCTGCGCCGAGGGC
TTCGCGCCCATTCCCCACGAGCCGCACAGGTGCCAGATGTTTTGCAACCA
GACTGCCTGTCCAGCCGACTGCGACCCCAACACCCAGGCTAGCTGTGGT
GCCGTGAAGGCTACATCTGGACGACGGTTTCATCTGCACGGACATCGAC
GAGTGCGAAAACGGCGGCTTCTGCTCCGGGGTGTGCCAGAACCTCCCCGG
TACCTTCGAGTGCATCTGCGGGCCCGACTCGGCCGTTGCCCGCCACATTG
GCACCGAGTGTGACTCCGGCAAGGTGGACGGTGGCACGGCGGCTCTGGC
GAGCCCCGCCCAGCCCGACGCCGGCTCCACCTTGACTCCTCCGGCCGT
GGGGCTCGTGCATTCGGGCTTGCTCATAGGCATCTCCATCGCGAGCCGT
GCCTGGTGGTGGCGCTTTTGGCGCTCCTCTGCCACCTGCGCAAGAAGCAG
GGCGCCGCCAGGGCCAAGATGGAGTACAAGTGCGCGGCCCCTTCCAAGGA
GGTAGTGCTGCAGCACGTGCGGACGCGACGCCGCAGAGACTCTGAG
CGGCCTCCGTCAGGAGGCTGGCTCCGTCCAGGAGCTGTGCCTCCTCAC
CCCCAGCTTTGCTACCAAAGCACCTTAGCTGGCATTACAGCTGGAGAAGA
CCCTCCCCGCACCCCCCAAGCTGTTTTCTTCTATTCCATGGCTAACTGGC
GAGGGGGTGATTAGAGGGAGAGGAATGAGCCTCGGCCTCTTCCGTGACGT
CACTGGACCACTGGGCAATGATGGCAATTTTGTAACGAAGACACAGACTG
CGATTTGTGCCAGGTCCTCACTACCGGGCGCAGGAGGTGAGCGTTATTG
GTCGGCAGCCTTCTGGGCAGACCTTGACCTCGTGGGCTAGGGATGACTAA
AATATTTATTTTTTTAAGTATTTAGGTTTTTGTTTTCCTTTGTTCT
TACCTGTATGTCTCCAGTATCCACTTTGCACAGCTCTCGGGTCTCTCT
CTCTACAAACTCCCACTTGTCATGTGACAGGTAAACTATCTTGGTGAATT
TTTTTTTCCTAGCCCTCTCACATTTATGAAGCAAGCCCCACTTATTCCCC
ATTCTTCCTAGTTTTCTCCTCCCAGGAACTGGGCCAACTCACCTGAGTCA
CCCTACGTGTGCCTGACCCTACTTCTTTTGCTCTTAGCTGTCTGCTCAGA
CAGAACCCCTACATGAAACAGAACAAAAACAGTAAAATAAAAATGGCC
ATTTGCTTTTTCACCAGATTTGCTAATTTATCCTGAAATTTCAGATTCCC
AGAGCAAAATAATTTTAACAAAGGTTGAGATGTAAAAGGTATTAAATTG
ATGTTGCTGGACTGTCATAGAAATTACACCCAAAGAGGTATTTATCTTTA
CTTTTAAACAGTGAGCCTGAATTTGTTGCTGTTTTGATTTGTACTGAAA
AATGGTAATTGTTGCTAATCTTCTTATGCAATTTCCTTTTTTGTTATTAT
TACTTATTTTTGACAGTGTTAAGATGTCAGAAGGTTGCTCTAGATTGA
GAGAAGAGACAAACACCTCCCAGGAGACAGTTCAAGAAAGCTTCAAACTG
CATGATTCATGCCAATTAGCAATTGACTGTCACTGTTCCTTGTCACTGGT
AGACCAAAATAAAACCAGCTCTACTGGTCTTGTGAATTGGGAGCTTGGG
AATGGATCCTGGAGGATGCCCAATTAGGGCCTAGCCTTAATCAGGTCCTC
AGAGAATTTCTACCATTTCAGAGAGGCCTTTTGGAATGTGGCCCCTGAAC
AAGAATTGGAAGCTGCCCTGCCCATGGGAGCTGGTTAGAAATGCAGAATC
CTAGGCTCCACCCCATCCAGTTCATGAGAATCTATATTTAACAAGATCTG
CAGGGGGTGTGTCTGCTCAGTAATTTGAGGACAACCATTCCAGACTGCTT
CCAATTTTCTGGAATACATGAAATATAGATCAGTTATAAGTAGCAGGCCA
```
```
AGTCAGGCCCTTATTTTCAAGAAACTGAGGAATTTTCTTTGTGTAGCTTT
GCTCTTTGGTAGAAAAGGCTAGGTACACAGCTCTAGACACTGCCACACAG
GGTCTGCAAGGTCTTTGGTTCAGCTAAGCTAGGAATGAAATCCTGCTTCA
GTGTATGGAAATAAATGTATCATAGAAATGTAACTTTTGTAAGACAAAGG
TTTTCCTCTTCTATTTTGTAAACTCAAAATATTTGTACATAGTTATTTAT
TTATTGGAGATAATCTAGAACACAGGCAAAATCCTTGCTTATGACATCAC
TTGTACAAAATAAACAAATAACAATGTGAAAAAAAAAAAAAAAAAAAAA
AAAAAAAAAAAAAAAAAGGTAGCAGTCGACAGATGAATTCCACCACACT
GGACTAGTGGATCCGAGCTCGGTACCAAGCTTAAGTTTGGGCTGCAGGAA
TTCTGATGGCTCTCAAATTCCTGCCTCCTTTAGGGATAAAAGACTTTAA
GACTTTTTAACAAAAAGAAAAGAAAAAAAAAATTCCTGCCTCCTGGTG
TACACACAGAAGGGTTCCCTCCCGTTGAATGTGACCAGGATCTGTGAA
AATAACGGGATAGCCGCTCCTGTGATTAGGTTATGTGGTAGACTAGAGCA
AGATTCTCCTGCTGGTTTTGAAGAAGTCAGCTGCCATGTTGTGAGACTGT
CATGGGCTAGGGCATGAGCCTTTAAATATCTGGGAGCAACCCCTGGCCAG
CAGCCAGTGAGAAAACGGGCCCTCAGTCCTACAATCACAAGGAACTAAAT
TCTGCCAACAACCTGAAGGAACTTTGAAGAGGATCATGAGTCCCTTGATT
CAGCTTGATGAGCCCCTGAGCAGAGGATACAGCTAACTTGTACTAGGGAA
GTATAAAAACATGCATGGGAATGATATATATCAACTTTAAGGATAATTG
TCATACTTCTGGGAATGAAGGGAAAGAAATGGGGCTTTAGTTGTATTATG
ATCTTTAATTTCTCAAAAAAAATAAGATCAGAAGCAAATATGGCAAAATG
TTAATACTTTTGTGGGTACGTAGGTATTCAGCATACCCTTTTTTCTGAGT
TCAAATATTTTATAATTAAAATGAAATGCAGGCCAGGCACAGTGGCTCA
TGCCTATAATACCAGCACTTTGCGAGGCCGAGGTGGGAGGATGGCTTGAG
GCCAGACCAGCCTGGCCAACATGGCAAAACCCCATCTCTACTTAAAAAAA
AAAAAACTATATATATATATATGTGTGTGTGTGTGTATATATATATATGT
ATATATATTATATATGTGTGTATATATATATATGTATATATATTTATAT
ATGTGTGTGTATATATATATACACACACACACATATATACATACATAC
ATACACACACACACACACACAATTAGCCAGGCATGGTGGCGCACACCTGT
AGTCCCAGCTACTTGGGAGGCTGAGACATGAGAATTGCTTGAACCTGGGA
GGCAGAGTAGTTAGTGAGCTGAGATCATACCACTGCACTCCAGCCTGGTG
ACAGAGTGAGACTCTGTCTTAAAAAAAATAAAAATTAAAATTAAATGCAA
AAGGTCCAAGTGAATTGAAGAGGAAAGGGGTATCAAGGAAGGTTTTGTGG
AGGTGACGTTTGAGCTGGGTCTTAAATGACTTAAACATGGGATAAGAAGG
GAGGGAATAAGGACATTTCAGGTACGAGAAATAAGGAGCAAACAGTGGAA
ACAACCTAACGTCTGTCAACCAGTGAATGGATAACAAAAATGTAATTCAG
ATGGTATCCAACTTACGATGGTTCAACATGAGATTTTTCTGACTTTAGGA
TAGATTTATCAAAGTAGTAAATCCATTTTCAACTTATGATATTTTCAACT
TCAGATGGGTTTATCAGGACACAGTTGAGGAACACCTGTCTATCCATACA
ATTTGGCAATAAAAAGGAAATGAGTGCAGATATACTCCACAACATGAATG
AACCTTGAAAACATTAAGTGAGAGAAGCCAGATACAAAAGGCCACATATT
GTATGATTCTATTTATACAAAAATGTCAGAATAGGCAAATCTTATAGACA
GCAAGTAGGTAGATGATCAGTTTGCTAGGTGCTGGGGGAAGGGGAAATGG
GGAGTGATGGCTAAGGGGATTGGGTTTCTTTGTGGGGCAATGAAAATGTT
TTAAAATTGAGCGTGATAATGATTGCACAATGCTGCATATATATATAATC
TATAGATTATATATATATAAGAGGCTGTTAGAGAGTGATAAGTGATA
TATATATATATATACATAGAGAGAGAGAGAGAGAGAGAGAGAGAGGCTGTTA
GTGATAAGTGATCAGGAAAATAAAAGTATTGAGGAGGAATACGAAGTTGA
CGGTGTGAAAACATGAGATTTTATATAGGATGGCCAGGGAAGGCCTTAAT
GAGAAAGTGACTTATGAGTAAAAACAAGGGATCCTAAACCTTAGCATGCA
TCAGAATCACTCGGAAACTTGTTAAAGACATAGCTTGCTGGGCCTCATCAC
AGATATTTTGATTCGGTAGGTTCTTGTCTGATATTAATACTTTTGGTCTA
GGGAACCACATTTTGAGAACCACTGAGCTAAAGGAAGTAAAGGTTTCCCT
TAGTTTACTAGCTGGTAACACTGGCCCAGGAGGCCTTTCTGGAAAAGGTG
GCAGTCCCCAAAGGAAGCTGGGGAGTCGCGTTCACATCGTCAAGGTTTAC
CAAGTTGTGGCGGGCCTTTCCGTCTTGAAAAAAGCCTCAAAATGGCAGAT
TAGGGTGTCCATGGGCGGCGGAAAGGGTCTTTGAAGTTGCAGACCAGGAG
GGAAGAAGATTCTGGGCCTCCCGCATGCAGTGTCAGCTGGGAACAGAATG
CACCCCGGCTGGGTTGGAGGCCGTGGGTACTGGCTCTTCCACACCAGGGG
CCCACCTACCAAGGGCAGCAGGACGCATCTGCACCTCCTGCGCCAGGCGCC
CTTGAGTGCTTCGACTTGAGCAGCTCTCCAGACACCAGCTAGGGTGACAG
TGGTACAAATACCAGACTCCCCTGGCCTGCTCACCTCACAGGGTAATGTG
CTGTGGAGTCAGGGGGACACAGCAACCACCAGATGACATGGCTGGCCCCG
GGGAAGGACGACACGGCAGATACGGCTACTTGGCACCTGTGATATTTACAC
ACTCGAGAGGGCCCGCACCATCCTCAGCCCTCTCCCCACATTCACTCTT
AGTTCATGTCACCTCCACCCAGAGGGGACACAGGCCCACAGCGATGGCC
CCACACCCTGCCTGAGGTCGCCCACTTCCGGAGGAGCAGTCTGGGACTT
CCACCCGACCCAGGCCCCAGAGCCCACCGACTTAACCCCTCCAGAGGCTTG
TCGTTCATTACCTTATTCAAGATGGAGAGCAGCCTTTTTCGGAGAAAAT
GCGGGTGAAGGTCCTGAAAGTGCATTGACGCCGTTTTCGGAAGCCATACA
AGTTTAGCTGGCGGAAGAACTCTTTTATCGAAGTTGTGGCAAACATTTG
TGTGCGACGTCCCTTTTGAGAATCTCCTTTTCAAAGAGTTTTTGATTGAT
CACTCTAGAAGCCCCACTGTCATCCCACCAGATGGACGAAACTGGTTGC
TGCTGACCAGTGTCCACAGTTTCTGTGGAAAGGGAGGGAGAGGAGATTA
TCTTCTCCCTGGGGCGGACGTCACCGTCAGCGTGCGGCCTTCTGAACGA
AGCTTCCTCGGCCAGAGGTTGGAAGCGGATTTCTTCTGTCAGCAGCCTCA
AGTTAGGGCTCCCAGTGGACCCCGGGTCGTCCCAGGCAGGGGAAGGATCT
GCTGGGTGAAGGTAGGTCTCTGACTGCAACTGGGGAGGGAAAGGCACCCT
TTCCAAGCCATGATCCTGTGCTCTCGAATTTCTTTCTTCACAGCGAGCCA
TACTCAATGATCGCTTGTCCTCCATCTGGCAAACTTGCTAGTGCAGTGTG
```

-continued

```
GCCAGCAGCACCCCTTGGCAGTCATGTAACCAGCCCCATGACATCATAAA
GGGGCTCTGACTGCCGGGGGGTGGGATCTCCACCCCCAGCAAGTTGTGTA
ATAAAGGGCCAAGGCAGACAAGTAGCTGCCCATCTGCATGTGCACATTCT
GGTCCTCACAGTCATTTCAATGGGAAAGATGACACTAGTGCACAAGAGTG
CCGAGGGGCCCTGCCACACCGTAGATGCAGACCTGGAGCGGTCCCCTTGT
CCTAGAGCTCCTGAGCCAGGCACAACTACAGCAAAGCCCTGGCTCAGGAA
GGTCAGAGCTCACCGTCTGAGTCATGGGCCCACAGACCCCAGCACATGAC
TGACACTCGGAAGCACAGAACAAAGGGTAGGACGGTGCCCATGGGTCAGG
CTGTAGCCACGCCACCCTTTCCACCCTGTCCTAGCCAGAGGCAGCAATGT
GCTCGATACAGATCCTCCTAACACACCCACACTGTCGGTCCCCAGCAGGC
AGATGCCCGACAGCCCCTTAGGCAAATGGCTTAGCTGACTGCCCCACCAC
ACGCCGTCGCCATGCAGTCCAGTGGGGAGTCGGAGGCAGCCTCCTTCCTG
CCTCTCCTCGGCCTGCACGTGTCGCCCCACCAGGCAGAGACCCTTCTACA
CCGCGGGTGTCTGCGGTCACATCGCGGTGGGGCATGCAGCTGTTGGCCTT
CGAGGATGTTTTGTTTTCCTTGGCGAGTGTCTCCAGAGAAACGCACGTGG
GTTTGTGTCCAGCGGTCCATCTCTGCAACAGTTGTTCCTTTGGGATTGGA
TGCTAGGAGGTCACGGGAGAGGTGTCATCCAAAGCAGTGTCTGTGTCAC
ACAGTGTCGCCACACAGAGGGCCACCTCTGCACAGACTCCCCCGACTCGA
TTCTGGGCACAGAGCTCAGTGACCTTCCAGAGACTGCCACGAACCGGTGA
TGCCTCCACGCTTGAGACATCCTGACCGCAGGGCCCAAGGCGCACTGGCT
CAGGGGGTGACAGTGAGGGGTGTGCAAACAGACTGCTGATGCTCAACCCG
GCCGCTGCCGAGCTGTGTGACTTGGGCACGTCACTTAACCTCTCTCGGCC
TCTGTCTCCTCCCGGGGATAAGAGTAGTAGCACCTGCTTCCCGGGGCTGT
GAGGATCCAGTGGGACGTATAGGAACTAGCGAGGCACCGGCAGTTGGGTC
AGAGCTACTGTTGTCACTTCACAAGGCATTTTCTTCAACAGCAAGTCGGA
AATCTCATGAGCGTAAGGCAGAATCCACCTGTGGCCTCTGGTTACAACCC
ACAGGACTGAAAATCCTTCCAGCCACAGCAACTGGTGAATTTCCTGGTCA
ATTGCCACAAGTCATGAGCTGAACCCCACTTGAGTTTCAGTTCAGGCAGA
ACTCTAGAGACGACTAGGGCAAGCTAGACAGCGACTGCAGAGCCTTTTGT
TGCAGCGTGAGCAGTCCTCAGCTGTTGACATCACTGGGGAGCAAACGAGG
ACCAGGAGCGGTGAAAGGACAGTGTCTGCTGCAGATTGTCGTAGCACGCA
AGGAAGACTCCAGAAAGCCTCCTAAGCAGTAACAAGTGTGGCAAGGTGTA
GCCCAGCCAACAGTGGCATCTGGGAGGCGTCCCCTCGTTCCTCCCACTAC
CCCGTATACCCTGGGACCTGTGCAGTGAAGGACTCATTCTAAAGGGTGTA
CCCCTGCAGCCGCCAGCCTCACTCACTGGCTGCCTGTGCCAGCTAGAGAT
TTCTTTCCTCTGAGGCTGGCTGAGAGGACCACTCCAGTTTCCTGGCCCAT
CCAGCAAAGAAGATACACATCATGCACGTGTAAAATGAGGAACCGGTTTA
TTGAACAGCTTAAGGAGAGCAAAAATAGTGGCTTTAGCTACATTTTTTAC
ACACTGAGCAGGAAAGTCTAAACCATCCCGTTCCCCTGTACCCCAAAGAG
AACAGGGCTTGCTGGAGGCCAGTGCCAAGGGCGGAGTCGTGCTCGCAGCA
GACTTGAATTAACCCCCATGTAGGCCGGCGAGCAGTTGCCCGCGTGAAAAC
ACCACCCTCTTCTCCTGGCTGAGAAGATCAAAGCTCTTTTTTTAACCTCT
TTTCAGCAAAGGACCTATTTGTTTTCAGGCAGGAGGGATGTTAAACTTGCA
GCCTCTGACACACGGTGGAACCTGCAGTGCTTGGAGAAACGGCACGCACA
CGTGAAAACATCATGCCTACTCCAAAGCCTTCTTGTTGCTGGCAGGAGGG
AAGCTTGAGACTTTCCCACGCATAGTCGTGACCCGCGTGGCCCTTGGTGG
TCTCAGCAACATTCTCTAGTGTTCCGCTTCAAGCAGCGCTTGTCAGGTT
TGAAGCTAGCCAGTATTCTGAGAACGTCAGAAAAGCATGGACCATCTCTT
GCTTGGTGTTGCCGTTGTGGCAGTAGCAGCTACTACGTACCTGCACGAGT
TCCAGGGCAGAAGTGGCAATGTCCCATGAAGGCGTGGCACCCCACGGGGG
GGGGGGGAGTGTGCCACGGGCGTCCACTTCTGCAGCAGAAGGCATGTG
CCTAGAGCACAAGCTTGTAAAAAAAATAGTTGAACAGAATATGCTGTACAG
AACTAGGGGTTAACACCGGATATGAAGATGCTAAAACATTTGTATAAATA
CTCTGTATACAAGCATGGAGTCACTCCCGTAGAAAAGGGCTCATCCGTGA
GCTATGAAAAACTGCTGTCAGCATGCCCAAAGAGAAACTACTTCCACAGT
AGGAACAGAAAAAAGGACTGTGCTGTGTCTAAACACGTGGTGCATCAGAG
ACATAGTTACAGTTCCTACTGACTGCCCCAGCCACGACCTGGGAGTGCTG
AGGACCTGGGAGTGCTCAGCGAGCTGCAGGAGGTCAGCCCTGTGGAGAAA
TACATTTCTAAACAATACTTTTGATTGGGATTTCAGCACCGTATAGACAG
ATGTTCCTTCTGGGGGCTGGCAAGCAGCCATCTCCCAGTGGGTCTGACG
GGGAAGAGGGGTACCTGGAGCCCCTCCCAGACAGACGGTAATCCCACGCC
TGTTCTCACACTCTTCCTGGCATCCGCATCTGCTGGCACACACCCCGTC
ACCTGCCACTTCCGCGTCCCGTCGTGGTGGAGGTGGCTGATAGGCGCTGAT
GCAAACAAGGCATGAGATGGACGTACCTGGAGACCCAGCTCCAGTACTGG
TTCTGGTCTGCGGGGTGAACGAGGGGGCAGAGGAAGGCGGAGAGAGTGCG
TCCCAGTCCACTTAAGCTCTGTCCCCGGAAGTGGCATCTAATCTGGCATT
TCGATATTTAATTTGGGAGGTGGGAGCACATACTTCCCAGGGCTCTGGGT
AATGACCACCCTGGCCTCTTTCGAAACATGGGTGCGATTTTAGGGGGCT
CCGGAACTGGGGTCTGTTGGGTTTCTTCATTATCTTCGTGATGGAGATCA
TAGGAAATGTTTCCATATTCTCGTAGAAATGGGAAGATTTCAAGCAGAAA
CTGACAGAAATCTTTGGGGATACAACCACCCTGAAAAGATTAGACAAG
TTATTTCACACACGAGGCTCAACTGACCTTCCTGTTAACTTTCTTTCCGT
AACAAGAAGTTTCACTCCTACAATGTCATAACATACTTTATCCGATCTCC
TGAGTCACAAAGCCTGAACAGGGCTTGAGTACCCAAAATGGGGAAGAAGT
AAGATGCTAGCTCTGTGGTGCTTGGAGTGGGGTTCCCGGAGCGGCAGGG
ACAGCGTCCACGGGGCTAGTTAGGGATGCCATTCTCGGGCCCCAGCCCA
GACCTGCAGAAACTGAGTCGGGCTAGGGTCGGCTCCAGCGGTCCCCTTTT
CCTGGCCCTTTTGGGATTCTGCTGGATGCCCAAATTTGAGAACTACTGCT
CCAGTGAGTCTCAAAATATCTGTGGTGCGCAGACTACGGTGTCTTCCGCT
AATCTTCTCCAGCCAGGATAAACTCATGGATGACAGTGCCACCCAAGAAC
AAGATTTCTGTCACCCTCTGGAATCCGTGAGGGCGGTAGTCATGCACGGG
TTGGCGAGGAGGGGGCCTGAAGTGATGGAGCCACCTTAAAGCCACTTTCC
CAGTCCCACTACTCCTCTCTGTAGGCTACTGGAGTGTCAGCTCGGTGCAA
GCCCTCCCTGCTCCCGGGTGCGGGGTAGGGGGCAGAGGCACAAACAGCAA
GGACAGCCCGGGCTGCTGGGCTGCAGTGAGGCCCTGCCCCCAAACCCACT
GGCTTTCCGAAGGGCAATGCTCTGGGCTTCGGTGCCATGGAGCCCACAGC
CTTGCCAGGAAGGCAGCCTCTGCAGAGATCGTTTTGGAAGTGTCTGCCTC
AGCAAGCAGGTGGAGGGGAATAGAGTGTTAGCAAGGGAAGACAGGCAAGA
CTCGAGGTGATGGCAGCAAGGATATGGGGAGGCAGAGCGGCCAACAGGGA
CCTAGGATGAATCCCAGGTTTGGGTGGGAGATGTGGATTTTCCATCAAAC
CCTCCGGGGCCTGGGAAGAATCTGTCTTGATCCCCATTTTGCAGAGGAGG
GAACGGGATCTCTGAGAGGTTGCCTGCCGTGTCTGGTTCTACCTCAAATG
GCAGCGTGCACTGCGAGAAAAGTCCCGGTGCAGGCCAGCAGAACACCAGA
GTTACGCATGCCCTTCCCTTAGAAAGGTCCCAGAATTTCCTCAGCCCTCA
CTTTCCCACACAAGCTTCTAAATTGGGGCCCTCGGGGACTCATCCCTTCC
TAGACTTCTATCCGCCACCCCCACCCCGTGGTCCCCCCCAGACACACA
CCAAGGACTTCTGAAATGCTGAGTACATACAGTGGTTTCCTCCCTTCTGT
CCAAATGTGGTTGCCATCAGCGTGATCAACGAGAGCCAAAGGGGGACAAA
GATCGGGATGCAGGAGAAGGCGTTGTGGCCATCCAGTTTGTGAACCAGCA
GAATCTAAAGAAAGAGACATAGTCCCGGTTGATGCCAGCACCGAAAATGG
GCAGAGGCGGAAGCCAGACTTCATTAGGCAGTTCCTCCCCACCACCCCAC
CCCCGCGTGAGCTCCCACAAGAGGGAACATCAGCACCGCCAGAAAAAGGC
AGGAAACCACCTATCCCTGGGGAAAGCTCGAAATGAGCTTTTATGTCCCT
CTTCAGAGCTCGGCAATAGCCTATCCACTTGAAAAGTTCCCAGTGCCAGC
AGTTTTATGGCAAACTCCTCCGGGTGTTTGTTCTAAGGAGTCAACAGCTC
CCATTCTAGAATTCTCCACGTGACTCCAATACACAAATCTGACATCCCAC
TCTGCTTTCCCCAGAGTGGAAACTGGAGCCATACAGAGGCACCATGGCTA
AAAAGGTGCACTCTTCTCCCTGCCAGCCCCACGTGCTGCCCCCAAGAGAA
AGGAAGGATGCTCTCCTTTCACCGAAGCTCCCTCTCGGAGATGGCTGTGT
TCTCTCCCCTCTCCTGGAGTGGGCTCACTGTGAGCTCGAGGGACAGGAGC
TGCCTTTCTAGGGGTGCAGAATCCTGTCAGGGGAAGCGCAAGCTTCAGGG
GCTGAAGAGGCTTGCCGTGGAACGCTTACCTCAAATGTAAGAAGGGGCAC
GACGATGGTCATCCAGCTCAGGGCCATGGTTATGTGTGTCCTGCGCTGTC
CGCAATCACATCCATAGAGCGCAAGAACAAGACGGACCACAATGTAGT
AGAGGACCACCAGGCACAGAAAGGACATGAGAATCCACAGCGGGACACAC
ACAACCTGGGGGTGGGTGAGAGAACAGCAAGAGAAGTCTCTTTAGAGCTT
CCAACCTGGCCTCTGATGGAAGGCATCTTTAGCACCTTGCTGTGTCTGTC
CAGTTAAGGCGGTCCTTCCTGTGAGCCGAATAAGGACCGTTCCATCTCCC
AGGACTGCTGGGAGCATCGCTCAGGACAGAAAAGGGTATGGTATGTTCACT
ATGGGGCCTGCTGCCACCAGGGGACACACACGCTCAGTGAGTCATCAGTC
CCTCTTCCTTTGGGTGACAGACAGCCCTGCACCTGGCTCCGCAGCCTCTA
CTCTTCCAGAGGCCCACTCTCCCACACTCTCTCAGGCTCCTCTAGGTTCT
GCTGCCATCACAGCTTCCCGGGAACATGGCACACAACTGTCACCCTGTGCA
CACACACAAGATCTCACCCCAACAGACTCTCTTCACAGGCAACATTCCCA
CAACCTGCTGGGGTACTTTGGCAACACAAATGGGAATGGGCTCCCCAGA
AAGTCTGGCTGCCTGGGCTCCTAAGGATCCCTAACCTCACCCCTACCAAG
TTAGTGAACTTGGCGGGTTGATGCTGGATACAGGTTGATGCTGGATACGT
AGCGCTGCCGGGTCGTGACCCCTAAGGAATTATCCAAACTCTTGTTTTTA
GATGCTTTATTATATCAAACTCTCCTTTAAACAAGTGGCCCATCTGCTGG
GATTTGGAAGCCTGTAATACTGAAATTTTCATCATAATGGAAATTTTAAA
AACAGAATTTGACCCAGCTGTTTTTAAAACACTTTTCATTACTTAACAAGA
GGTCTAATCTTGGGGAAGTGTTGAAATTTCTCTGGCCTTAGTTTCCCATG
TGTTAAATGAAACTTGAAGCAGTTGGTCTCTTATAGTCTCCTGACTCTAA
CATTCTAAGAATTATATTTGTACAATAACTCAAAAATCACATAATTTAAT
TTACCATATGCTCAAAATATATTTTCTCATTAGGCTAAACTTGATCT
GCATTTTCTGGATGTGTCCATATTCTTGGACTACACTAAAACATGATACC
AATGCTTCCTCTCACCATAAACCCTCACTTCGCTTTCTACATTTAAGAAT
TTTATAGGTGGAAGAGTCGTTAACAGAAAATACCATCTAATAATTACCCC
TCAAAATCAGAAAGTCCTATCTGTTCTTATGCTAGTTATTATAAGAATGAG
CAGCATTTCACATAATGGTTATAAAGACTGCCACAAGAAGATTCATGATG
TGTTGTTTATCTGTAGGTCTCATCATACTCTGTCATATAACTATAGCATT
AAGATTTTAATGTTCTATATATTCTTCTAAGACAGTGTTTACCAGAGTAA
GGACAAAAGATCCACTGGTTTGCAAGAAAGATTAGAACTTTTAAATTTT
TTACCTCACCTTGTTTAATCTATATTTTTGTATGTATTTTGTAACATATA
TATTATTATTACCATAAATCATATATAATTTAAAATGCATATATTAGGGG
TAAATGCTCAGGAAACTTTTTATAAATTGGGCATGCAAATACAAGTTTGA
AGACTCACTGTTCTAGGTATTAAAAGTAAAGTTATAACCAAGTAAAGCTT
CCACCTTTTCATGTCTCAAAGCAGTTTATTGTTGGAGGTAAGATCTCTTA
GAAGCCTAAACAGGTCCAAGTACAGAATGAAGTAAGGCTAGCCCATAACT
TGTGGCAAGCAATTCATACTATTTCTCTCATGCTGAGCTCTCCTCAGTGA
AGCAGCTACTATAGACAACTGCAGCCTATTGGTAGCTCTATTTTACAGGCA
GGAAAAAAATTACTTTTTATTCAAAGTGGAACTCAGGACATGGGGAGAAA
ATGAATACAAAAATAGGGTCAATCCAAAGGCACACAGCAAATGAGTAAC
ACAGTTATGTTTTTTCCCATTTGTATGAGGTCCCAGTAAATTCTAAGTA
AACTGCAAATTTAATAATACTAAAAAAGACCATGCAATTGTTCAAATGA
ATCCCAGCATGGTACAAGGAGTACAGACACTAGAGTCTAAAAAACAAAAG
AATGCCATTATTGAGTTTTTGAATTATATCAAGTAGTTACATCTCTACTT
AATAAATGAGAAAACGAGGATAAGAGGCCATTTGATAAATGAAAATAG
CCAAGAAGTGGTATTAGAGAGTTGAATACAGGTATTCGGGTCCAAAGTTG
ATCTGCTCAAATACTAACTGGGGAAAAGAGGGAAAAATATTTATATACAT
```

-continued

```
ATATATCTGCACACAAAATACCCCCAAAAAGACAAAATGAGGCCAGGCAG
GGTGGCTCACACCCGTAATCCCGGTACTTTGGGAGGCTGAGGCAGGTGGA
TACCTGAGATCAGGAGTTGGAGATCAGCCTGGTCAACATGGTGAAACCCT
GTCTCTACTAAAGATAAAAAATTAGCCAGGCATGGTGGCGTGCGCCTGT
AATCCCAGCTACTTGGGAGTCTGAGGCAGGAGAATCACTTGAACTGGGAA
GGGGAGGTTGCAGTGAGCCAAGATCGTACTACTGCACTCCAGCCTGGGCA
GCAGAGTGAGACTCCATCACAAAATAAATAAATAAATAAAATACAATGA
AACAGAAAGTTCAAATAATCCCATAATCTTACCACCAAGAAATAACTTTC
ACTCGTTATACTTATTGATTTTTCACATAATAAATGTACTTTACTGTGACT
ATCATGAAAAGAAAGTTATTTTAGAAACAGAGAACTGTTTCAGATCAAAT
CTATGTAGTAGAACAGAGCCATTAGGTGGGAAAGACGAGATCAAACTAAA
TCTCAGAAGGCCTAAAAGGCTAGGTCCATTCCAGCACTAAAAACTGACCA
GACAAGTAATGGCTTCAACAGCTTCTAAATATGGACAAAGCATGCTGAAA
GGGAAGGACAGGTCTAACAGTGGTATATGAAATGAACAGGAGGGGCAAAG
CTCATTTCTCCTCTGAAGTTTTCCAAAGATGGTGAGGAGGACATTAGTTT
GACATGACCCTGATATGGGACAAGATAATTTCACAGAAGTTTTACATGTT
AAAGTTTTCTTATAGATACTCATTCAAGTAAGCAATGAACACTAAAATCT
AAAGAAAGAAAAGAGCTTTAGAGTCAGGTCTGTATTCAAATTCAAGCTCT
ACCACTTAGTGGTTCTGTGACTTTGGGCAAGTCTTTTAACCTTATTAAGT
CTTAATTTCCTGATTTGTAAAATGGGGATATCGTCTCCCTCACAGGATTG
TTGTGAAACTTTTATGAGATTAATGCCTTTATATTTGGCATAGTGTAAGT
AAACAATAACTGGCAGCTTCAAAAAAAAAAGCAGTAGCATTCCATCATT
TATTATTGGTTACTCTCAAAAAGTTTTTCAATGTACTAGAAGATAAATAT
TCAAATACCTTAATATCTCCATTATTTTCAGGTAAACAGCATGCTCCTGA
ACAACCAATGGGTGAACAAATAAATTAAAAGGGAAATCTAAAACATCTT
GATATTAAACATACATGGAAGCACAATATACCAAAACCAATGGTTCACACT
AGGAGAATTTTAAGGTACAAGAAACTCTTTGAGATTCTTAAAATAATA
GTATGTCTGAATTTATTGAGTGATTTACCAGAAACTGTTGTAAGAGCTCT
ACTTGCATTATAGCACTTAATCCTCTTAACTCTATGCTGCTATTATCAA
CCTCACCCTAATCACATATGGGACACAGAGAGGTTAAGTAACTTGCCAA
GGTCAGAGTTAGGAAGTACTAAGCCATGCTTTGAATCAGTTGTCAGGCTC
CGGAACTCACACTTTCAGCCACTACATAATACTGCTTTGCTATCTTTTAG
GAAACTATGTGAGTCTACCTCACATAGACTCACATAGGTTTGTTTTTTT
TTTTTTTTTAAAGCTATCTTTTCCCCCATCAGTGTTTTTGAAGGATCCC
AAATTAGAGTCCCACAGAGGCAGACAGCAGTACTTGACAATATGGACATT
TAAGGTTAATGTTGGATTCTACTGTCTTTTACTACATGACCTAGGGAAC
GATAATTAACCTAGACTGCTTCCAAGGGTTAAATAACCCATTTAGTTATA
CTATGTAAATTATCTCTTAGTGATTGATTGAAAGCACACTGTTACTAATT
GACTCGGTATGAAGTGCTTTTTTTTCTTCCCTTTCAAGATACATACCTTT
CCAGTTAAAGTTGAGAGATCATCTCCACCCAATTACTTTTATGTCCCCTGT
TGACTGGTCATTCTAGTTAAAAAAAAAAAAACTATATATATATATATCT
ACACACACATATGTATATGTATATCCCTTATGTACACACACAAACTTCAAA
TTAAATGAGAACTAGAAGATTTGAGAAGTTAGCTAGCTAATATCCATAGC
ATTATGATATTCTAAATGATATGAATTATAAGAATTAGGTTTCCTGAAAT
GAATGACTAGAAAACTTTCAAGTAGAGATTAGTAAAAATTAAAAAGTCCT
AATCGGCCATTACTGATTTGATGTTTTTAAGAGTCCTAAAAAATGGGTTA
CATCCATTTTTAAGTGGGTAGTATTATAACAGCCACCCATCTTCAATCAC
AGTGATTTCTGAATTGTGAGGGAAGTTATTAGCATGACAGGTGTCTGTT
CTGGCCCTGTACGATTCCCATGAGTCAAGCAAATTGTAAGGGCTGGTCTA
TATCAGACCCAACCCCAAGGATATGTCCCTCAAAAGTCTAAGAAAAAACCC
CGTCATCTTCAGCATCATCTGGGAAACAGGTCTGATTAGTAGTCCTTTA
AGGAATACCTCTTAGGCTCCCATTTTACTGCTATCACAGAATCCAATAAA
ACCCTTACAGGAGATTCAATGGGAAATGCTCAACACCCACTGTAGTTGGT
GGTGACAATGACCATAATTTGGCTGTGCTGGATTCAGGACAGAAAATTTG
GGTGAAAGAGCAGGTGAACAAAAGAGCTTCGACTTGCCCTAGCAGAGAGC
AAGCCATACCATCACAAAGCCACGCAATTACAACGGTGCAGTACCAG
CACAGTAAATGAACAAAGTAGAGCCCAGAAACAGACCCAGAACTATATGA
GGATTTAGTATACAATAAAGATGGTATTTCGAGTCAGTAGGGAAAAGATG
AATTATTCAATAAATGATGTTTGGCCTTCAGCGATCTGTCTATTTGTTGT
ATAAAAGTATGGTCCCTACCTCACAGCATACACAAAATAAATTCCAGAC
GGATTAAAATCTAAATGTAAAAAATAAAGCCATAAGTGGACTGGAAGAAA
ATAGAGAATTTTTTTTAACATCCGTAGAAAGGGTAAAAACCCAGGCATGA
CATGAACCAAAACTGAAGAGGTTCTGTAACAAATACCCCCTTTTATATAT
TGGGCTCCAACAATAAGAACCCATAGGAAAATGGAGAATGAACACAAATA
GACAATTTATGAAGAGAAGGTTATAAGGTGTAAAATTATATCTATCTGA
GAAACAAACACTAAAACAATGTGATTCTACTGTTCTCCCACCGATACTGG
CAAAACTTAAGCCTGATAATATGCTGAGGGGAAATAAGCACTGTTGTTGG
TGAGAGTATTAATTGGCATAGCTTCTTTTGAAAATGAGATAGCAATACCT
GTTAAAATTGCAAACATGCATGTCACTTAATCCAGTAATGCCACTTCTGG
GAATCAATGCTACAAAACACTGACAAGTATACAAAGATACATTCAAGAG
TGTTCACTGGGCCGGGTGCGGTGGCTTCATGCCTGTAATCCCAGGGAGGC
AGAGGCAAGACGATCGCTTGACCCCAGGAGTTCAAGGCCAGCCCGAGAAA
CACAGCAAGACCGTGTCTCTCTTTTTTTATTTAAAAAATAAATGTTCAC
TGTATCAGTTGTTCACAAAAACAAACCAACATGTCCATTAACAGGGAACC
ATTTAATCAAGTCATCTACACAATGTAATACCATGCACTATATTA
AAAAGCACCTCGATAATCCAAAGCACACTGAGACAGAATAATGGTATTAAA
AACACCAAGTAGTGGACACTGTGTTGCCTATGACACCATTTTTATTCAA
CATTTAAACAAATTTGTAACAGCAATTACATGAGTAGTGACAATGGCGTT
TATGAGACTTTTCACTTTTATGTGCTTCTATTTTTGTTATGCTTCTATAT
ATACATCCATTTATTATGGAGTGTTACTTTCAAAAATCACAAATGGGCCA
GTATTATTTGGTGTTGCAAGGTGAGCATATGACTTCTGATATCAACCTTT
GCATATTACTTCTCAATTTAGGGAAATTACAGACATCCCTTATTCTAACT
AACTTAAAACCCAGCATTTTCAAACATACAGAATTGATGGGGAAAAAAAG
AAAGAAGAAAGAAAGAAAAGGCAACAAGCTTCAGATGACAGTGACTCACA
TCAAATTATTTATAAAATCTGTTAATAGTGCCATCTTCTGGAGATACCT
GGTATTACAGTCCAACTCCAGTTGATGTCTTTACAGAGACAAGAGGAATA
AAGGAAAAATATTCAAGAACTGAAAAGTATGGAGTCATGGAAAATTGC
TGTGATCCAAAGGCTACGGTGATAGGACAAGAAACAAGAGAACTCCAAGC
AGTAAGACACTGCTGTTCTATTAGCATCGAAACCTCCATACTCCTGTTTG
CCCCAAGGCTTTTTTAAAAAATAGAGACAGGATCTCACTATTTTGCTCAG
GCTGGTCTTGAACTCCTGGACTCAAGCTATCCTCCTGCCTCGGCCTCCTA
AAGTGCCGAGATTACAGGCTTGAGTCACCATACCTGGCTATTTATTTTTT
CTTAACTCTCTTGCCTGGCCTATAGCCACCATGGAAGCTAATAAGAATAT
TAATTTAAGAGTAATGGTATAGTTCACTACATTGGAATACAGGTATAAGT
GCCTACATTGTACATGAATGGCATACATGGATCAATTACCGCACCTGGGT
GGCCAAAGGAACTGCGCGAACCTCCCTCCTTGGCTGTCTGGAAGAAGCTT
CCCACTAGATCCCTTTACTGAGTGCCTCCCTCATCTTTAATTATGGTTAA
GTCTAGGATAACAGGACTGGCAAAGGTGAGGGGAAAGCTTCCTCCAGAGT
TGCTCTACCCTCTCCTCTACCGTCCTATCTCCTCACTCCTCTCAGCCAAG
GAGTCCAATCTGTCCTGAACTCAGAGCGTCACTGTCAACTACATAAAATT
GCCAGAGAGCTCTTTGGGACTACAAACACATACCCTTAATGTCTTTATT
TCTATTTTGTGTACCTCTTCAGTGTAGGTGAAAAAATAGGAAGGATAATA
GGGAAGAACTTTGTTTATGCCTACTTATCCGCCCCTAGGAATTTTGAAAA
CCTCTAGGTAGCAATAAGAACTGCAGCATGGTATAGAAAAAGAGGAGGAA
AGCTGTATAGAAATGCATAATAAATGGGCAGGAAAAGAAGCTGCTTGGAAC
AAACAGGGAGGTTGAACTATAAGGAGAGAAAGCAGAGAGGCTAATCAACA
AGGGTGGGTTCCCAAGAGGGCATGATGAGACTATTACTAAGGTAGGAATT
ACTAAGGGCTCCATGTCCCCTTAGTGGGTTAGTACTATGTAGCTTGCTTT
CTGCAGTGAACTTCAGACCCCTTCTTTTAGGATCCTAGAATGGACTTTTTT
TTTTTATCGGAAAACAGTCATTCTCTCAACATTCAAGCAGGCCCCAAGTC
TACCACACTCAATCACATTTTTCTCTTCATATCATAATCTCTCAACCATTC
TCTGTCCTTTTAACTGTTTTTCTATACCCTGATCAAATGCCAACAAAAGT
GAGAATGTTAGAATCATGTATTTTTAGAGGTAGAGTGTATCTCAGATAAA
AAAAAAGGCAGATATTCCATTTTCCAAAATATGATGCAGAAAAAA
GTATGAAAGGACATATGCTCAGGTAACAAGTTAATTTGTTTACTTGTATT
TTATGAATTCCCTAAAACCTACGTCACCCGCGCCGTTCCCACGCCCGCG
CCACGTCACAAACTCCACCCCCTCATTATCATATTGGCTTCAATCCAAA
TAAGGTATATTATTGATGATGTTAATTAACATGCATGGATCCATATGCGG
TGTGAAATACCGCACAGATGCGTAAGGAGAAAATACCGCATCAGGCGCTC
TTCCGCTTCCTCGCTCACTGACTCGCTGCGCTCGGTCGTTCGGCTGCGGC
GAGCGGTATCAGCTCACTCAAAGGCGGTAATACGGTTATCCACAGAATCA
GGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCC
CTGACGAGCATCACAAAATTGACGCTCAAGTCAGAGGTGGCGAAACCCG
ACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACC
CGGTAAGACACGACTTATCGCCACTGGCAGCAGCCACTGGTAACAGGATT
AGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGA
AGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCG
CAGAAAAAAAGGATGTCAAGAAGATCCTTTGATCTTTTCTACGGGGTCTG
ACGCTCAGTGGAACGAAAACTCACGTTAAGGGATTTTGGTGATGAGATTA
TCAAAAAGGATCTTCACCTAGATCCTTTTAAATTAAAATGAAGTTTTAA
ATCAATCTAAAGTATATATGAGTAAACTTGGTCTGACAGTTACCAATGCT
TAATCAGTGAGGCACCTATCTCAGCGATCTGTCTATTTCGTTCATCCATA
GTTGCGTGACTCCCCGTCGTGTAGATAACTACGATACGGGAGGGCTTACC
ATCTGGCCCCAGTGCTGCAATGATACCGCGAGACCCACGCTCACCGGCTC
CAGATTTATGAGCAATAAACCAGCCAGCCGGAAGGGCCGAGCGCAGAAGT
GGTCCTGCAACTTTATCCGCCTCCATCCAGTCTATTAATTGTTGCCGGGA
AGCTAGAGTAAGTATTCGCCAGTTAATAGTTTGCGCAACGTTGTTGCCA
TTGCTGCAGCCATGAGATTATCAAAAAGGATCTTCACCTAGATCCTTTTC
ACGTAGAAAGCCAGTCCGCAGAAACGGTGCTGAGCCCGGATGAATGTCAG
CTACTGGGCTATCTGGACAAGGGAAAACGCAAGCGCAAAGAGAAAGAG
TAGCTTGCAGTGGGCTTACATGGCGATAGCTAGACTGGGCGGTTTTATGG
ACAGCAAGCGAACCGGAATTGCCAGCTGGGGCGCCCTCTGGTAAGGTTGG
GAAGCCCTGCAAAGTAAACTGGATGGCTTTCTTGCCGCCAAGGATCTGAT
GGCGCAGGGGATCAAGCTCTGATCAAGAGACAGGATGAGGATCGTTTCGC
ATGATTGAACAAGATGGATTGCACGCAGGTTCTCCGGCCGCTTGGGTGGA
GAGGCTATTCGGCTATGACTGGGCACAACAGACAATCGGCTGCTCTGATG
CCGCCGTGTTCCGGCTGTCAGCGCAGGGGCGCCCGGTTCTTTTTGTCAAG
ACCGACCTGTCCGGTGCCCTGAATGAACTGCAAGACGAGGCAGCGCGGCT
ATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAG
GATCTCCTGTCATCTCACCTTGCTCCTGCCGAGAAAGTATCCATCATGGC
TGATGCAATGCGGCGGCTGCATACGCTTGATCCGGCTAGCTGCCCATTCG
ACCACCAAGCGAAACATCGCATCGAGCGAGCACGTACTCGGATGGAAGCC
```

```
GGTCTTGTCGATCAGGATGATCTGGACGAAGAGCATCAGGGGCTCGCGCC
AGCCGAACTGTTCGCCAGGCTCAAGGCGAGCATGCCCGACGGCGAGGATC
TCGTCGTGACCCATGGCGATGCCTGCTTGCCGAATATCATGGTGGAAAAT
GGCCGCTTTTCTGGATTCATCGACTGTGGCCGGCTGGGTGTGGCGGACCG
CTATCAGGACATAGCGTTGGCTACCCGTGATATTGCTGAAGAGCTTGGCG
GCGAATGGGCTGACCGCTTCCTCGTGCTTTACGGTATCGCCGCTCCCGAT
TCGCAGCGCATCGCCTTCTATCGCCTTCTTGACGAGTTCTTCTGAATTTT
GTTAAAATTTTTGTTAAATCAGCTCATTTTTTAACCAATAGGCCGAAATC
GGCAAAATCCCTTATAAATCAAAAGAATAGACCGAGATAGGGTTGAGTGT
TGTTCCAGTTTGGAACAAGAGTCCACTATTAAAGAACGTGGACTCCAACG
TCAAAGGGCGAAAAACCGTCTATCAGGGCGATGGCCCACTACGTGAACCA
TCACCCTAATCAAGTTTTTTGGGGTCGAGGTGCCGTAAAGCACTAAATCG
GAACCCTAAAGGGAGCCCCCGATTTAGAGCTTGACGGGGAAAGCCGGCGA
ACGTGGCGAGAAAGGAAGGGAAGAAAGCGAAAGGAGCGGGCGCTAGGGCG
CTGGCAAGTGTAGCGGTCACGCTGCGCGTAACCACCACACCCGCCGGGCT
TAATGCGCCGCTACAGGGCGCGTCCATTCGCCATTCAGGAATCGATTAAT
TCTTAATTAACATCATCAATAATATACCTTATTTTGGATTGAAGCCAATA
TGATAATGAGGGGGTGGAGTTTGTGACGTGGCGCGGGGCGTGGGAACGGG
GCGGGTGACGTAGTAGTGTGGCGGAAGTGTGATGTTGCAAGTGTGGCGGA
ACACATGTAAGCGAGGGATGTGGCAAAAGTGACGTTTTTGGTGTGCGCCG
GTGTACAGAGGAAGTGACAATTTTCGCGCGGTTTTAGGCGGATGTTGTAG
TAAATTTGGGCGTAACCGAGTAAGATTTGGCCATTTTCGCGGGAAAACTG
AATAAGAGGAAGTGAAATCTGAATAATTTTGTGTTACTCATAGCGCGTAA
TACTG
```

What is claimed is:

1. A method for reducing re-occlusion or intimal hyperplasia in a blood vessel graft in a mammal, said method comprising the steps of:
   infecting a segment of blood vessel in vitro using a gutless adenoviral vector comprising a polynucleotide encoding a thrombomodulin protein which comprises SEQ ID NO: 2; and
   grafting the virus-treated blood vessel in said mammal;
   wherein the thrombomodulin protein is under the control of a regulatory element and is expressed in an amount sufficient to reduce re-occlusion or intimal hyperplasia in the grafted blood vessel, and wherein said gutless adenoviral vector comprises the nucleotide sequence of SEQ ID NO:13 or SEQ ID NO:15.

2. The method of claim 1, wherein said gutless adenoviral vector comprises the nucleotide sequence of SEQ ID NO: 13 and SEQ ID NO: 15.

3. The method of claim 1, wherein said gutless adenoviral vector is produced by transfecting 293FLP cells with a linearized plasmid having the nucleotide sequence of SEQ ID NO: 16 followed with infection of a helper virus.

4. The method of claim 1, wherein said regulatory element is a CMV promoter or a RSV promoter.

5. The method of claim 1, wherein said infecting step further comprises:
   filling the blood vessel with a complete viral delivery system comprising of 1:1 mixture of Ham's F12 medium and DMEM, an effective amount of the gutless adenovirus vector, and an acellular oxygen carrier; and
   incubating the blood vessel with the complete viral delivery system for a desired period of time.

6. The method of claim 5, wherein said acellular oxygen carrier is selected from the group consisting of unmodified hemoglobin, chemically modified hemoglobin and perfluorochemical emulsions.

7. The method of claim 6, wherein said unmodified hemoglobin or chemically modified hemoglobin is used in the range of 3 g/dl to 10 g/dl.

8. The method of claim 7, wherein the complete viral delivery system further comprises at least one of L-glutamine, sodium bicarbonate, or antibiotic-antimycotic.

9. The method of claim 8, wherein the desired period of time is between 10 to 45 minutes.

* * * * *